United States Patent
Kim et al.

(10) Patent No.: US 10,193,082 B2
(45) Date of Patent: Jan. 29, 2019

(54) CONDENSED-CYCLIC COMPOUND AND ORGANIC LIGHT EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Hyunjung Kim, Suwon-si (KR); Miyoung Chae, Suwon-si (KR); Sangmo Kim, Hwaseong-si (KR); Soonok Jeon, Seoul (KR); Yeonsook Chung, Seoul (KR); Dalho Huh, Suwon-si (KR); Namheon Lee, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 41 days.

(21) Appl. No.: 15/093,412

(22) Filed: Apr. 7, 2016

(65) Prior Publication Data
US 2017/0054082 A1    Feb. 23, 2017

(30) Foreign Application Priority Data
Aug. 20, 2015  (KR) .......................... 10-2015-0117335

(51) Int. Cl.
| | |
|---|---|
| C07D 405/10 | (2006.01) |
| H01L 51/00 | (2006.01) |
| C09K 11/02 | (2006.01) |
| C07D 401/10 | (2006.01) |
| H01L 51/50 | (2006.01) |

(52) U.S. Cl.
CPC ........ *H01L 51/0072* (2013.01); *C07D 401/10* (2013.01); *C07D 405/10* (2013.01); *C09K 11/025* (2013.01); *H01L 51/0073* (2013.01); *H01L 51/5016* (2013.01)

(58) Field of Classification Search
CPC .................................................. H01L 51/0072
See application file for complete search history.

(56) References Cited

U.S. PATENT DOCUMENTS

| | | | |
|---|---|---|---|
| 9,318,709 B2 * | 4/2016 | Mizuki | ............... H01L 51/0067 |
| 2009/0030202 A1 | 1/2009 | Iwakuma et al. | |
| 2014/0374720 A1 | 12/2014 | Kato et al. | |
| 2015/0057445 A1 | 2/2015 | Anemian et al. | |

FOREIGN PATENT DOCUMENTS

| | | | |
|---|---|---|---|
| JP | 2012-033892 A | | 2/2012 |
| JP | 2013-075891 A | | 4/2013 |
| KR | 2013-0127994 A | | 11/2013 |
| KR | 2014046541 | * | 4/2014 |
| KR | 2014132244 | * | 11/2014 |
| KR | 2014-0138393 A | | 12/2014 |

OTHER PUBLICATIONS

Deng et al., Simple bipolar host materials incorporating CN group for highly efficient blue electrophosphorescence with slow efficiency roll-off, Journal of Materials Chemistry C: Materials for Optical and Electronic Devices (2013), 1(48), 8140-8145.*

* cited by examiner

*Primary Examiner* — Paul V Ward
(74) *Attorney, Agent, or Firm* — Cantor Colburn LLP

(57) ABSTRACT

A condensed-cyclic compound represented by Formula 1:

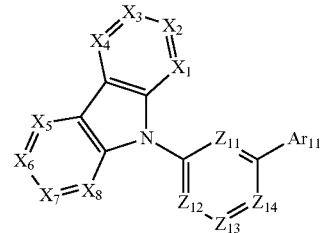

Formula 1 wherein, in Formula 1, $Ar_{11}$, $X_1$ to $X_8$, and $Z_{11}$ to $Z_{14}$ are the same as described in the specification.

20 Claims, 3 Drawing Sheets

CONDENSED-CYCLIC COMPOUND AND ORGANIC LIGHT EMITTING DEVICE INCLUDING THE SAME

CROSS-REFERENCE TO RELATED APPLICATION

This application claims priority to and the benefit of Korean Patent Application No. 10-2015-0117335, filed on Aug. 20, 2015, in the Korean Intellectual Property Office, the content of which is incorporated herein in its entirety by reference.

BACKGROUND

1. Field

The present disclosure relates to a condensed-cyclic compound and an organic light-emitting device including the same.

2. Description of the Related Art

Organic light-emitting devices (OLEDs) are self-emission devices that have wide viewing angles, high contrast ratios, and short response times. In addition, the OLEDs exhibit high luminance, driving voltage, and response speed characteristics, and produce full-color images.

A typical organic light-emitting device includes an anode, a cathode, and an organic layer that is disposed between the anode and the cathode, wherein the organic layer includes an emission layer. A hole transport region may be between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons change from an excited state to a ground state to thereby generate light.

Different types of organic light emitting devices are known. However, there still remains a need in OLEDs having low driving voltage, high efficiency, high brightness, and long lifespan.

SUMMARY

Provided are a condensed-cyclic compound and an organic light-emitting device including the same.

Additional aspects will be set forth in part in the description which follows and, in part, will be apparent from the description, or may be learned by practice of the presented exemplary embodiments.

According to one or more exemplary embodiments, a condensed-cyclic compound represented by Formula 1 is provided:

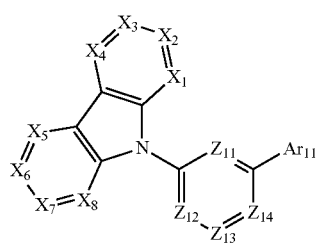

Formula 1 wherein, in Formula 1,
$Ar_{11}$ is represented by one of Formulae 10-1 to 10-4:

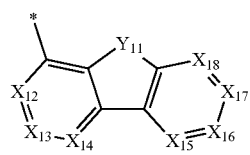

10-1

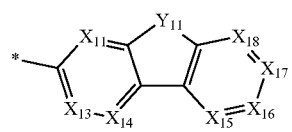

10-2

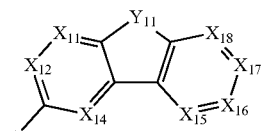

10-3

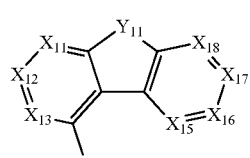

10-4 wherein, in Formulae 1 and 10-1 to 10-4,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, and $X_{18}$ is N or $C(R_{18})$;
$Y_{11}$ is O, S, $N(R_{101})$, $C(R_{101})(R_{102})$, or $Si(R_{101})(R_{102})$;
$Z_{11}$ to $Z_{14}$ are each independently selected from N, $C(A_{11})$, and $C(A_{12})$; and at least one of $Z_{11}$ to $Z_{14}$ is $C(A_{11})$; and
$A_{11}$ may include at least one cyano group (CN); and $A_{11}$ is represented by one of Formulae 2-1 to 2-10:

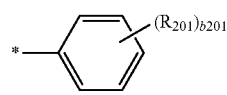

2-1

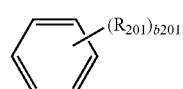

2-2

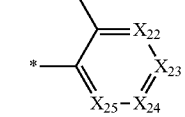

2-3

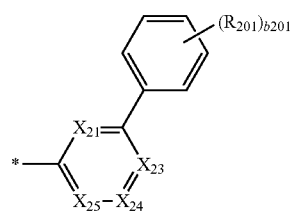

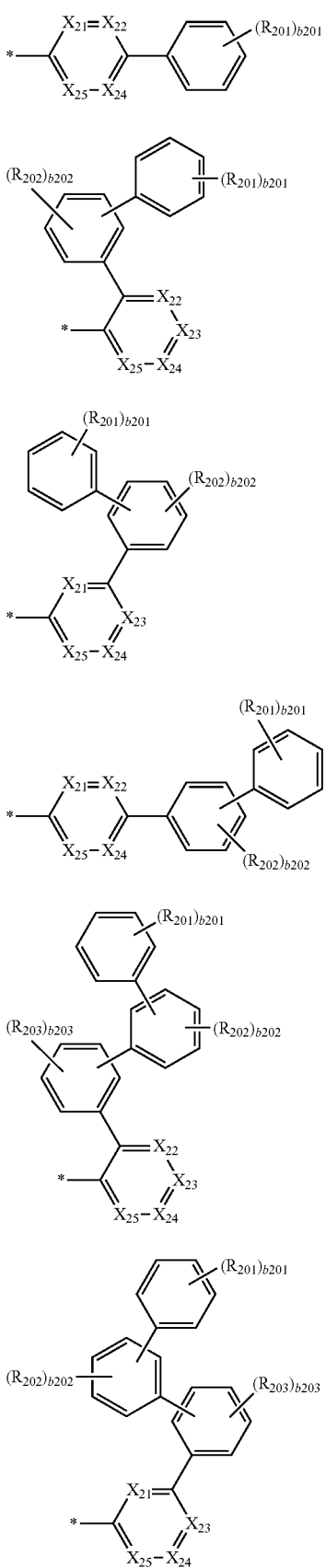

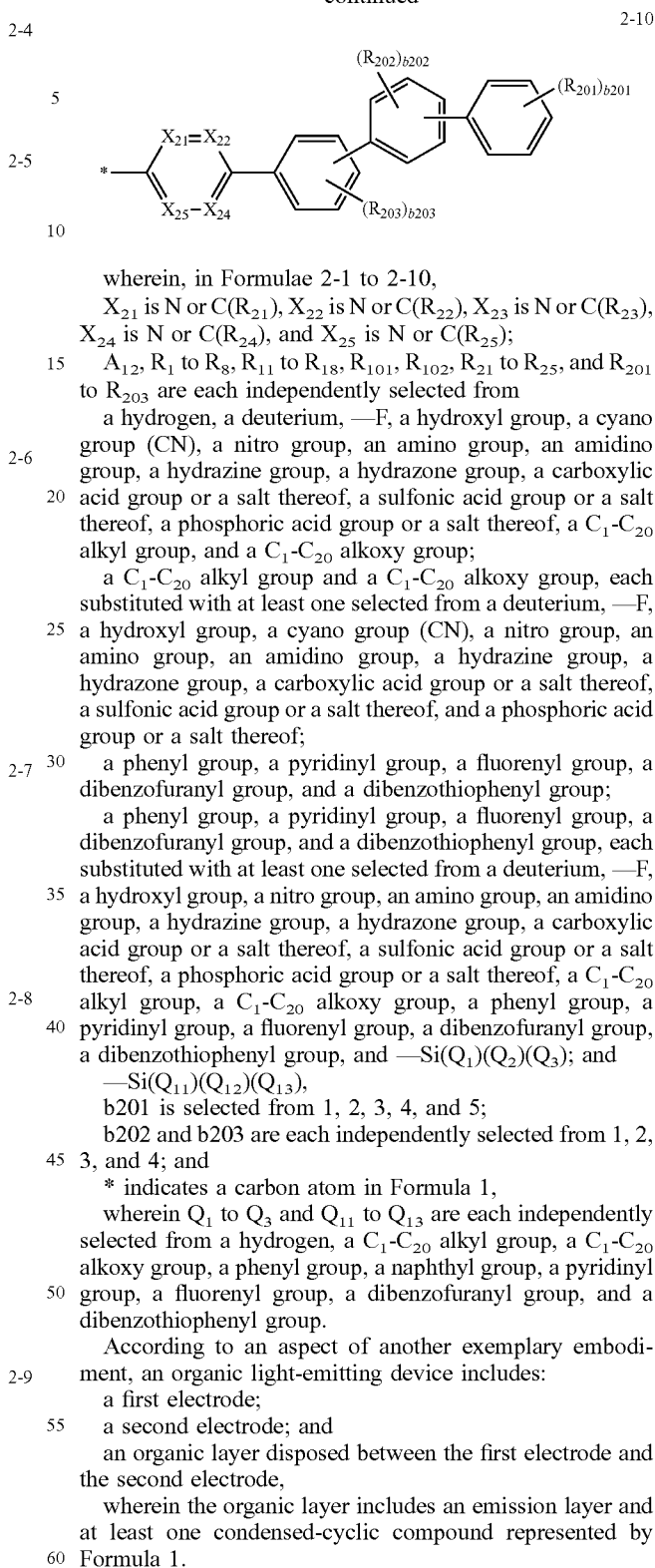

wherein, in Formulae 2-1 to 2-10,
$X_{21}$ is N or $C(R_{21})$, $X_{22}$ is N or $C(R_{22})$, $X_{23}$ is N or $C(R_{23})$, $X_{24}$ is N or $C(R_{24})$, and $X_{25}$ is N or $C(R_{25})$;

$A_{12}$, $R_1$ to $R_8$, $R_{11}$ to $R_{18}$, $R_{101}$, $R_{102}$, $R_{21}$ to $R_{25}$, and $R_{201}$ to $R_{203}$ are each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$); and —Si($Q_{11}$)($Q_{12}$)($Q_{13}$), b201 is selected from 1, 2, 3, 4, and 5;

b202 and b203 are each independently selected from 1, 2, 3, and 4; and

* indicates a carbon atom in Formula 1, wherein $Q_1$ to $Q_3$ and $Q_{11}$ to $Q_{13}$ are each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

According to an aspect of another exemplary embodiment, an organic light-emitting device includes:
a first electrode;
a second electrode; and
an organic layer disposed between the first electrode and the second electrode,
wherein the organic layer includes an emission layer and at least one condensed-cyclic compound represented by Formula 1.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
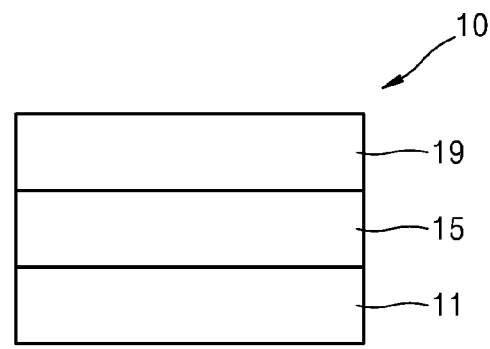
FIG. 1 is a schematic cross-sectional view illustrating an organic light-emitting device according to an embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present inventive concept. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed-cyclic compound may be represented by Formula 1:

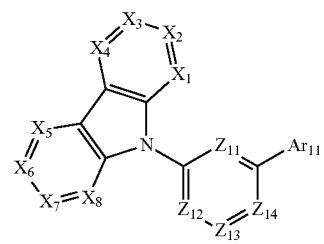

Formula 1 wherein, in Formula 1, $Ar_{11}$ may be represented by one of Formulae 10-1 to 10-4:

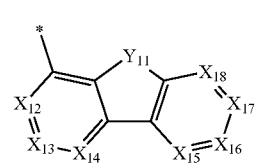

10-1

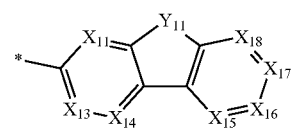

10-2

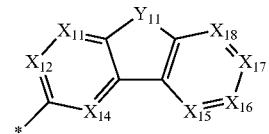

10-3

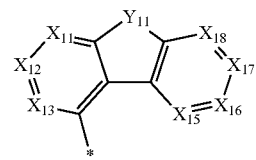

10-4 wherein, in Formulae 10-1 to 10-4,

* indicates a carbon atom in Formula 1, and $Y_{11}$ and $X_{11}$ to $X_{18}$ may be understood by referring to descriptions thereof provided herein.

In some embodiments, in Formula 1, $Ar_{11}$, may be represented by one of Formulae 10-2 and 10-3, but embodiments are not limited thereto.

In Formulae 1 and 10-1 to 10-4, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_{11}$, may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{16})$, $X_{16}$ may be N or $C(R_{16})$, $X_{17}$ may be N or $C(R_{17})$, and $X_{18}$ may be N or $C(R_{18})$.

In some embodiments, in Formulae 1 and 10-1 to 10-4, $X_1$ may be N, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be N, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be N, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be $C(R_3)$, $X_4$ may be N, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be $C(R_3)$, $X_4$ may be $C(R_4)$, $X_5$ may be N, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be N, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be N, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be N, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formulae 1 and 10-1 to 10-4, $X_1$ may be $C(R_1)$, $X_2$ may be $C(R_2)$, $X_3$ may be N, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$;

$X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be N, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, $X_{18}$ may be $C(R_{18})$; or $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In Formulae 10-1 to 10-4, $Y_{11}$ may be O, S, $N(R_{101})$, $C(R_{101})(R_{102})$, or $Si(R_{101})(R_{102})$, and $R_{101}$ and $R_{102}$ may be understood by referring to descriptions thereof provided herein.

In some embodiments, in Formulae 10-1 to 10-4, $Y_{11}$ may be O, S, or $N(R_{101})$, but embodiments are not limited thereto.

In Formula 1, $Z_{11}$ to $Z_{14}$ may be each independently selected from N, $C(A_{11})$, and $C(A_{12})$; at least one of $Z_{11}$ to $Z_{14}$ may be $C(A_{11})$; and $A_{11}$ and $A_{12}$ may be understood by referring to descriptions thereof provided herein.

In some embodiments, in Formula 1, $Z_{11}$ may be N, $Z_{12}$ may be $C(A_{12})$, $Z_{13}$ may be $C(A_{11})$, and $Z_{14}$ may be $C(A_{12})$;

$Z_{11}$ may be $C(A_{12})$, $Z_{12}$ may be N, $Z_{13}$ may be $C(A_{11})$, and $Z_{14}$ may be $C(A_{12})$;

$Z_{11}$ may be $C(A_{12})$, $Z_{12}$ may be $C(A_{12})$, $Z_{13}$ may be $C(A_{11})$, and $Z_{14}$ may be N; or $Z_{11}$ may be $C(A_{12})$, $Z_{12}$ may be $C(A_{12})$, $Z_{13}$ may be $C(A_{11})$, and $Z_{14}$ may be $C(A_{12})$, but embodiments are not limited thereto.

In some embodiments, in Formula 1, $Z_{11}$ may be $C(A_{12})$, $Z_{12}$ may be $C(A_{12})$, $Z_{13}$ may be $C(A_{11})$, and $Z_{14}$ may be $C(A_{12})$, but embodiments are not limited thereto.

In some embodiments, in Formula 1, $Z_{11}$ may be N, $Z_{12}$ may be CH, $Z_{13}$ may be $C(A_{11})$, and $Z_{14}$ may be CH;

$Z_{11}$ may be CH, $Z_{12}$ may be N, $Z_{13}$ may be $C(A_{11})$, and $Z_{14}$ may be CH;

$Z_{11}$ may be CH, $Z_{12}$ may be CH, $Z_{13}$ may be $C(A_{11})$, and $Z_{14}$ may be N; or $Z_{11}$ may be CH, $Z_{12}$ may be CH, $Z_{13}$ may be $C(A_{11})$, and $Z_{14}$ may be CH, but embodiments are not limited thereto.

In some embodiments, in Formula 1, $Z_{11}$ may be CH, $Z_{12}$ may be CH, $Z_{13}$ may be $C(A_{11})$, and $Z_{14}$ may be CH, but embodiments are not limited thereto.

In Formula 1, $A_{11}$ may include at least one cyano group (CN); and $A_{11}$ may be represented by one of Formulae 2-1 to 2-10, but embodiments are not limited thereto:

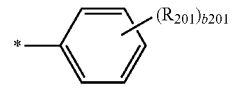

2-1

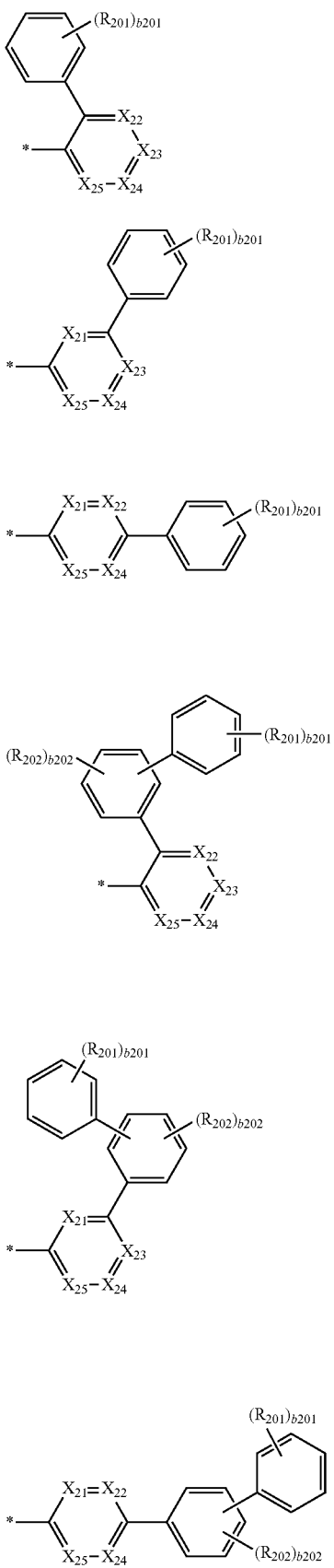

wherein, in Formulae 2-1 to 2-10,
$X_{21}$ may be N or $C(R_{21})$, $X_{22}$ may be N or $C(R_{22})$, $X_{23}$ may be N or $C(R_{23})$, $X_{24}$ may be N or $C(R_{24})$, and $X_{25}$ may be N or $C(R_{25})$; and
$R_{21}$ to $R_{25}$, $R_{201}$ to $R_{203}$, and b201 to b203 may be understood by referring to descriptions thereof provided herein.

In some embodiments, in Formula 1, $A_{11}$ may be represented by one of Formulae 2-1 to 2-7, but embodiments are not limited thereto.

In some embodiments, in Formula 1, $A_{11}$ may be represented by one of Formulae 2-2, 2-5, and 2-8,
wherein, in Formula 2-2, 2-5 and 2-8,
$X_{22}$ may be N, $X_{23}$ may be $C(R_{23})$, $X_{24}$ may be $C(R_{24})$, and $X_{25}$ may be $C(R_{25})$;
$X_{22}$ may be $C(R_{22})$, $X_{23}$ may be N, $X_{24}$ may be $C(R_{24})$, and $X_{25}$ may be $C(R_{25})$;
$X_{22}$ may be $C(R_{22})$, $X_{23}$ may be $C(R_{23})$, $X_{24}$ may be N, and $X_{25}$ may be $C(R_{25})$; or
$X_{22}$ may be $C(R_{22})$, $X_{23}$ may be $C(R_{23})$, $X_{24}$ may be $C(R_{24})$, and $X_{25}$ may be N, but embodiments are not limited thereto.

In some embodiments, in Formula 1, $A_{11}$ may be represented by one of Formulae 2-3, 2-6, and 2-9,
wherein, in Formula 2-3, 2-6 and 2-9,
$X_{21}$ may be N, $X_{23}$ may be $C(R_{23})$, $X_{24}$ may be $C(R_{24})$, and $X_{25}$ may be $C(R_{25})$;

$X_{21}$ may be $C(R_{21})$, $X_{23}$ may be N, $X_{24}$ may be $C(R_{24})$, and $X_{25}$ may be $C(R_{25})$;

$X_{21}$ may be $C(R_{21})$, $X_{23}$ may be $C(R_{23})$, $X_{24}$ may be N, and $X_{25}$ may be $C(R_{25})$; or $X_{21}$ may be $C(R_{21})$, $X_{23}$ may be $C(R_{23})$, $X_{24}$ may be $C(R_{24})$, and $X_{25}$ may be N, but embodiments are not limited thereto.

In some embodiments, in Formula 1, $A_{11}$ may be represented by one of Formulae 2-4, 2-7, and 2-10, wherein, in Formula 2-4, 2-7 and 2-10, $X_{21}$ may be N, $X_{22}$ may be $C(R_{22})$, $X_{24}$ may be $C(R_{24})$, and $X_{25}$ may be $C(R_{25})$;

$X_{21}$ may be $C(R_{21})$, $X_{22}$ may be N, $X_{24}$ may be $C(R_{24})$, and $X_{25}$ may be $C(R_{25})$;

$X_{21}$ may be $C(R_{21})$, $X_{22}$ may be $C(R_{22})$, $X_{24}$ may be N, and $X_{25}$ may be $C(R_{25})$; or $X_{21}$ may be $C(R_{21})$, $X_{22}$ may be $C(R_{22})$, $X_{24}$ may be $C(R_{24})$, and $X_{25}$ may be N, but embodiments are not limited thereto.

In some embodiments, in Formula 1, $A_{11}$ may be represented by one of Formulae 3-1 to 3-110, but embodiments are not limited thereto:

3-1
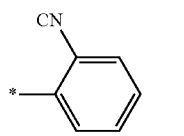

3-2
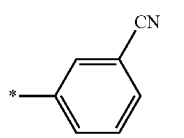

3-3
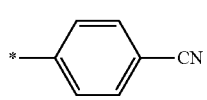

3-4
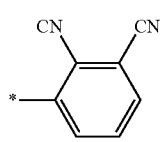

3-5
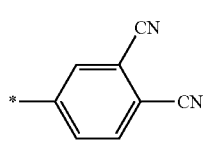

3-6
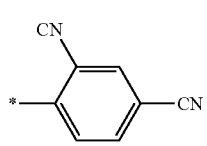

3-7
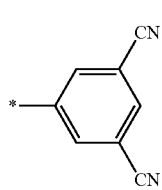

-continued 3-8
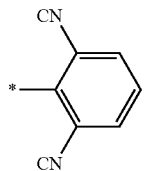

3-9
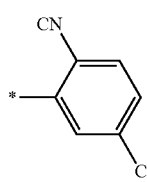

3-10
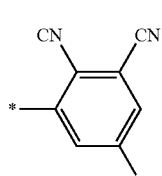

3-11
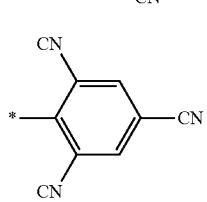

3-12
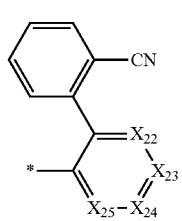

3-13
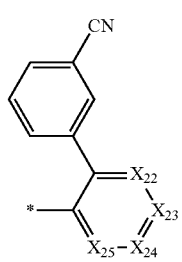

3-14
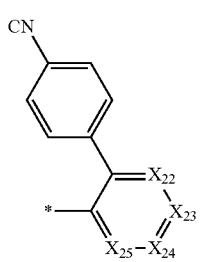

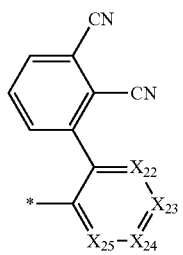
3-15
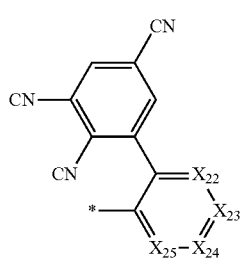
3-21
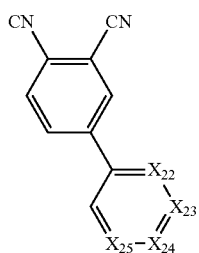
3-16
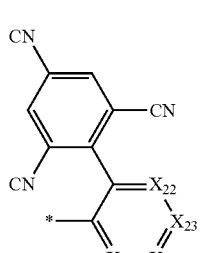
3-22
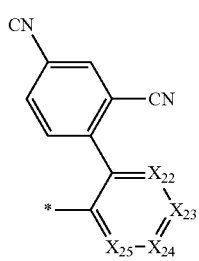
3-17
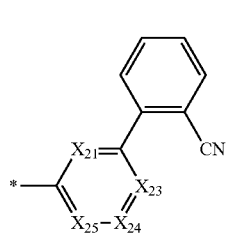
3-23
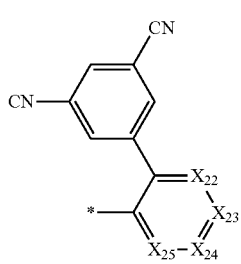
3-18
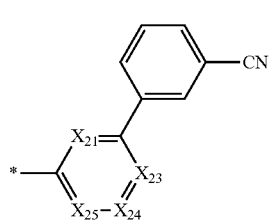
3-24
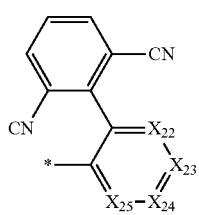
3-19
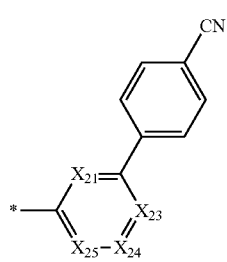
3-25
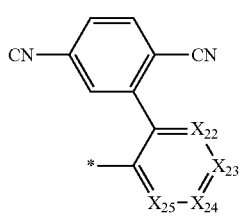
3-20
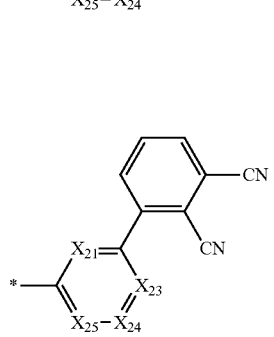
3-26

3-27 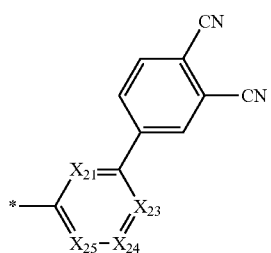
3-28 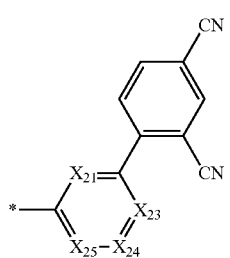
3-29 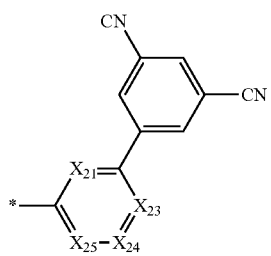
3-30 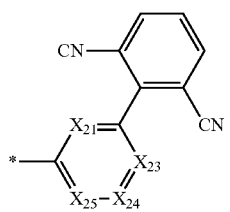
3-31 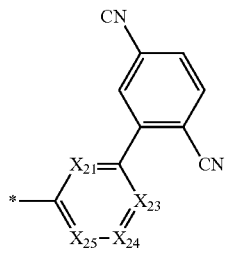
3-32 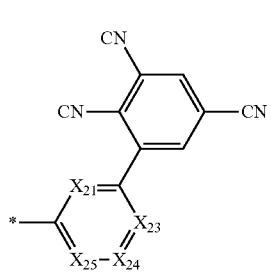
3-33 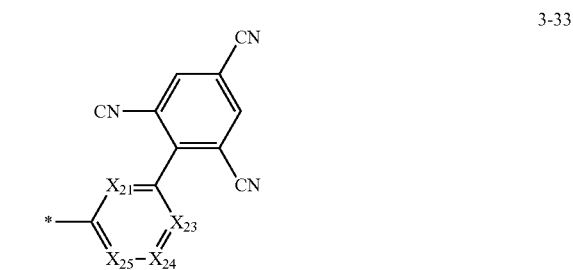
3-34 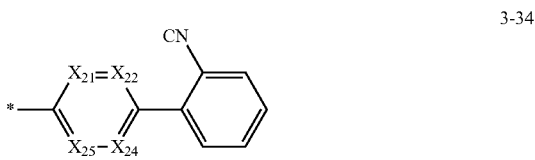
3-35 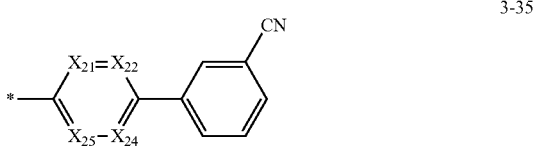
3-36 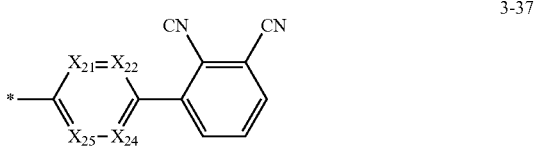
3-37 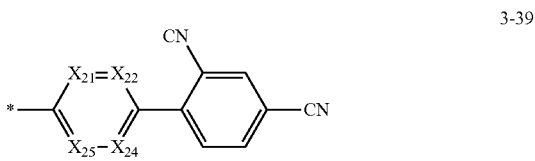
3-38 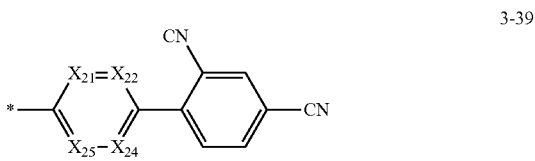
3-39 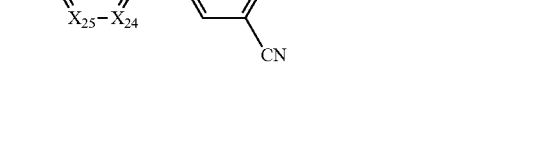
3-40 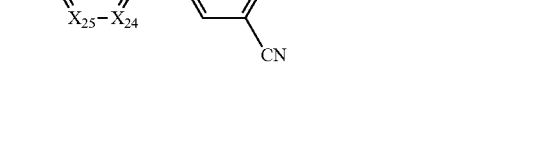
3-41 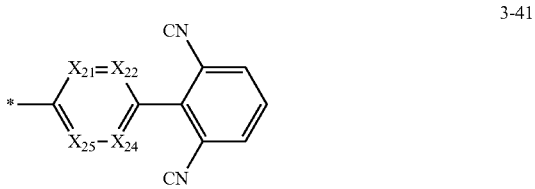

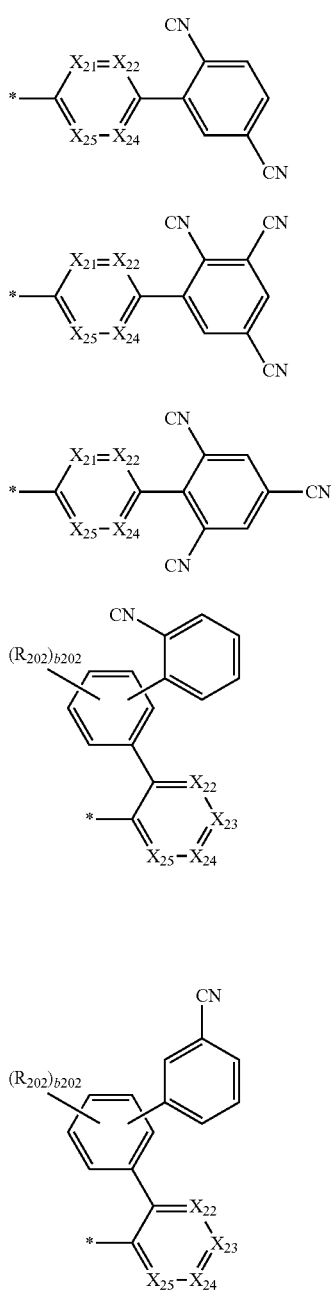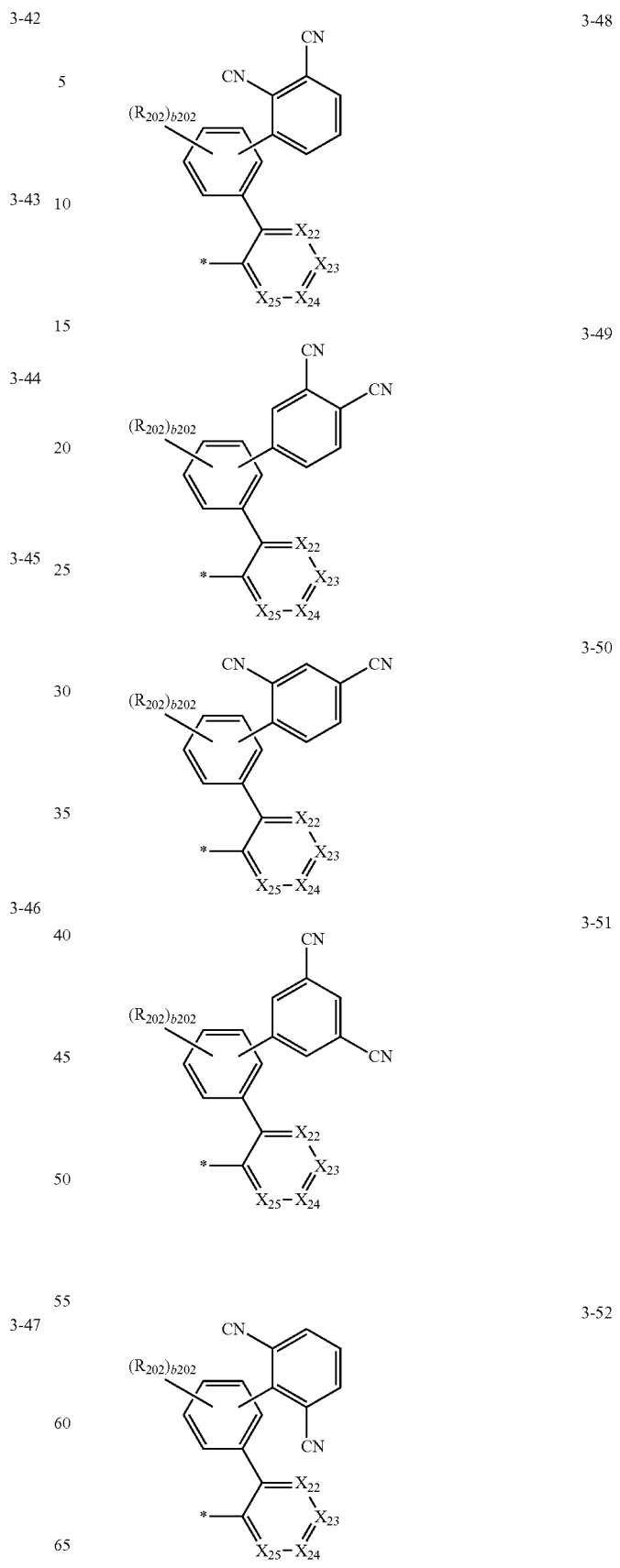

-continued
3-53
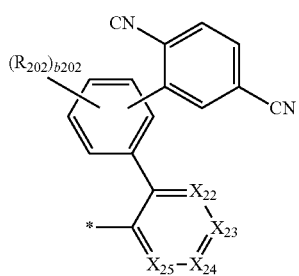
3-54
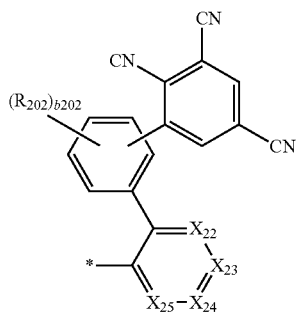
3-55
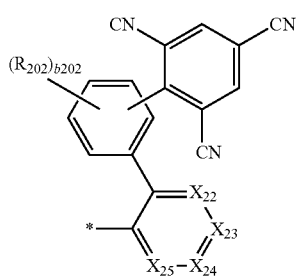
3-56
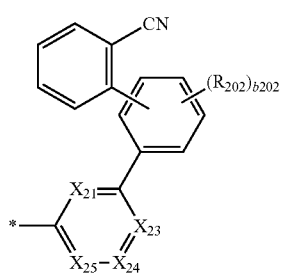
3-57
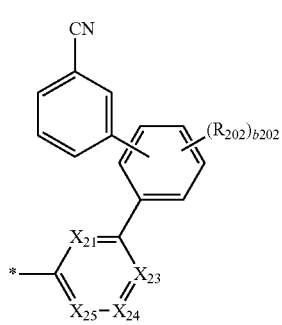
-continued
3-58
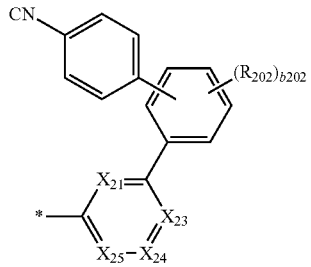
3-59
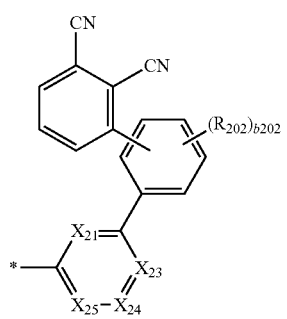
3-60
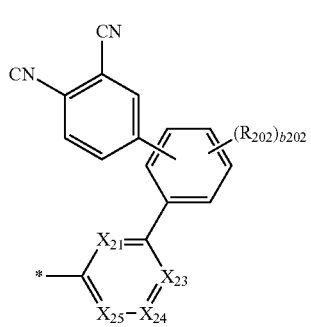
3-61
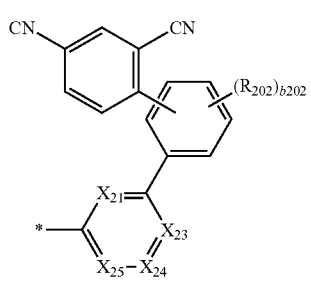
3-62
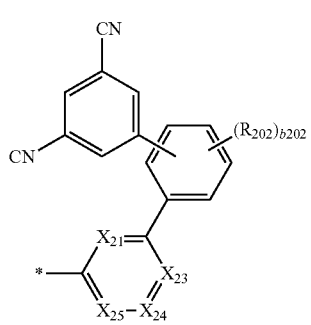

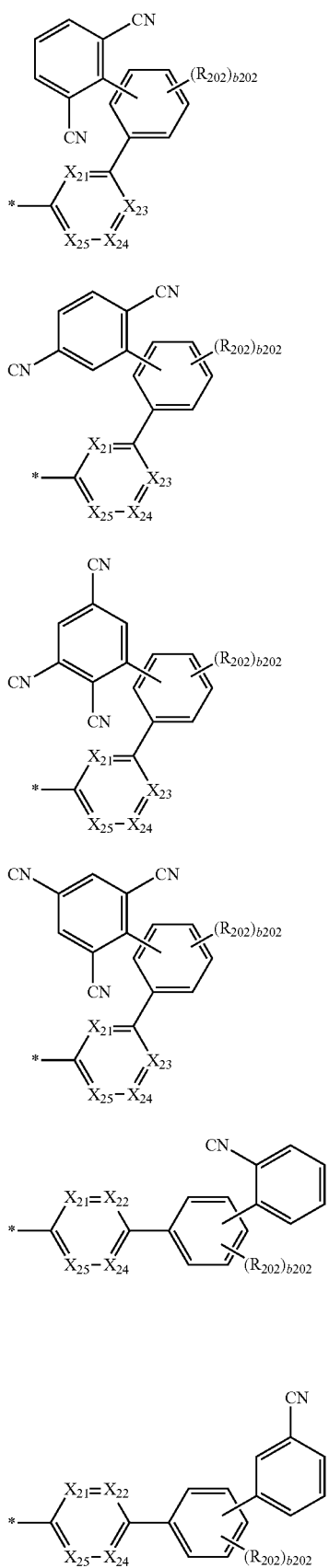
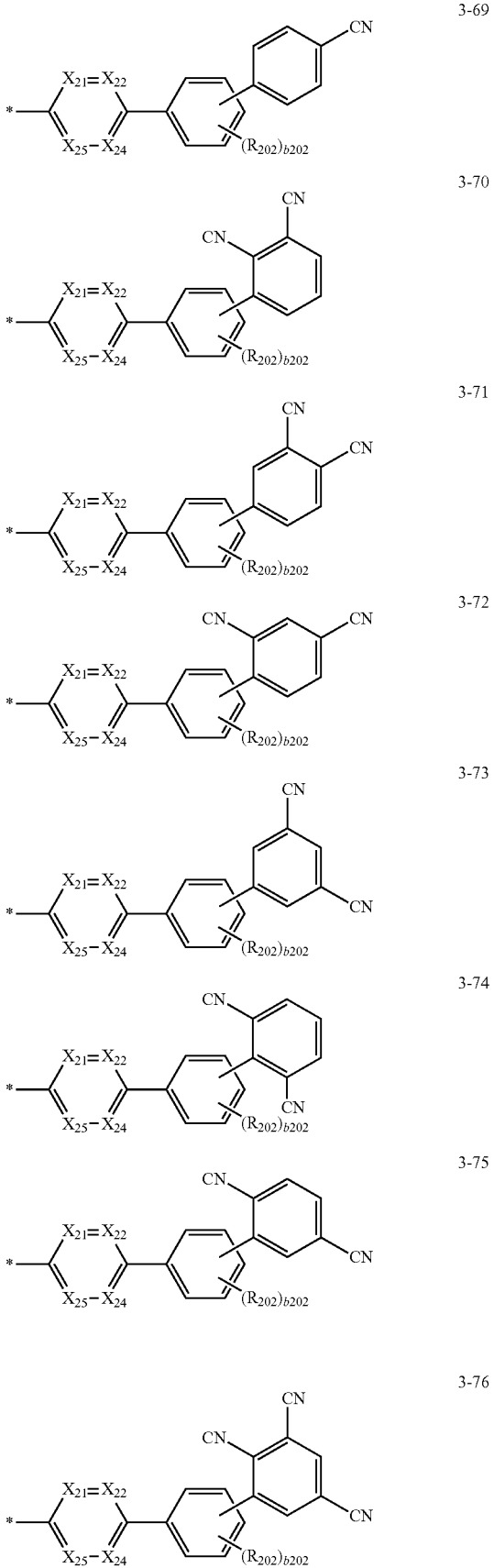

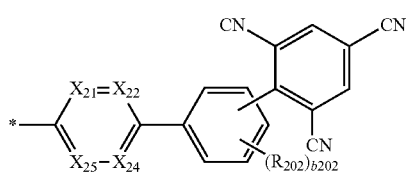
3-77
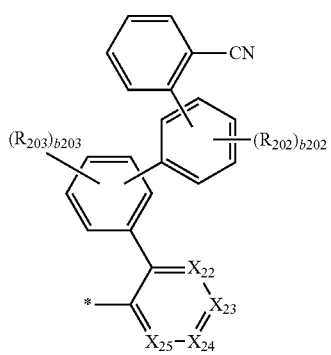
3-78
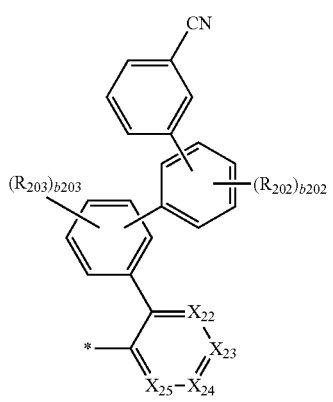
3-79
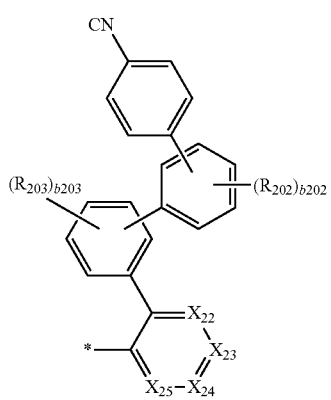
3-80
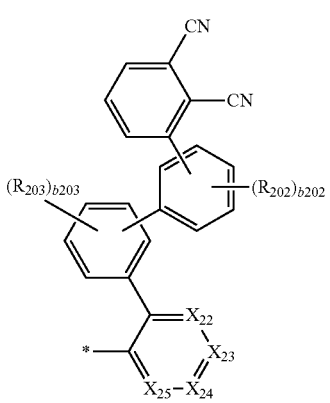
3-81
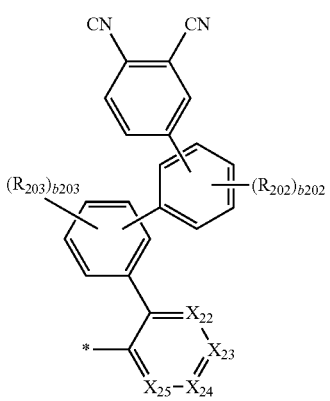
3-82
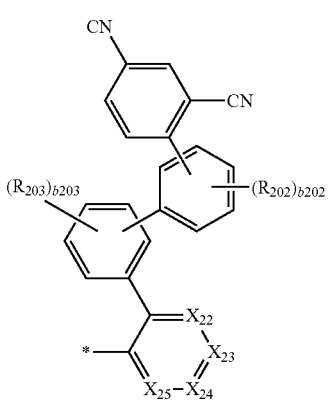
3-83
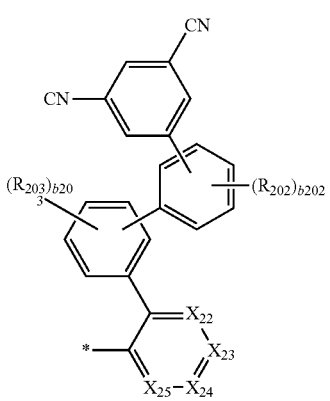
3-84

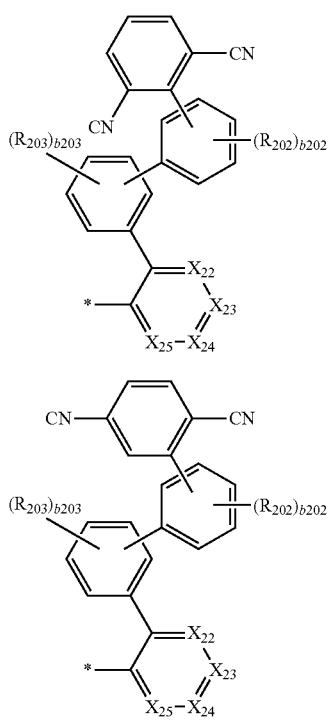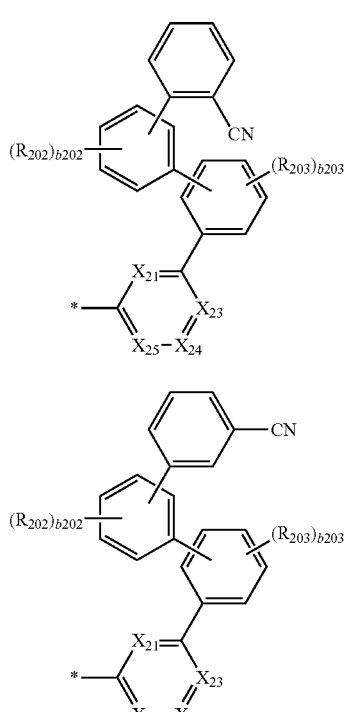

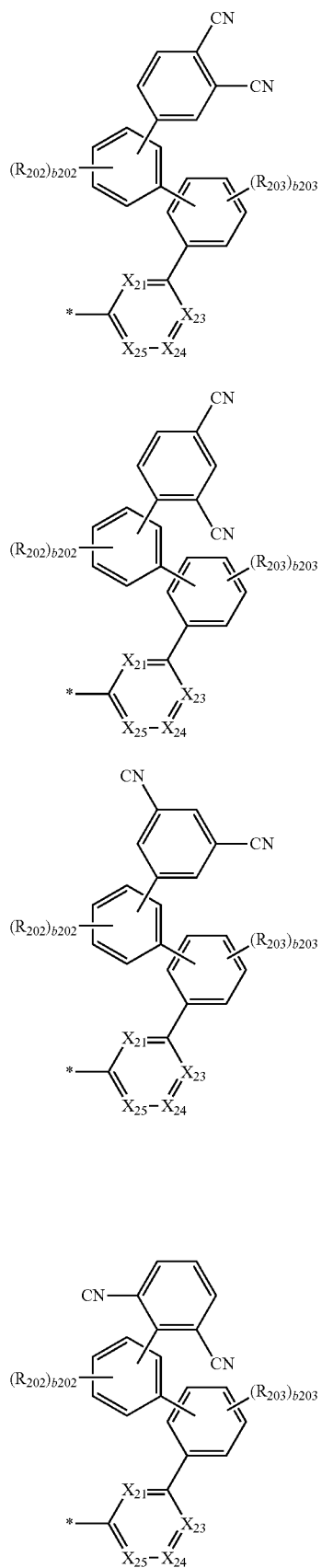
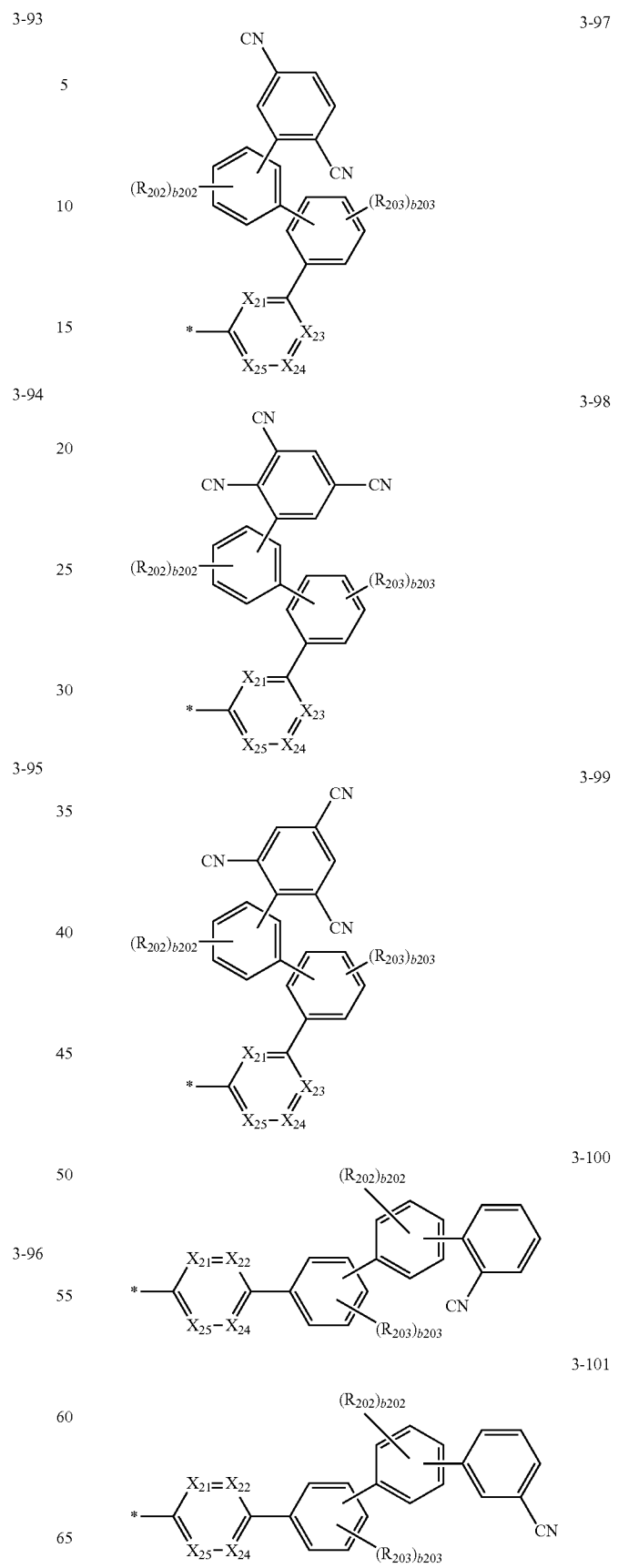

3-102

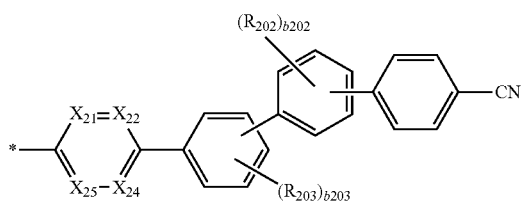

3-103

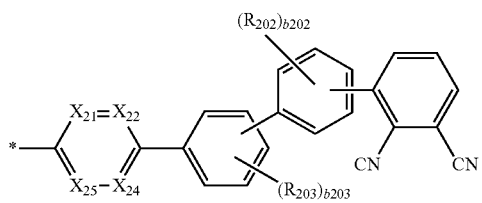

3-104

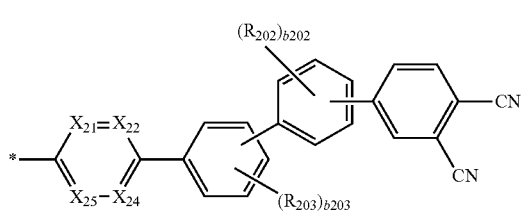

3-105

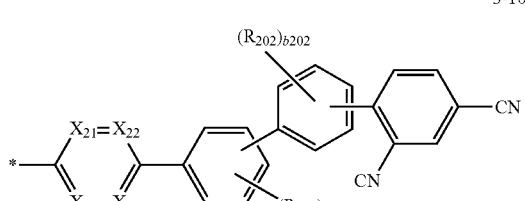

3-106

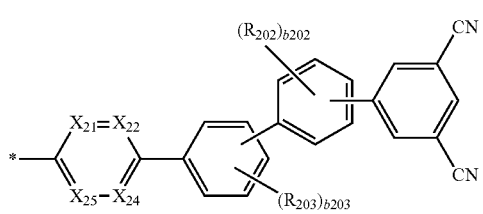

3-107

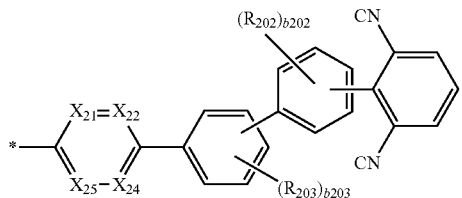

3-108

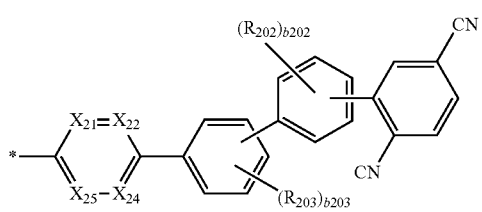

3-109

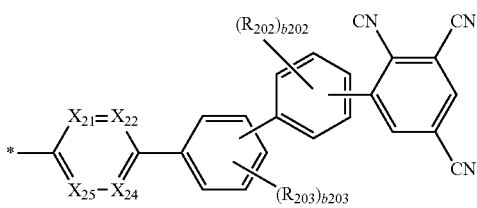

3-110

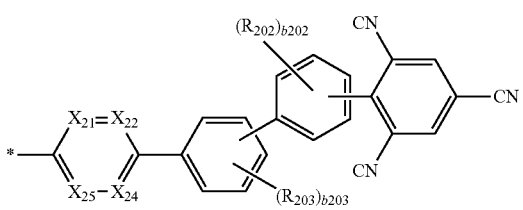

wherein, in Formulae 3-1 to 3-110,

* indicates a carbon atom in Formula 1, and $X_{21}$ to $X_{25}$, $R_{21}$ to $R_{25}$, $R_{202}$, $R_{203}$, b202, and b203 may be understood by referring to descriptions thereof provided herein.

In some embodiments, in Formulae 3-12 to 3-22, 3-45 to 3-55, and 3-78 to 3-88, $X_{22}$ may be N, $X_{23}$ may be $C(R_{23})$, $X_{24}$ may be $C(R_{24})$, and $X_{25}$ may be $C(R_{25})$;

$X_{22}$ may be $C(R_{22})$, $X_{23}$ may be N, $X_{24}$ may be $C(R_{24})$, and $X_{25}$ may be $C(R_{25})$;

$X_{22}$ may be $C(R_{22})$, $X_{23}$ may be $C(R_{23})$, $X_{24}$ may be N, and $X_{25}$ may be $C(R_{25})$; or $X_{22}$ may be $C(R_{22})$, $X_{23}$ may be $C(R_{23})$, $X_{24}$ may be $C(R_{24})$, and $X_{25}$ may be N, but embodiments are not limited thereto.

In some embodiments, in Formulae 3-23 to 3-33, 3-56 to 3-66, and 3-89 to 3-99, $X_{21}$ may be N, $X_{23}$ may be $C(R_{23})$, $X_{24}$ may be $C(R_{24})$, and $X_{25}$ may be $C(R_{25})$;

$X_{21}$ may be $C(R_{21})$, $X_{23}$ may be N, $X_{24}$ may be $C(R_{24})$, and $X_{25}$ may be $C(R_{25})$;

$X_{21}$ may be $C(R_{21})$, $X_{23}$ may be $C(R_{23})$, $X_{24}$ may be N, and $X_{25}$ may be $C(R_{25})$; or $X_{21}$ may be $C(R_{21})$, $X_{23}$ may be $C(R_{23})$, $X_{24}$ may be $C(R_{24})$, and $X_{25}$ may be N, but embodiments are not limited thereto.

In some embodiments, in Formulae 3-34 to 3-44, 3-67 to 3-77, and 3-100 to 3-110, $X_{21}$ may be N, $X_{22}$ may be $C(R_{22})$, $X_{24}$ may be $C(R_{24})$, and $X_{25}$ may be $C(R_{25})$;

$X_{21}$ may be $C(R_{21})$, $X_{22}$ may be N, $X_{24}$ may be $C(R_{24})$, and $X_{25}$ may be $C(R_{25})$;

$X_{21}$ may be $C(R_{21})$, $X_{22}$ may be $C(R_{22})$, $X_{24}$ may be N, and $X_{25}$ may be $C(R_{25})$; or $X_{21}$ may be $C(R_{21})$, $X_{22}$ may be $C(R_{22})$, $X_{24}$ may be $C(R_{24})$, and $X_{25}$ may be N, but embodiments are not limited thereto.

In some embodiments, in Formula 1, $A_{11}$ may be represented by one of Formulae 4-1 to 4-110, but embodiments are not limited thereto:

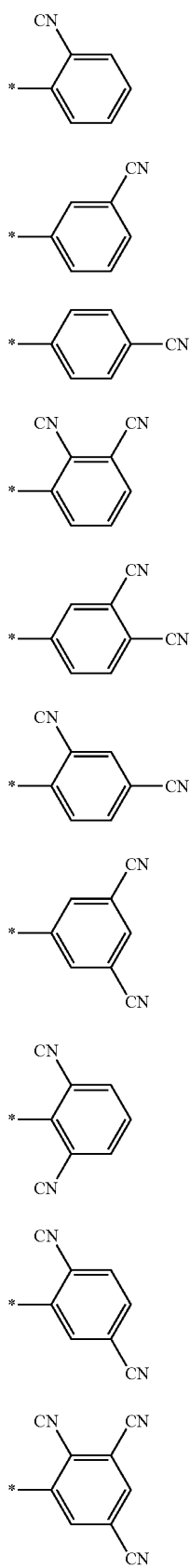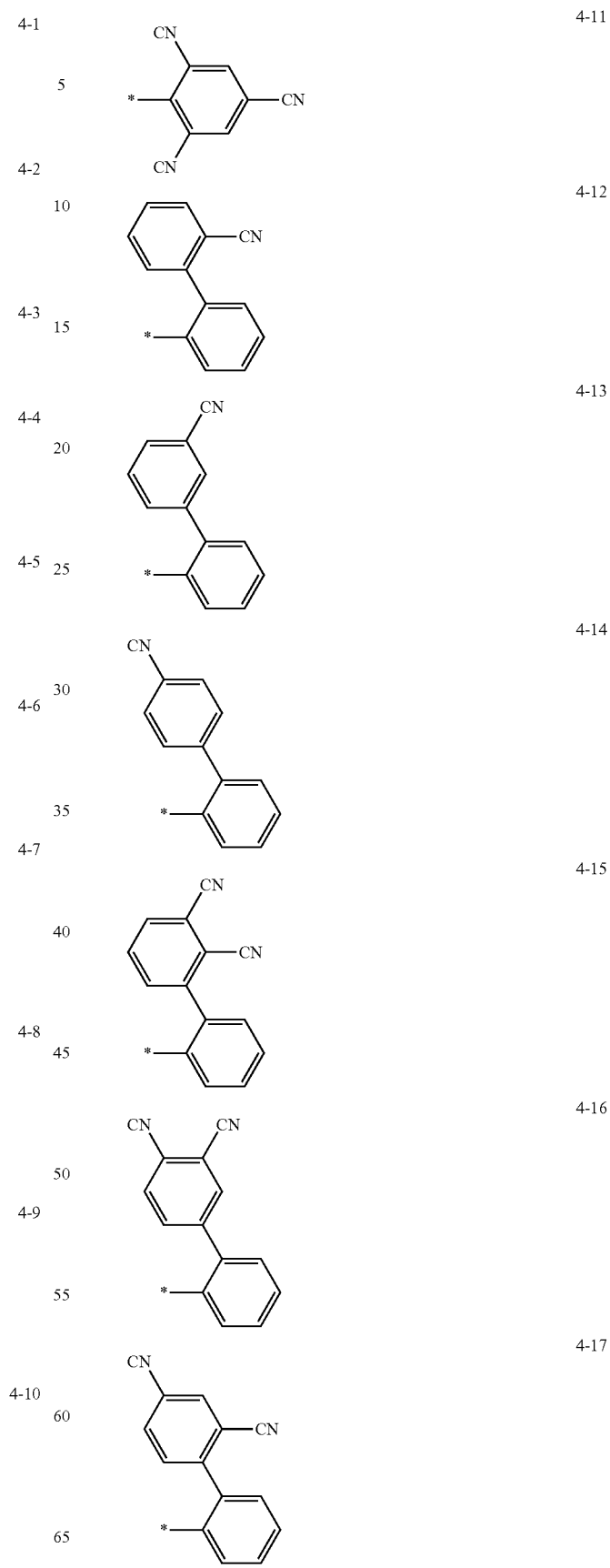

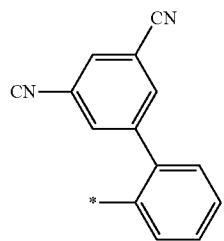
4-18
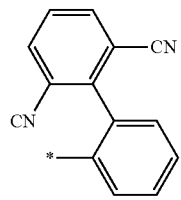
4-19
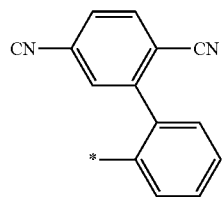
4-20
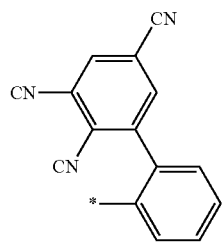
4-21
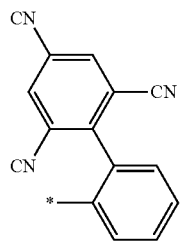
4-22
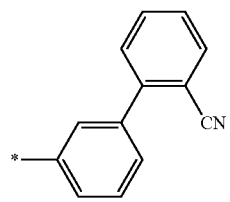
4-23
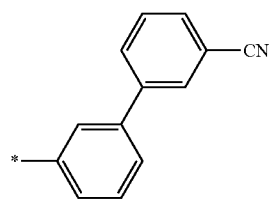
4-24
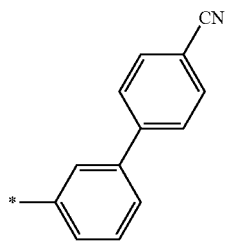
4-25
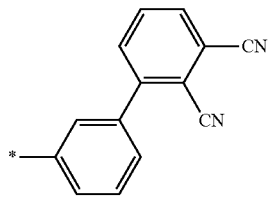
4-26
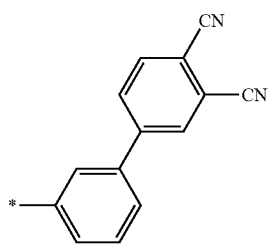
4-27
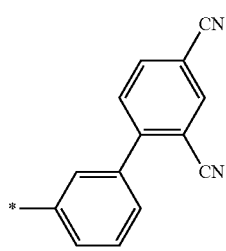
4-28
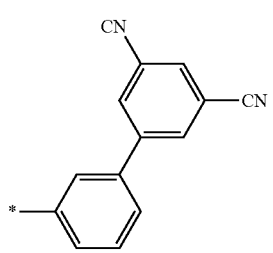
4-29
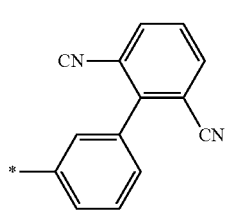
4-30
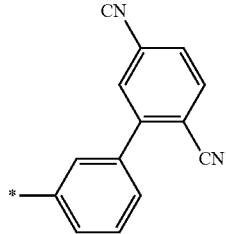
4-31

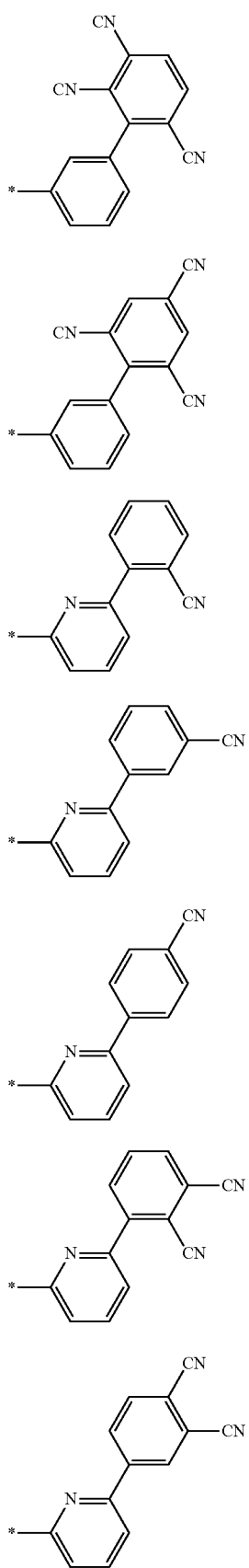
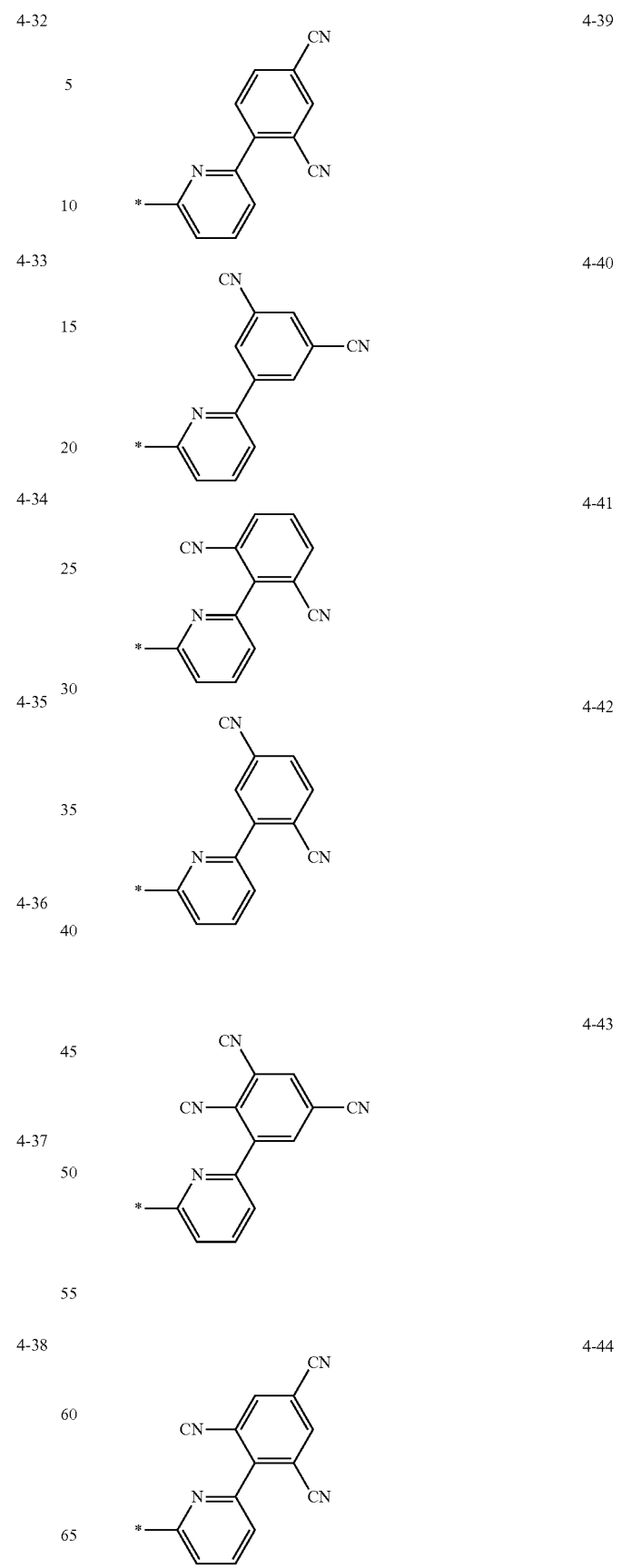

| | |
|---|---|
| 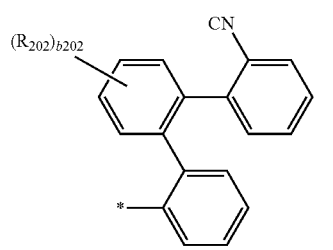 4-45 | 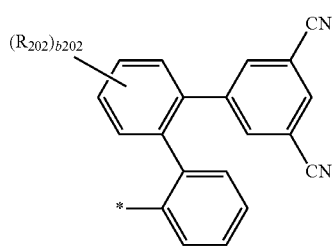 4-51 |
| 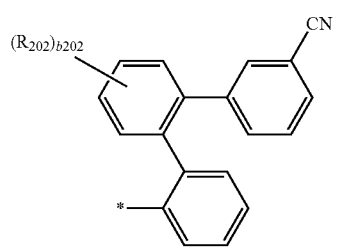 4-46 | 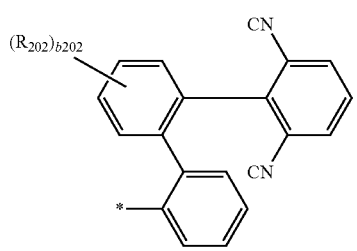 4-52 |
| 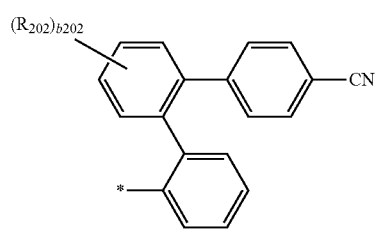 4-47 | 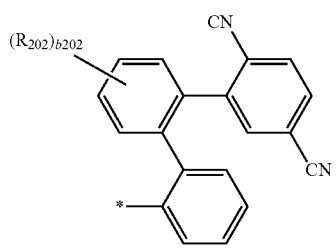 4-53 |
| 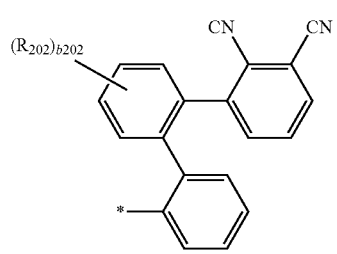 4-48 | 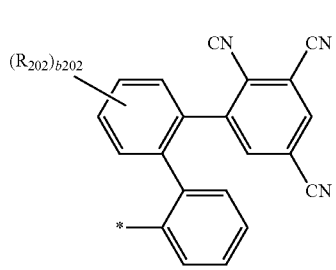 4-54 |
| 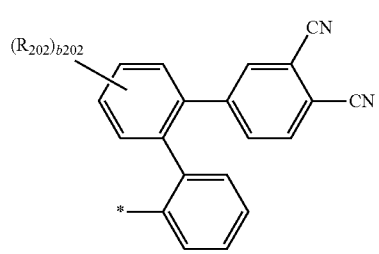 4-49 | 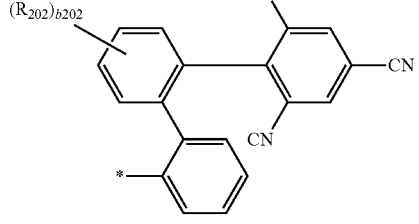 4-55 |
| 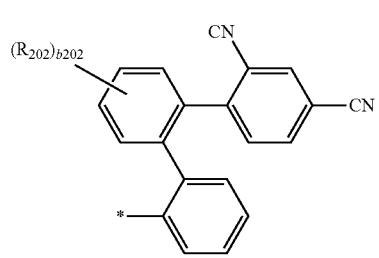 4-50 | 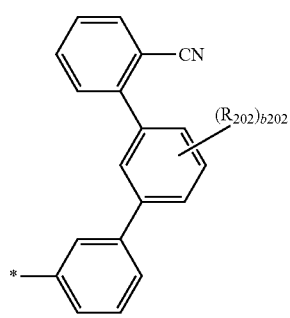 4-56 |

4-57
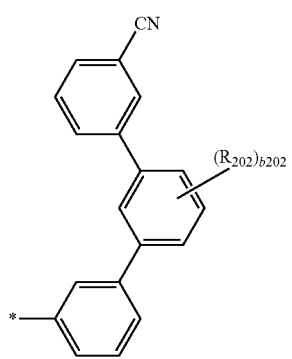
4-58
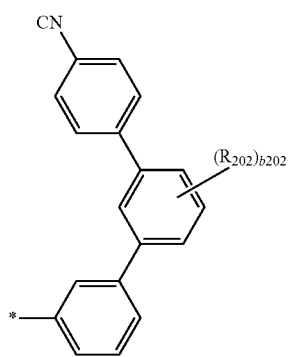
4-59
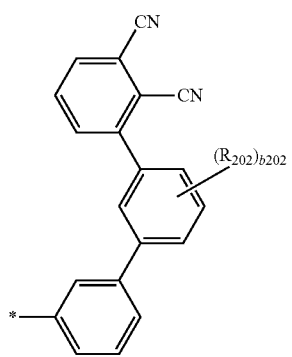
4-60
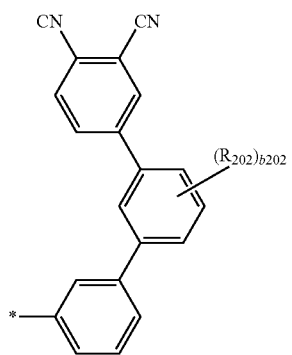
4-61
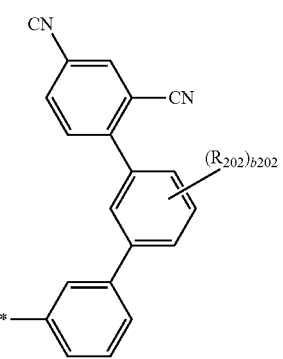
4-62
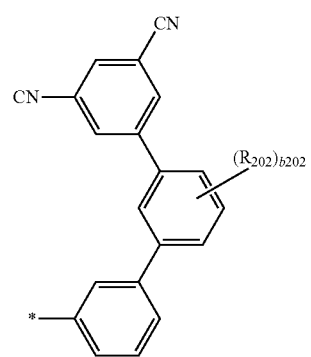
4-63
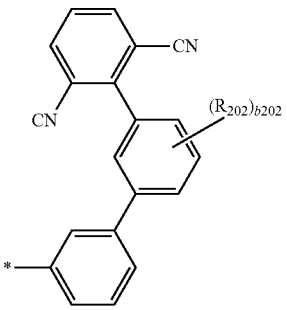
4-64
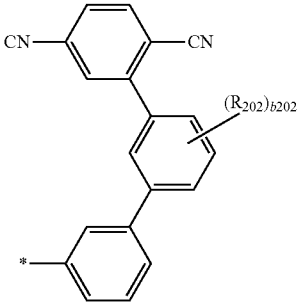

4-65 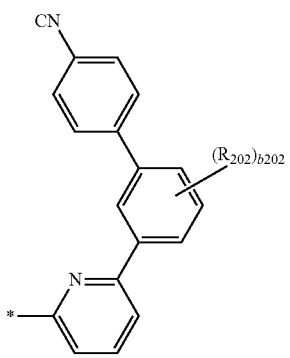
4-66 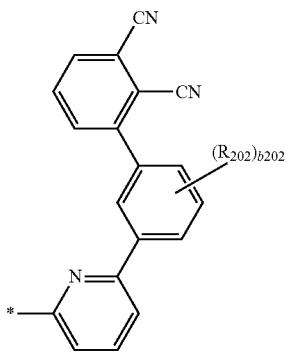
4-67 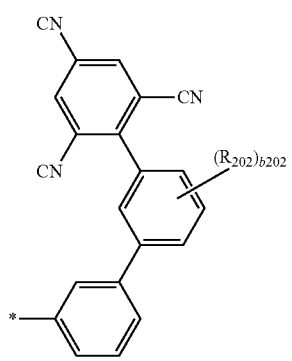
4-68 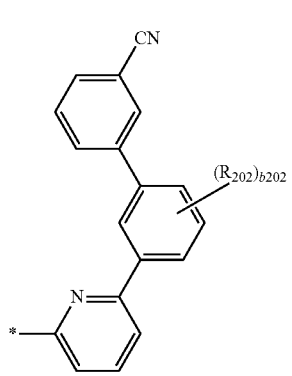
4-69 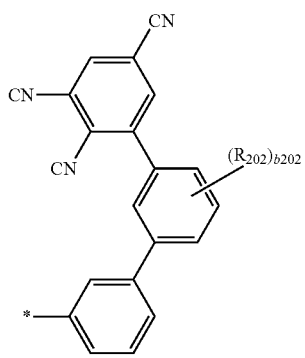
4-70 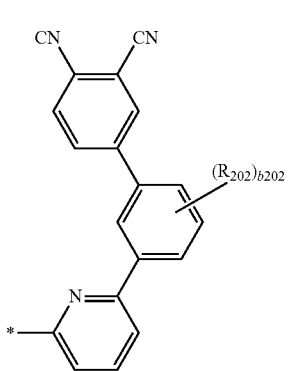
4-71
4-72 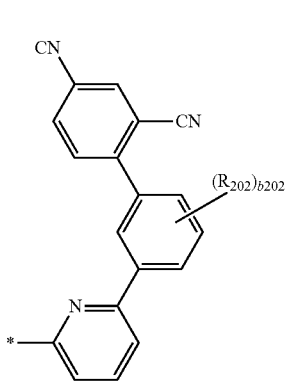

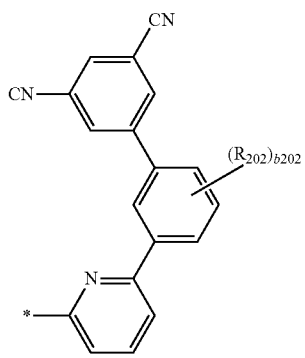
4-73
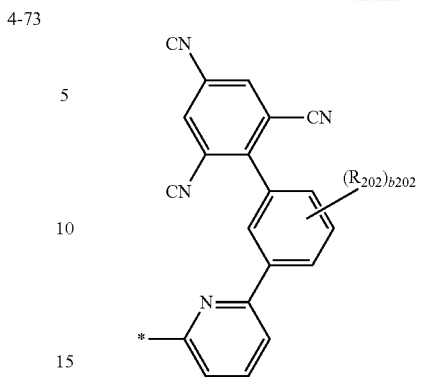
4-77
4-74
4-78
4-75
4-79
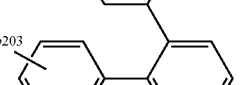
4-76
4-80
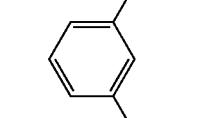

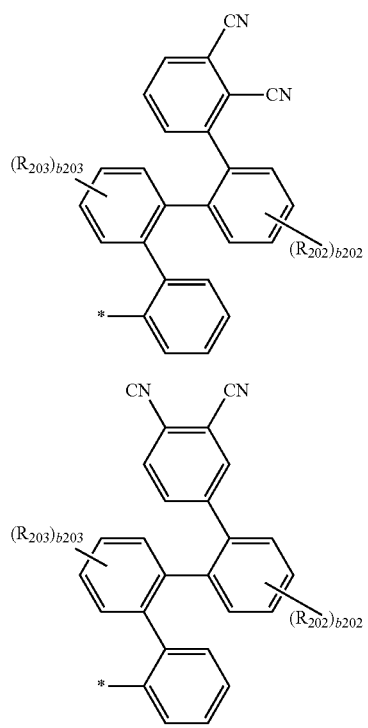
4-81
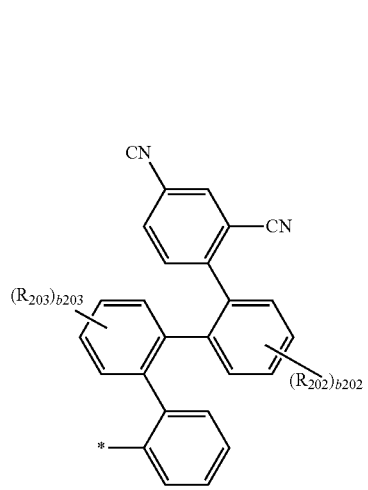
4-82
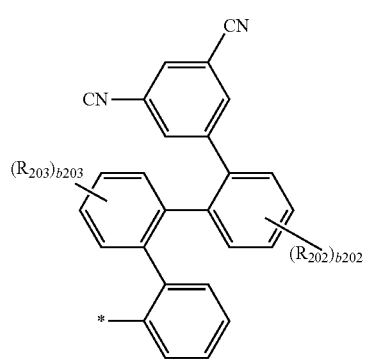
4-83
4-84
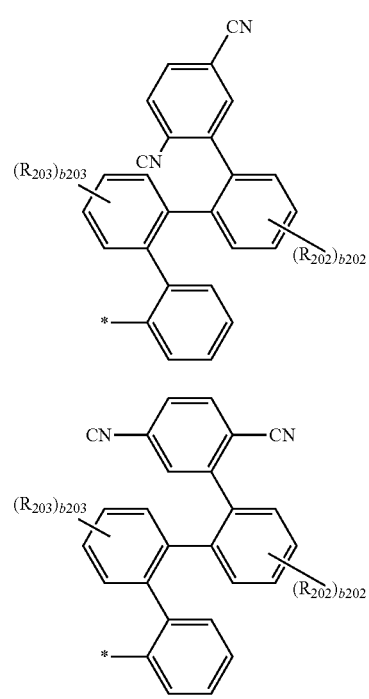
4-85
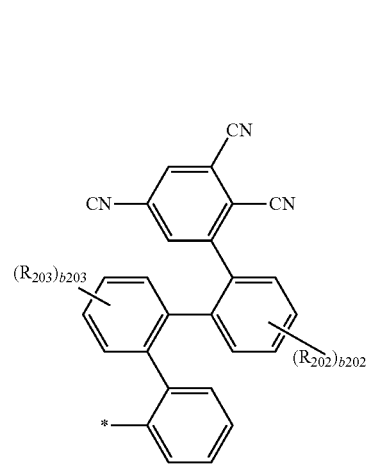
4-86
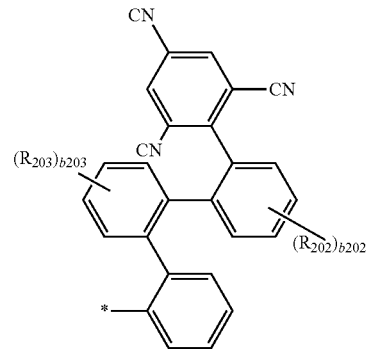
4-87
4-88

4-89
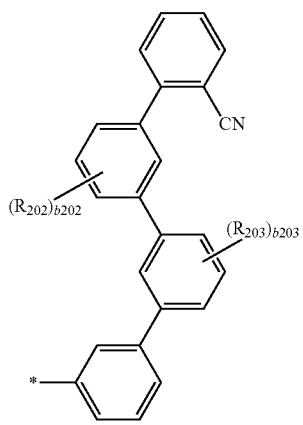
4-90
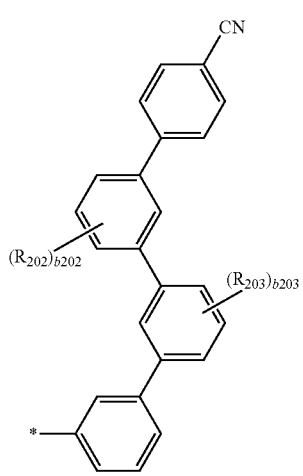
4-91
4-92
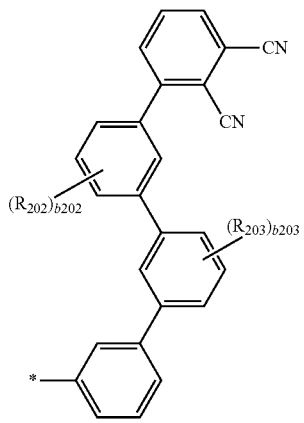
4-93
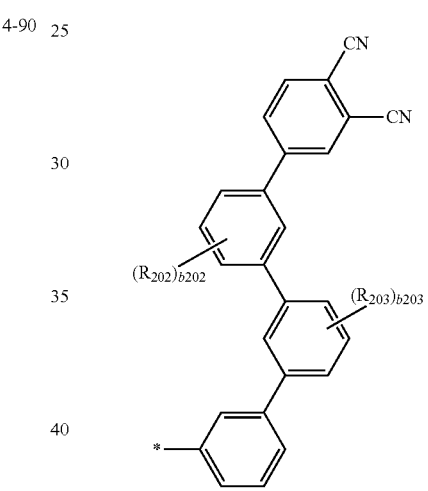
4-94
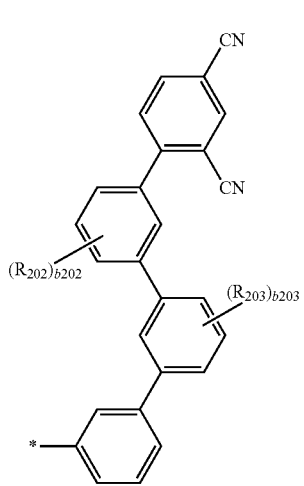

4-95
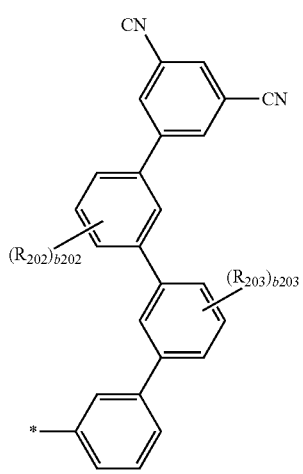
4-98
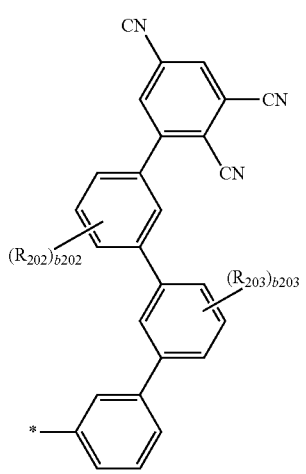
3-96
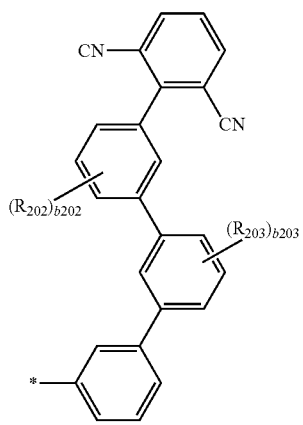
3-99
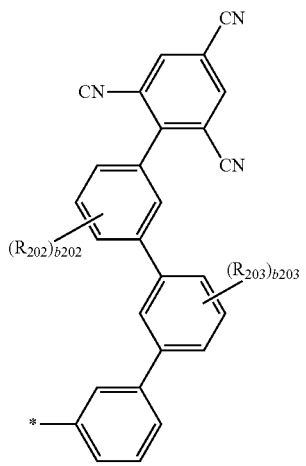
3-97
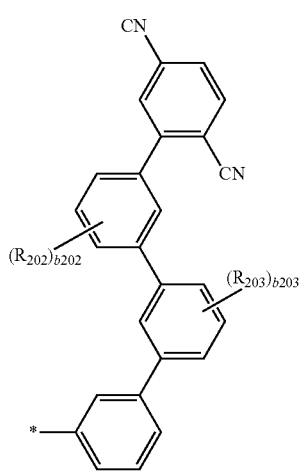
4-100
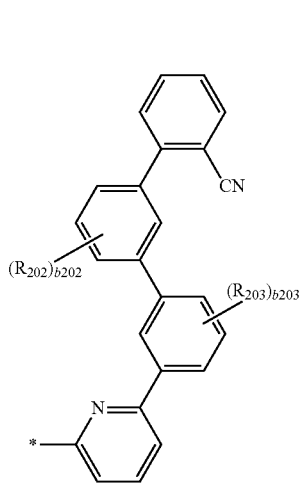

-continued
4-101
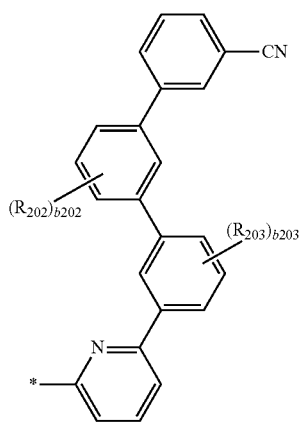
4-102
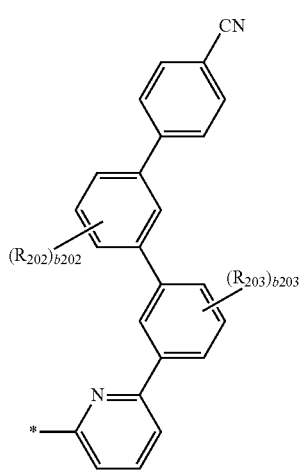
4-103
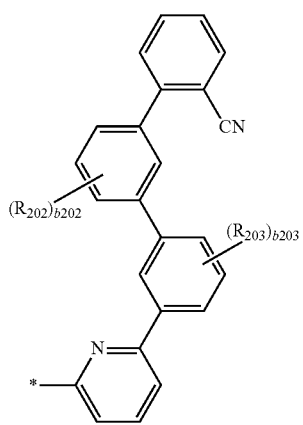
-continued
4-104
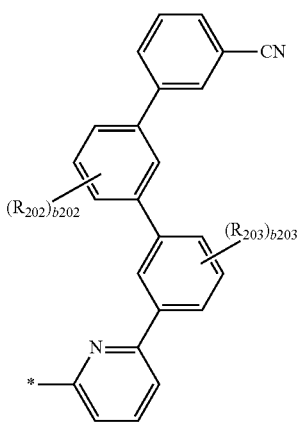
4-105
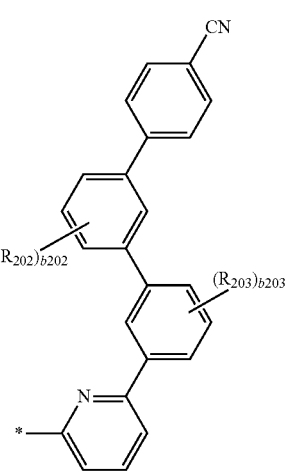
4-106
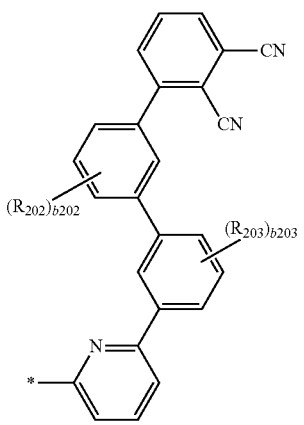

-continued 4-107

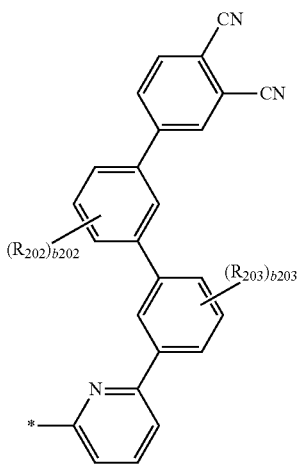

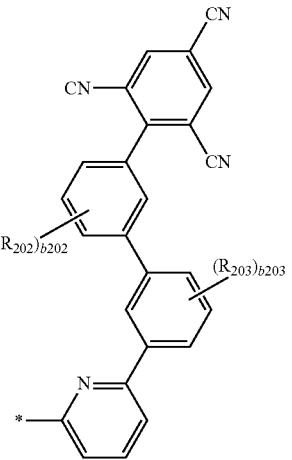

4-108

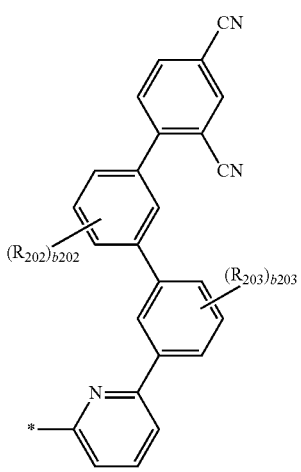

4-109

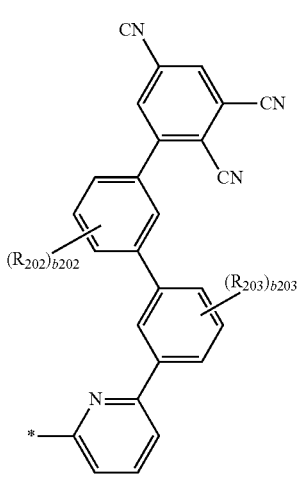

-continued 4-110 wherein, in Formulae 4-1 to 4-110,

* indicates a carbon atom in Formula 1, and $R_{202}$, $R_{203}$, b202, and b203 may be understood by referring to descriptions thereof provided herein.

In Formulae 1, 10-1 to 10-4 and 2-1 to 2-10, $A_{12}$, $R_1$ to $R_8$, $R_{11}$ to $R_{18}$, $R_{101}$, $R_{102}$, $R_{21}$ to $R_{25}$, and $R_{201}$ to $R_{203}$ may be each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{20}$ alkyl group and $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$); and —Si($Q_{11}$)($Q_{12}$)($Q_{13}$), wherein $Q_1$ to $Q_3$ and $Q_{11}$ to $Q_{13}$ may be each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

In some embodiments, in Formula 1, $A_{12}$ may be selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a pyridinyl group, a fluorenyl group, a dibenzofuranyl group, and a dibenzothiophenyl group; and
—Si($Q_{31}$)($Q_{32}$)($Q_{33}$),
wherein $Q_{31}$ to $Q_{33}$ may be each independently selected from a $C_1$-$C_{10}$ alkyl group, a $C_1$-$C_{10}$ alkoxy group, a phenyl group, a naphthyl group, and a pyridinyl group, but embodiments are not limited thereto.

In some embodiments, in Formulae 10-1 to 10-4, and 2-1 to 2-10, $R_1$ to $R_8$, $R_{11}$ to $R_{18}$, $R_{101}$, $R_{102}$, $R_{21}$ to $R_{25}$, and $R_{201}$ to $R_{203}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group;

a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and
—Si($Q_{11}$)($Q_{12}$)($Q_{13}$),
wherein $Q_{11}$ to $Q_{13}$ may be each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group, but embodiments are not limited thereto.

In some embodiments, in Formulae 10-1 to 10-4 and 2-1 to 2-10, $R_1$ to $R_8$, $R_{11}$ to $R_{18}$, $R_{101}$, $R_{102}$, $R_{21}$ to $R_{25}$, and $R_{201}$ to $R_{203}$ may be each independently selected from a hydrogen, a deuterium, a cyano group, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, and
—Si($Q_{11}$)($Q_{12}$)($Q_{13}$);

wherein $Q_{11}$ to $Q_{13}$ may be each independently selected from a hydrogen, a $C_1$-$C_{20}$ alkyl group, a $C_1$-$C_{20}$ alkoxy group, and a phenyl group, but embodiments are not limited thereto.

In Formulae 2-1 to 2-10, b201 indicates the number of groups $R_{201}$, and b201 may be selected from 1, 2, 3, 4, and 5. When b201 is 2 or more, groups $R_{201}$ may be identical to or different from each other.

In Formulae 2-1 to 2-10, b202 indicates the number of groups $R_{202}$, and b202 may be selected from 1, 2, 3, and 4. When b202 is 2 or more, groups $R_{202}$ may be identical to or different from each other.

In Formulae 2-1 to 2-10, b203 indicates the number of groups $R_{203}$, and b203 may be selected from 1, 2, 3, and 4. When b203 is 2 or more, groups $R_{203}$ may be identical to or different from each other.

In some embodiments, in Formulae 1 and 10-1 to 10-4, at least one of $X_3$, $X_6$, $X_{13}$, and $X_{16}$ may be C(CN), but embodiments are not limited thereto.

In some embodiments, in Formula 1, $X_3$ may be C(CN), but embodiments are not limited thereto.

In some embodiments, in Formula 1, $X_3$ and $X_6$ may be C(CN), but embodiments are not limited thereto.

In some embodiments, in Formulae 1 and 10-1 to 10-4, $R_1$, $R_2$, $R_4$, $R_5$, $R_7$, $R_8$, $R_{11}$, $R_{12}$, $R_{14}$, $R_{15}$, $R_{17}$, and $R_{18}$ may not be a cyano group, but embodiments are not limited thereto.

The condensed-cyclic compound represented by Formula 1 may be represented by one of Formulae 1-1 to 1-8, but embodiments are not limited thereto:

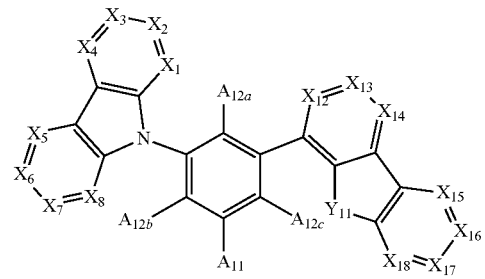

1-1

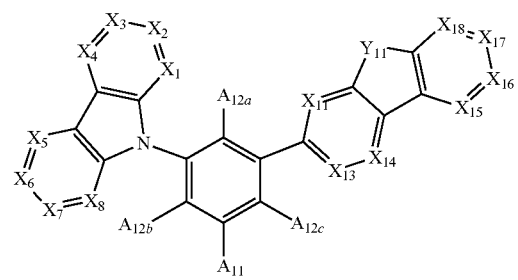

1-2

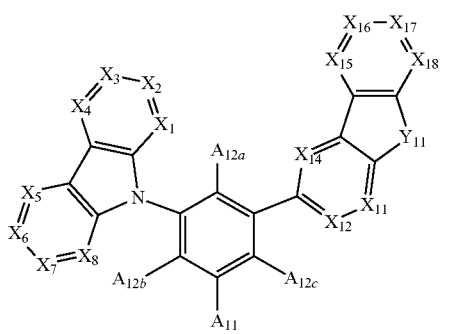

1-3

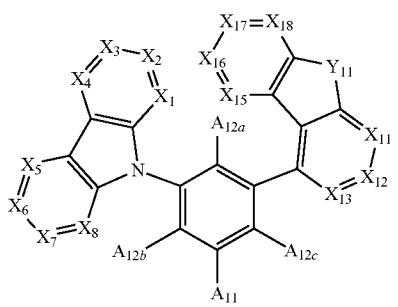

1-4

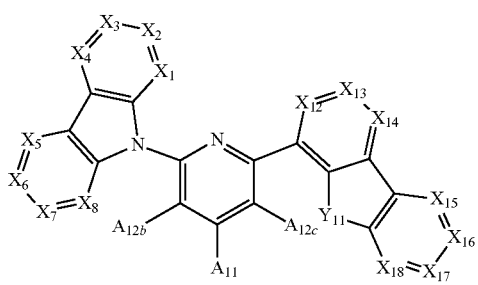

1-5

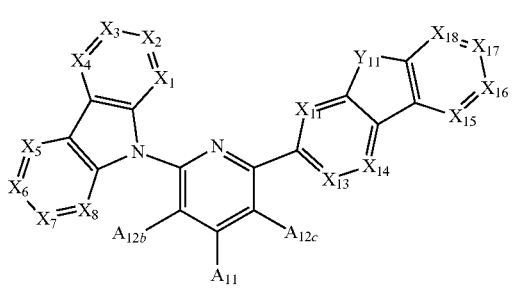

1-6

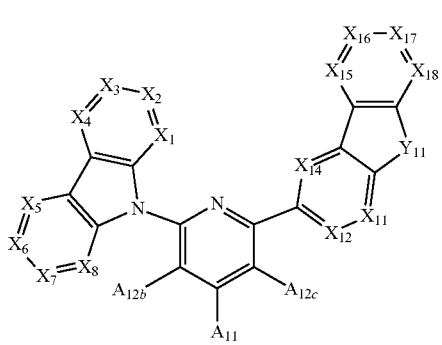

1-7

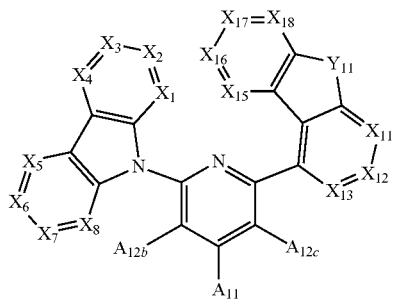

1-8 wherein, in Formulae 1-1 to 1-8, $X_1$ to $X_8$ and $A_{11}$ are the same as in Formula 1;

$X_{11}$ to $X_{18}$ and $Y_{11}$ are the same as in Formulae 10-1 to 10-4; and $A_{12a}$, $A_{12b}$, and $A_{12c}$ may be each independently the same as in connection with $A_{12}$ in Formula 1.

In some embodiments, in Formulae 1-1 to 1-8, $A_{11}$ may be represented by one of Formulae 3-1 to 3-110, but embodiments are not limited thereto.

In some embodiments, in Formulae 1-1 to 1-8, $A_{11}$ may be represented by one of Formulae 4-1 to 4-110, but embodiments are not limited thereto.

In some embodiments, in Formulae 1-1 to 1-8, at least one of $X_3$, $X_6$, $X_{13}$, and $X_{16}$ may be C(CN), but embodiments are not limited thereto.

In some embodiments, in Formulae 1-1 to 1-8, $X_3$ may be C(CN), but embodiments are not limited thereto.

In some embodiments, in Formulae 1-1 to 1-8, $X_3$ and $X_6$ may be C(CN), but embodiments are not limited thereto.

The condensed-cyclic compound represented by Formula 1 may be represented by one of Formulae 1-11 to 1-18, 1-21 to 1-28, and 1-31 to 1-38, but embodiments are not limited thereto:

1-11

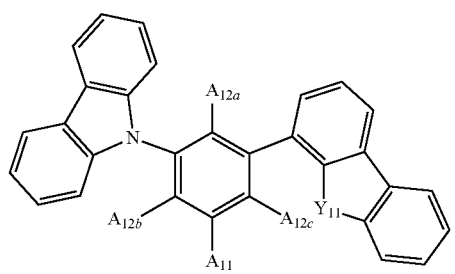

1-12

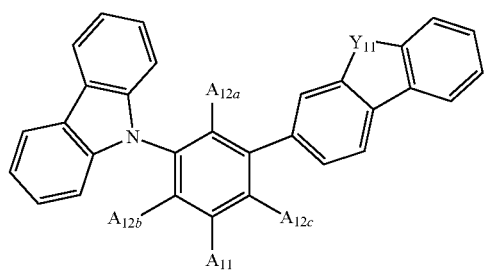

1-13
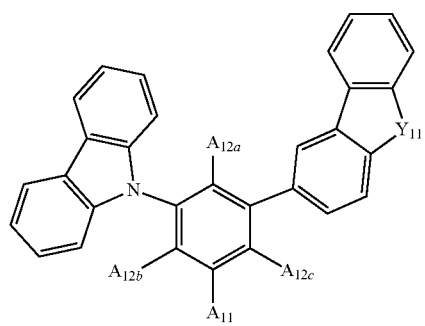
1-14
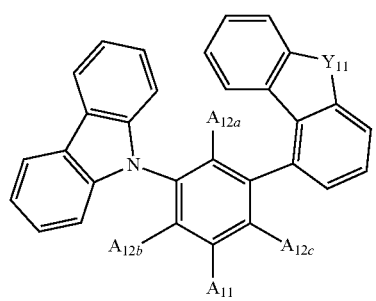
1-15
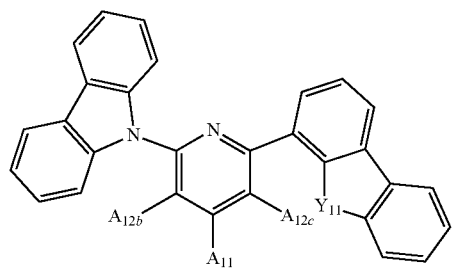
1-16
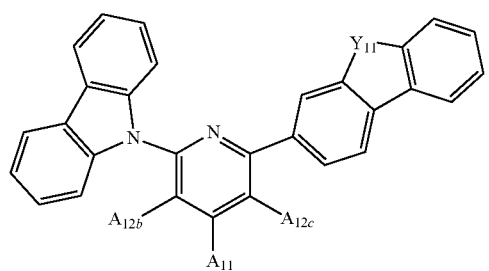
1-17
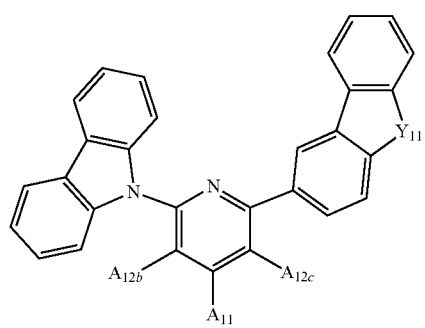
1-18
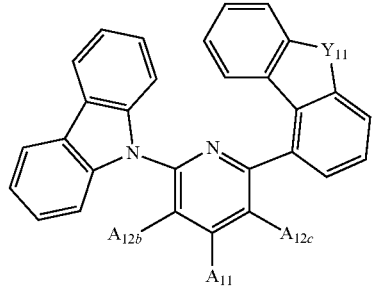
1-21
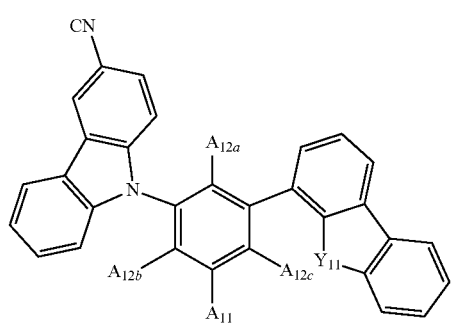
1-22
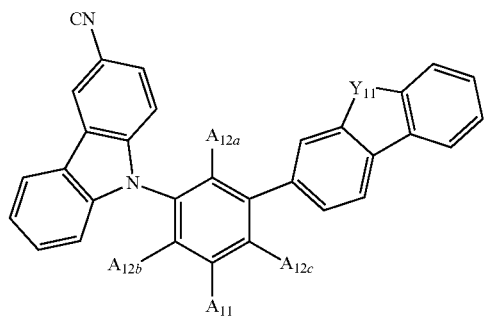
1-23
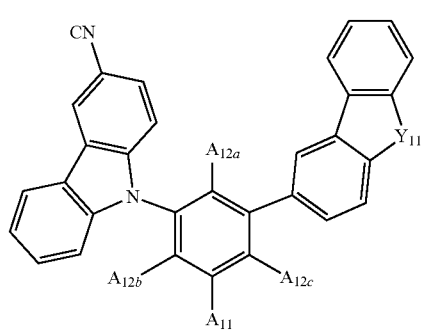
1-24
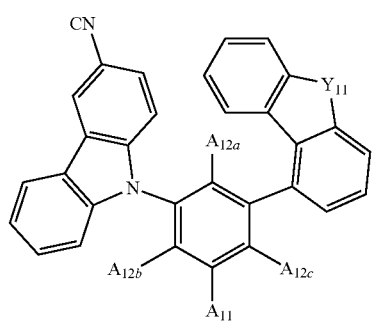

1-25
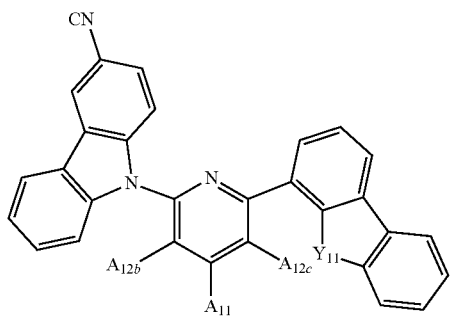
1-26
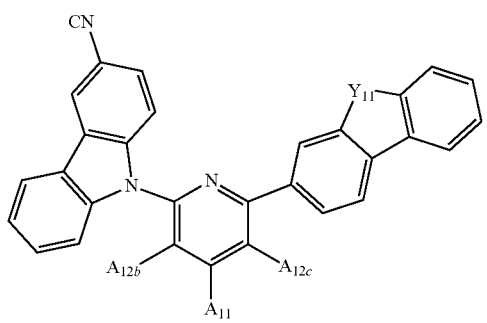
1-27
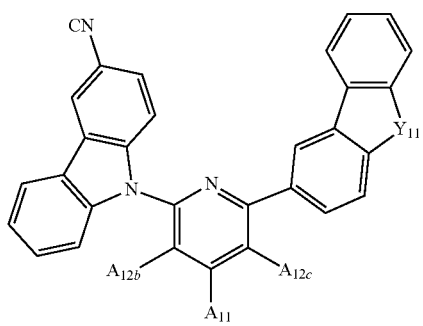
1-28
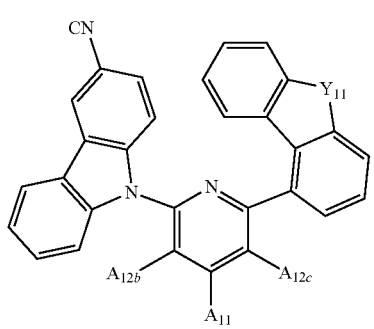
1-31
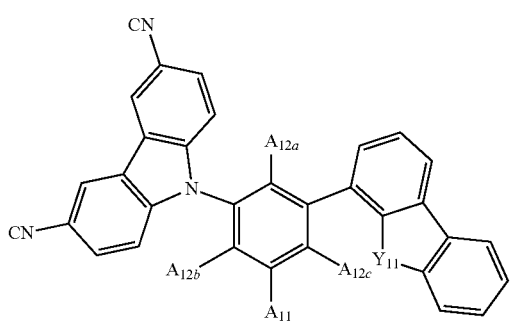
1-32
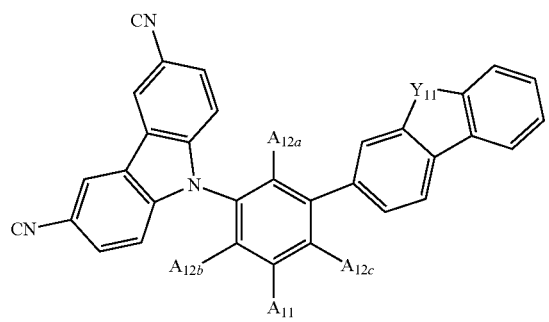
1-33
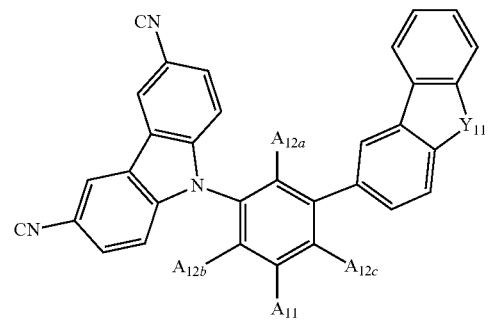
1-34
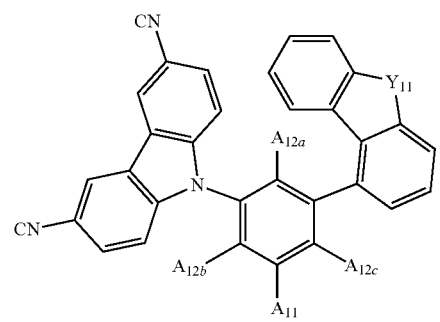
1-35
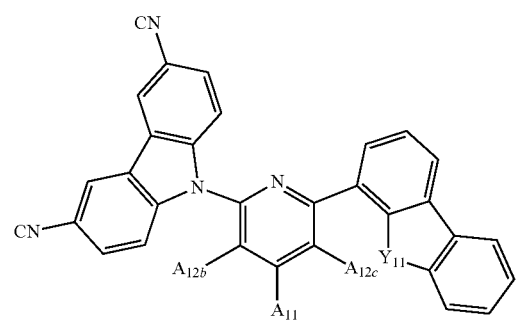

-continued

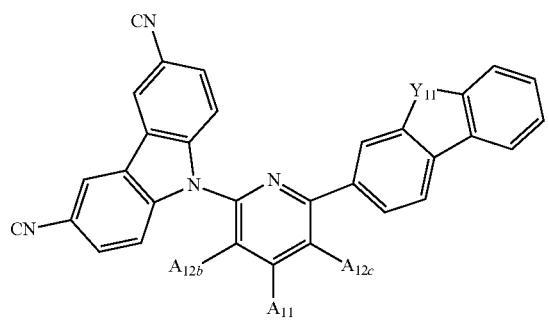
1-36

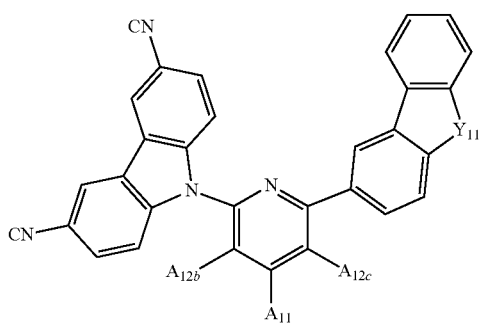
1-37

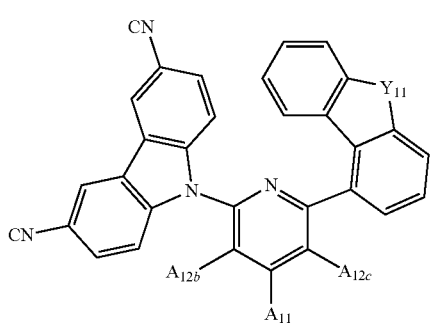
1-38

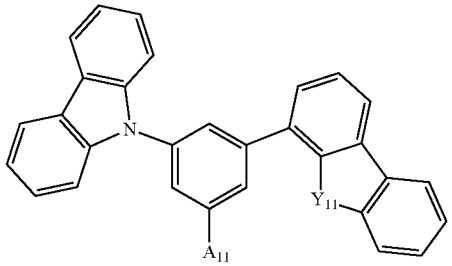
1-41

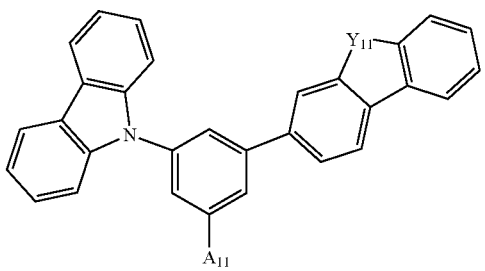
1-42

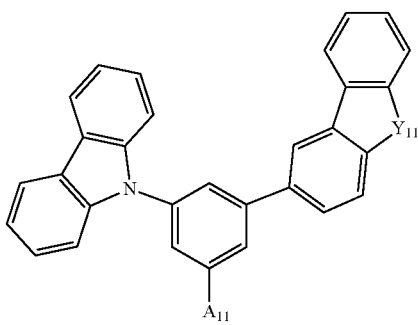
1-43

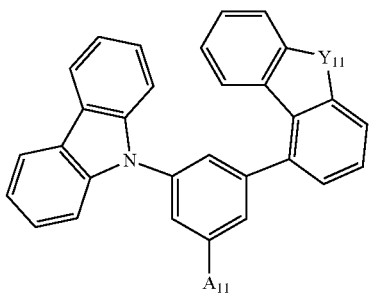
1-44

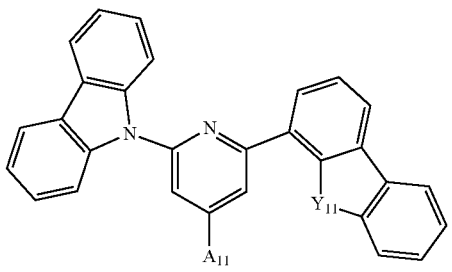
1-45 wherein, in Formulae 1-11 to 1-18, 1-21 to 1-28, and 1-31 to 1-38, $A_{11}$ is the same as in Formula 1;

$Y_{11}$ is the same as in Formulae 10-1 to 10-4; and $A_{12a}$, $A_{12b}$, and $A_{12c}$ may be each independently the same as $A_{12}$ in Formula 1.

In some embodiments, in Formula 1-11 to 1-18, 1-21 to 1-28, and 1-31 to 1-38, $A_{11}$ may be represented by one of Formulae 3-1 to 3-110, but embodiments are not limited thereto.

In some embodiments, in Formula 1-11 to 1-18, 1-21 to 1-28, and 1-31 to 1-38, $A_1$ may be represented by one of Formulae 4-1 to 4-110, but embodiments are not limited thereto.

The condensed-cyclic compound represented by Formula 1 may be represented by one of Formulae 1-41 to 1-48, 1-51 to 1-58, and 1-61 to 1-68, but embodiments are not limited thereto:

1-46
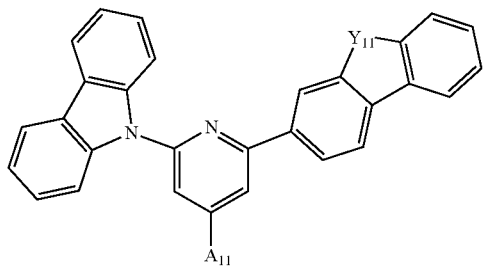
1-47
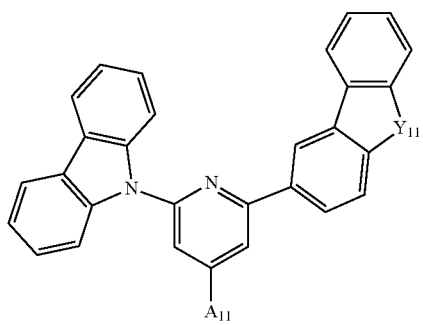
1-48
1-51
1-52
1-53
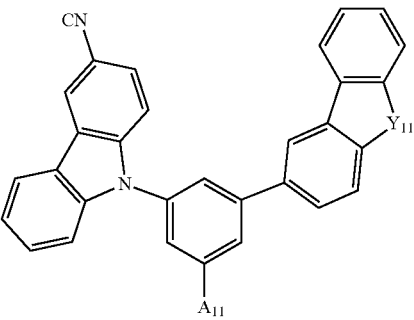
1-54
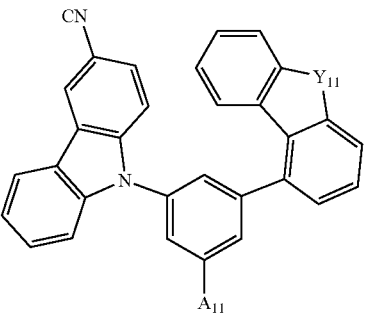
1-55
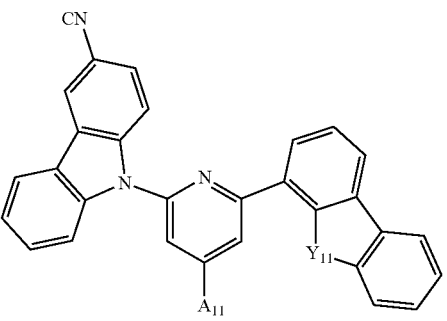
1-56
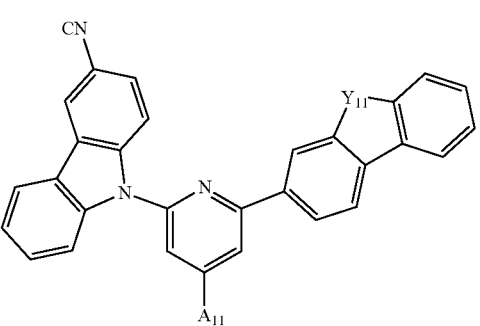
1-57
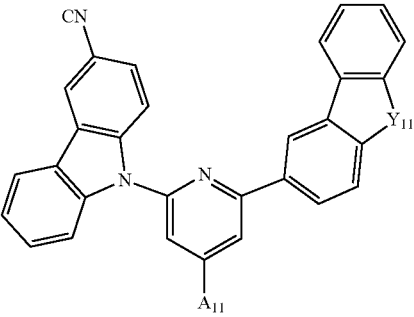

1-58
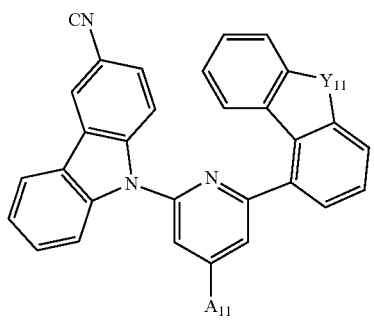
1-61
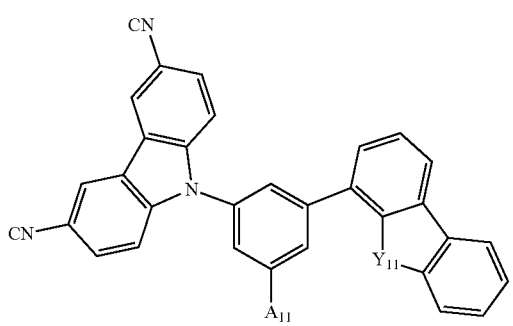
1-62
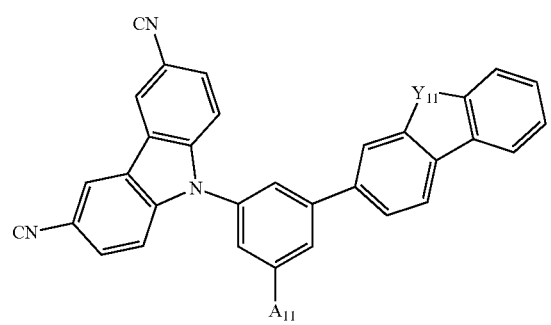
1-63
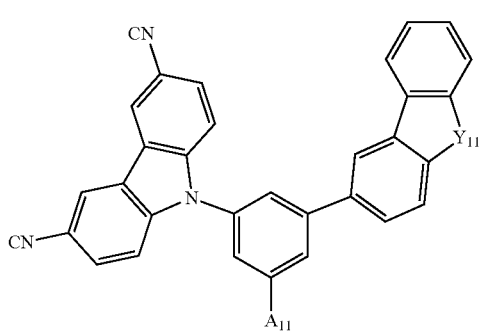
1-64
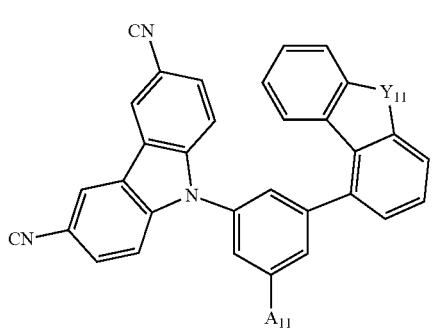
1-65
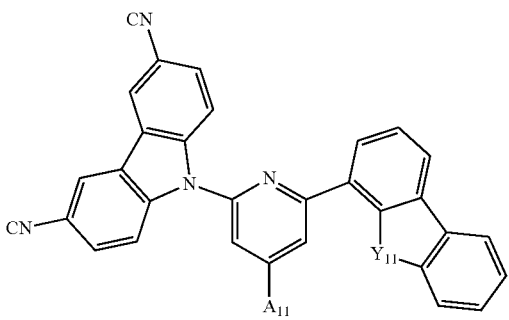
1-66
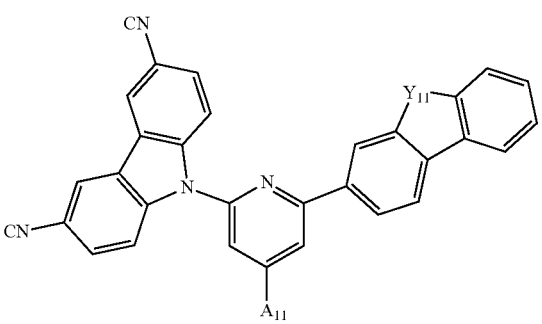
1-67
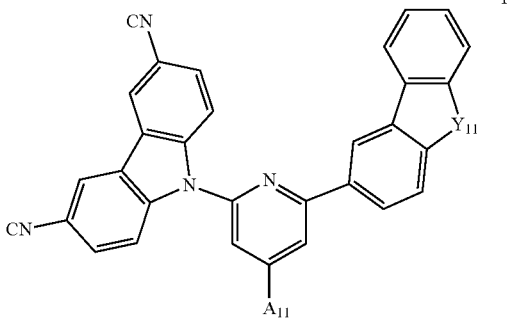
1-68
wherein, in Formulae 1-41 to 1-48, 1-51 to 1-58, and 1-61 to 1-68,
$A_{11}$ is the same as in Formula 1; and
$Y_{11}$ is the same as in Formulae 10-1 to 10-4.
In some embodiments, in Formula 1-41 to 1-48, 1-51 to 1-58, and 1-61 to 1-68, $A_{11}$ may be represented by one of Formulae 4-1 to 4-110, but embodiments are not limited thereto.
The condensed-cyclic compound represented by Formula 1 may be selected from Compounds 1 to 90, but embodiments are not limited thereto:

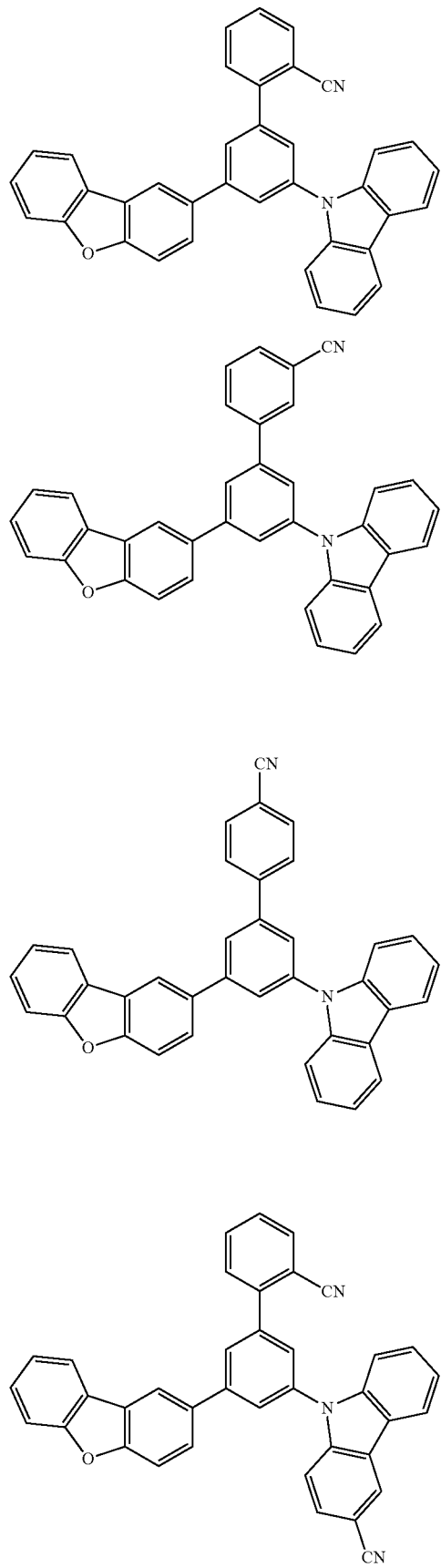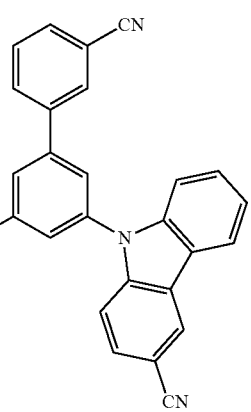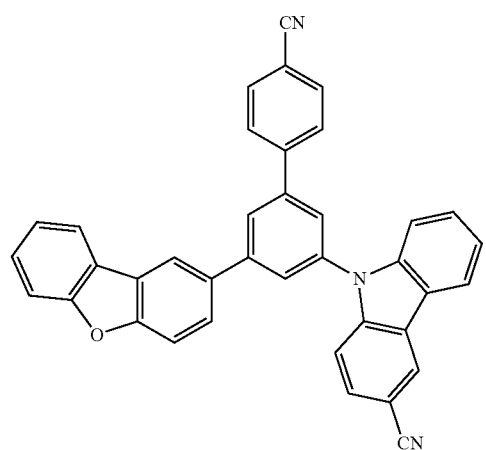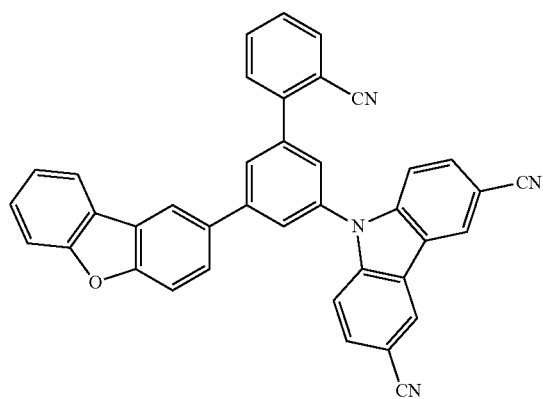

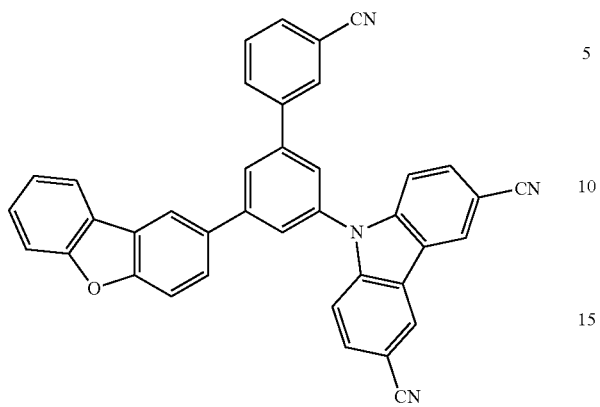
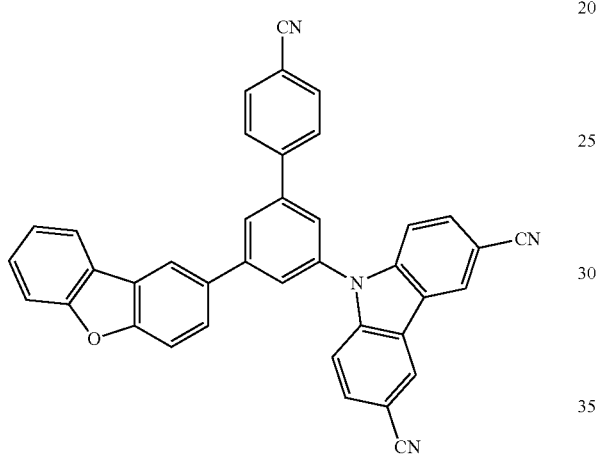
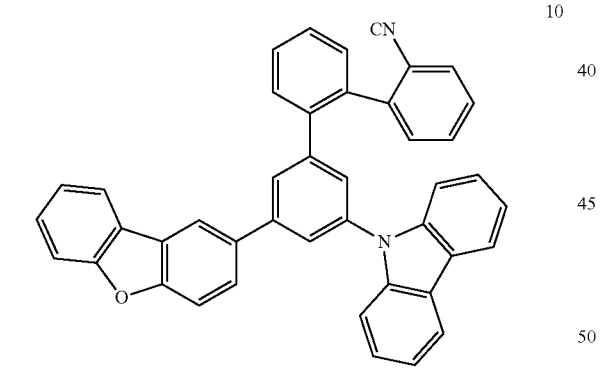
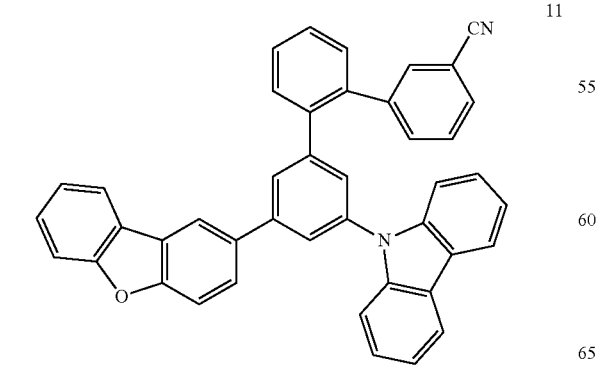
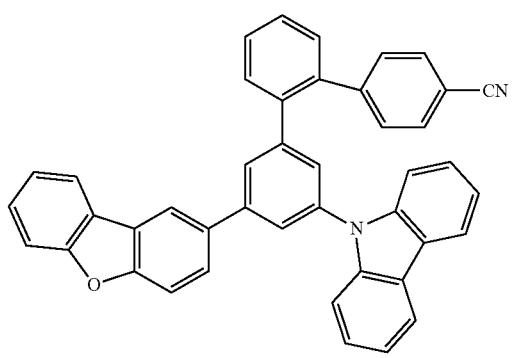
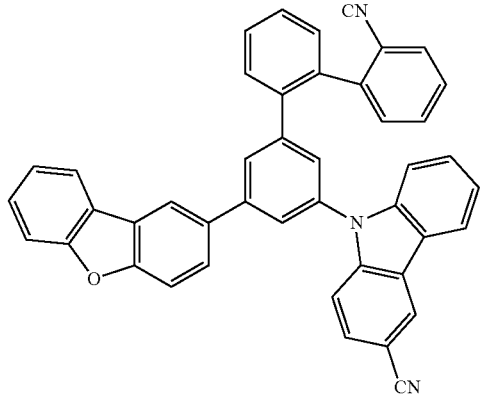
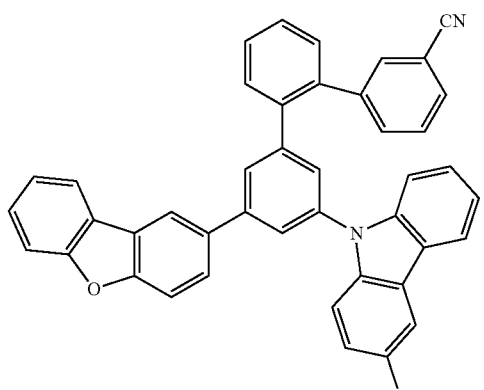
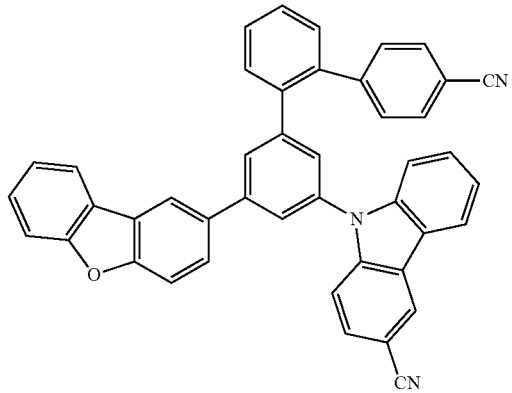

16
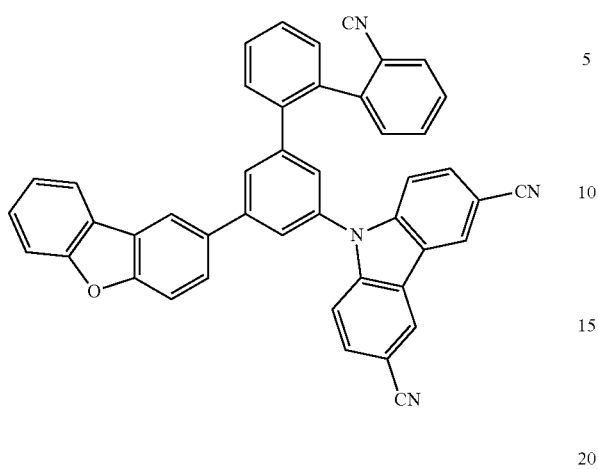
17
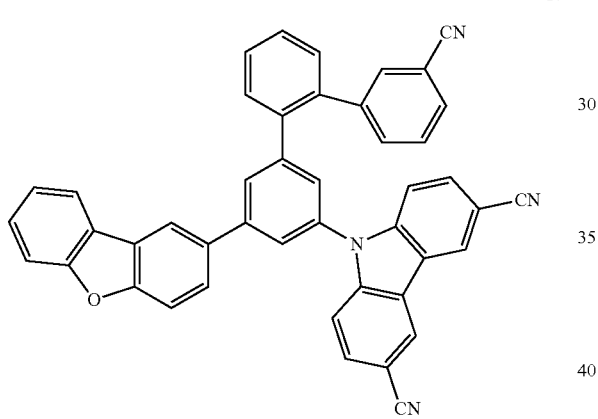
18
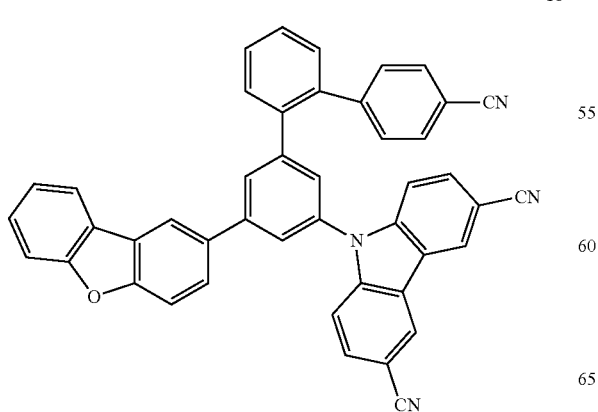
19
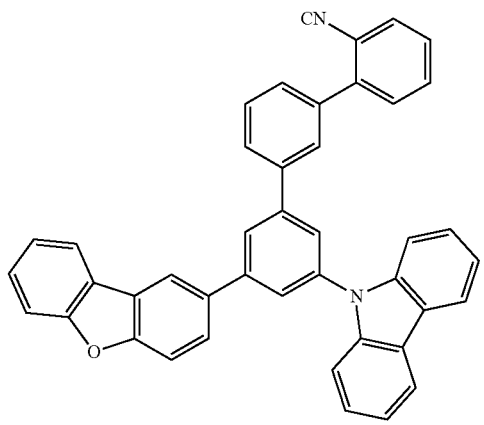
20
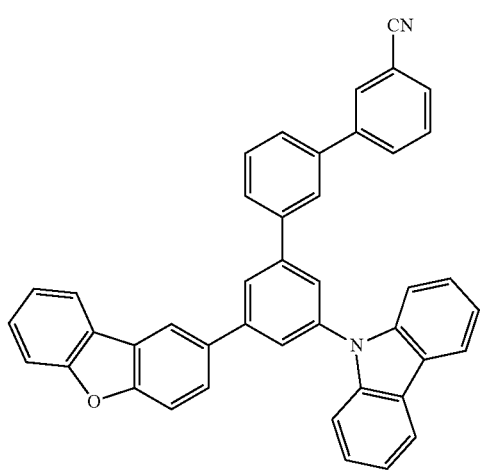
21
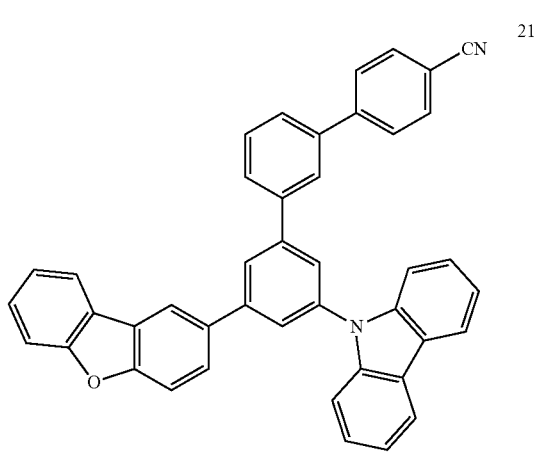

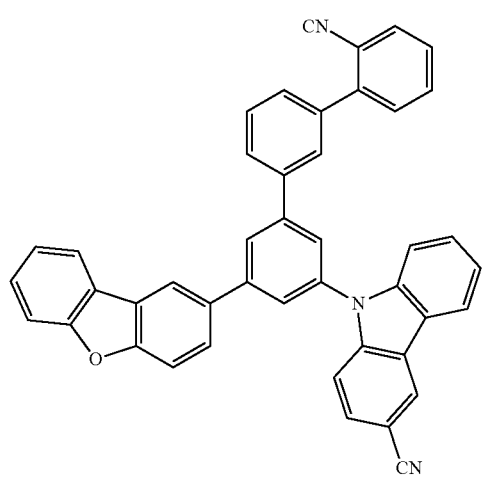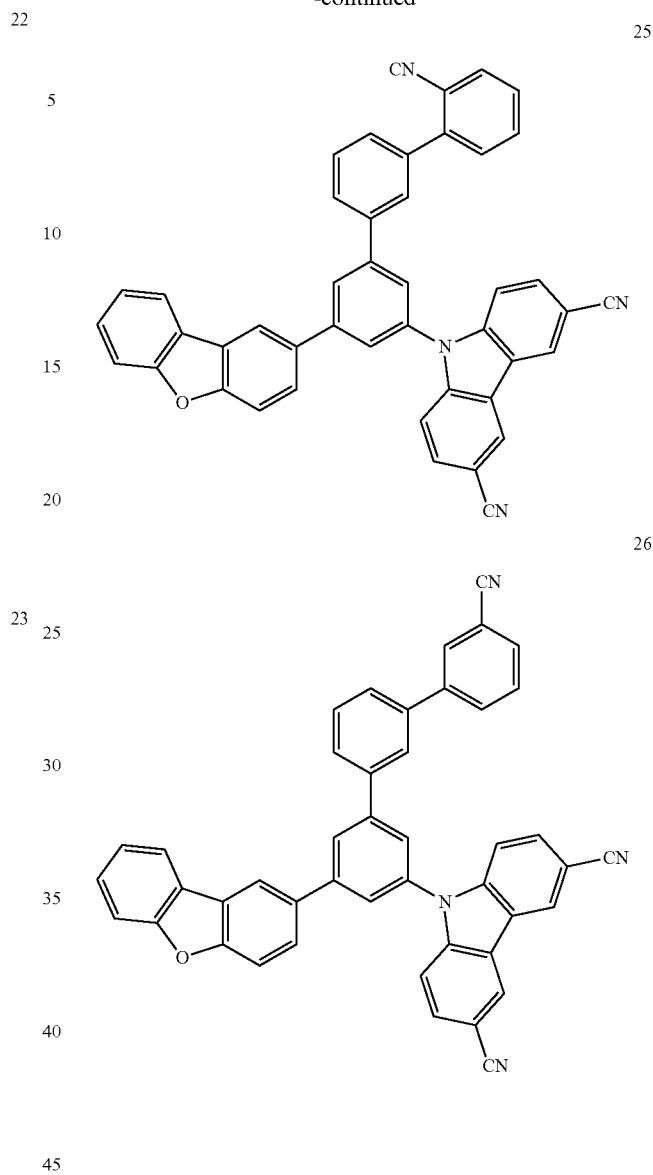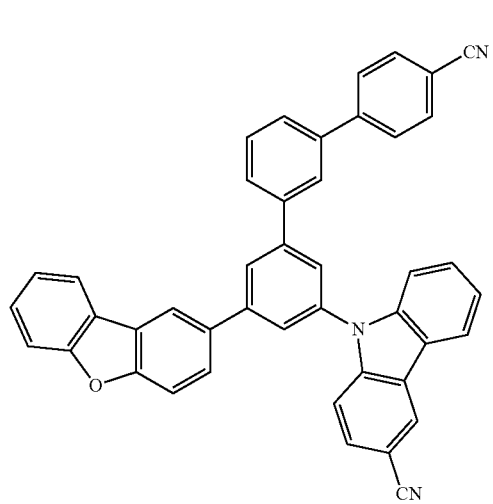

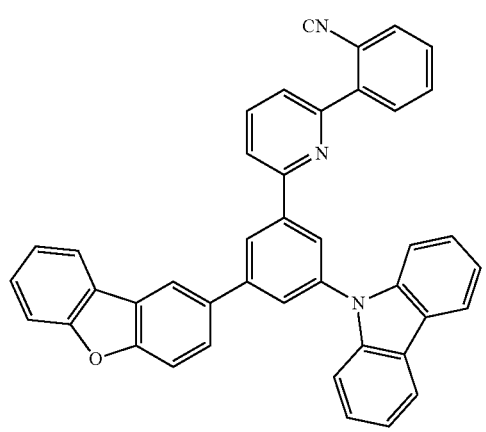
28
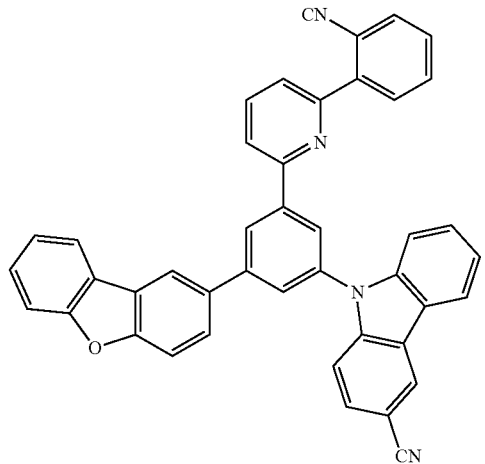
31
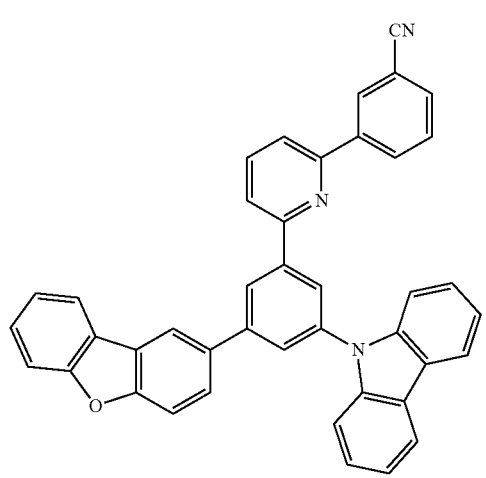
29
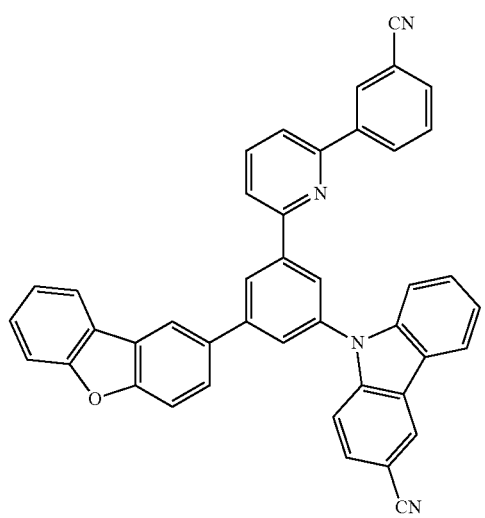
32
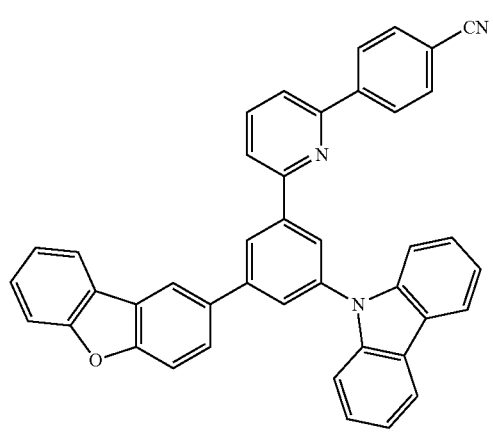
30
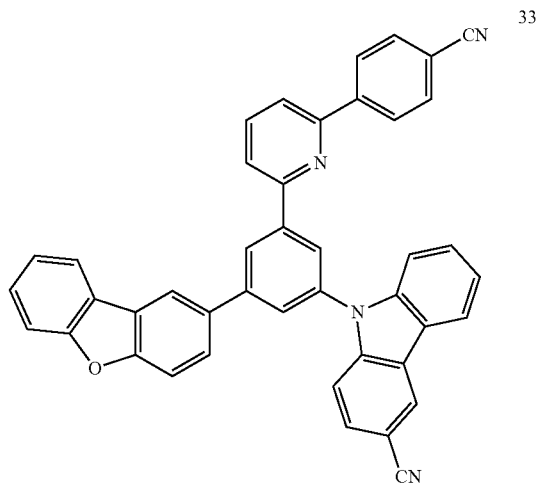
33

34
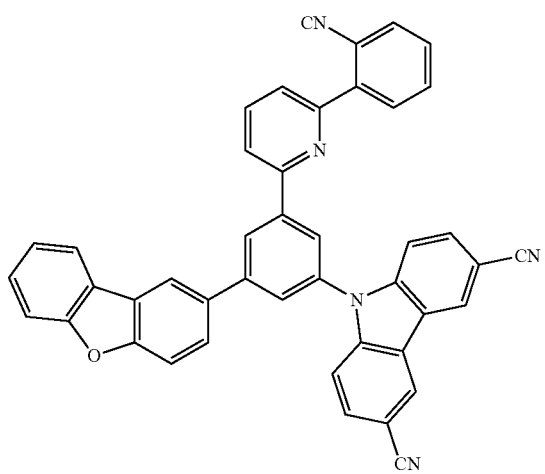
35
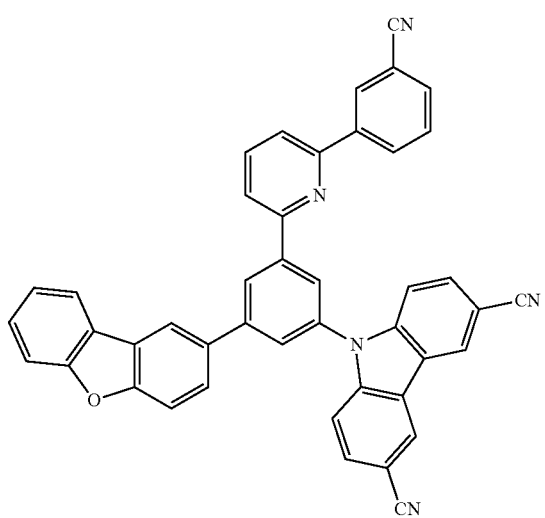
36
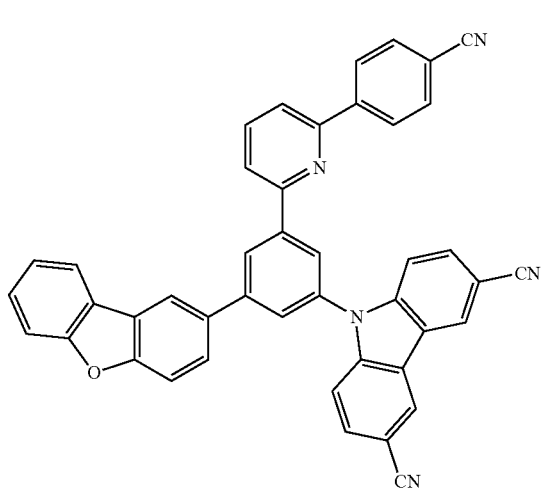
37
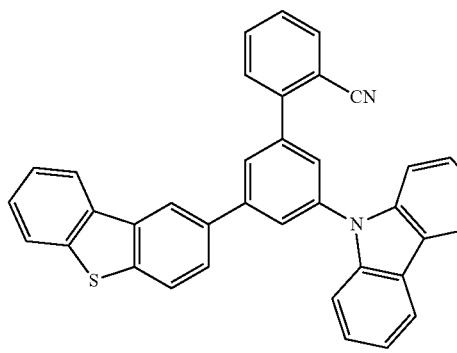
38
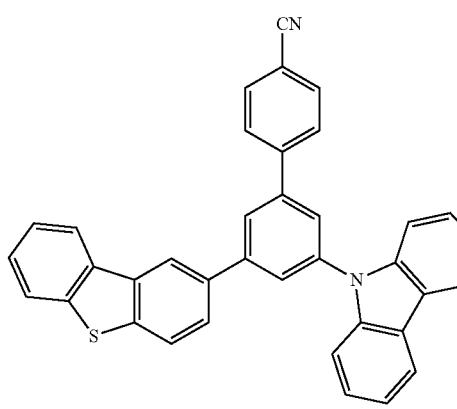
39
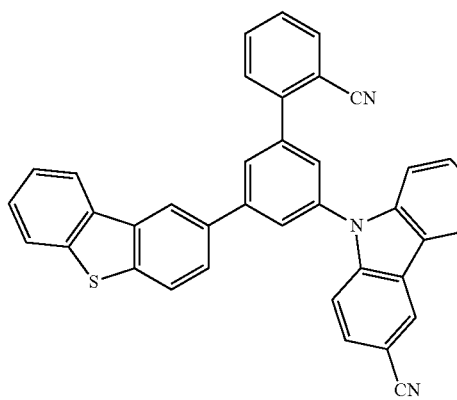
40

41
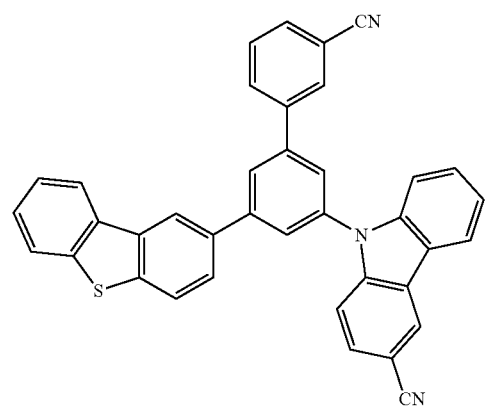
42
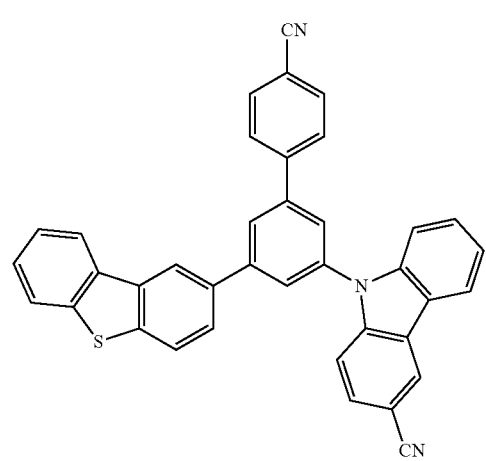
43
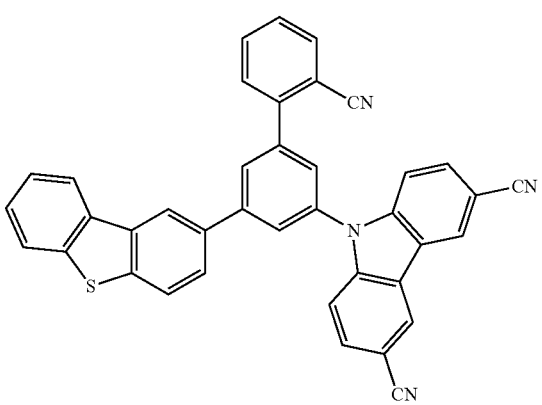
44
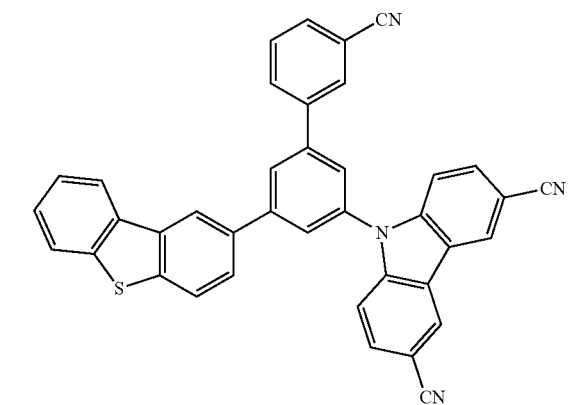
45
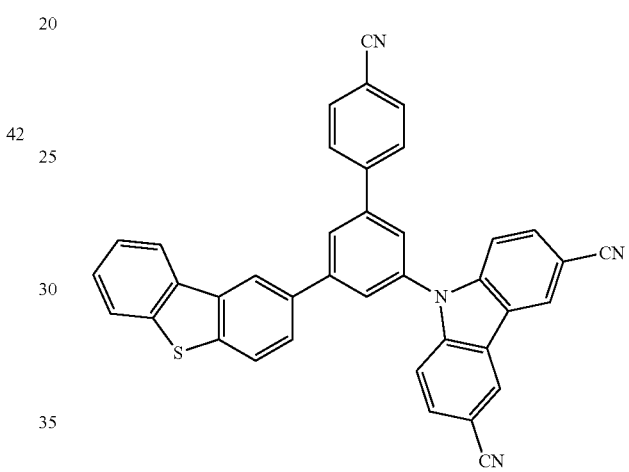
46
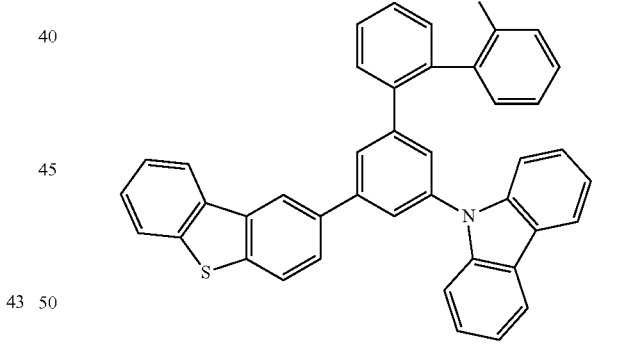
47
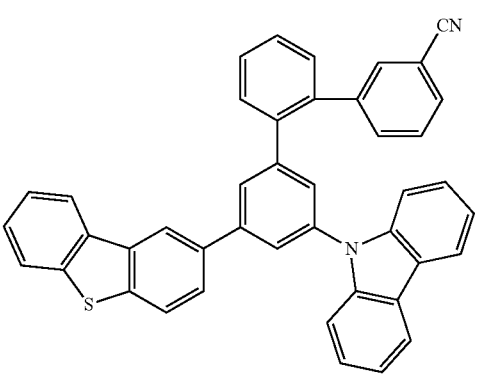

48
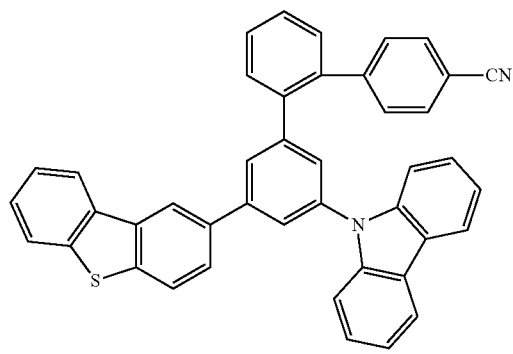
49
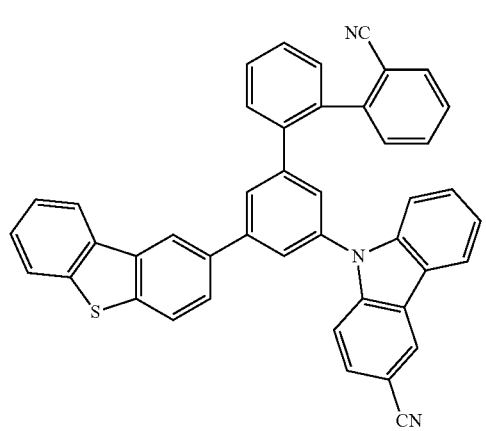
50
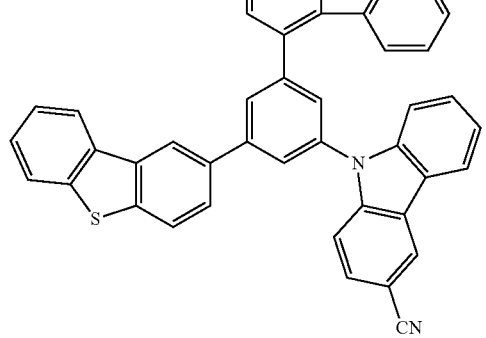
51
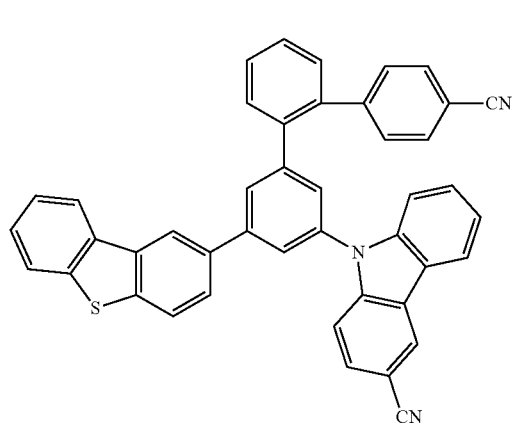
52
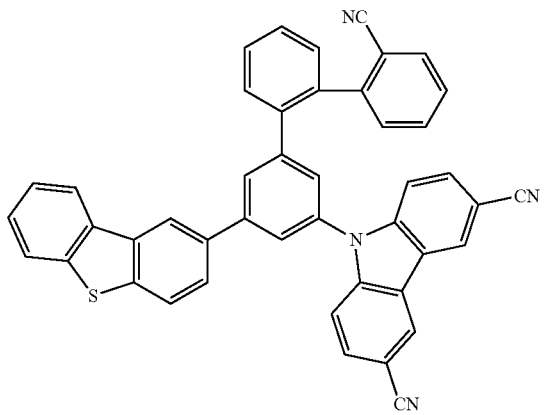
53
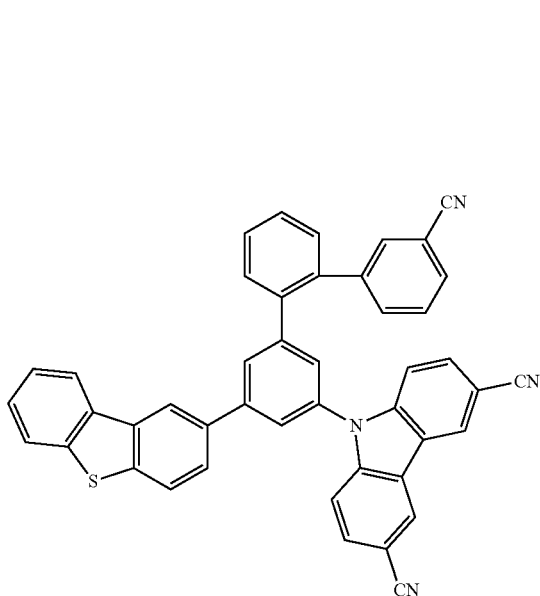
54
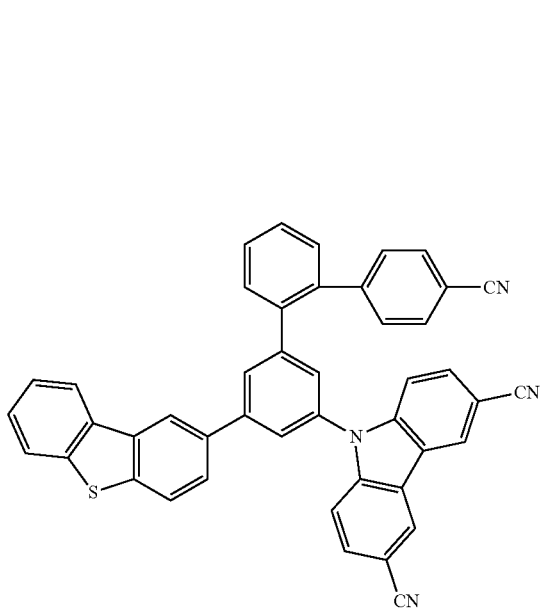

55
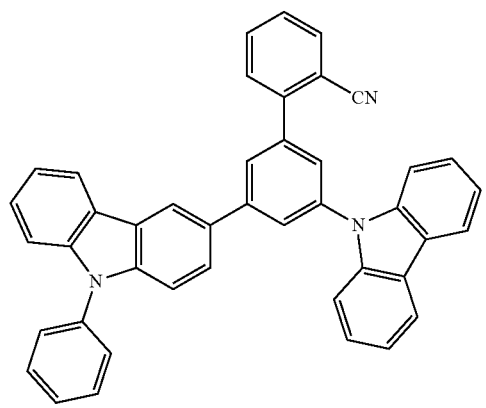
58
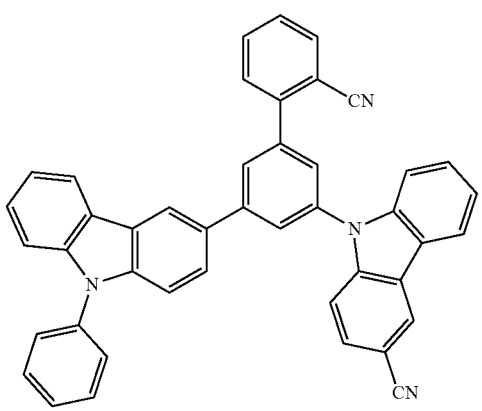
56
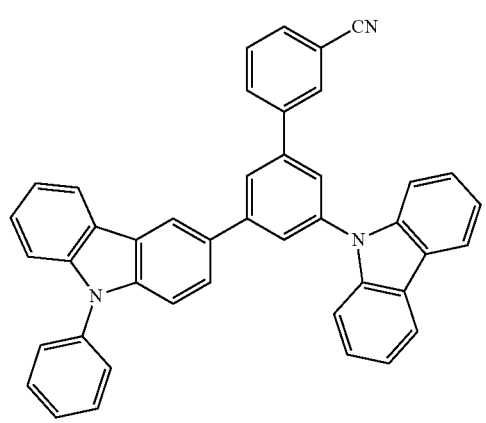
59
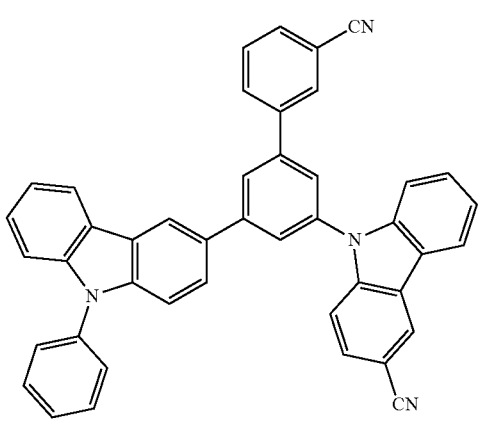
57
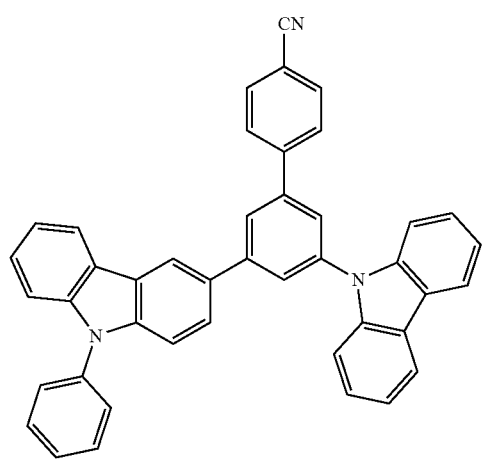
60
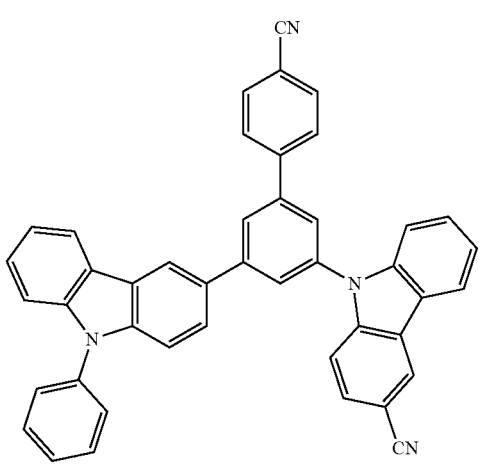

61
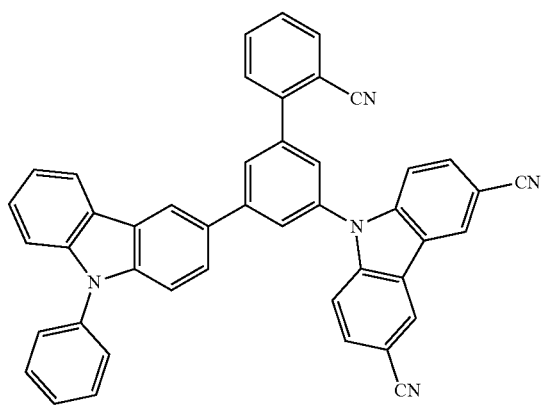
62
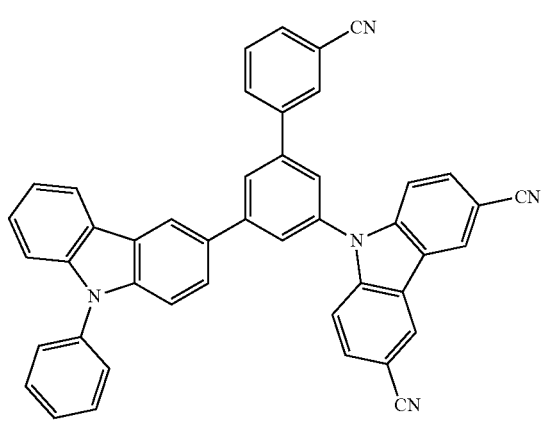
63
64
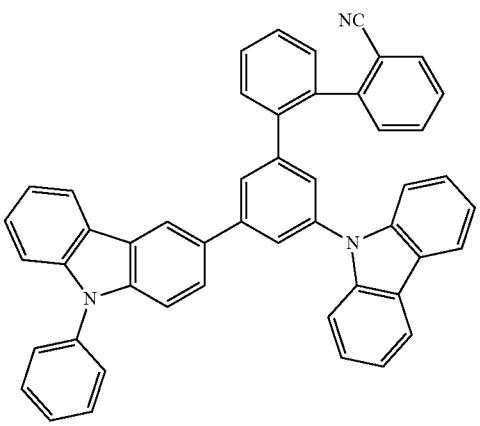
65
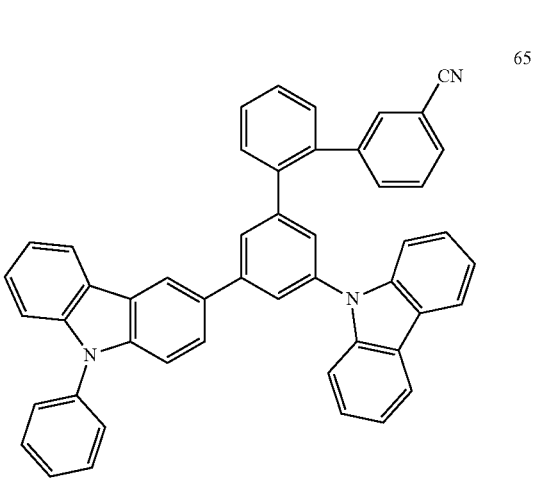
66
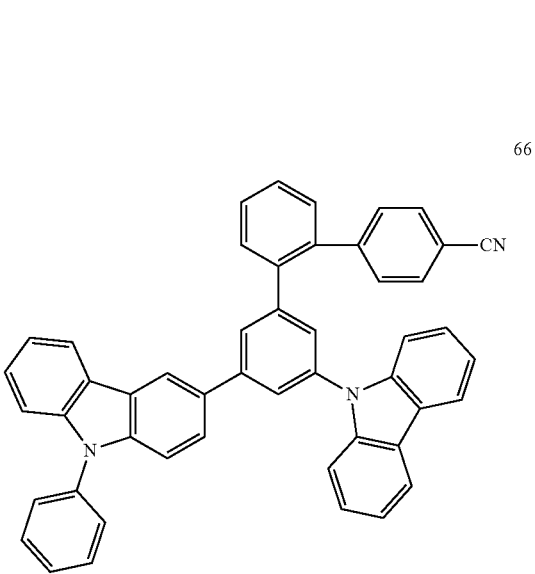

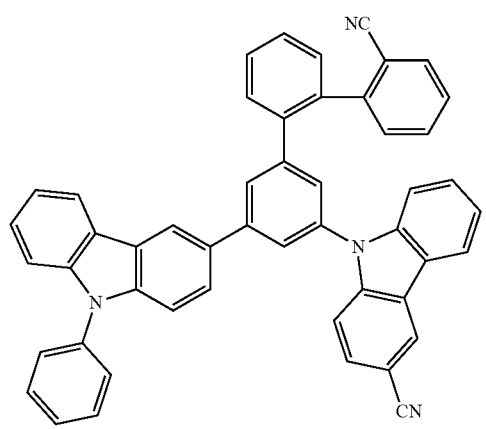
67
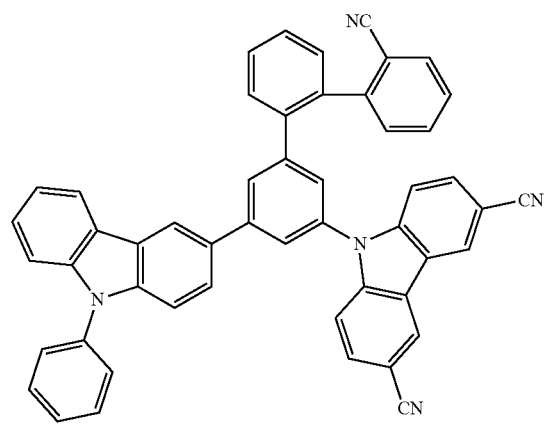
70
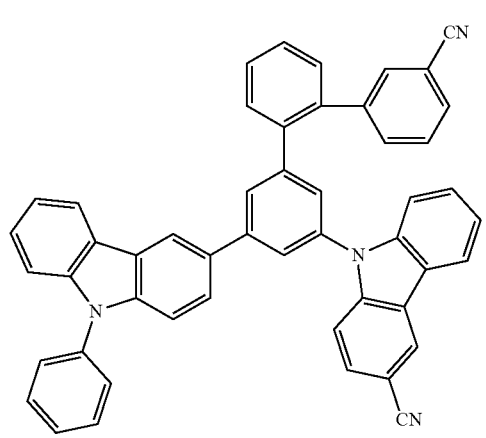
68
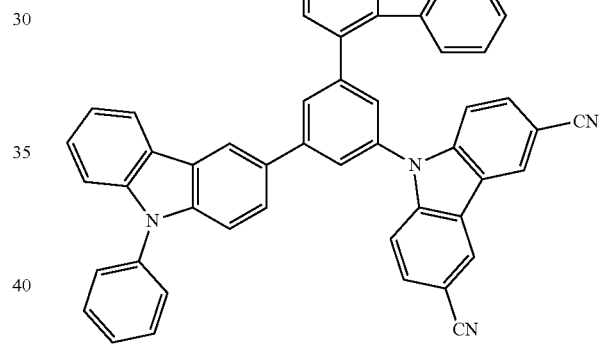
71
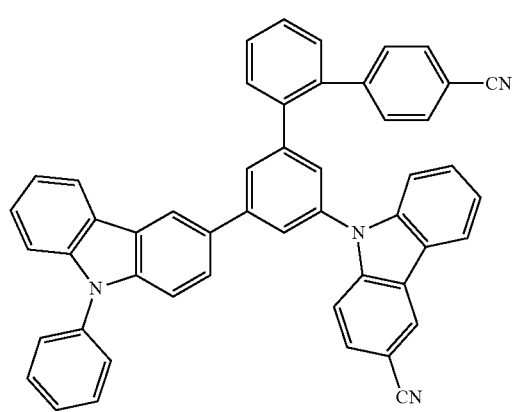
69
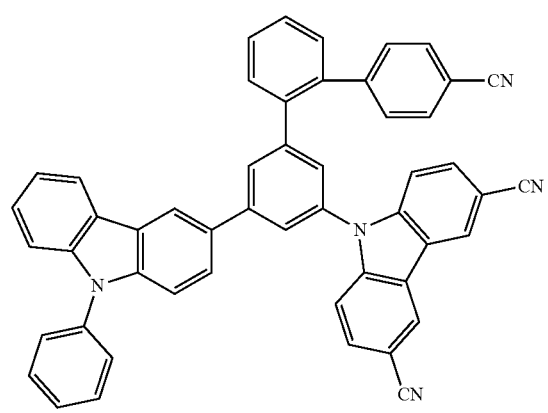
72

73
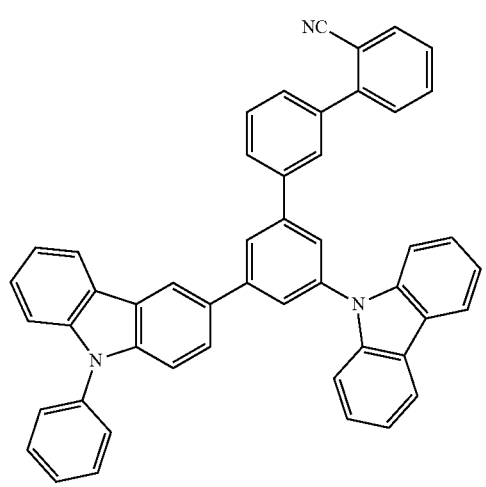
76
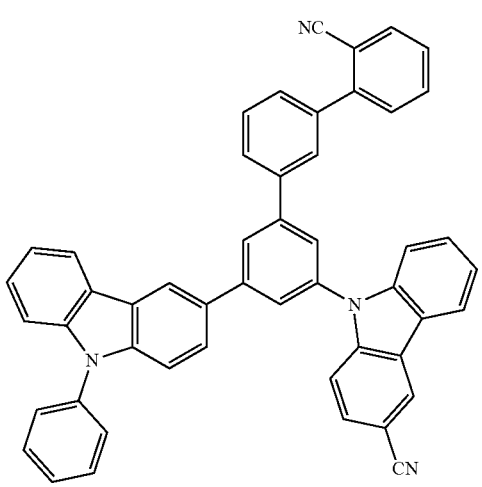
74
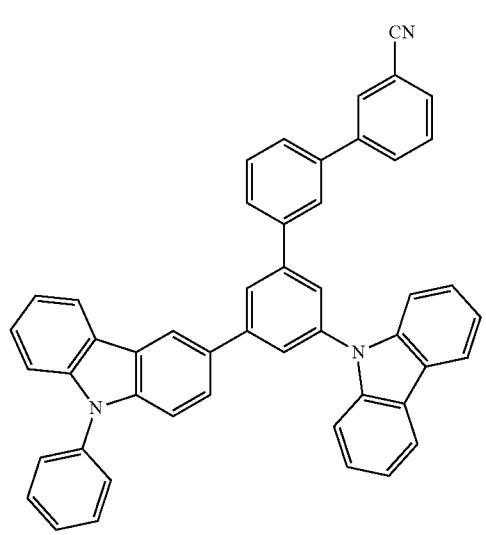
77
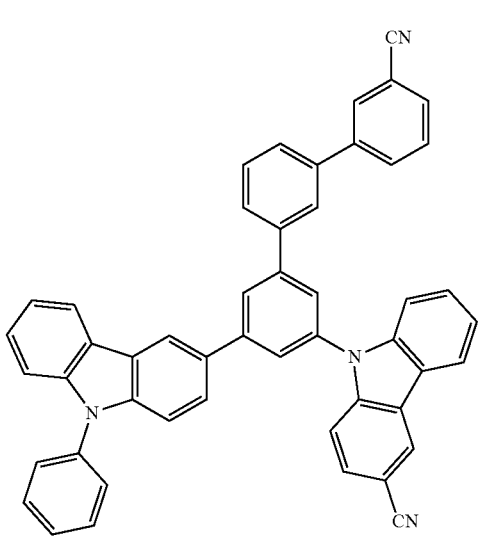
75
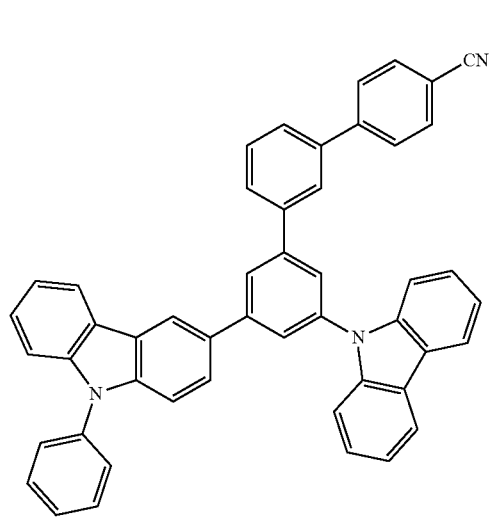
78
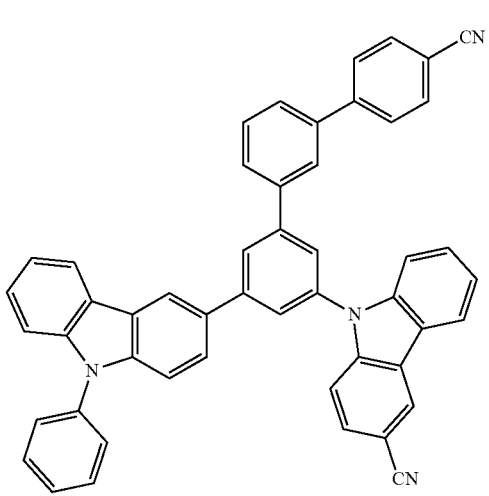

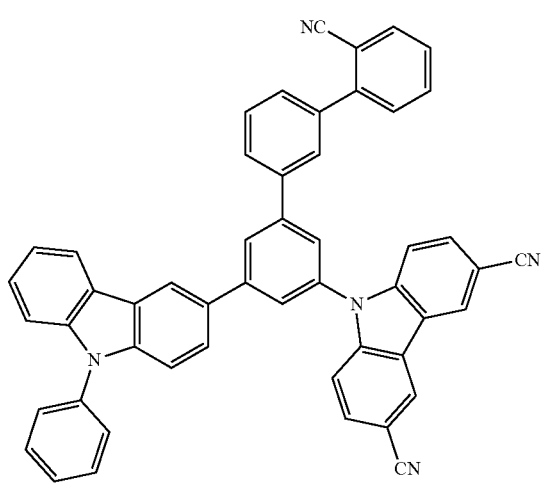
79
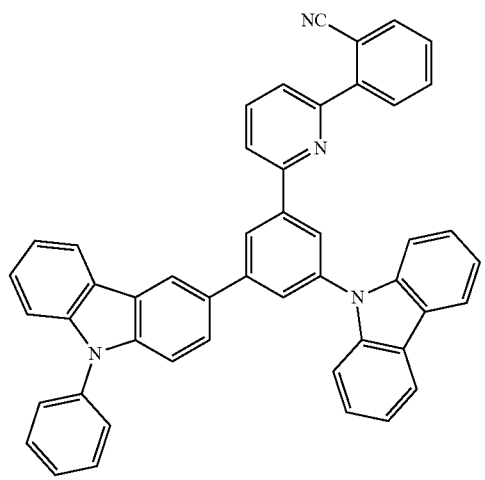
82
80
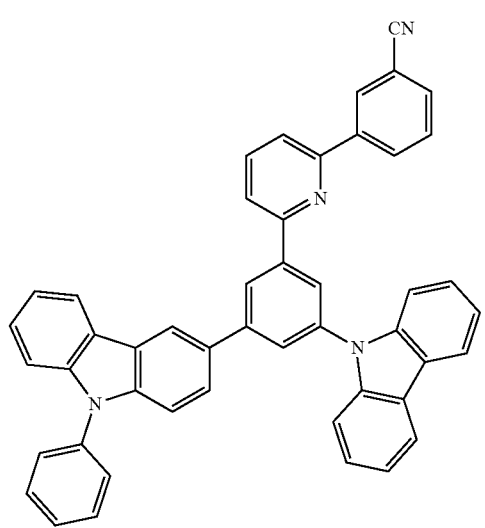
83
81
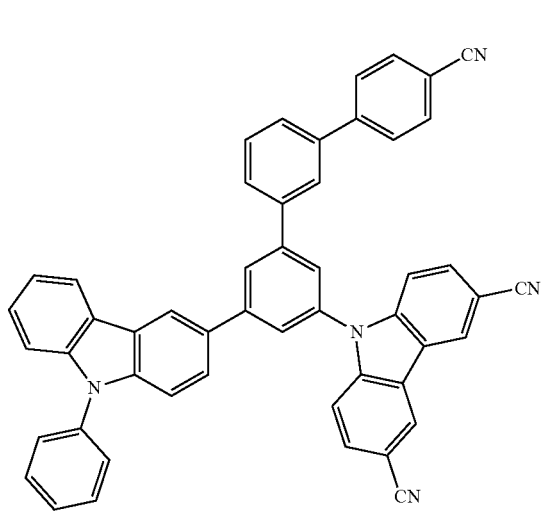
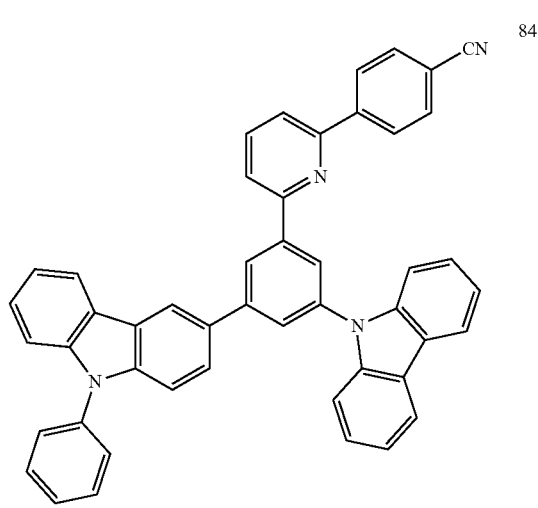
84

85
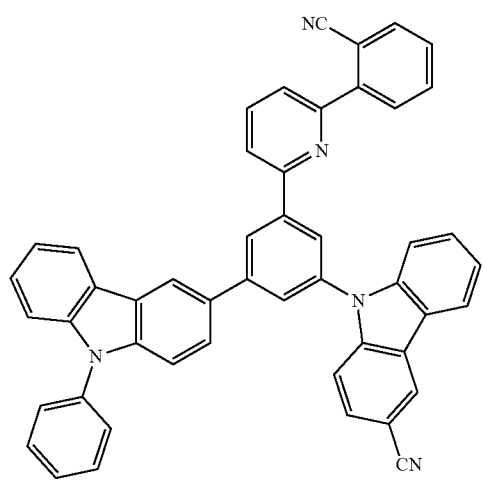
86
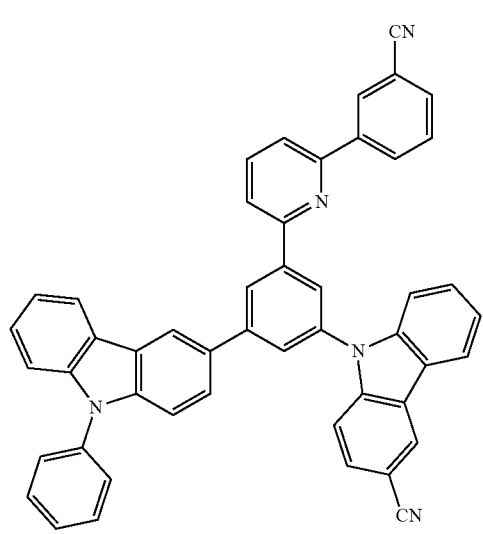
87
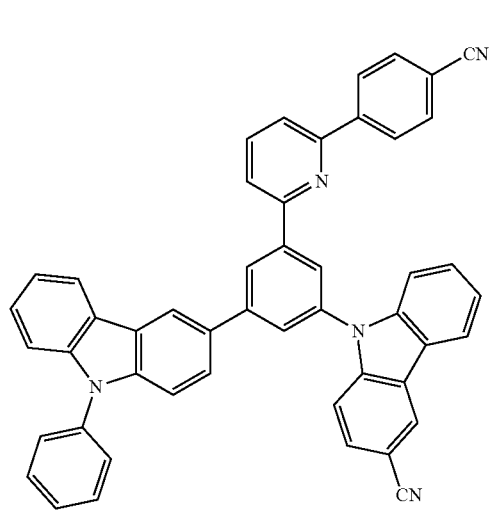
88
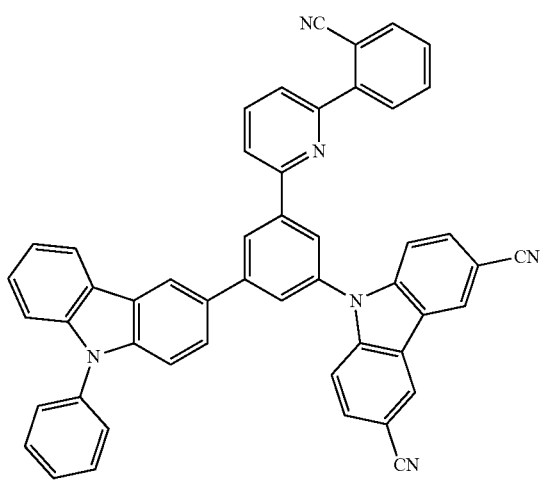
89
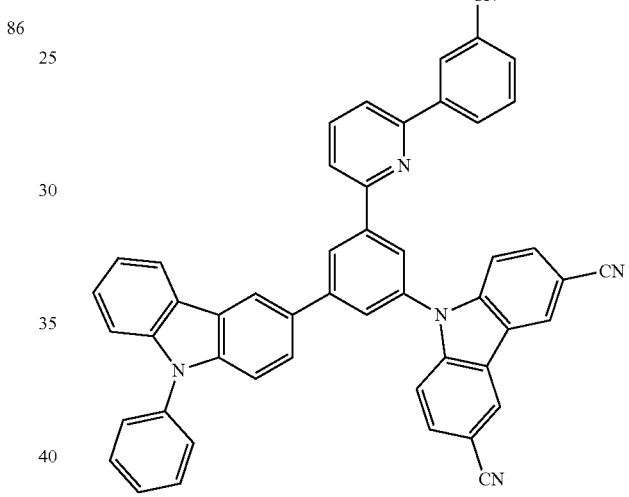
90
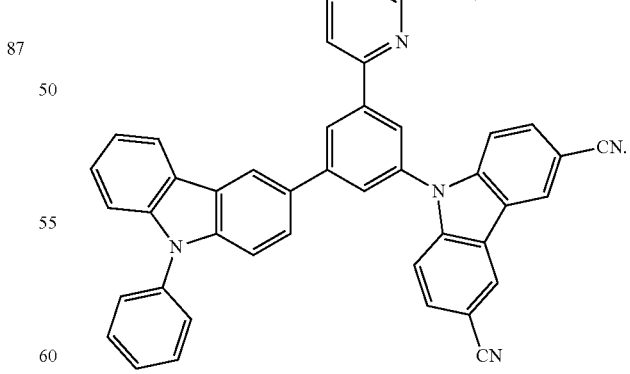
Since the condensed-cyclic compound represented by Formula 1 may essentially include $A_{11}$ including at least one cyano group, thermal stability and electric characteristics of the condensed-cyclic compound may improve. In addition, since the condensed-cyclic compound represented by Formula 1 may essentially include $A_{11}$ including at least one cyano group, holes and electrons transfer in the condensed-cyclic compound may easily occur. Therefore, organic light-emitting device including the condensed-cyclic compound represented by Formula 1 may have improved lifespan and efficiency.

Furthermore, by varying the number of cyano groups in the condensed-cyclic compound represented by Formula 1, a desired level of the highest occupied molecular orbital (HOMO) energy level and lowest unoccupied molecular orbital (LUMO) energy level may be easily derived therefrom, and by varying the number of phenyl groups in the condensed-cyclic compound represented by Formula 1, holes and electrons mobility of the condensed-cyclic compound may be readily controlled.

The condensed-cyclic compound represented by Formula 1 may have a molecular weight in a range of about 350 to about 800 grams per mole (g/mL). Thus, the condensed-cyclic compound represented by Formula 1 may have excellent thermal stability, for example, the condensed-cyclic compound may have a decomposition temperature that is higher than a sublimation temperature under a vacuum degree in a range of about $10^{-8}$ torr to about $10^{-3}$ torr. Therefore, an organic light-emitting device employing the condensed-cyclic compound represented by Formula 1 may have long lifespan.

For example, HOMO, LUMO, $T_1$, and $S_1$ energy levels of Compounds A to D were simulated by using the Gaussian. Simulation evaluation results are shown in Table 1.

TABLE 1

| Compound No. | HOMO (eV) | LUMO (eV) | $T_1$ (eV) | $S_1$ (eV) |
| --- | --- | --- | --- | --- |
| 1 | −5.29 | −1.67 | 3 | 3.13 |
| 2 | −5.48 | −1.62 | 3.04 | 3.38 |
| 3 | −5.53 | −1.86 | 2.94 | 3.2 |
| 4 | −5.73 | −1.85 | 3.07 | 3.38 |
| 5 | −5.91 | −1.8 | 3.06 | 3.63 |
| 6 | −5.97 | −2.04 | 2.97 | 3.45 |
| 7 | −6.13 | −2.03 | 3.08 | 3.61 |
| 8 | −6.31 | −1.97 | 3.06 | 3.84 |
| 9 | −6.36 | −2.21 | 2.98 | 3.66 |
| 10 | −5.36 | −1.59 | 3.07 | 3.29 |
| 11 | −5.38 | −1.52 | 3.08 | 3.4 |
| 12 | −5.37 | −1.73 | 3.05 | 3.16 |
| 13 | −5.8 | −1.76 | 3.09 | 3.56 |
| 14 | −5.82 | −1.68 | 3.08 | 3.68 |
| 15 | −5.8 | −1.9 | 3.07 | 3.43 |
| 16 | −6.2 | −1.9 | 3.08 | 3.82 |
| 17 | −6.22 | −1.8 | 3.08 | 3.94 |
| 18 | −6.2 | −2.03 | 3.08 | 3.71 |
| 19 | −5.3 | −1.6 | 3.04 | 3.33 |
| 20 | −5.37 | −1.55 | 3.04 | 3.46 |
| 21 | −5.47 | −1.76 | 2.98 | 3.35 |
| 22 | −5.72 | −1.76 | 3.03 | 3.58 |
| 23 | −5.81 | −1.68 | 3.05 | 3.73 |
| 24 | −5.9 | −1.89 | 2.99 | 3.66 |
| 25 | −6.07 | −1.93 | 2.99 | 3.75 |
| 26 | −6.22 | −1.77 | 3.06 | 3.95 |
| 27 | −6.29 | −1.97 | 2.99 | 3.94 |
| 28 | −5.42 | −1.8 | 2.94 | 3.26 |
| 29 | −5.46 | −1.75 | 2.93 | 3.3 |
| 30 | −5.47 | −2 | 2.85 | 3.13 |
| 31 | −5.85 | −1.93 | 2.96 | 3.55 |
| 32 | −5.9 | −1.87 | 2.95 | 3.55 |
| 33 | −5.9 | −2.12 | 2.86 | 3.44 |
| 34 | −6.24 | −2.04 | 2.97 | 3.78 |
| 35 | −6.28 | −2.02 | 2.95 | 3.74 |
| 36 | −6.28 | −2.24 | 2.86 | 3.67 |
| A | −5.46 | −0.77 | 3.17 | 4.01 |
| B | −5.259 | −0.870 | 3.050 | 3.338 |
| C | −5.357 | −1.099 | 3.114 | 3.372 |
| D | −5.587 | −1.743 | 3.048 | 3.356 |

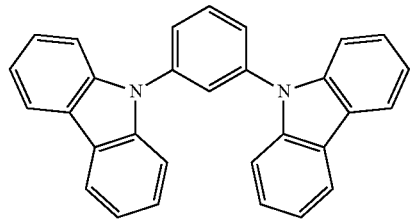

A

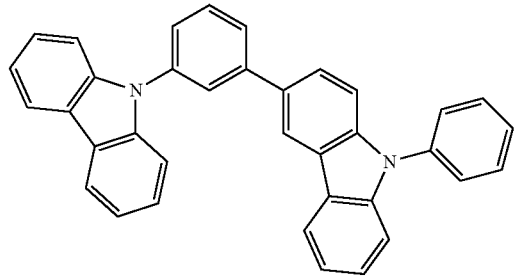

B

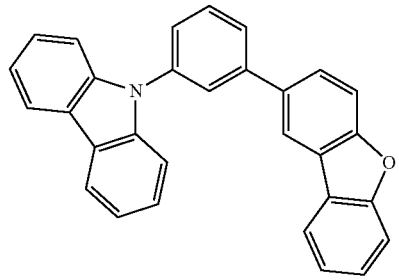

C

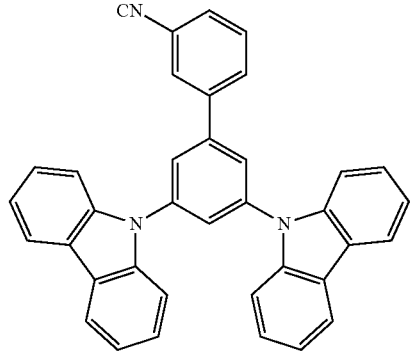

D

Referring to Table 1, the condensed-cyclic compound represented by Formula 1 may have a HOMO energy level and a LUMO energy level suitable for a material for an organic light-emitting device, and maintained a high $T_1$, e.g., 2.8 electron volts (eV) or greater, particularly, 2.9 eV or greater, and a small $\Delta E_{ST}$ value.

A method of synthesizing the condensed-cyclic compound represented by Formula 1 may be understood by one of ordinary skill in the art by referring to Synthesis Examples described below.

Therefore, the condensed-cyclic compound represented by Formula 1 may be appropriate to be used in an organic layer of an organic light-emitting device, for example as a host in an emission layer of the organic layer. Thus, according to another aspect, provided is an organic light-emitting device that may include: a first electrode;

a second electrode; and an organic layer disposed between the first electrode and the second electrode, wherein the organic layer includes an emission layer and the condensed-cyclic compound represented by Formula 1.

Since the organic light-emitting device has an organic layer including the condensed-cyclic compound represented by Formula 1, the organic light-emitting device may have a low driving voltage, high efficiency, high luminance, high quantum efficiency, and long lifespan.

The condensed-cyclic compound represented by Formula 1 may be included in between a pair of electrodes of the organic light-emitting device. In some embodiments, the condensed-cyclic compound represented by Formula 1 may be included in the emission layer. In this case, the condensed-cyclic compound may serve as a host, and the emission layer may further include a dopant.

As used herein, the expression the "(organic layer) includes a condensed-cyclic compound" may be construed as meaning the "(organic layer) may include one condensed-cyclic compound represented by Formula 1 or two different condensed-cyclic compounds represented by Formula 1".

For example, the organic layer may include only Compound 1 as the condensed-cyclic compound. In this case, Compound 1 may be included in the emission layer of the organic light-emitting device. In some embodiments, the organic layer may include Compound 1 and Compound 2 as the condensed-cyclic compounds. In this regard, Compound 1 and Compound 2 may be included in the same layer (for example, both Compound 1 and Compound 2 may be included in the emission layer).

The first electrode may be anode, which is a hole injection electrode, and the second electrode may be a cathode, which is an electron injection electrode.

Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole transport region disposed between the first electrode and the emission layer, wherein the hole transport region may include at least one selected from a hole injection layer, a hole transport layer, and an electron blocking layer; and ii) an electron transport region between the emission layer and the second electrode, wherein the electron transport region may include at least one selected from a hole blocking layer, an electron transport layer, and an electron injection layer.

As used herein, the term the "organic layer" refers to a single and/or a plurality of layers between the first electrode and the second electrode in an organic light-emitting device. The "organic layer" may include not only organic compounds but also organometallic complexes including metals.

FIG. 1 is a schematic view of an organic light-emitting device 10 according to an exemplary embodiment. Hereinafter a structure and a method of manufacturing the organic light-emitting device according to an exemplary embodiment will be described with reference to FIG. 1. The organic light-emitting device 10 may include a first electrode 11, an organic layer 15, and a second electrode 19, which may be sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum depositing or sputtering a material for forming the first electrode on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag).

The first electrode 11 may have a single layer structure or a multi-layer structure including a plurality of layers. For example, the first electrode 11 may have a triple-layer structure of ITO/Ag/ITO, but embodiments are not limited thereto.

The organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may include a hole injection layer only or a hole transport layer only. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer (HIL), the hole injection layer may be formed on the first electrode 11 by using a suitable method, such as vacuum deposition, spin coating, casting, and a Langmuir-Blodgett (LB) method.

When a hole injection layer is formed by vacuum-deposition, for example, the vacuum-deposition may be performed at a deposition temperature in a range of about 100° C. to about 500° C., at a vacuum degree in a range of about $10^{-8}$ torr to about $10^{-3}$ torr, and at a deposition rate in a range of about 0.01 Angstroms per second (Å/sec) to about 100 Å/sec, although the conditions may vary depending on a compound that is used as a hole injection material and a structure and thermal properties of a desired hole injection layer, but embodiments are not limited thereto.

When a hole injection layer is formed by spin coating, the spin coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired hole injection layer, but embodiments are not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201, and a compound represented by Formula 202:

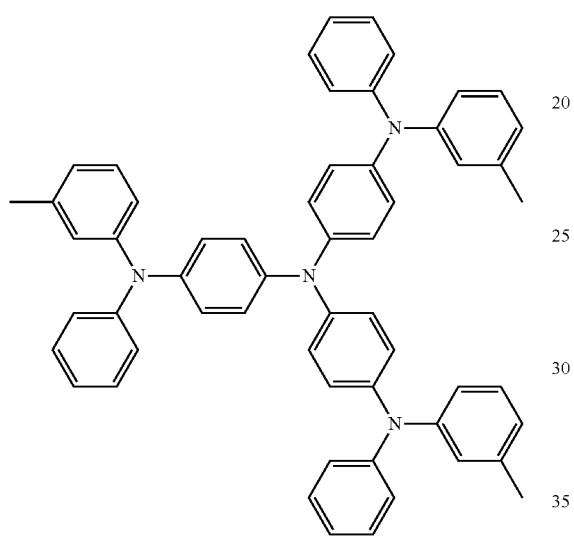

m-MTDATA

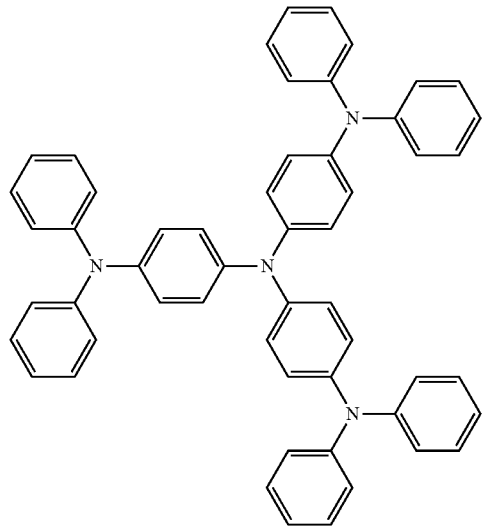

TDATA

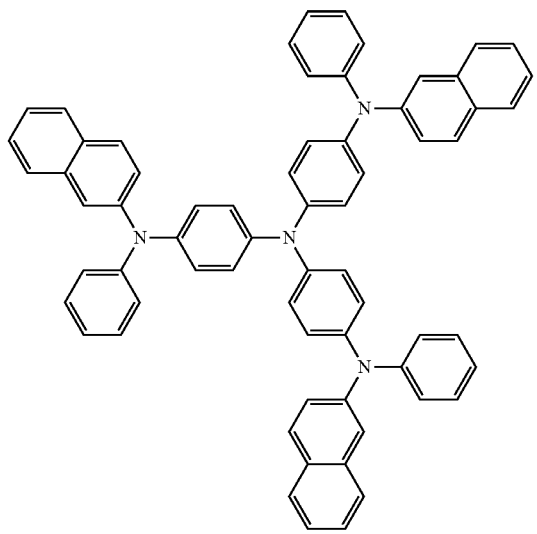

2-TNATA

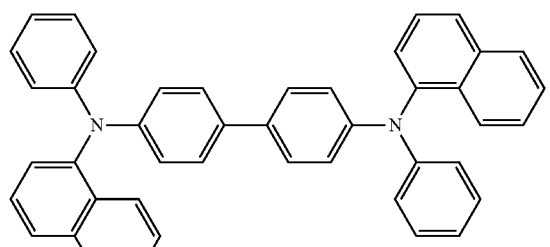

NPB

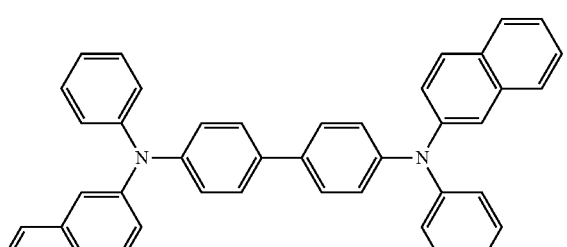

β-NPB

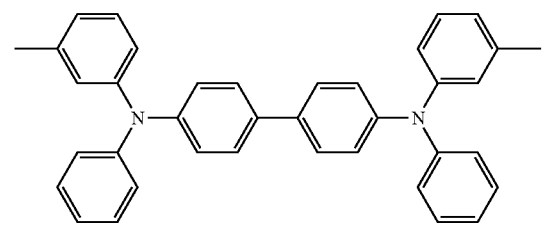

TPD

-continued

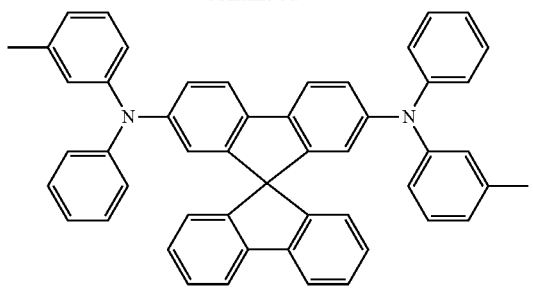

Spiro-NPB

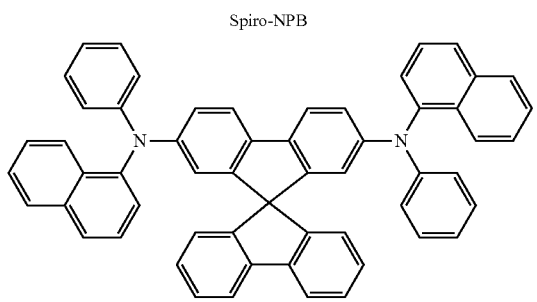

Spiro-NPB

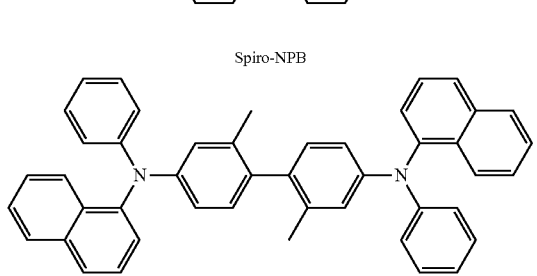

methylated NPB

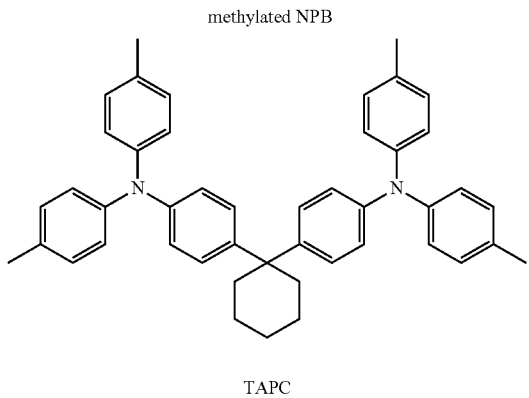

TAPC

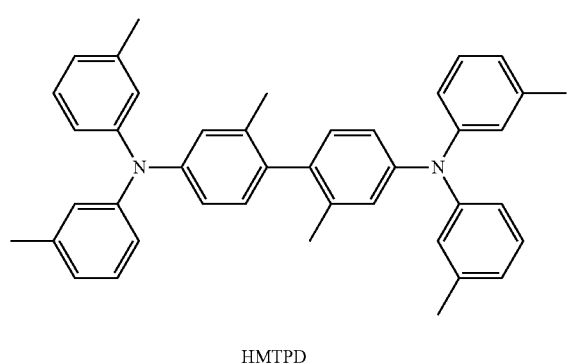

HMTPD

-continued

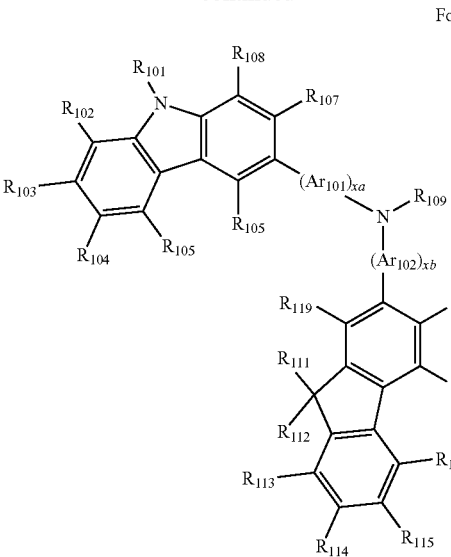

Formula 201

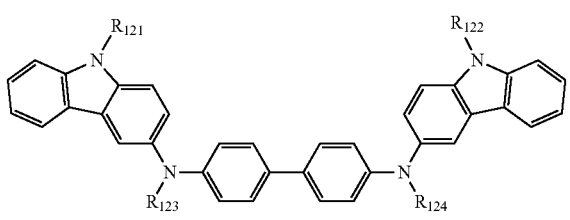

Formula 202 wherein, in Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5. Alternatively, xa and xb may be each independently an integer selected from 0, 1, and 2. In some embodiments, xa may be 1 and xb may be 0, but embodiments are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, e.g., a methyl group, an ethyl group, a propyl group, a butyl group, pentyl group, or a hexyl group, and a $C_1$-$C_{10}$ alkoxy group, e.g., a methoxy group, an ethoxy group, a propoxy group, a butoxy group, or a pentoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A, but embodiments are not limited thereto:

Formula 201A

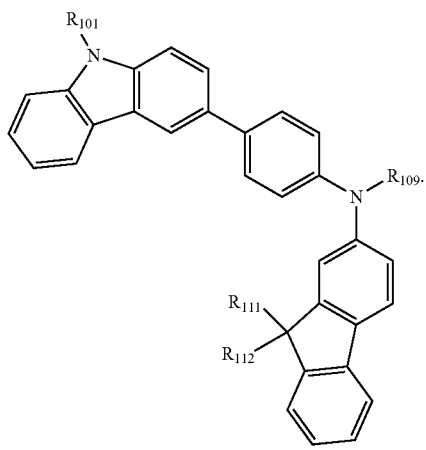

$R_{101}$, $R_{111}$, $R_{112}$, and $R_{109}$ in Formula 201A may be understood by referring to the descriptions thereof provided herein.

For example, the compound represented by Formula 201 and the compound represented by Formula 202 may include Compounds HT1 to HT20, but embodiments are not limited thereto:

HT1

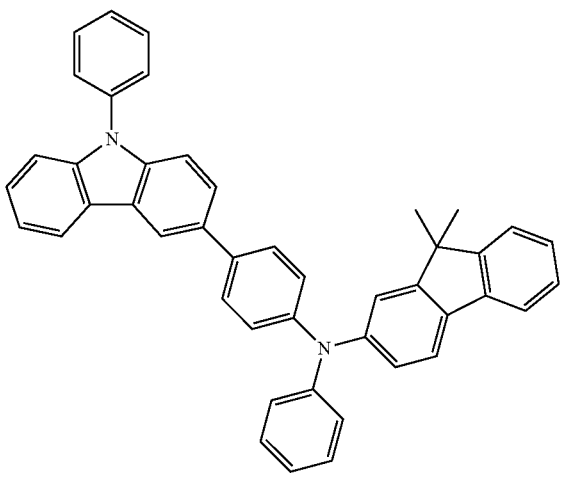

HT2

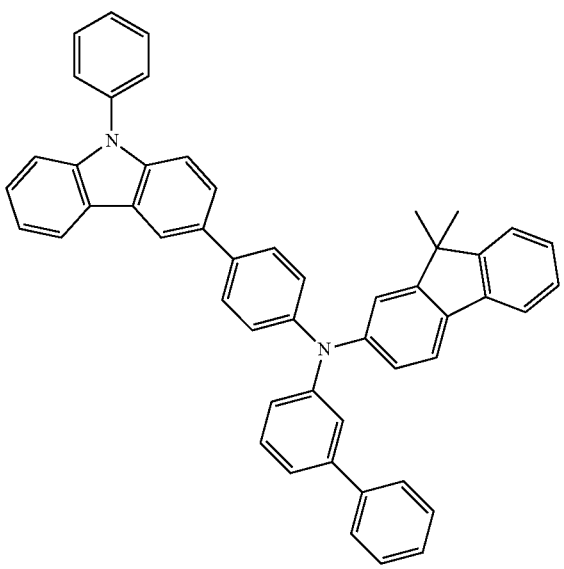

HT3
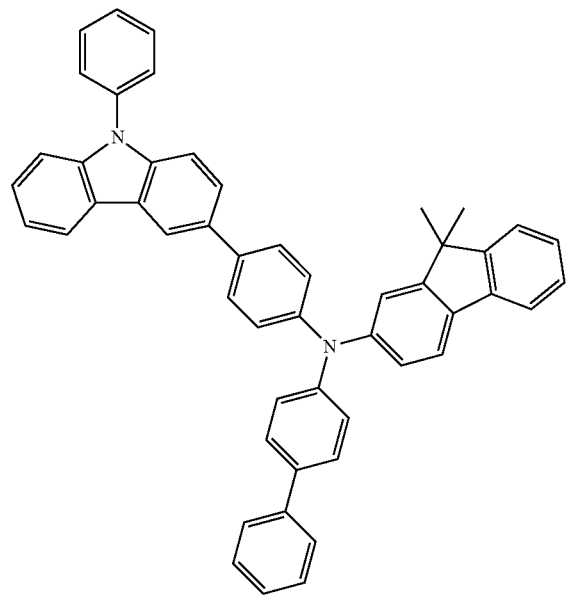
HT4
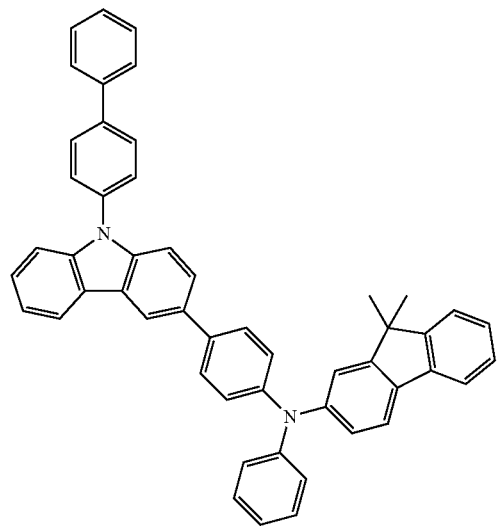
HT5
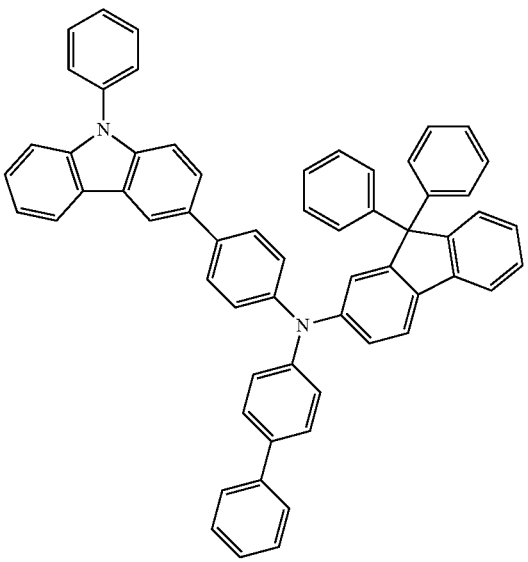
HT6
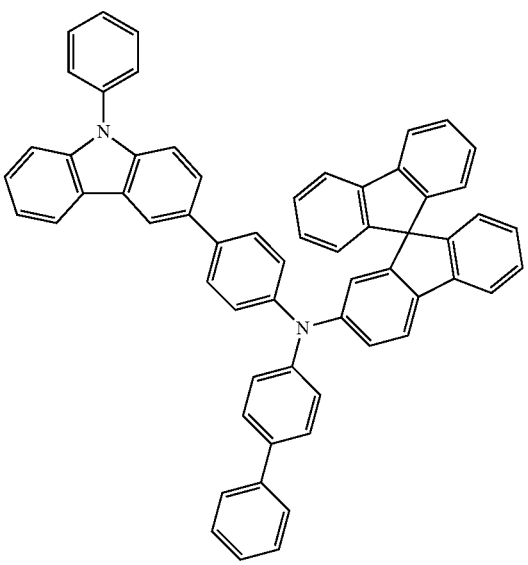

-continued
HT7
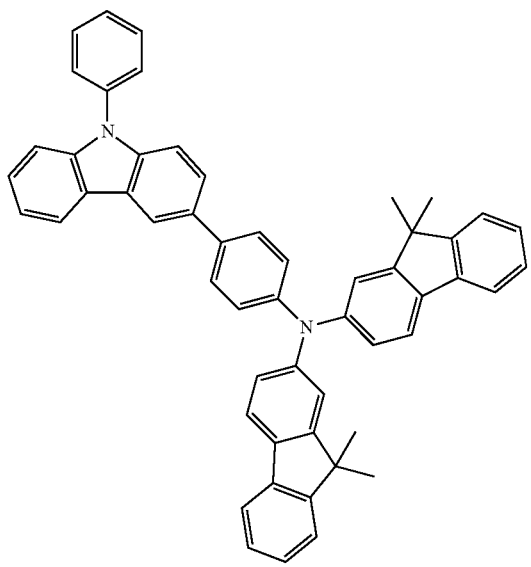
HT8
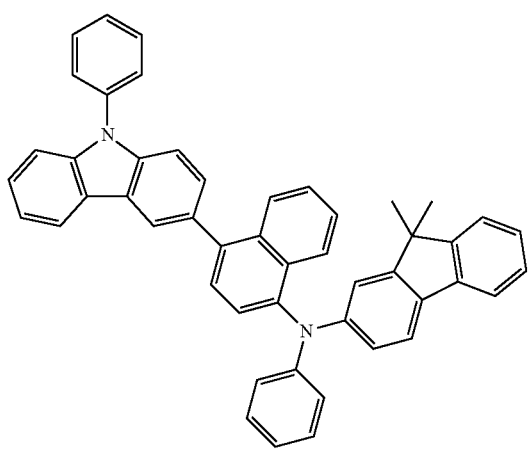
HT9
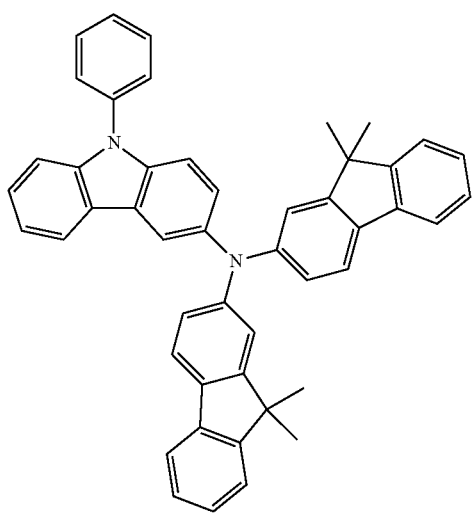
-continued
HT10
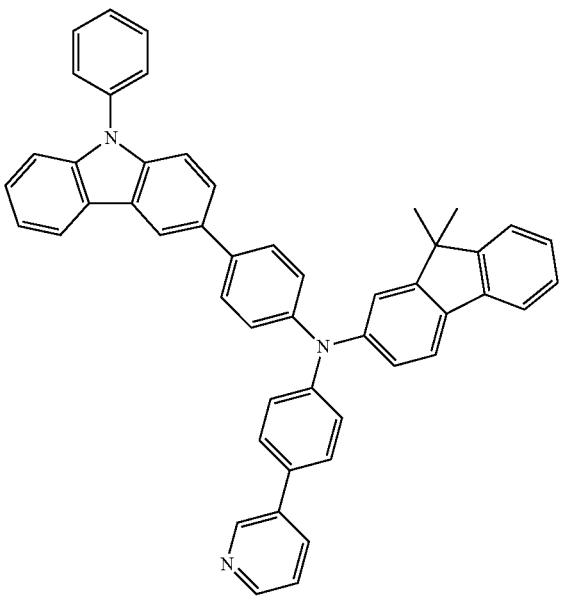
HT11
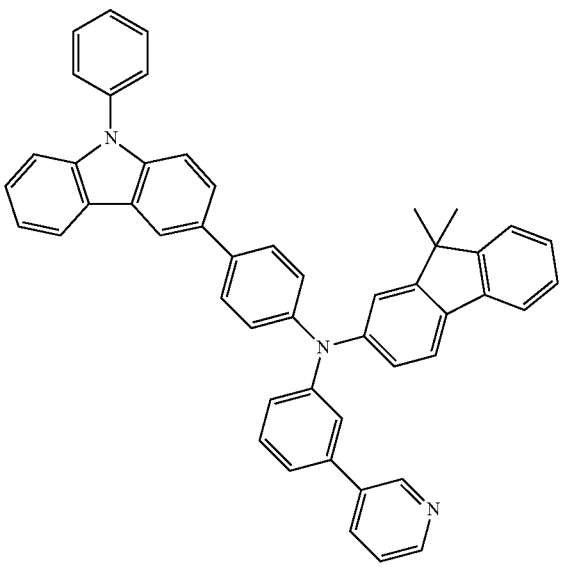

HT12
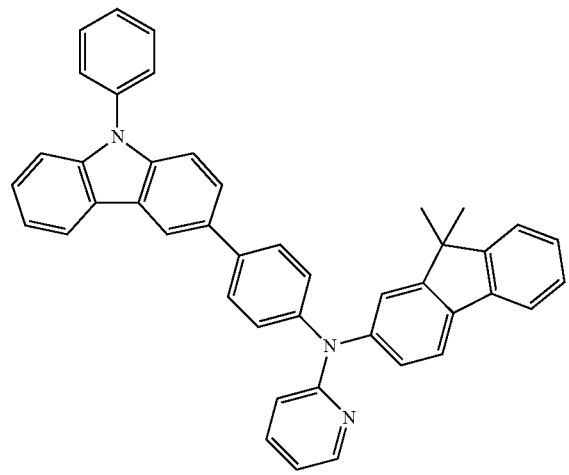
HT13
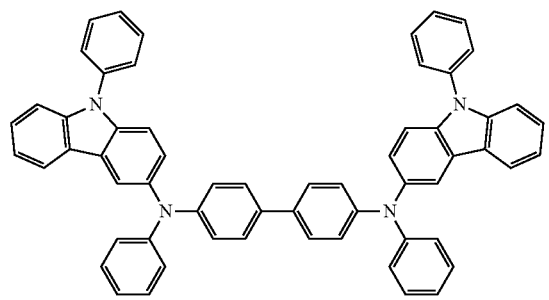
HT14
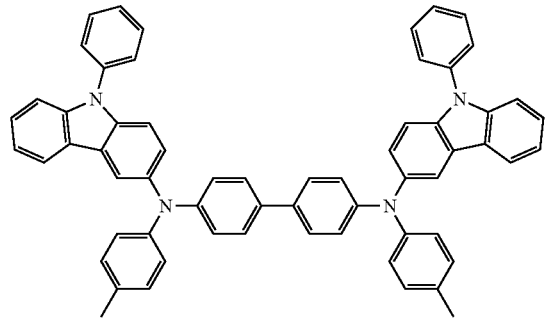
HT15
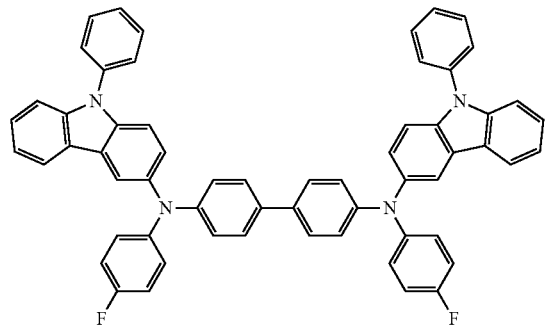
HT16
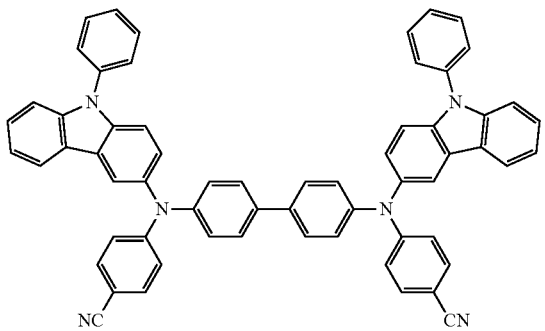
HT17
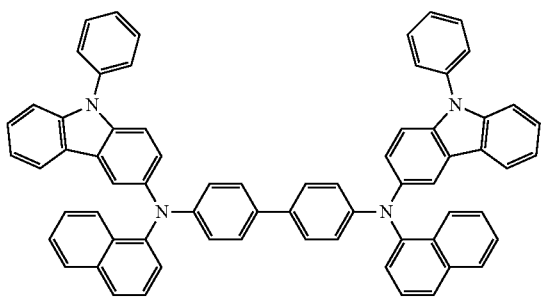
HT18
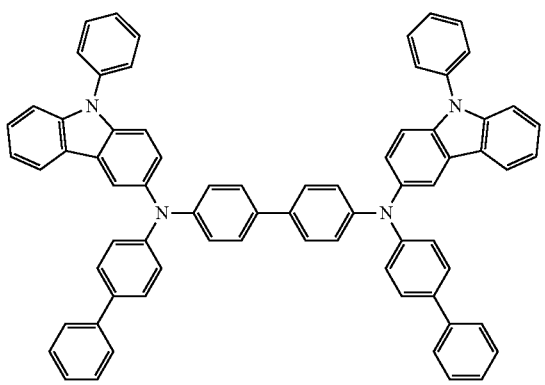
HT19
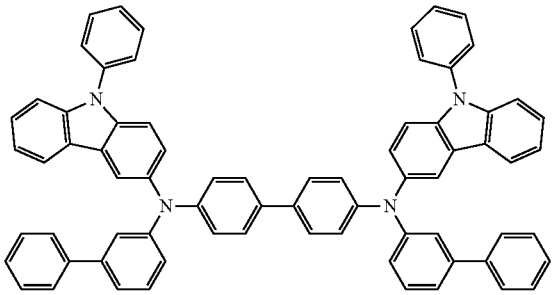

HT20

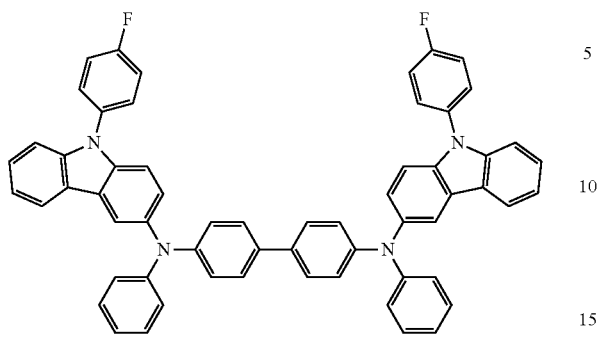

The thickness of the hole transport region may be in a range of about 100 Angstroms (Å) to about 10,000 Å, for example, about 100 Å to about 1,000 Å. While not wishing to be bound by theory, it is understood that when the hole transport region includes a hole injection layer and a hole transport layer, the thickness of the hole injection layer may be in a range of about 100 Å to about 10,000 Å, for example, about 100 Å to about 1,000 Å, a thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, excellent hole transport characteristics may be obtained without a substantial increase in driving voltage.

The hole transport region may include a charge-generating material as well as the mentioned materials above, to improve conductive properties. The charge-generating material may be homogeneously or non-homogeneously dispersed throughout the hole transport region.

The charge-generating material may be, for example, a p-dopant. The p-dopant may be selected from a quinone derivative, a metal oxide, and a cyano group-containing compound, but embodiments are not limited thereto. For example, non-limiting examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or HT-D2, but embodiments are not limited thereto:

Compound HT-D1

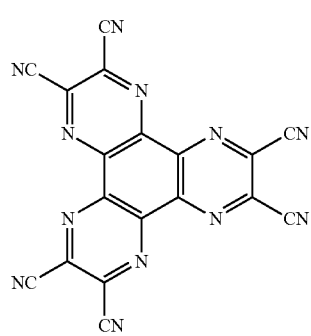

F4-TCNQ

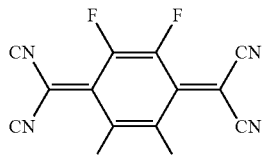

Compound HT-D2

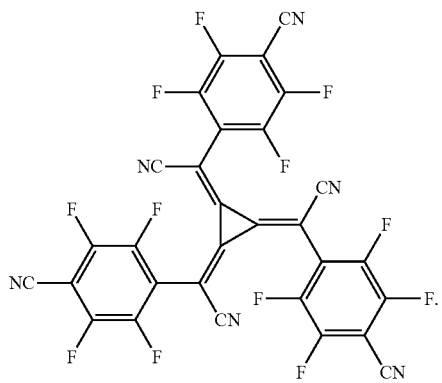

The hole transport region may further include a buffer layer.

The buffer layer may compensate for an optical resonance distance according to a wavelength of light emitted from the emission layer to improve the efficiency of an organic light-emitting device.

An emission layer (EML) may be formed on the hole transport region by using one or more suitable methods, such as vacuum deposition, spin coating, casting, or an LB method. When the emission layer is formed by vacuum deposition or spin coating, vacuum deposition and coating conditions for the emission layer may be generally similar to the conditions for forming a hole injection layer, though the conditions may vary depending on the compound used.

The hole transport region may further include an electron blocking layer. The electron blocking layer may include any suitable material, e.g., mCP, but embodiments are not limited thereto:

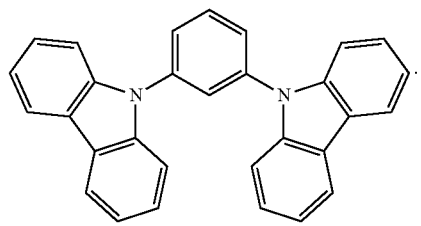

mCP

When the organic light-emitting device 10 is a full color organic light-emitting device, the emission layer may be patterned into a red emission layer, a green emission layer, and a blue emission layer. In some embodiments, the emission layer may have a structure in which the red emission layer, the green emission layer, and/or the blue emission layer are layered to emit white light or other various embodiments are possible.

The emission layer may include the condensed-cyclic compound represented by Formula 1. The emission layer may further include a dopant. The dopant may include at least one selected from a fluorescent dopant and a phosphorescent dopant.

For example, a host in the emission layer may include the condensed-cyclic compound represented by Formula 1.

The dopant in the emission layer may include a fluorescent dopant which emits light according to a fluorescent emission mechanism or a phosphorescent dopant which emits light according to a phosphorescent emission mechanism.

According to an embodiment, the dopant in the emission layer may be a phosphorescent dopant, and the phosphorescent dopant may include an organometallic compound represented by Formula 81:

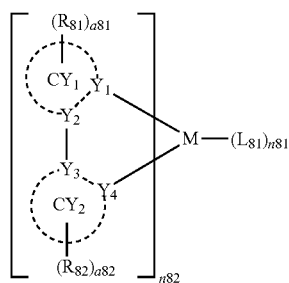

Formula 81 wherein, in Formula 81,

M may be iridium (Ir), platinum (Pt), osmium (Os), titanium (Ti), zirconium (Zr), hafnium (Hf), europium (Eu), terbium (Tb), or thulium (Tm);

$Y_1$ to $Y_4$ may be each independently carbon (C) or nitrogen (N);

$Y_1$ and $Y_2$ may be linked to each other via a single bond or a double bond, and $Y_3$ and $Y_4$ are linked to each other via a single bond or a double bond;

$CY_1$ and $CY_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, wherein $CY_1$ and $CY_2$ may be, optionally, line to each other via a single bond or an organic linking group;

$R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$;

a81 and a82 may be each independently an integer selected from 1 to 5;

n81 may be an integer selected from 0 to 4;

n82 may be an integer selected from 1, 2, and 3; and $L_{81}$ may be any suitable monovalent, divalent, or trivalent organic ligand.

$R_{81}$ to $R_{82}$ may be the same as defined in connection with $R_{41}$ provided herein.

The phosphorescent dopant may include at least one selected from Compounds PD1 to PD78 and Flr6, but embodiments are not limited thereto:

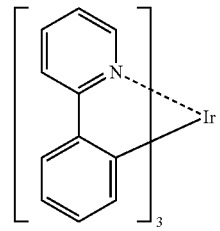

PD1

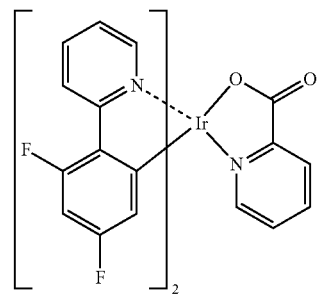

PD2

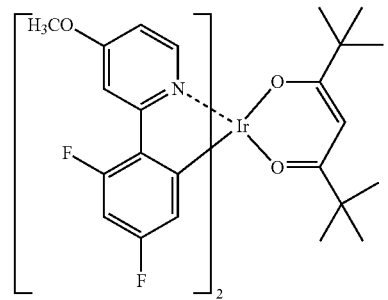

PD3

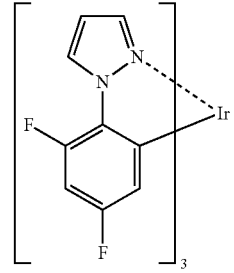

PD4

PD5 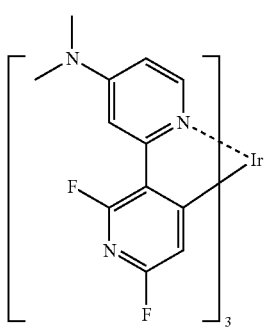
PD6 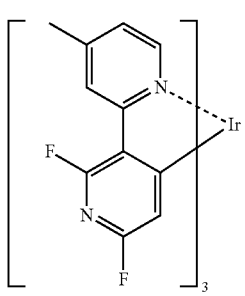
PD7 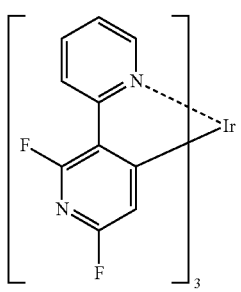
PD8 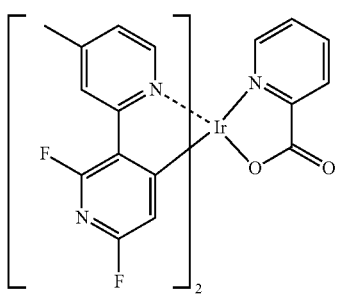
PD9 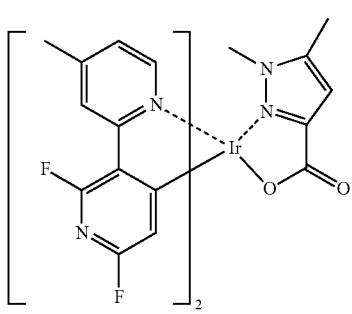
PD10 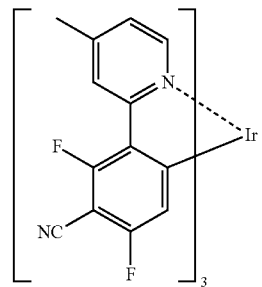
PD11 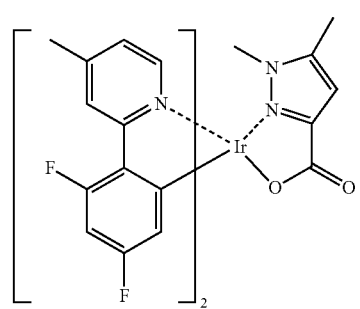
PD12 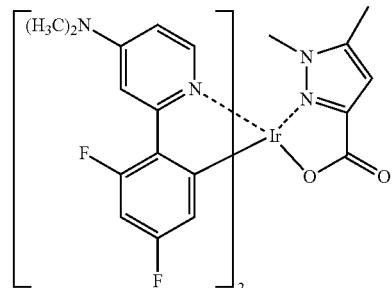
PD13 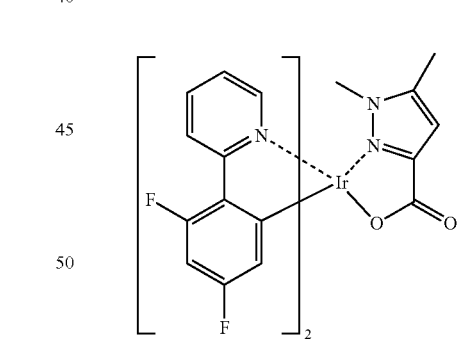
PD14 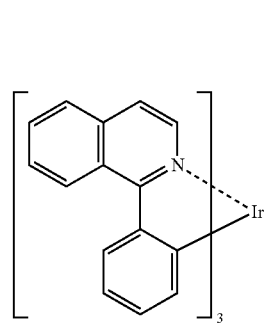

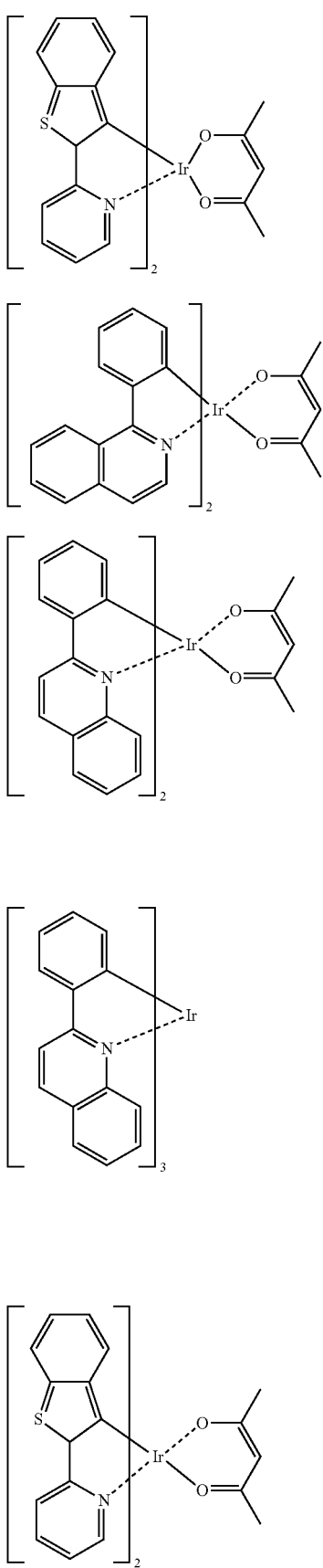
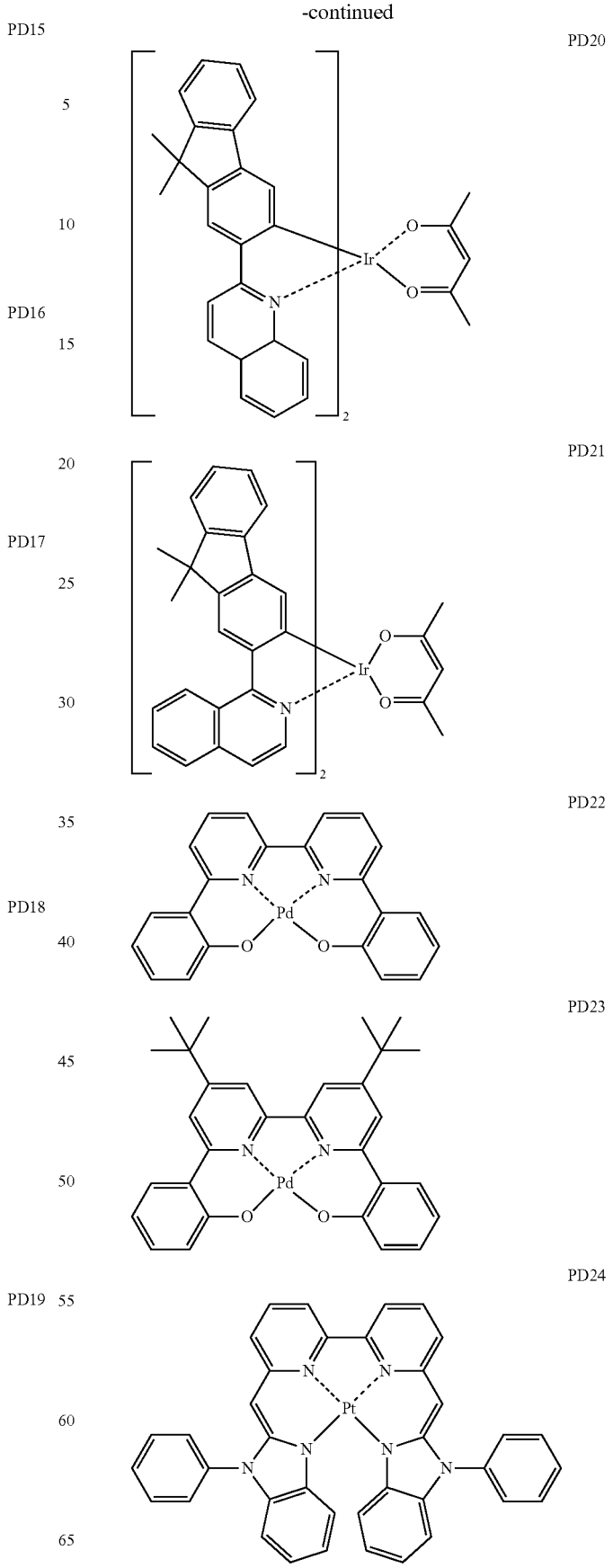

PD25 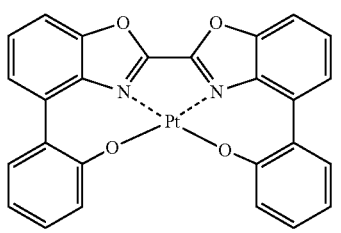
PD26 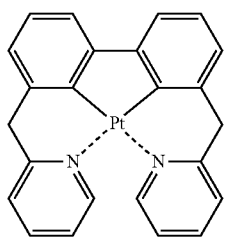
PD27 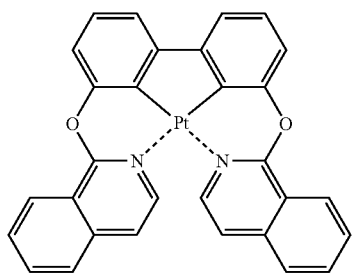
PD28 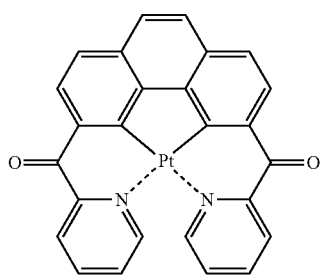
PD29 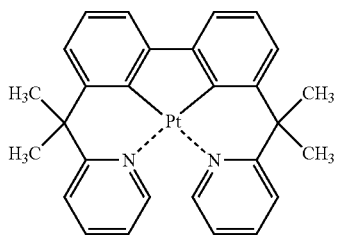
PD30 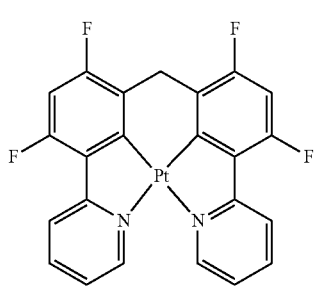
PD31 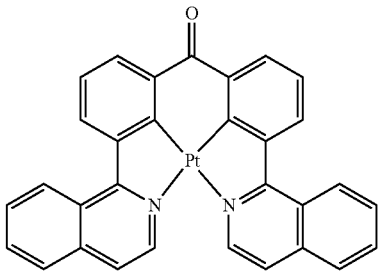
PD32 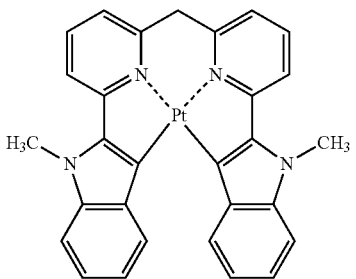
PD33 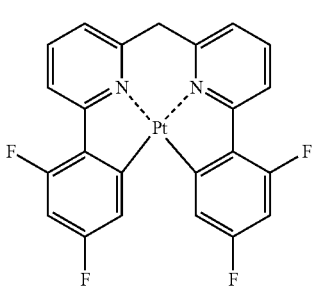
PD34 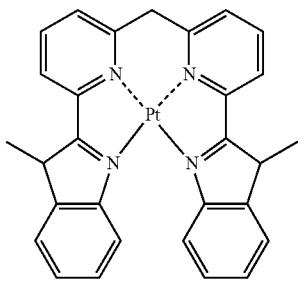
PD35 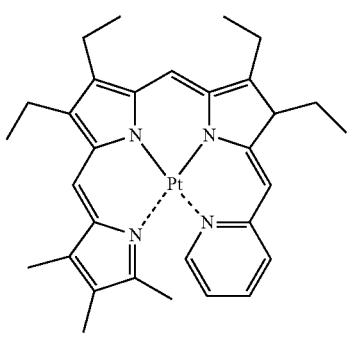

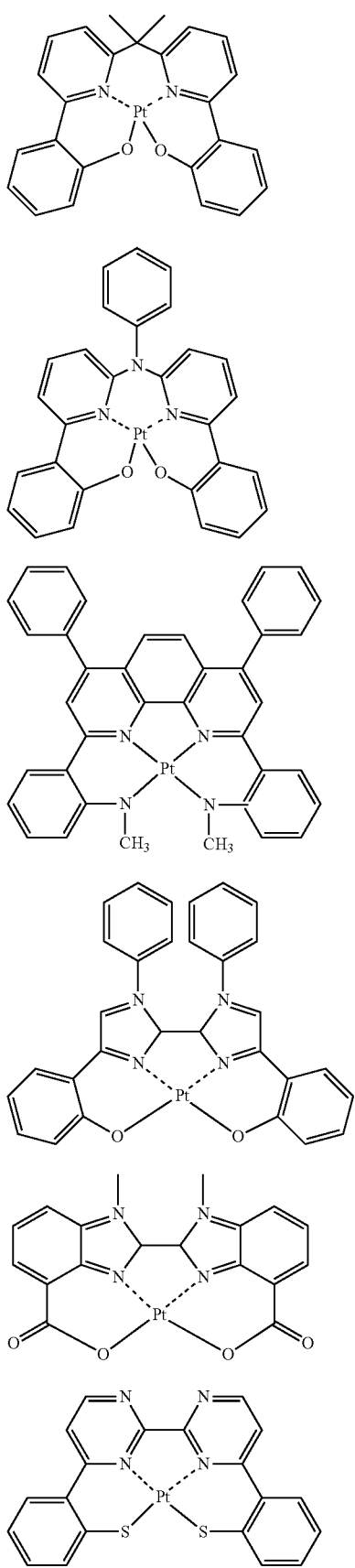
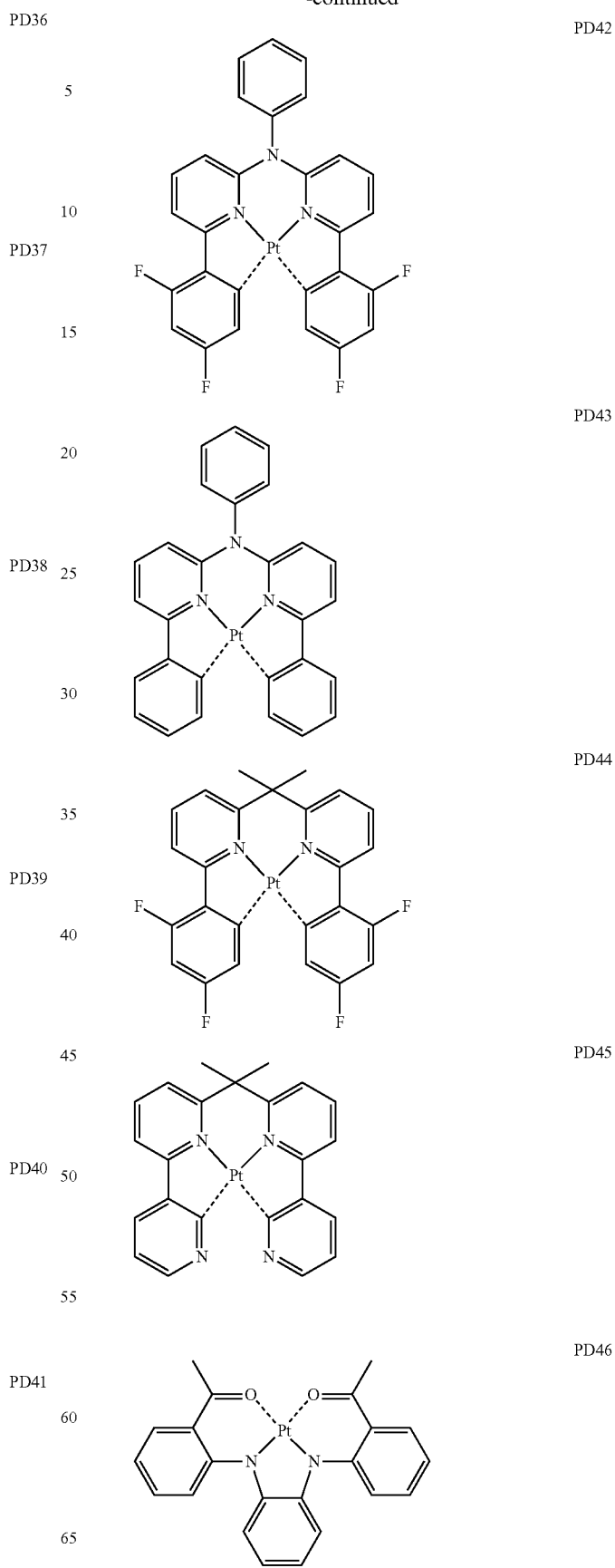

PD47 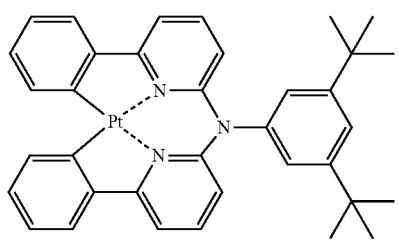
PD48 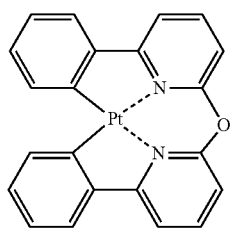
PD49 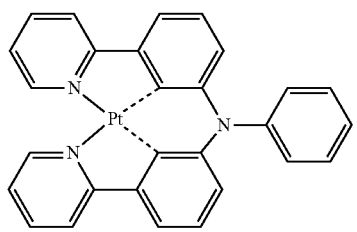
PD50 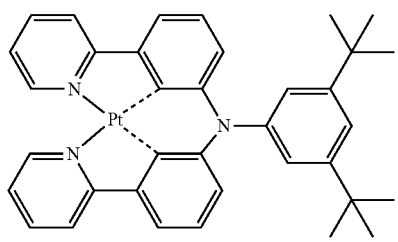
PD51 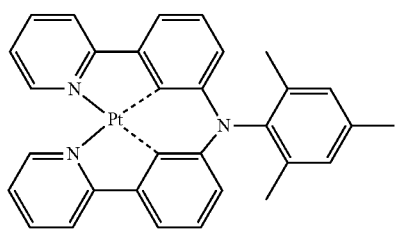
PD52 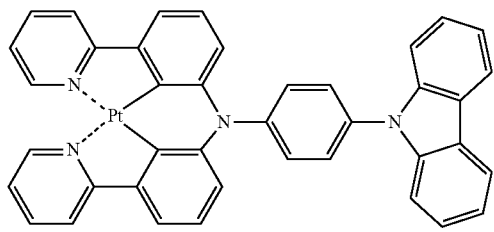
PD53 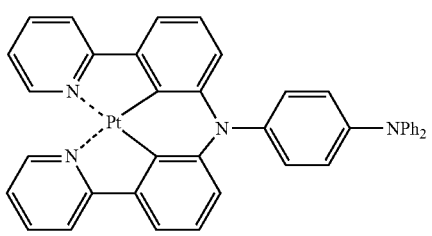
PD54 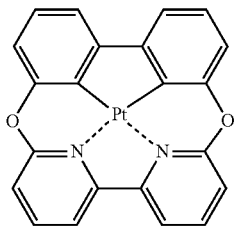
PD55 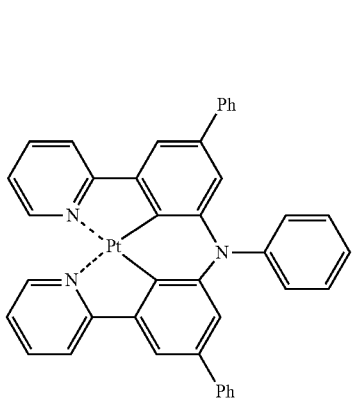
PD56 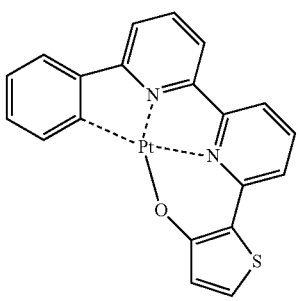
PD57 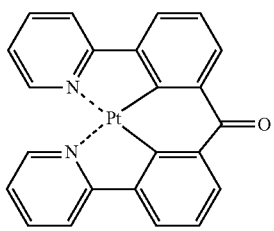

-continued
PD58
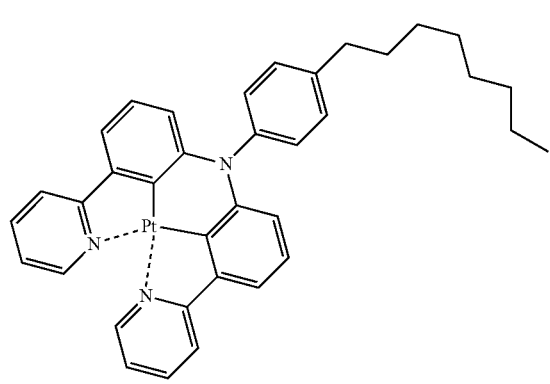
PD59
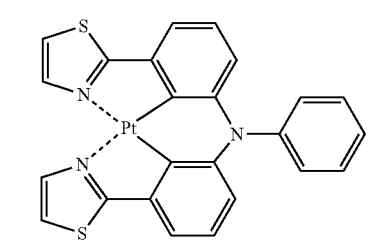
PD60
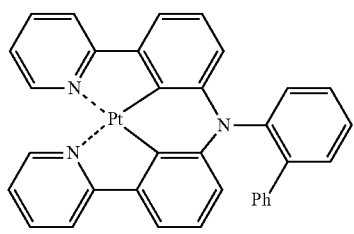
PD61
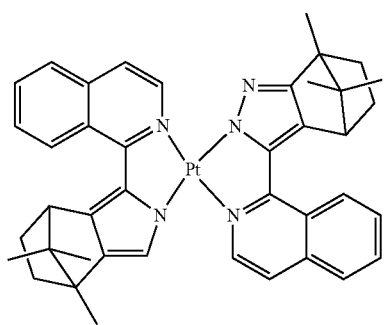
PD62
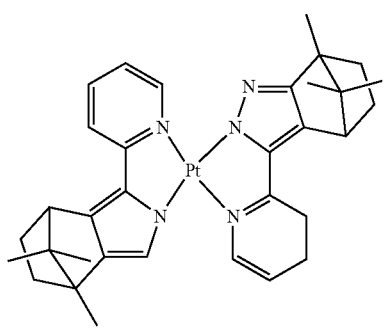
-continued
PD63
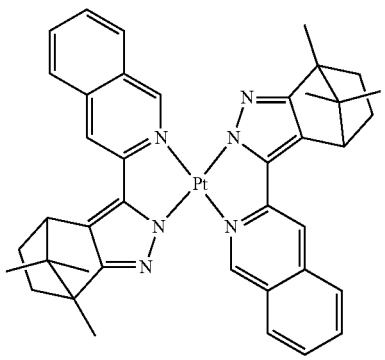
PD64
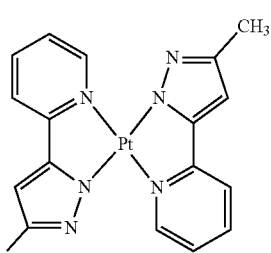
PD65
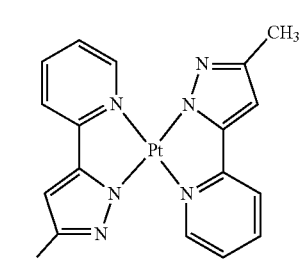
PD66
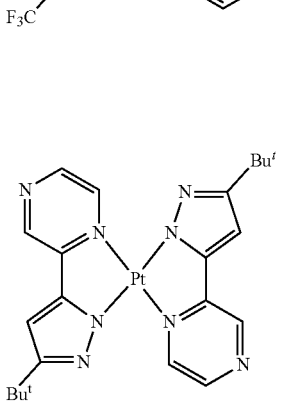
PD67
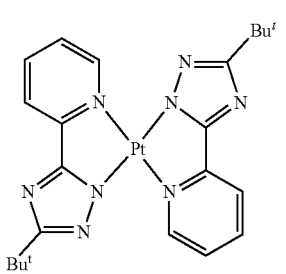

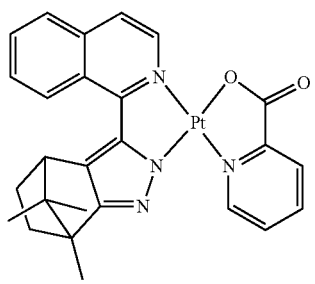
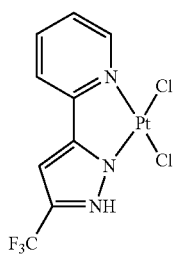
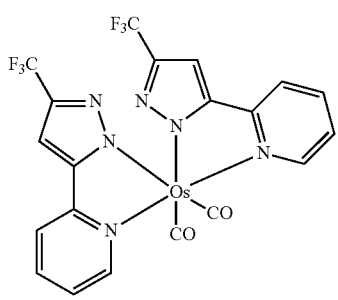
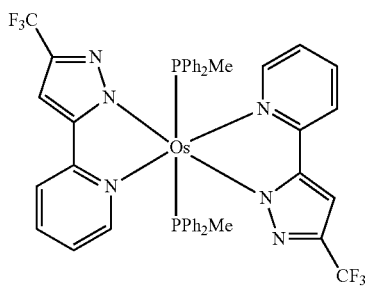
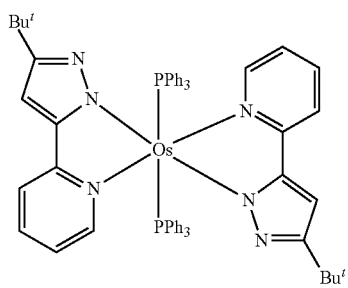
PD68
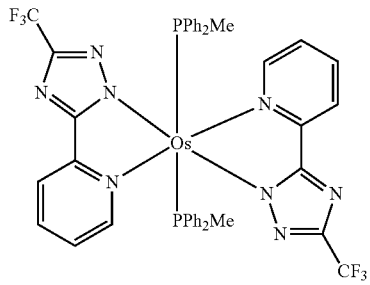
PD69
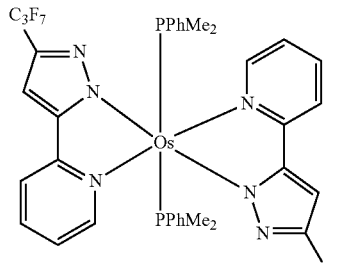
PD70
PD71
PD72
PD73
PD74
PD75
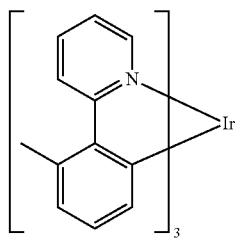
PD76
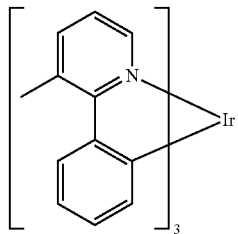
PD77
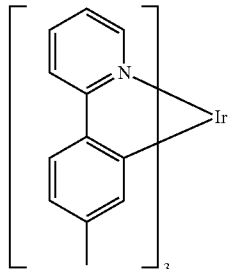
PD78

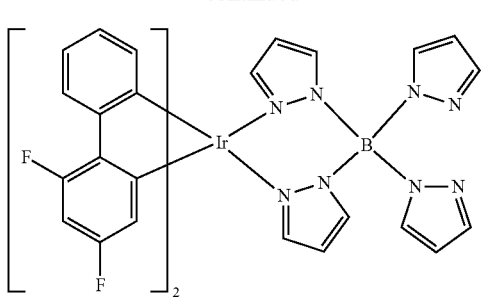

Flr6

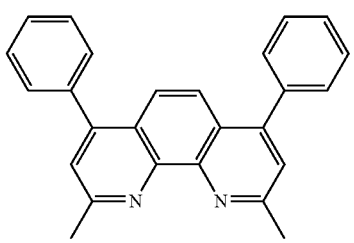

BCP

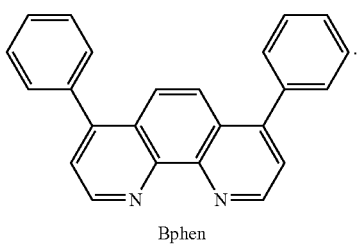

Bphen

In some embodiments, the phosphorescent dopant may include PtOEP:

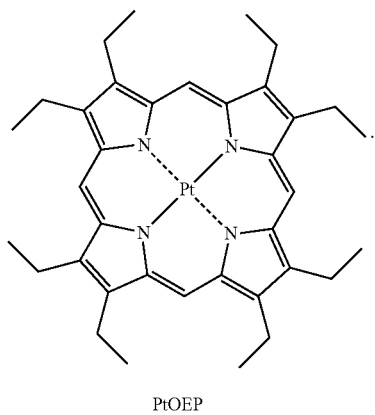

PtOEP

When the emission layer includes the host and the dopant, the amount of the dopant may be selected from a range of about 0.01 part by weight to about 20 parts by weight based on about 100 parts by weight of the host, but embodiments are not limited thereto.

The thickness of the emission layer may be in a range of about 100 Å to about 1,000 Å, for example, about 200 Å to about 600 Å. While not wishing to be bound by theory, it is understood that when the thickness of the emission layer is within these ranges, excellent light-emission characteristics may be achieved without a substantial increase in driving voltage.

Then, an electron transport region may be formed on the emission layer.

The electron transport region may include at least one selected from a hole blocking layer, an electron transport layer, and an electron injection layer, but embodiments not limited thereto.

In some embodiments, the electron transport region may have a structure of a hole blocking layer/an electron transport layer/an electron injection layer or an electron transport layer/an electron injection layer, but embodiments are not limited thereto.

The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer, for example, may include at least one of BCP and Bphen, but embodiments are not limited thereto:

The thickness of the hole blocking layer may be in a range of about 20 Å to about 1,000 Å, for example, about 30 Å to about 300 Å. When the thickness of the hole blocking layer is within these ranges, excellent hole blocking characteristics may be achieved without a substantial increase in driving voltage.

The electron transport layer may further include at least one selected from BCP, Bphen, Alq$_3$, BAlq, TAZ, and NTAZ:

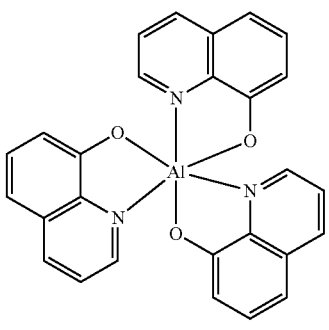

Alq$_3$

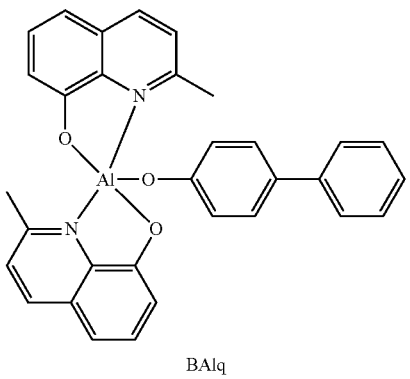

BAlq

133
-continued
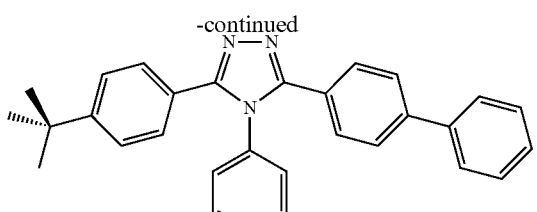
TAZ
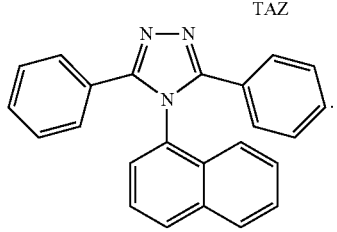
NTAZ
Alternatively, the electron transport layer may include at least one selected from Compounds ET1 to ET19, but embodiments are not limited thereto:
ET1
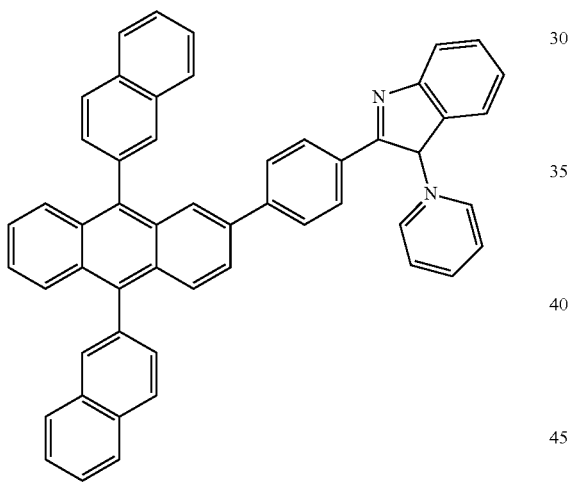
ET2
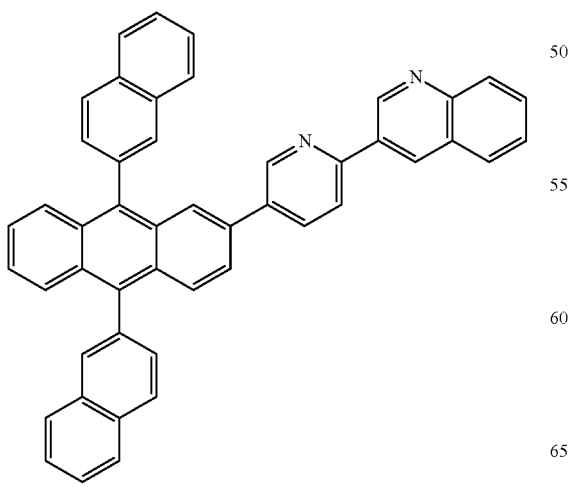
134
-continued
ET3
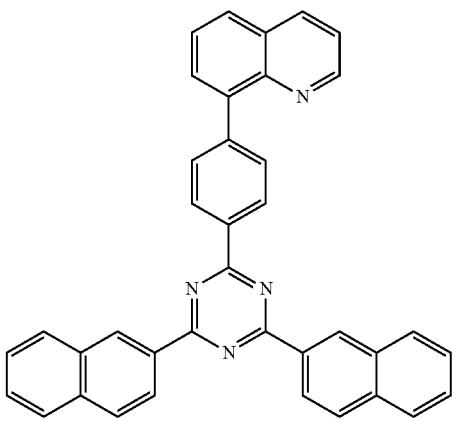
ET4
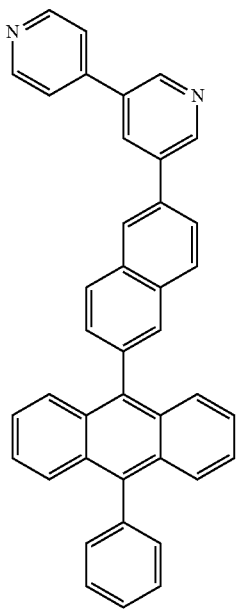
ET5
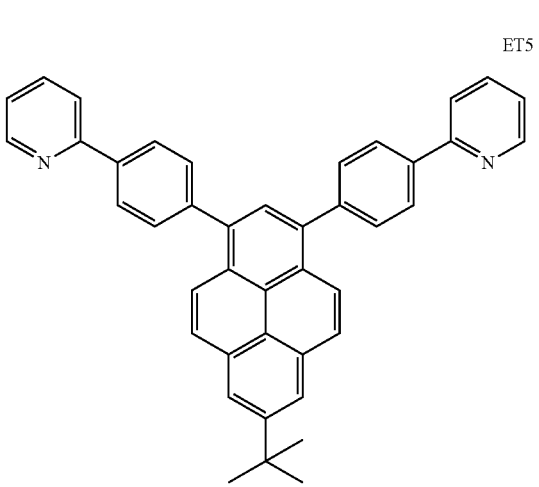

135
-continued
ET6
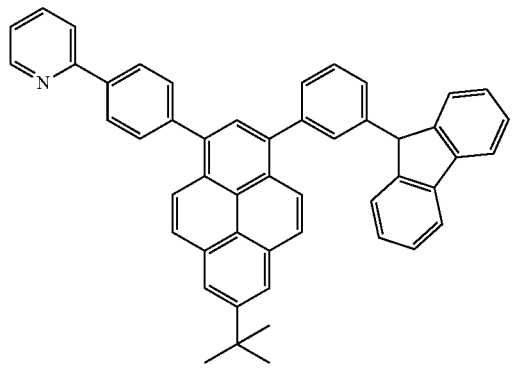
ET7
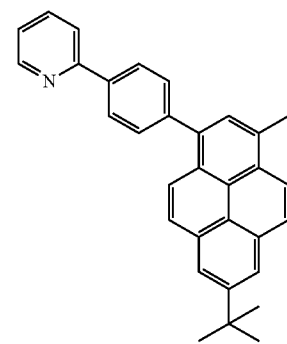
ET8
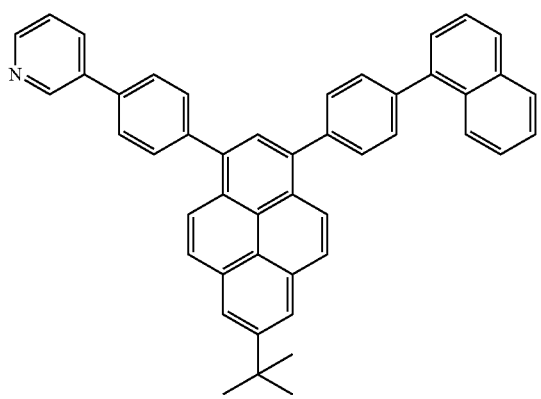
136
-continued
ET9
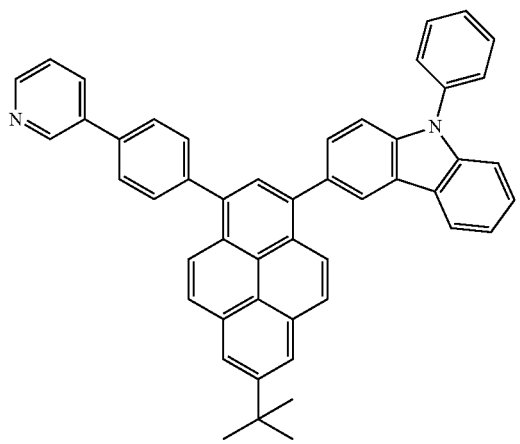
ET10
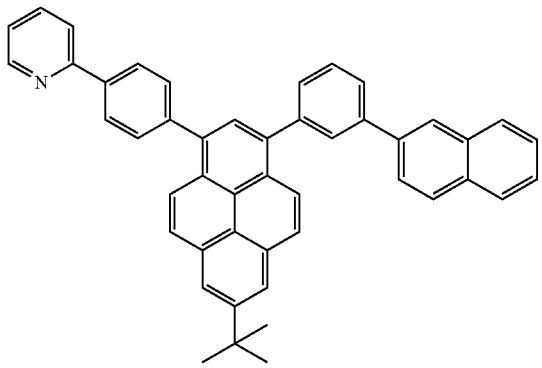
ET11
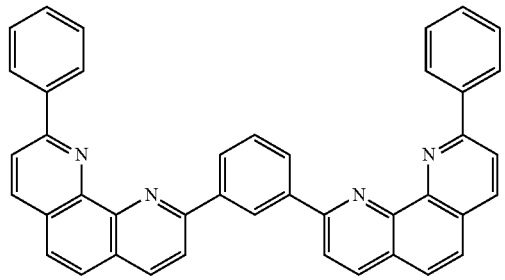
ET12

ET13
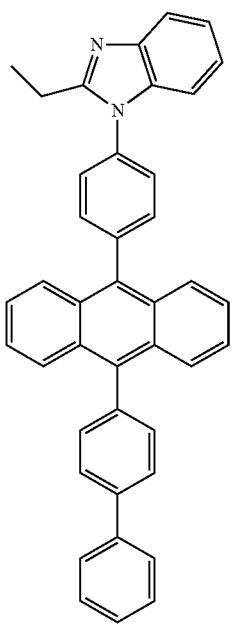
ET14
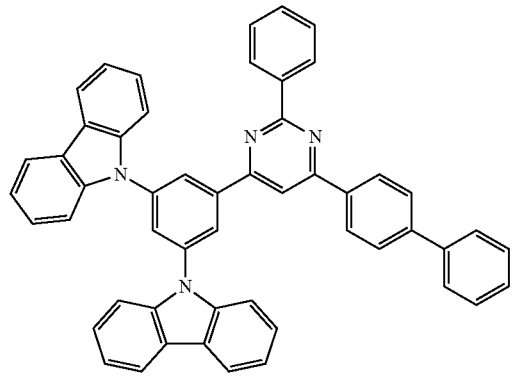
ET15
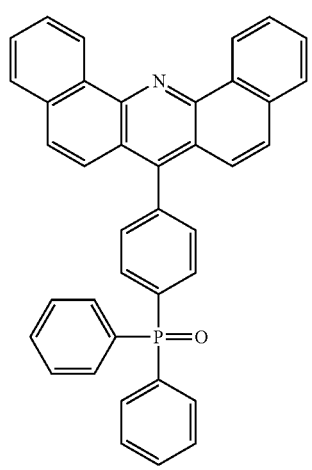
ET16
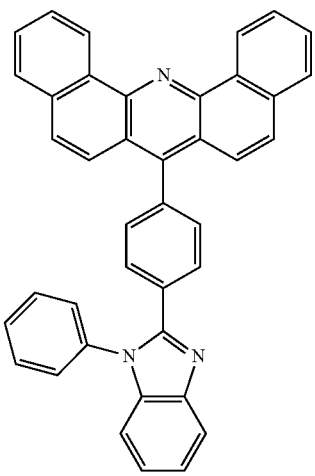
ET17
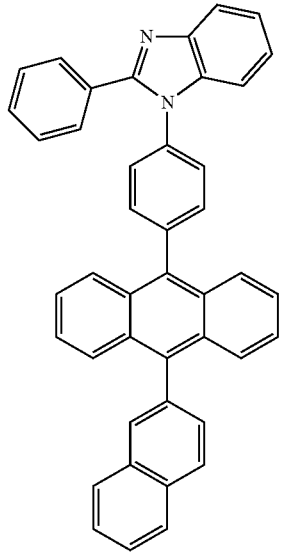
ET18
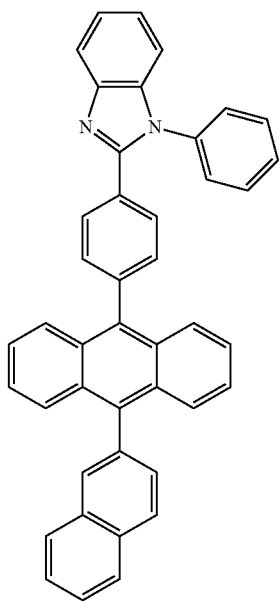

ET19

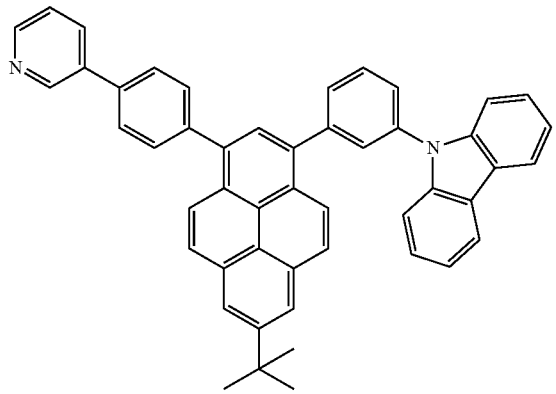

The thickness of the electron transport layer may be in a range of about 100 Å to about 1,000 Å, for example, about 150 Å to about 500 Å. When the thickness of the electron transport layer is within these ranges, excellent electron transport characteristics may be achieved without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2:

ET-D1

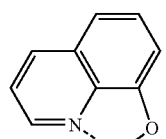

ET-D2

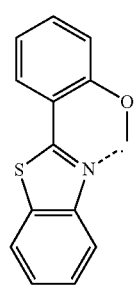

The electron transport region may include an electron injection layer that facilitates electron injection from the second electrode 19.

The electron injection layer may include at least one selected from, LiF, NaCl, CsF, $Li_2O$, and BaO.

The thickness of the electron injection layer may be in a range of about 1 Å to about 100 Å, for example, about 3 Å to about 90 Å. While not wishing to be bound by theory, it is understood that when the thickness of the electron injection layer is within these ranges, excellent electron injection characteristics may be achieved without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device, and such a variation may be possible.

Hereinbefore the organic light-emitting device 10 has been described with reference to FIG. 1, but embodiments are not limited thereto.

A $C_1$-$C_{60}$ alkyl group as used herein refers to a linear or branched saturated aliphatic hydrocarbon monovalent group having 1 to 60 carbon atoms. Detailed examples thereof may include a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (where $A_{101}$ is the $C_1$-$C_{60}$ alkyl group). Detailed examples thereof may include a methoxy group, an ethoxy group, and an isopropyloxy group.

A $C_2$-$C_{60}$ alkenyl group as used herein refers to a group formed by placing at least one carbon double bond in the middle or at the terminal of the $C_2$-$C_{60}$ alkyl group. Detailed examples thereof may include an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a group formed by placing at least one carbon triple bond in the middle or at the terminal of the $C_2$-$C_{60}$ alkyl group. Detailed examples thereof may include an ethenyl group and a propenyl group. A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof may include a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one heteroatom selected from N, O, P, and S as a ring-forming atom and 1 to 10 carbon atoms. Detailed examples thereof may include a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in its ring, and is not aromatic. Detailed examples thereof may include a cyclopentenyl group, a cyclohexenyl group, and a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one heteroatom selected from N, O, P, and S as a ring-forming atom, 1 to 10 carbon atoms, and at least one double bond in its ring.

Detailed examples of the $C_1$-$C_{10}$ heterocycloalkenyl group may include a 2,3-dihydrofuranyl group and a 2,3-dihydrothiophenyl group. A $C_1$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms. A $C_6$-$C_{60}$ arylene group as used herein refers to a divalent group having a carbocyclic aromatic system having 6 to 60 carbon atoms. Detailed examples of the $C_6$-$C_{60}$ aryl group may include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the plurality of rings may be fused to each other.

A $C_1$-$C_{60}$ heteroaryl group as used herein refers to a monovalent group having a carbocyclic aromatic system having at least one heteroatom selected from N, O, P, and S as a ring-forming atom and 1 to 60 carbon atoms. A $C_1$-$C_{60}$ heteroarylene group as used herein refers to a divalent group having a carbocyclic aromatic system having at least one heteroatom selected from N, O, P, and S as a ring-forming atom and 1 to 60 carbon atoms. Detailed examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

A $C_6$-$C_{60}$ aryloxy group as used herein is represented by —$OA_{102}$ (where $A_{102}$ is the $C_6$-$C_{60}$ aryl group). A $C_6$-$C_{60}$ arylthio group as used herein is represented by —$SA_{103}$ (where $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as ring forming atoms, wherein the molecular structure as a whole is non-aromatic. A detailed example of the non-aromatic condensed polycyclic group may include a fluorenyl group. A divalent non-aromatic condensed polycyclic group as used herein refers to a divalent group having the same structure as the monovalent non-aromatic condensed polycyclic group.

A monovalent non-aromatic condensed hetero-polycyclic group as used herein refers to a monovalent group that has a plurality of rings condensed with each other, has a heteroatom selected from N, O, P, and S, other than carbon atoms (for example, the number of carbon atoms may be in a range of 1 to 60), as ring-forming atoms, wherein the molecular structure as a whole is non-aromatic. The monovalent non-aromatic condensed heteropolycyclic group includes a carbazolyl group. A divalent non-aromatic condensed hetero-polycyclic group as used herein refers to a divalent group having the same structure as the monovalent non-aromatic condensed hetero-polycyclic group.

In the present specification, at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ may be each independently selected from a hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

A biphenyl group as used herein refers to a phenyl group substituted with at least one phenyl group.

Hereinafter the organic light-emitting device according to an embodiment will be described in detail with reference to Synthesis Examples and Examples; however, the inventive concept is not limited thereto. The wording "B was used instead of A" used in describing Synthesis Examples means that an amount of B used was identical to an amount of A used based on molar equivalence.

EXAMPLE

Synthesis Example 1

Synthesis of Compound 1

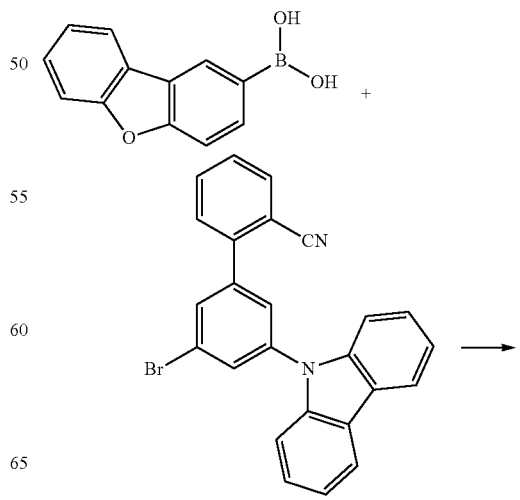

-continued

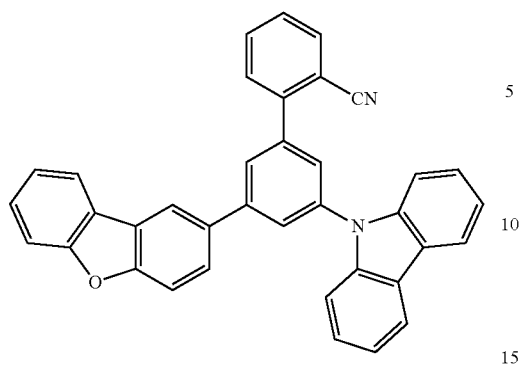

Compound 1

In a round bottom flask, 8.969 grams (g) (42.30 millimoles (mmol)) of dibenzo[b,d]furan-2-ylboronic acid, 14.923 g (35.25 mmol) of 3'-bromo-5'-(9H-carbazol-9-yl)-[1,1'-biphenyl]-2-carbonitrile, 2.037 g (1.76 mmol) of tetrakis(triphenylphosphine)palladium [Pd(PPh$_3$)$_4$], and 9.745 g (70.51 mmol) of potassium carbonate were added to 50 milliliters (mL) of tetrahydrofuran (THF) and 25 mL of distilled water, and the reaction mixture was heated under reflux for about 12 hours. Once the reaction was complete, the mixture was cooled to room temperature, and the THF and distilled water layers were separated. The separated THF layer was added dropwise to 100 mL of methanol for crystallization. The obtained solid therefrom was separated by filtering, and was subsequently washed with water and methanol.

The resulting solid was dried in a vacuum oven to obtain 13 g of Compound 1 (yield: 72%).

MS (m/z, [M]$^+$): 510.58

Synthesis Example 2

Synthesis of Compound 55

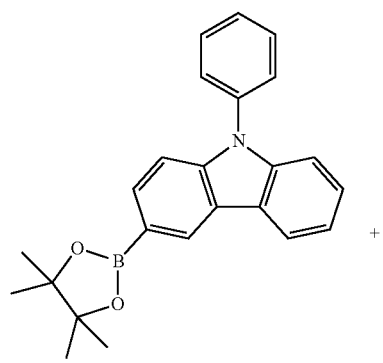

+

-continued

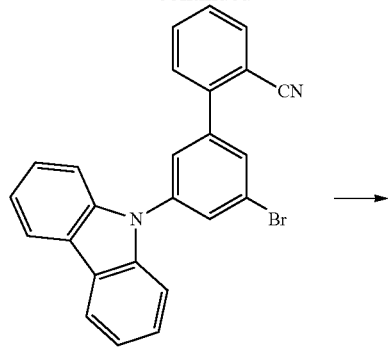

→

Compound 55

In a round bottom flask, 15.7 g (42.52 mmol) of 9-phenyl-3-(4,4,5,5-tetramethyl-1,3,2-dioxaborolan-2-yl)-9H-carbazole, 15 g (35.44 mmol) of 3'-bromo-5'-(9H-carbazol-9-yl)-[1, 1'-biphenyl]-2-carbonitrile, 1.228 g (1.06 mmol) of tetrakis(triphenylphosphine)palladium [Pd(PPh$_3$)$_4$], and 9.795 g (70.87 mmol) of potassium carbonate were added to 50 mL of THF and 25 mL of distilled water, and the reaction mixture was heated under reflux for about 12 hours. Once the reaction was complete, the mixture was cooled to room temperature, and the THF and distilled water layers were separated. The separated THF layer was added dropwise to 100 mL of methanol for crystallization. The obtained solid therefrom was separated by filtering, and was subsequently washed with water and methanol. The result solid was dried in a vacuum oven to obtain 12.45 g of Compound 55 (yield: 60%).

MS(m/z, [M]$^+$): 585.69

Evaluation Example 1

Evaluation on HOMO, LUMO, and Triplets (T1) Energy Levels

HOMO, LUMO, and T1 energy levels of Compounds 1, 55, B, and C were evaluated using the method of Table 2. The results thereof are shown in Table 2.

TABLE 2

| | |
|---|---|
| HOMO energy level evaluation method | A potential (Volts, V) versus current (Amperes, A) graph of each compound was obtained by using cyclic voltammetry (CV) (electrolyte: 0.1 molar (M) $Bu_4NClO_4$/solvent: $CH_2Cl_2$/electrode: 3-electrode system (working electrode: GC, reference electrode: Ag/AgCl, auxiliary electrode: Pt)). Subsequently, from reduction onset of the graph, a HOMO energy level of the compound was calculated. |
| LUMO energy level evaluation method | Each compound was diluted at a concentration of $1 \times 10^{-5}$ M in $CHCl_3$, and an UV absorption spectrum thereof was measured at room temperature by using a Shimadzu UV-350 spectrometer. A LUMO energy level thereof was calculated by using an optical band gap (Eg) from an edge of the absorption spectrum. |
| T1 energy level evaluation method | A mixture (each compound was dissolved in an amount of 1 milligram (mg) in 3 cubic centimeters (cc) of toluene) of toluene and each compound was loaded into a quartz cell. Subsequently, the resultant quartz cell was loaded into liquid nitrogen (77 Kelvins (K)), a photoluminescence spectrum thereof was measured by using a device for measuring photoluminescence. The obtained spectrum was compared with a photoluminescence spectrum measured at room temperature, and peaks observed only at a low temperature were analyzed to calculate T1 energy levels. |

B

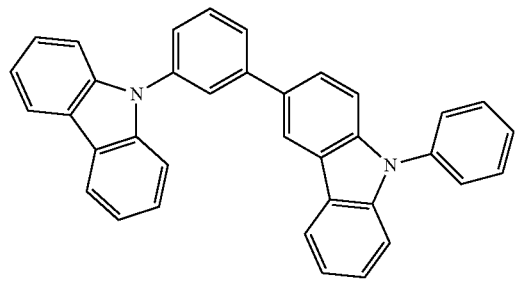

C

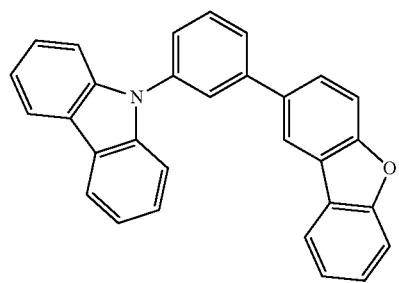

TABLE 3

| Compound No. | HOMO (eV) | LUMO (eV) | $T_1$ (eV) |
|---|---|---|---|
| Compound 1 | −5.68 | −2.11 | 3.04 |
| Compound 55 | −5.34 | −1.84 | 3.05 |
| Compound B | −5.91 | −2.46 | 2.74 |
| Compound C | −5.91 | −2.34 | 2.77 |

From Table 3, it was found that Compounds 1 and 55 had electric characteristics that are suitable as a material for forming an organic light-emitting device.

Evaluation Example 2

Thermal Characteristics Evaluation

Thermal analysis ($N_2$ atmosphere, temperature range: from room temperature to 800° (10° C./min)-TGA, from room temperature to 400° C.-DSC, Pan Type: Pt Pan in disposable Al Pan (TGA) and disposable Al pan (DSC)) was performed on Compounds 1, 55, B, and C by using thermo gravimetric analysis (TGA) and differential scanning calorimetry (DSC). The evaluation results are shown in Table 4. Referring to Table 4, it was found that Compounds 1 and 55 had excellent thermal stability.

TABLE 4

| Compound No. | Tg (° C.) |
|---|---|
| Compound 1 | 106 |
| Compound 55 | 129 |
| Compound B | 96 |
| Compound C | 64 |

Example 1

A glass substrate having 1,500 Å of Indium tin oxide (ITO) electrode deposited thereon was washed with distilled water in the presence of ultrasound waves. Once the washing with distilled water was complete, ultrasound wave washing was performed on the substrate by using a solvent, such as isopropyl alcohol, acetone, or methanol.

Subsequently, the substrate was dried, transferred to a plasma washer, washed for 5 minutes using oxygen plasma, and mounted in a vacuum depositor.

Compound HT3 and Compound HT-D2 were co-deposited on the ITO electrode of the glass substrate to form a hole injection layer having a thickness of about 100 Å.

Then, Compound HT3 was vacuum deposited on the hole injection layer to form a hole transport layer having a thickness of about 1,300 Å. mCP was next vacuum deposited on the hole transport layer to form an electron blocking layer having a thickness of about 150 Å, thereby forming a hole transport region.

Subsequently, Compound 1 (host) and FIr6 (dopant, 10 percent by weight (wt %)) were co-deposited on the hole transport region to form an emission layer having a thickness of about 300 Å.

BCP was vacuum deposited on the emission layer to form a hole blocking layer having a thickness of about 100 Å. Compound ET3 and Liq were then co-deposited on the hole blocking layer to form an electron transport layer having a thickness of about 250 Å. Next, Liq was vacuum deposited on the electron transport layer to form an electron injection layer having a thickness of about 5 Å, and then, Al second electrode (a cathode) having a thickness of 1,000 Å was formed on the electron injection layer, thereby completing manufacturing of an organic light-emitting device.

Comparative Example 1

An organic light-emitting device was manufactured in the same manner as in Example 1, except that Compound A was used instead of Compound 1 as a host in the formation of the emission layer.

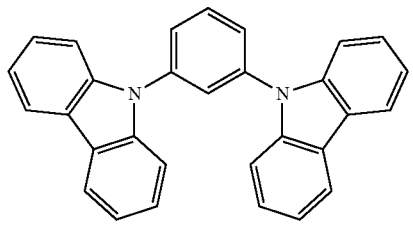

A

Comparative Example 2

An organic light-emitting device was manufactured in the same manner as in Example 1, except that Compound D was used instead of Compound 1 as a host in the formation of the emission layer.

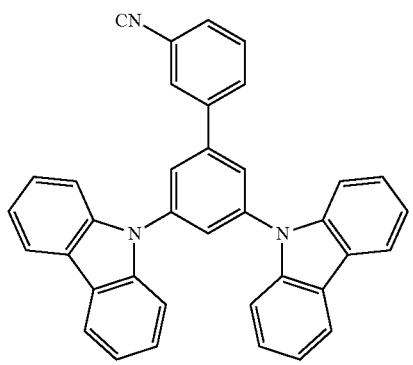

D

Evaluation Example 3

Evaluation of Characteristics of Organic Light-emitting Device

The driving voltage, efficiency, efficiency/y, quantum efficiency, and lifespan of the organic light-emitting devices manufactured in Example 1 and Comparative Examples 1 and 2 were measured by using a current voltmeter (Keithley 2400) and a luminance meter (Minolta Cs-1000A). The evaluation results are shown in Table 5.

Lifespan is a period taken for the luminance (at 500 (candelas per square meter, $cd/m^2$) to reach 80% with respect to 100% of the initial luminance. In addition, a graph of efficiency/y (arbitrary units, a. u.) versus luminance ($cd/m^2$), a graph of luminance ($cd/m^2$) versus time (hours), and a graph of external quantum efficiency (percent) versus luminance ($cd/m^2$) of the organic light-emitting devices manufactured in Example 1 and Comparative Examples 1 and 2 are each shown in FIGS. 2 to 4, respectively.

TABLE 5

|  | Host | Driving voltage (V) | Efficiency (Cd/A) | Efficiency/y | Quantum efficiency (%) | Lifespan (Hours) |
| --- | --- | --- | --- | --- | --- | --- |
| Example 1 | Compound 1 | 5.03 | 37.99 | 141.2 | 20.0 | 44.67 |
| Comparative Example 1 | Compound A | 5.85 | 29.30 | 1 | 16.3 | 0.67 |
| Comparative Example 2 | Compound D | 5.05 | 32.83 | 130.1 | 18.1 | 21.71 |

Figure 2:
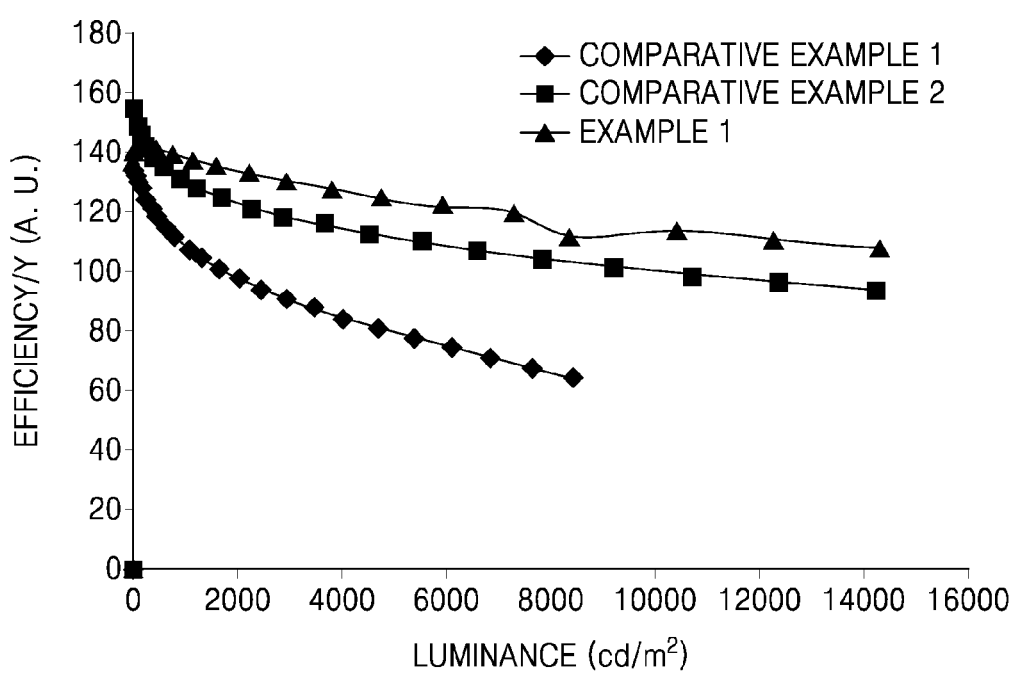
FIG. 2 is a graph of efficiency/y (arbitrary units, a. u.) versus luminance (candelas per square meter, cd/m²) of organic light-emitting devices manufactured in Example 1 and Comparative Examples 1 and 2.
Figure 3:
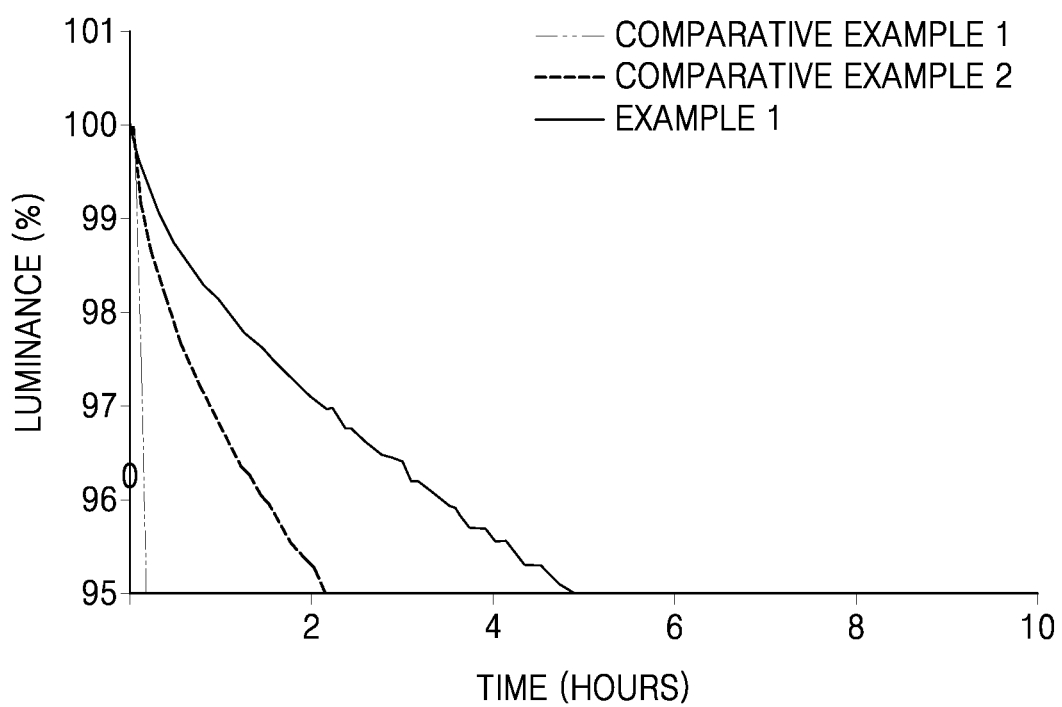
FIG. 3 is a graph of luminance (cd/m²) versus time (hours) of organic light-emitting devices manufactured in Example 1 and Comparative Examples 1 and 2.
Figure 4:
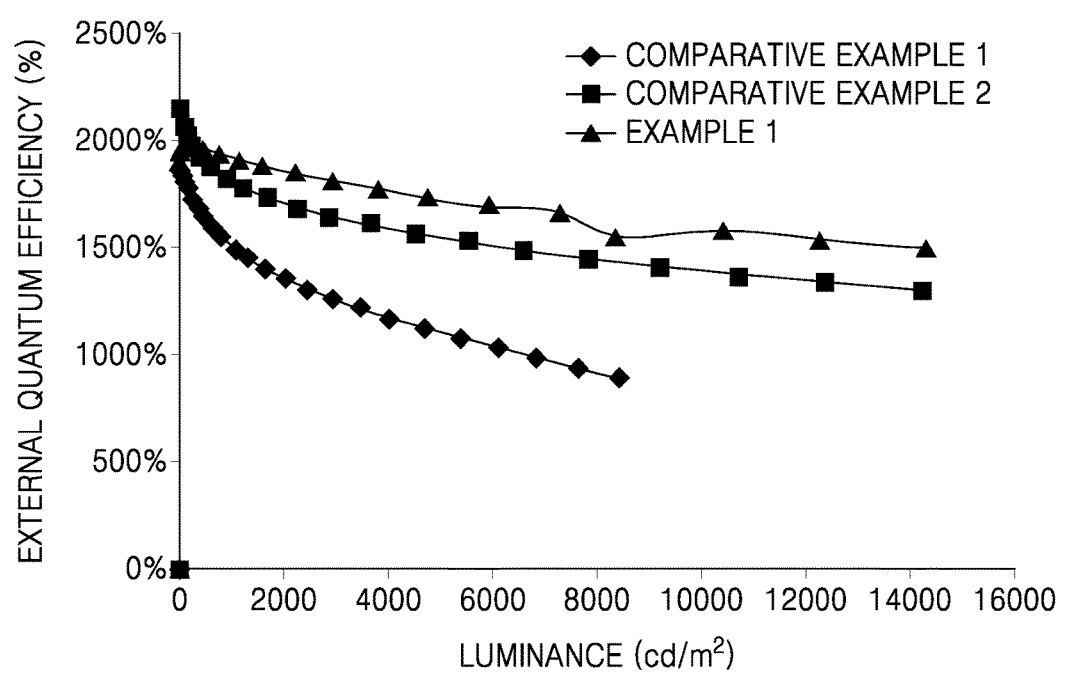
FIG. 4 is a graph of external quantum efficiency (percent) versus luminance (cd/m²) of organic light-emitting devices manufactured in Example 1 and Comparative Examples 1 and 2.

Referring to Table 5 and FIGS. 2 to 4, it was found that the organic light-emitting device manufactured in Example 1 had low driving voltage and improved luminous efficiency and lifespan compared to the organic light-emitting devices manufactured in Comparative Examples 1 and 2.

As described above, according to one or more exemplary embodiment, the condensed-cyclic compound may have excellent electric characteristics and thermal stability. Accordingly, an organic light-emitting device including the condensed-cyclic compound may have a low driving voltage, high efficiency, high power, high quantum yield, and long lifespan.

It should be understood that exemplary embodiments described herein should be considered in a descriptive sense only and not for purposes of limitation.

Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present disclosure as defined by the following claims.

What is claimed is:

1. A condensed-cyclic compound represented by Formula 1:

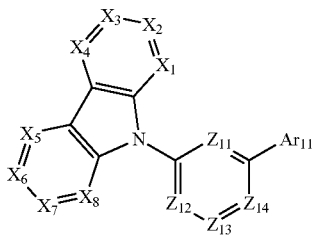

Formula 1 wherein, in Formula 1, $Ar_{11}$ is represented by one of Formulae 10-1 to 10-4:

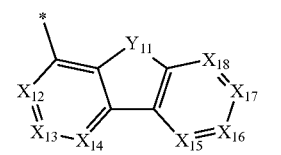

10-1

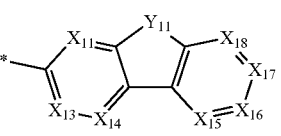

10-2

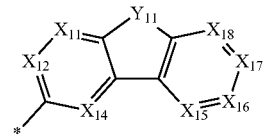

10-3

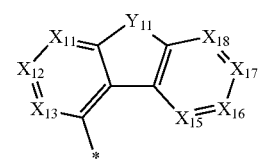

10-4 wherein, in Formulae 1 and 10-1 to 10-4, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, and $X_{18}$ is N or $C(R_{18})$;

$Y_{11}$ is O, S, $N(R_{101})$, $C(R_{101})(R_{102})$, or $Si(R_{101})(R_{102})$;

$Z_{11}$ is selected from N and $C(A_{12})$;

$Z_{12}$ to $Z_{14}$ are each independently selected from $C(A_{11})$ and $C(A_{12})$; and at least one of $Z_{12}$ to $Z_{14}$ is $C(A_{11})$; and $A_{11}$ comprises at least one cyano group (CN); and $A_{11}$ is represented by one of Formulae 2-1 to 2-10:

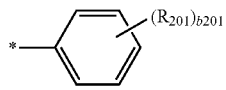

2-1

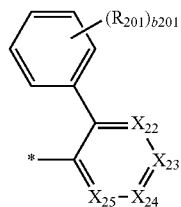

2-2

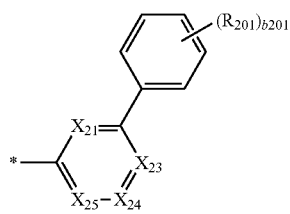

2-3

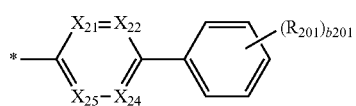

2-4

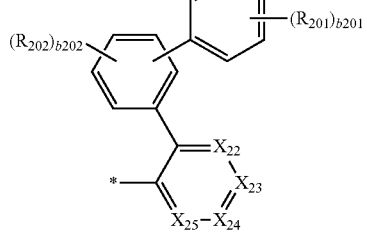

2-5

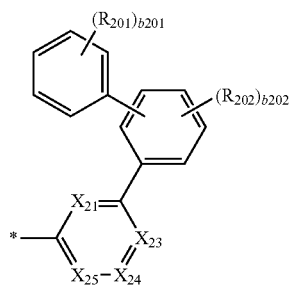

2-6

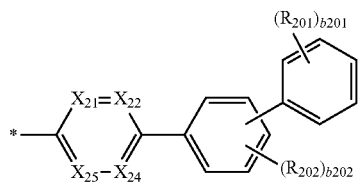

2-7

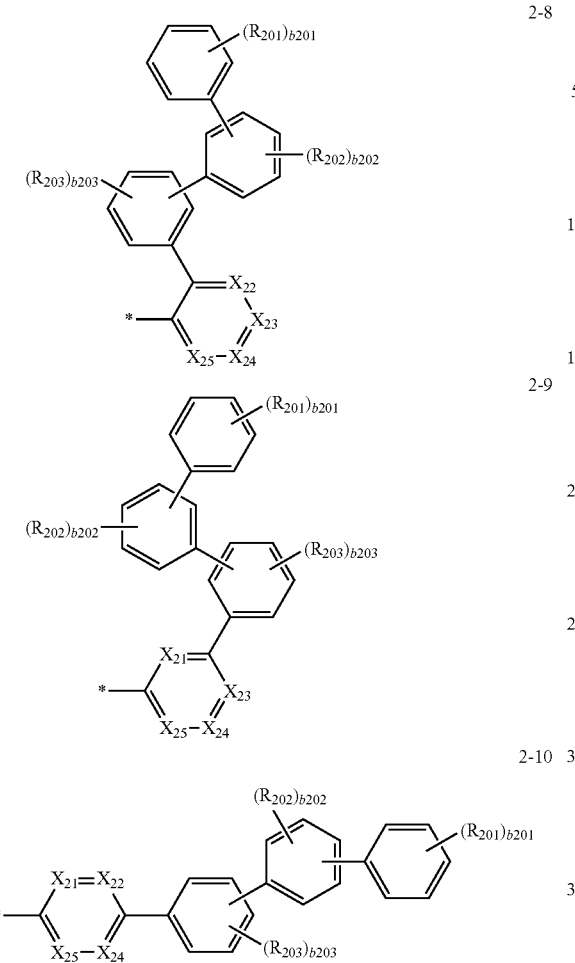

wherein, in Formulae 2-1 to 2-10, $X_{21}$ is N or $C(R_{21})$, $X_{22}$ is N or $C(R_{22})$, $X_{23}$ is N or $C(R_{23})$, $X_{24}$ is N or $C(R_{24})$, and $X_{25}$ is N or $C(R_{25})$;

$A_{12}$, $R_1$ to $R_8$, $R_{11}$ to $R_{18}$, $R_{101}$, $R_{102}$, $R_{21}$ to $R_{25}$, and $R_{201}$ to $R_{203}$ are each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$); and —Si($Q_{11}$)($Q_{12}$)($Q_{13}$), b201 is selected from 1, 2, 3, 4, and 5;

b202 and b203 are each independently selected from 1, 2, 3, and 4; and

* indicates a carbon atom in Formula 1, wherein $Q_1$ to $Q_3$ and $Q_{11}$ to $Q_{13}$ are each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

2. The condensed-cyclic compound of claim 1, wherein $X_1$ is N, $X_2$ is $C(R_2)$, $X_3$ is $C(R_3)$, $X_4$ is $C(R_4)$, $X_5$ is $C(R_5)$, $X_6$ is $C(R_6)$, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$;

$X_1$ is $C(R_1)$, $X_2$ is N, $X_3$ is $C(R_3)$, $X_4$ is $C(R_4)$, $X_5$ is $C(R_5)$, $X_6$ is $C(R_6)$, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$;

$X_1$ is $C(R_1)$, $X_2$ is $C(R_2)$, $X_3$ is N, $X_4$ is $C(R_4)$, $X_5$ is $C(R_5)$, $X_6$ is $C(R_6)$, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$;

$X_1$ is $C(R_1)$, $X_2$ is $C(R_2)$, $X_3$ is $C(R_3)$, $X_4$ is N, $X_5$ is $C(R_5)$, $X_6$ is $C(R_6)$, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ $C(R_{16})$, $X_{17}$ is $C(R_{17})$, and $X_{18}$ is $C(R_{18})$ $X_1$ is $C(R_1)$, $X_2$ is $C(R_2)$, $X_3$ is $C(R_3)$, $X_4$ is $C(R_4)$, $X_5$ is N, $X_6$ is $C(R_6)$, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$;

$X_1$ is $C(R_1)$, $X_2$ is $C(R_2)$, $X_3$ is $C(R_3)$, $X_4$ is $C(R_4)$, $X_5$ is $C(R_5)$, $X_6$ is N, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$;

$X_1$ is $C(R_1)$, $X_2$ is $C(R_2)$, $X_3$ is $C(R_3)$, $X_4$ is $C(R_4)$, $X_5$ is $C(R_5)$, $X_6$ is $C(R_6)$, $X_7$ is N, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$;

$X_1$ is $C(R_1)$, $X_2$ is $C(R_2)$, $X_3$ is $C(R_3)$, $X_4$ is $C(R_4)$, $X_5$ is $C(R_5)$, $X_6$ is $C(R_6)$, $X_7$ is $C(R_7)$, $X_8$ is N, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$; or $X_1$ is $C(R_1)$, $X_2$ is $C(R_2)$, $X_3$ is $C(R_3)$, $X_4$ is $C(R_4)$, $X_5$ is $C(R_5)$, $X_6$ is $C(R_6)$, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, $X_{14}$ is $C(R_{14})$, $X_{15}$ is $C(R_{15})$, $X_{16}$ is $C(R_{16})$, $X_{17}$ is $C(R_{17})$, and $X_{18}$ is $C(R_{18})$.

3. The condensed-cyclic compound of claim 1, wherein $Y_{11}$ is O, S, or $N(R_{101})$.

4. The condensed-cyclic compound of claim 1, wherein $Z_{11}$ is N, $Z_{12}$ is $C(A_{11})$, $Z_{13}$ is $C(A_{11})$, and $Z_{14}$ is $C(A_{12})$; or $Z_{11}$ is $C(A_{12})$, $Z_{12}$ is $C(A_{12})$, $Z_{13}$ is $C(A_{11})$, and $Z_{14}$ is $C(A_{12})$.

5. The condensed-cyclic compound of claim 1, wherein $A_{11}$ is represented by one of Formulae 2-1 to 2-7.

6. The condensed-cyclic compound of claim 1, wherein $A_{11}$ is represented by one of Formulae 3-1 to 3-110:

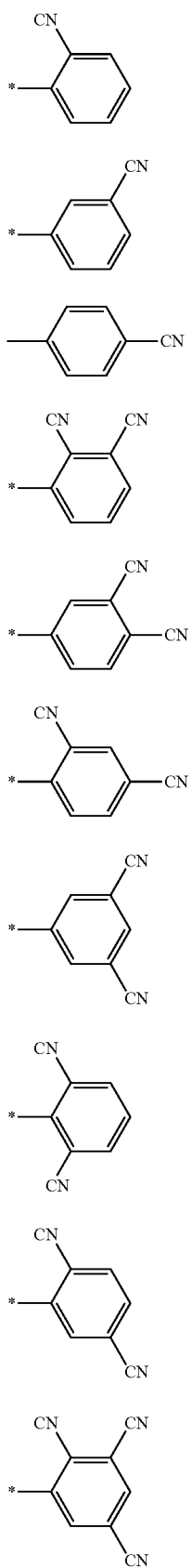
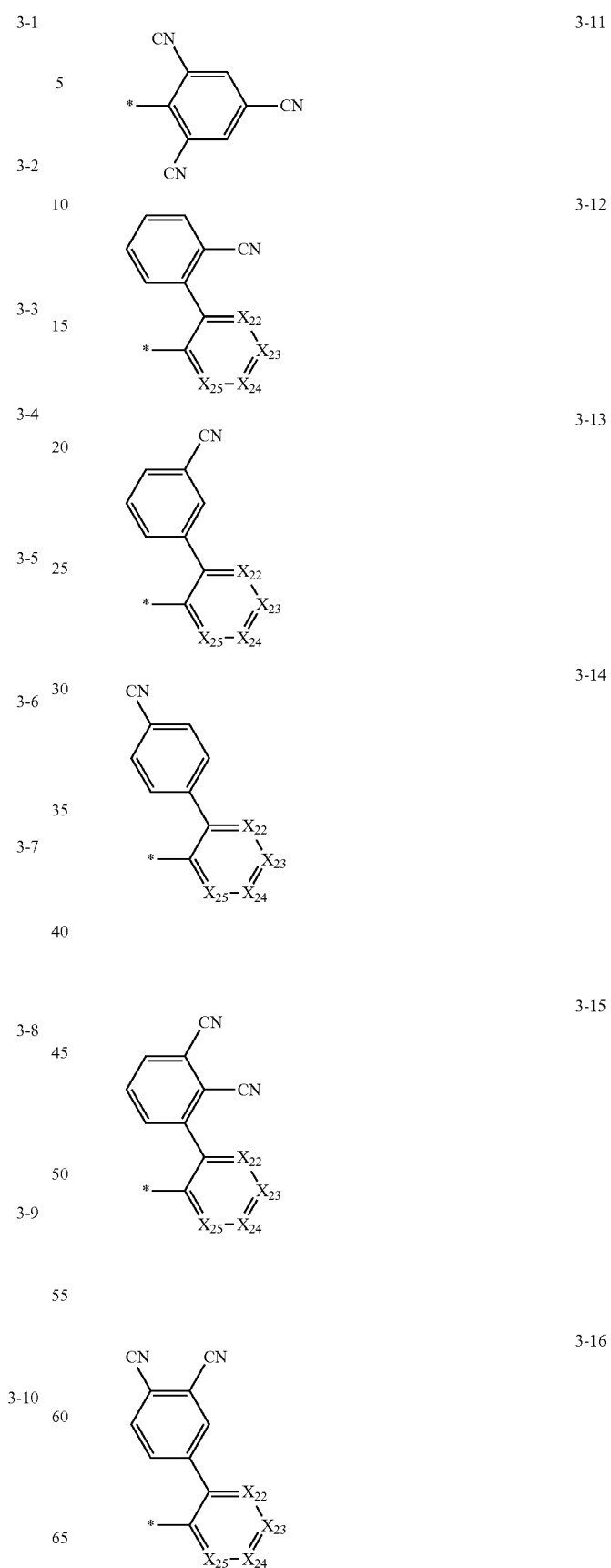

3-17
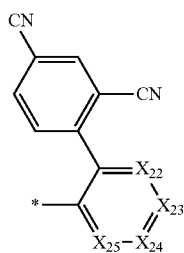
3-18
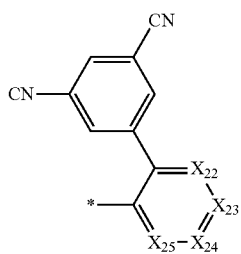
3-19
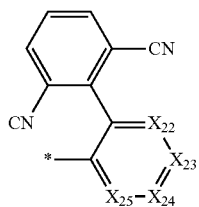
3-20
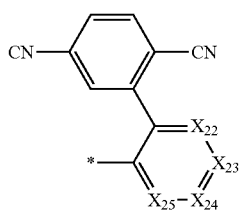
3-21
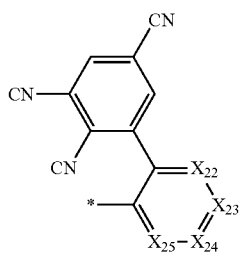
3-22
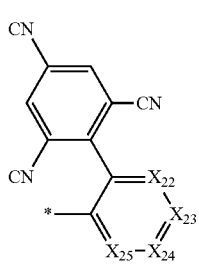
3-23
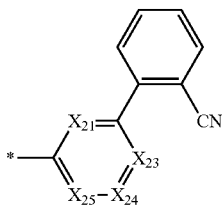
3-24
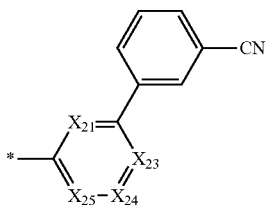
3-25
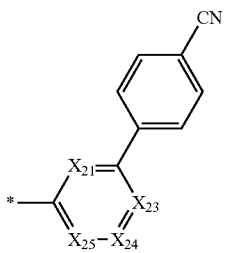
3-26
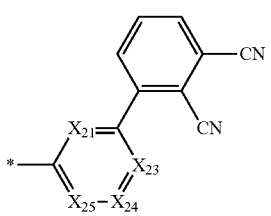
3-27
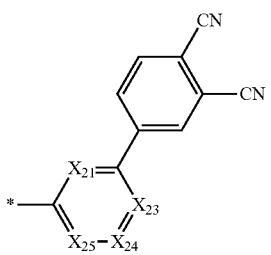
3-28
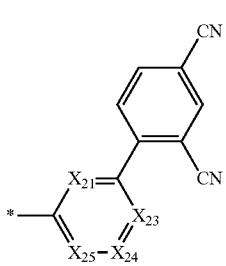

3-29 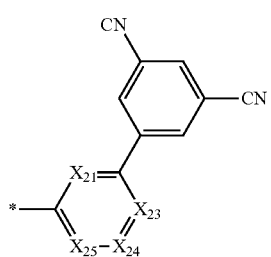
3-30 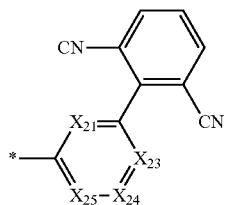
3-31 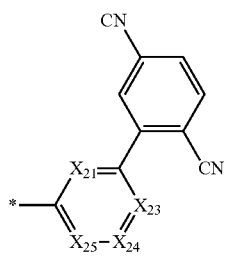
3-32 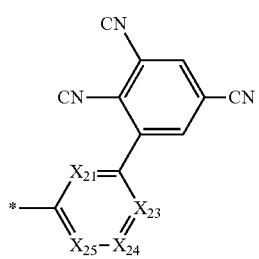
3-33 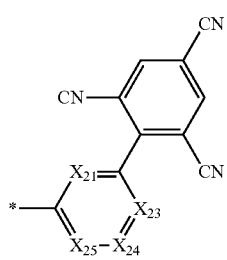
3-34 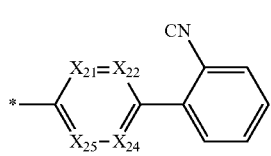
3-35 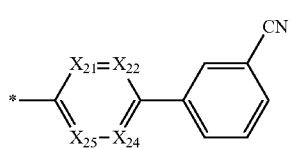
3-36 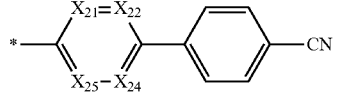
3-37 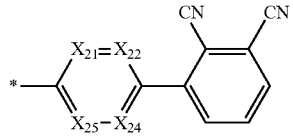
3-38 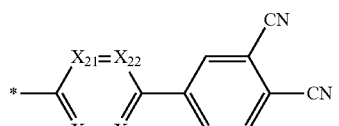
3-39 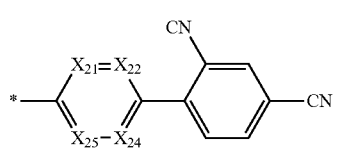
3-40 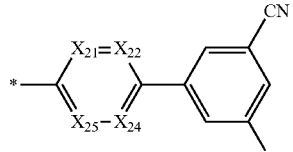
3-41 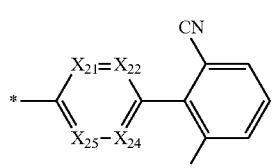
3-42 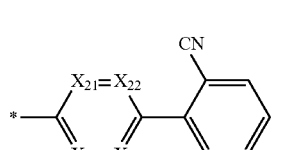
3-43 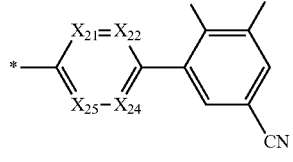
3-44 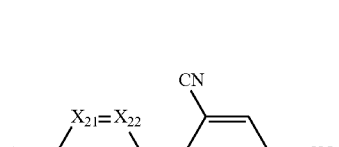

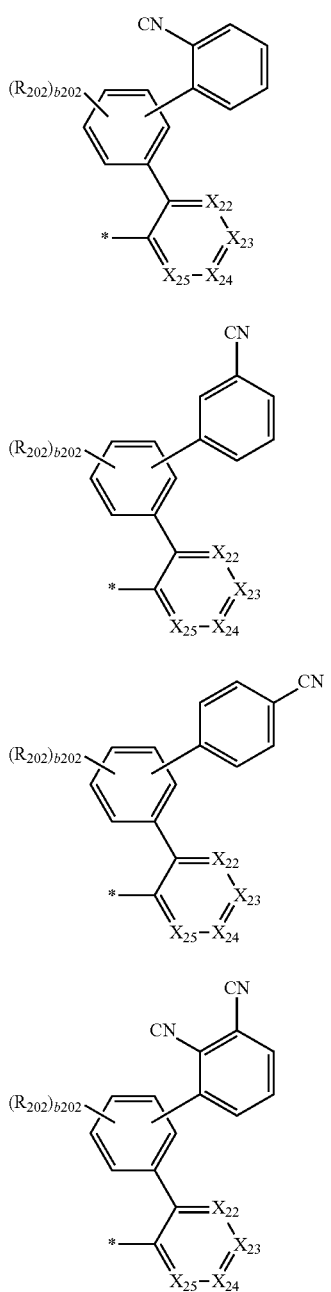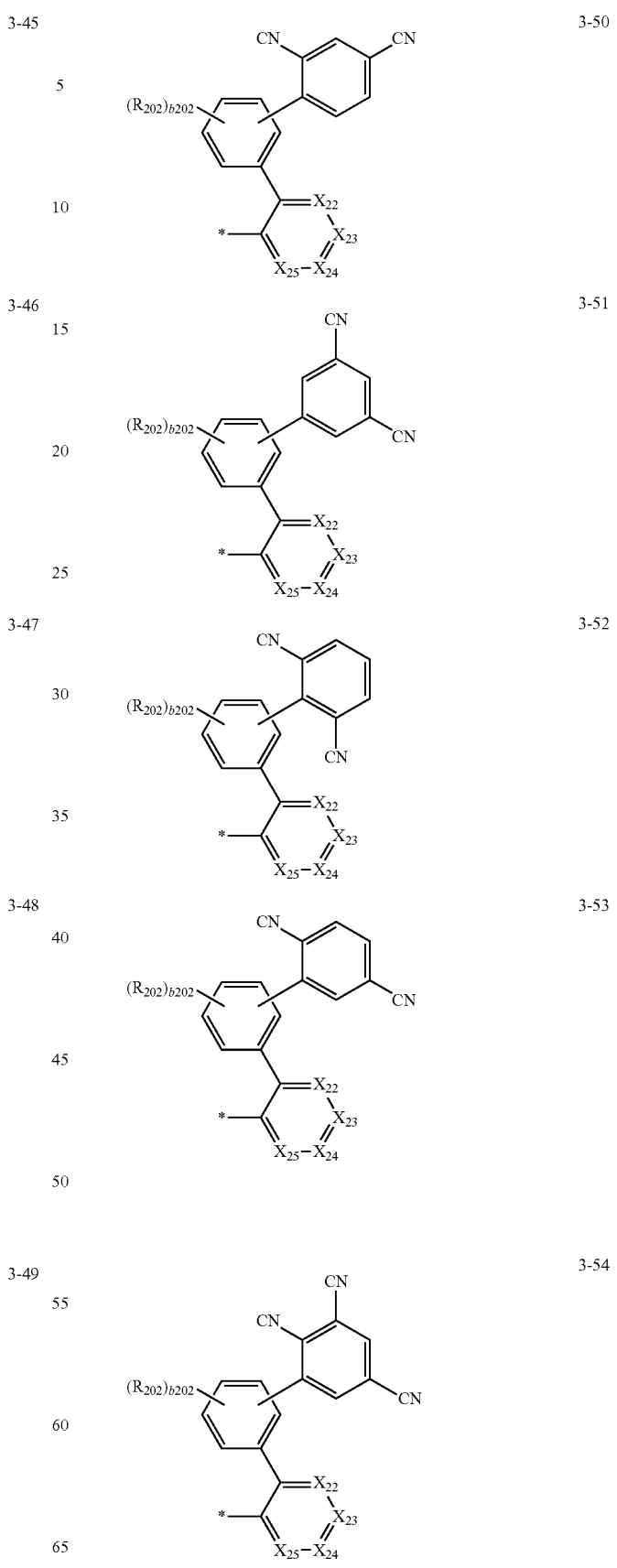

3-55
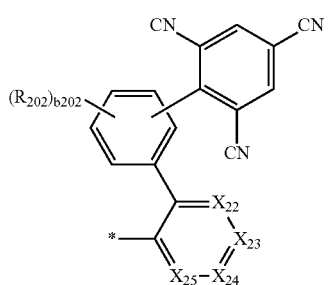
3-56
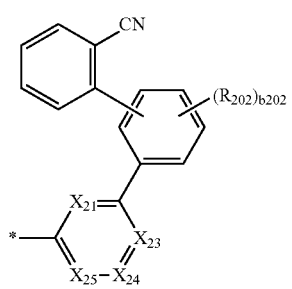
3-57
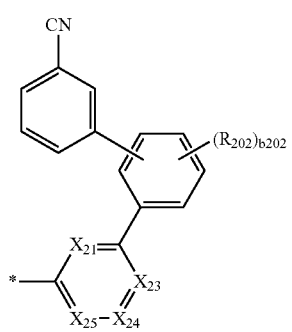
3-58
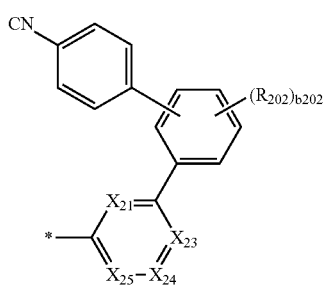
3-59
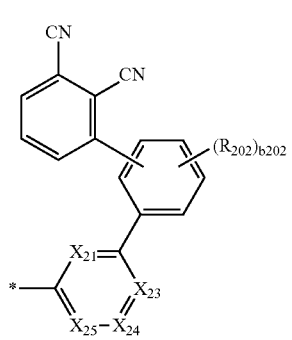
3-60
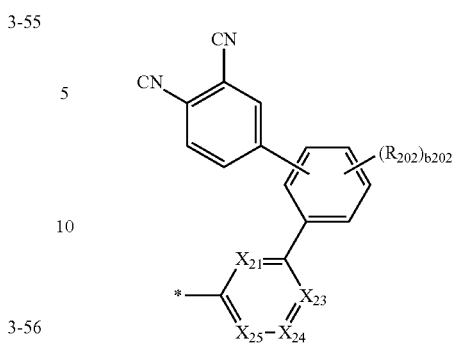
3-61
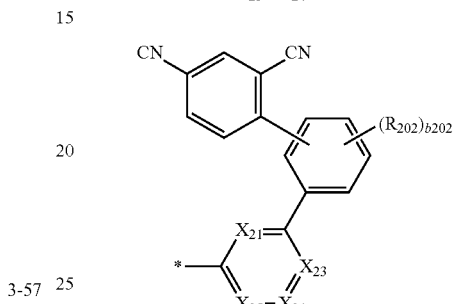
3-62
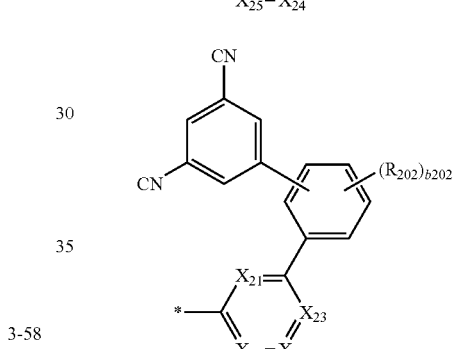
3-63
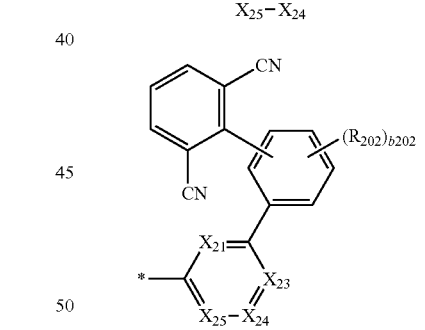
3-64

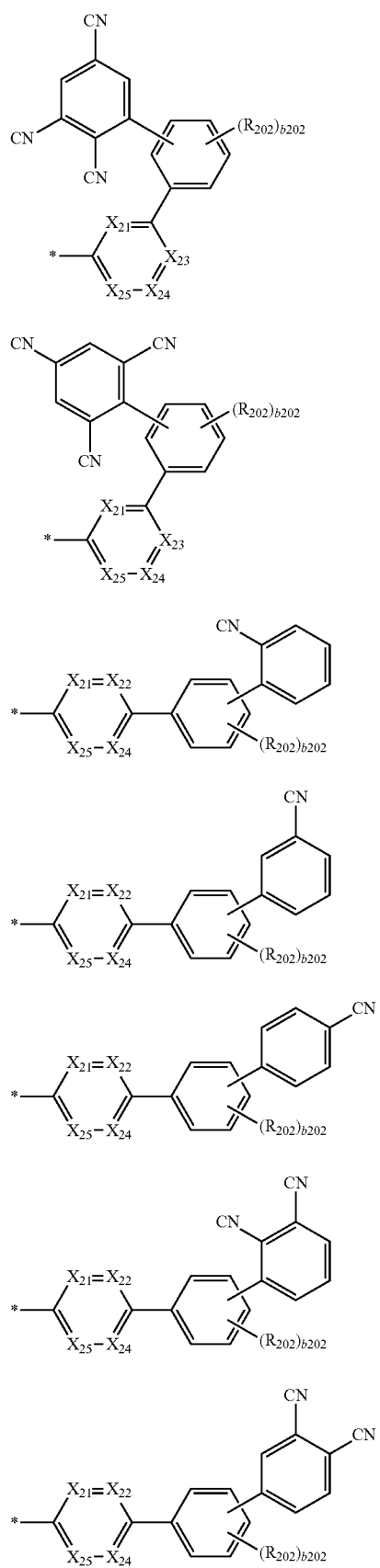

3-79
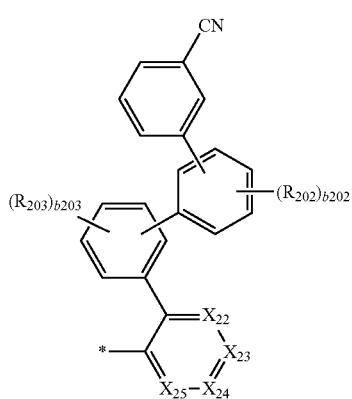
3-80
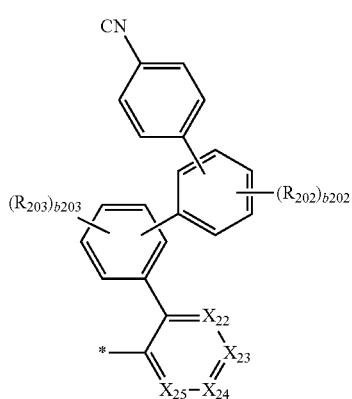
3-81
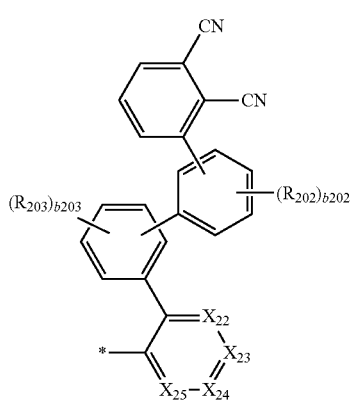
3-82
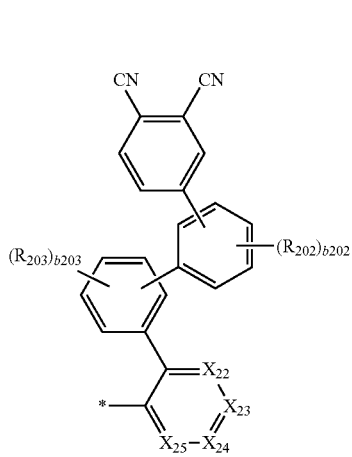
3-83
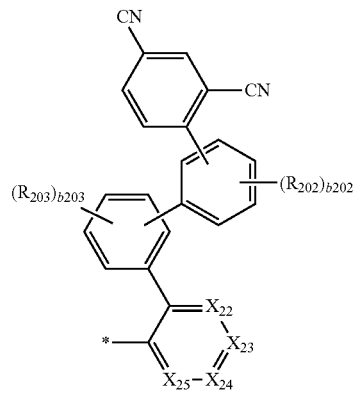
3-84
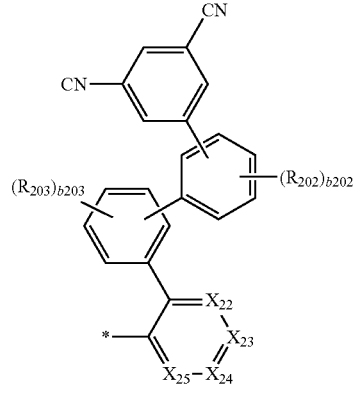
3-85
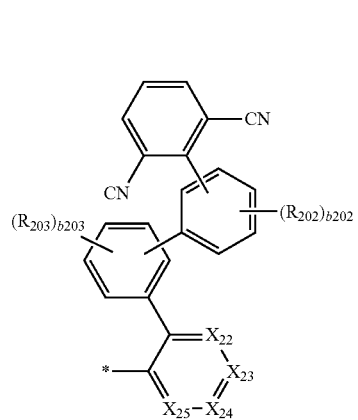
3-86
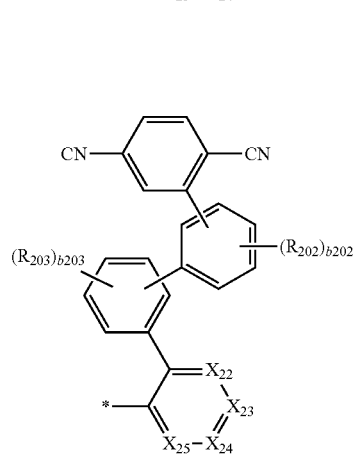

3-87
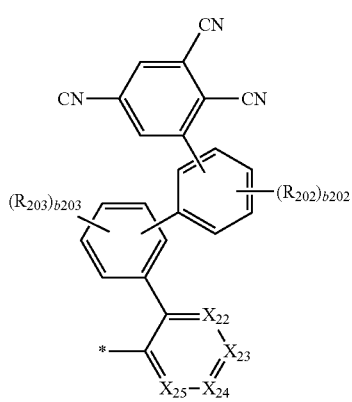
3-88
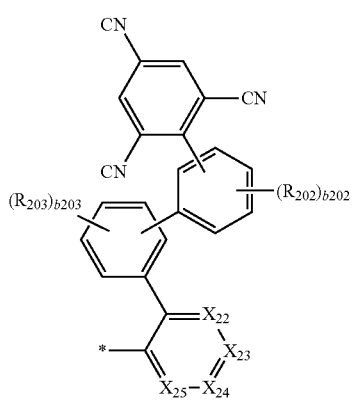
3-89
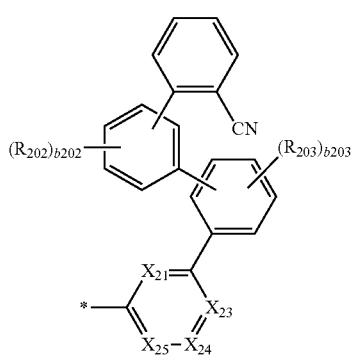
3-90
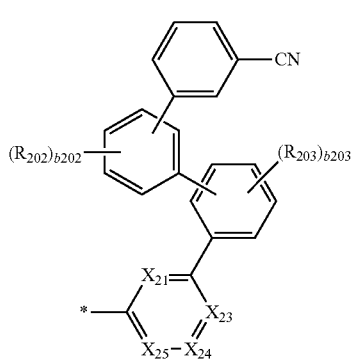
3-91
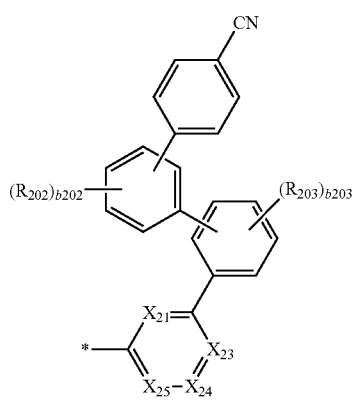
3-92
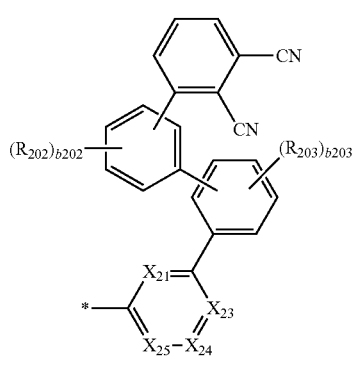
3-93
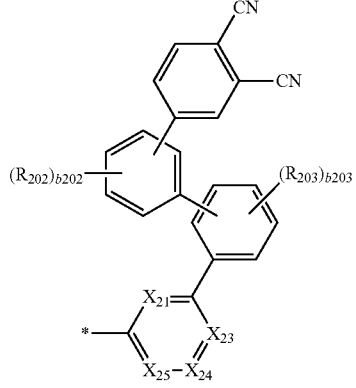
3-94
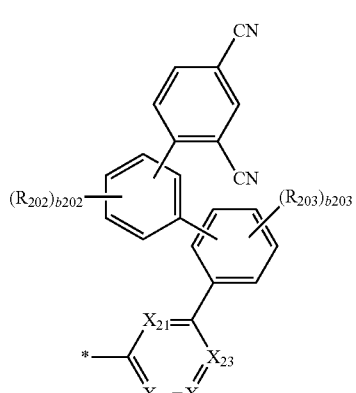

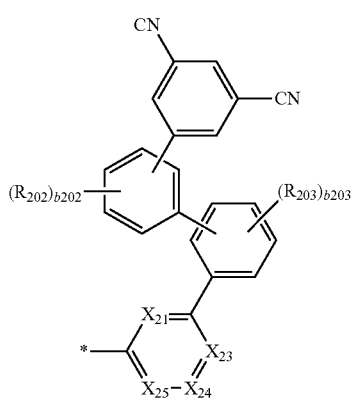
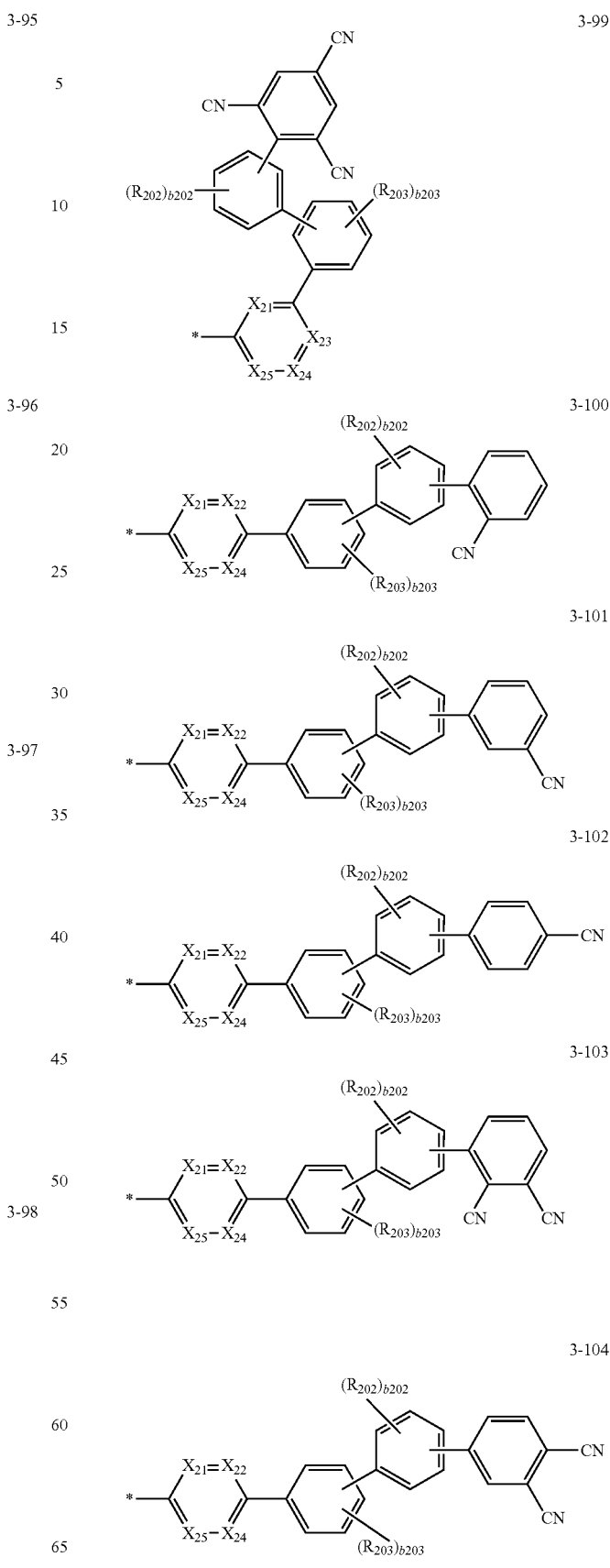

-continued
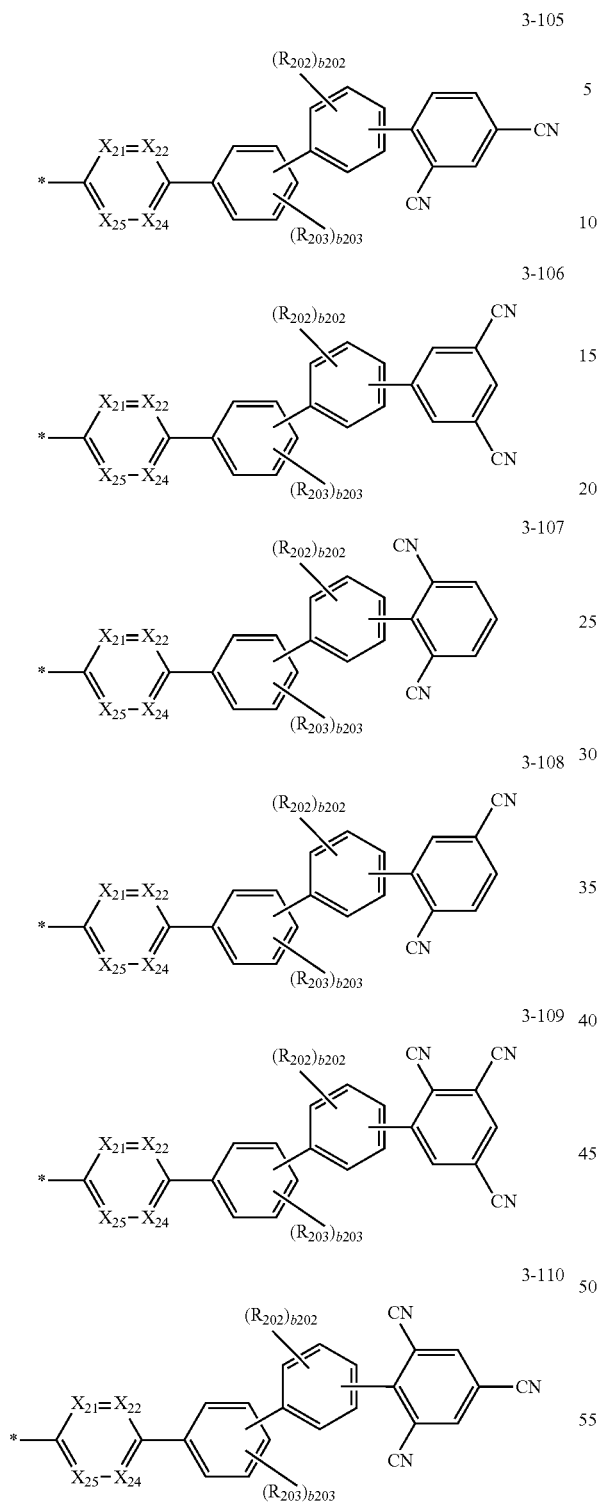
3-105
3-106
3-107
3-108
3-109
3-110
wherein, in Formulae 3-1 to 3-110,
* indicates a carbon atom in Formula 1, and
$X_{21}$ to $X_{25}$, $R_{21}$ to $R_{25}$, $R_{202}$, $R_{203}$, $b202$, and $b203$ are the same as in Formulae 2-1 to 2-10.
7. The condensed-cyclic compound of claim 1, wherein $A_{11}$ is represented by one of Formulae 4-1 to 4-110:
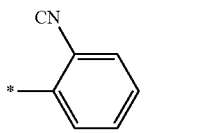
4-1
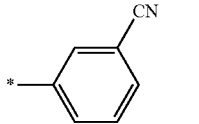
4-2
4-3
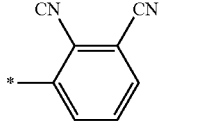
4-4
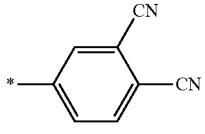
4-5
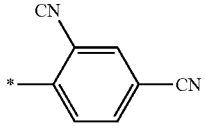
4-6
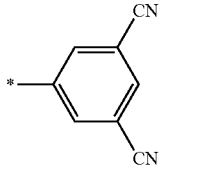
4-7
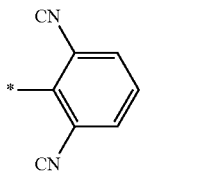
4-8
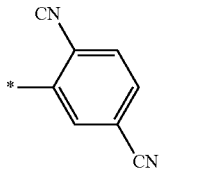
4-9
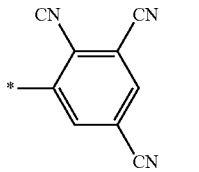
4-10

-continued
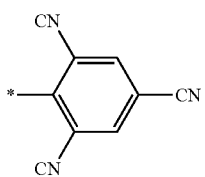
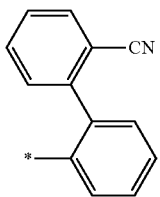
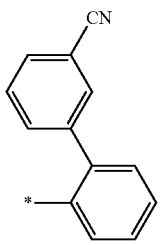
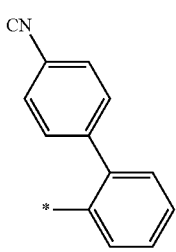
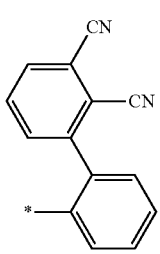
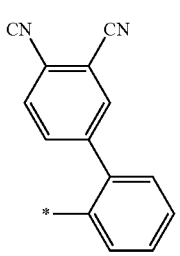
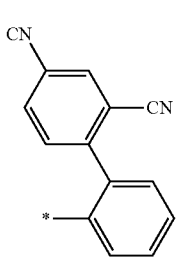
4-11
4-12
4-13
4-14
4-15
4-16
4-17
-continued
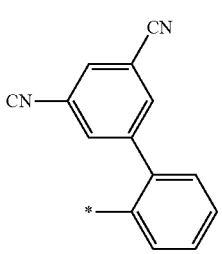
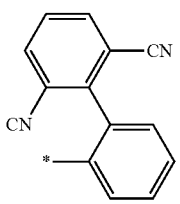
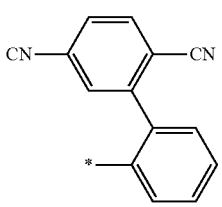
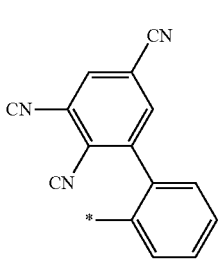
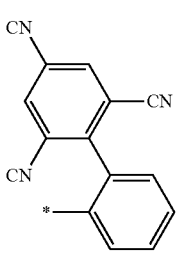
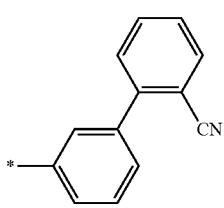
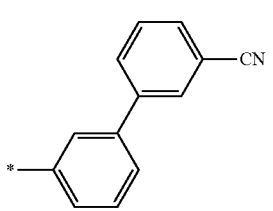
4-18
4-19
4-20
4-21
4-22
4-23
4-24

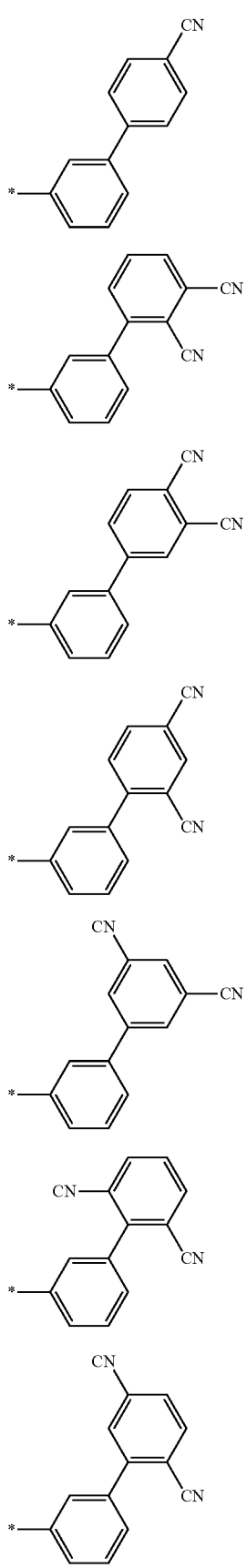
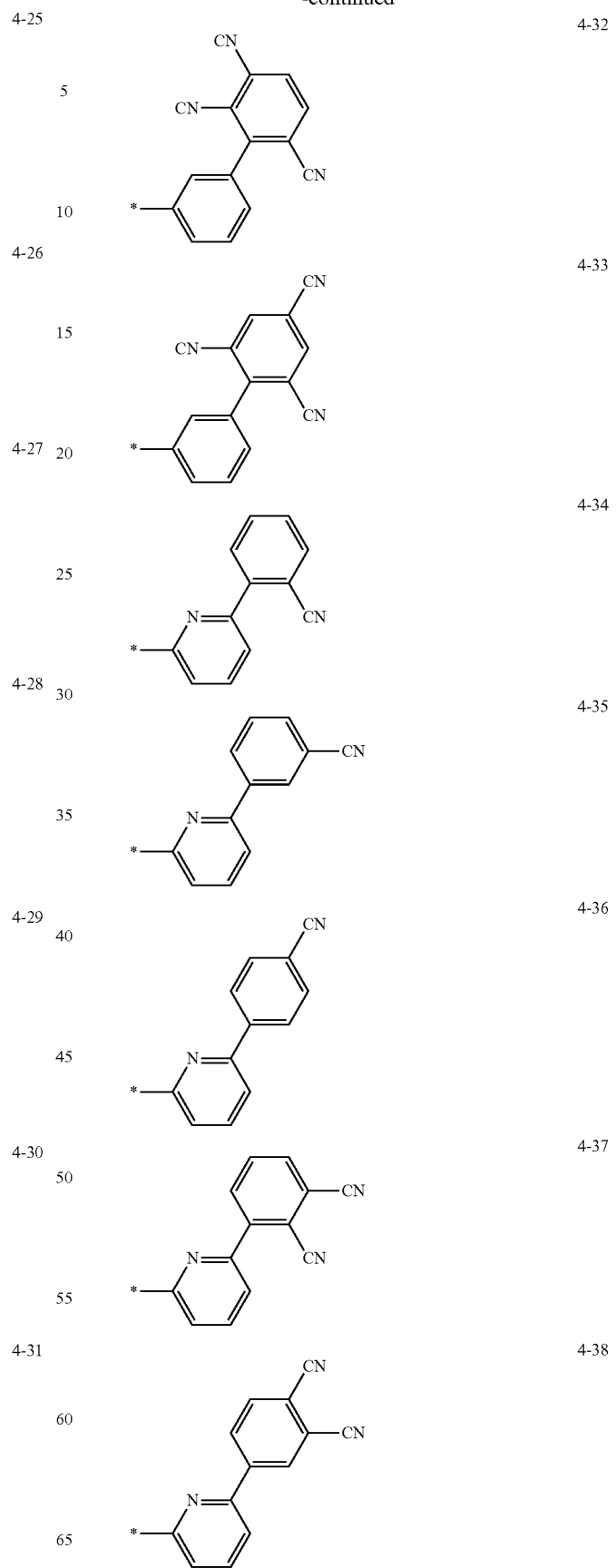

4-39 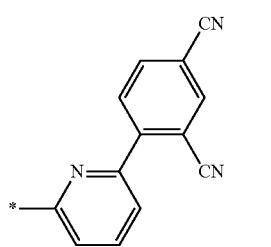
4-40 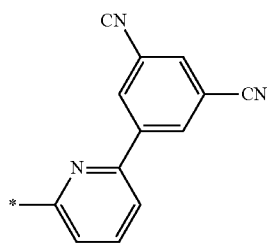
4-41 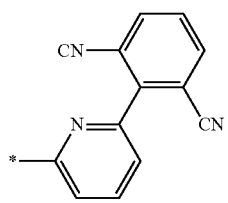
4-42 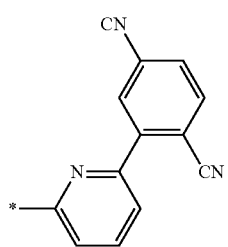
4-43 
4-44 
4-45 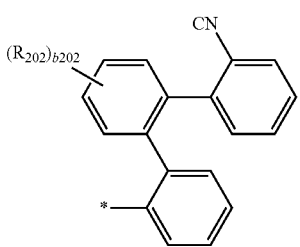
4-46 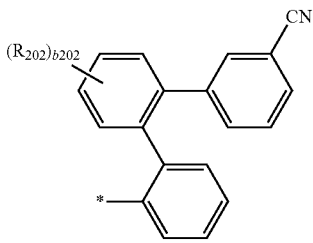
4-47 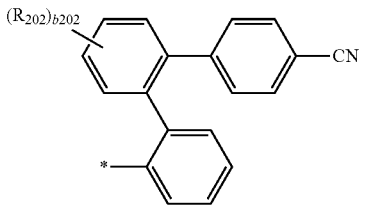
4-48 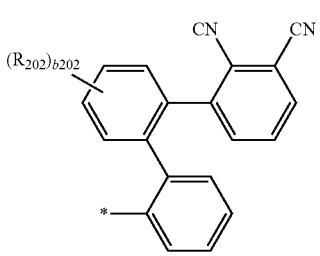
4-49 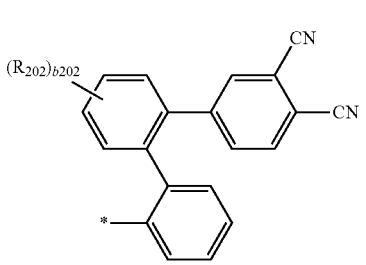
4-50 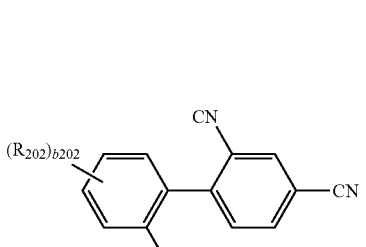

4-51 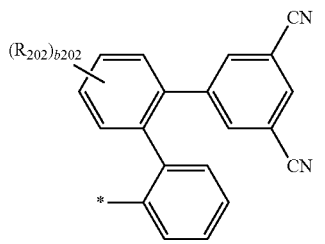
4-52 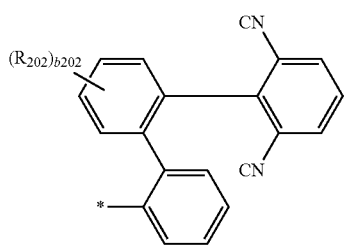
4-53 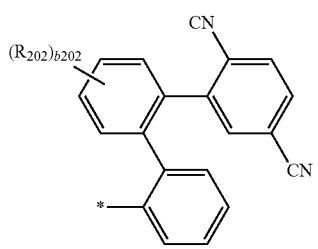
4-54 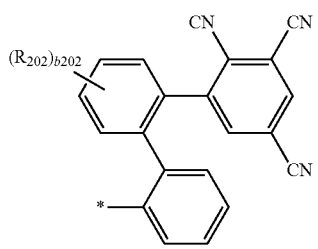
4-55 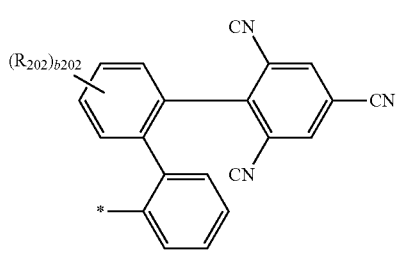
4-56 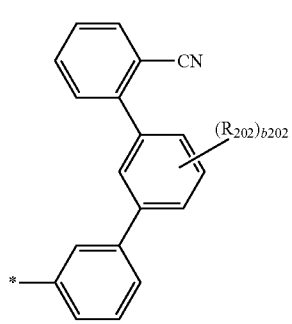
4-57 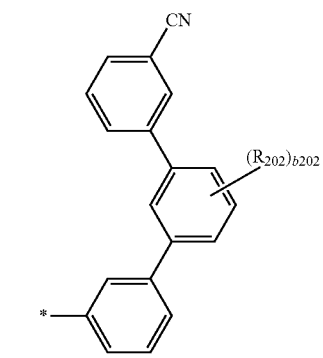
4-58 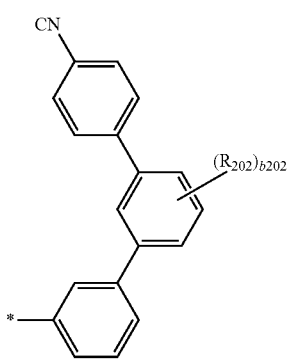
4-59 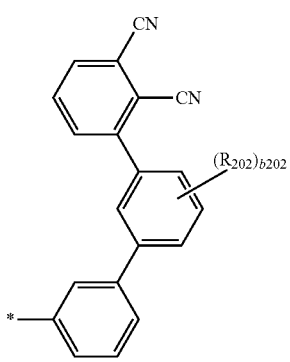
4-60 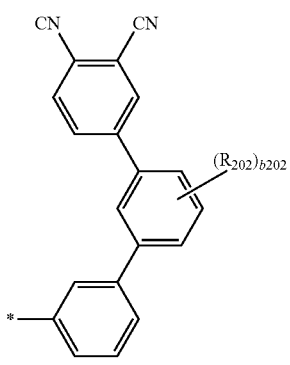

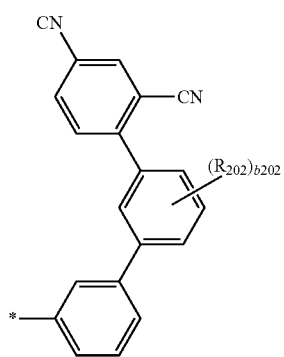
4-61
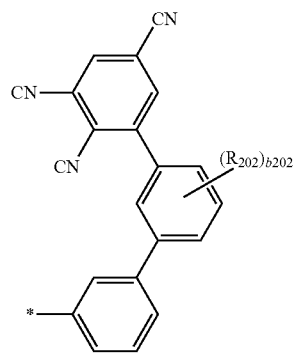
4-65
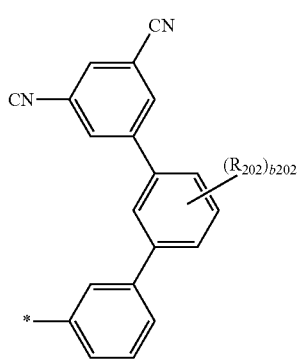
4-62
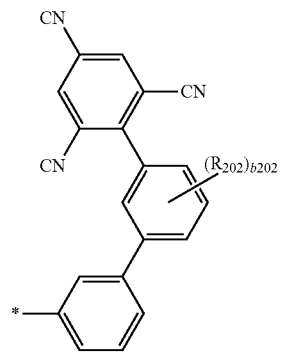
4-66
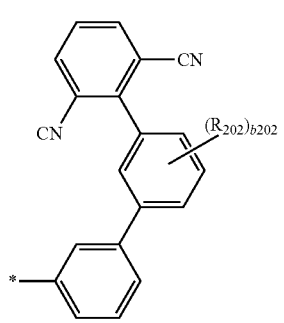
4-63
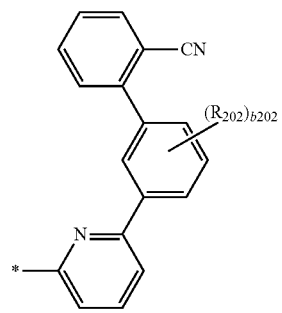
4-67
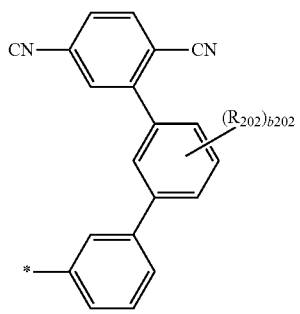
4-64
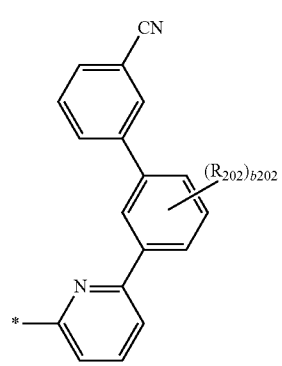
4-68

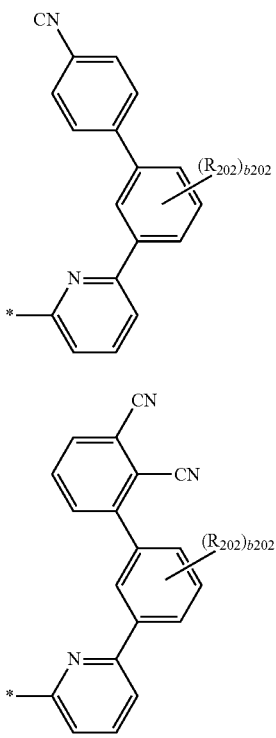
4-69
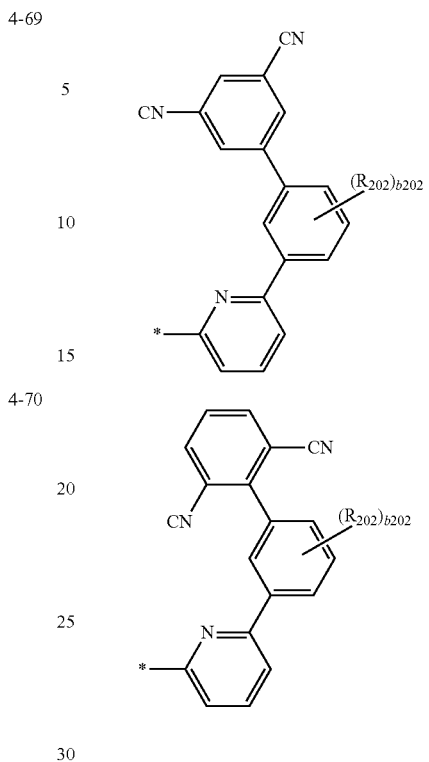
4-70
4-71
4-72
4-73
4-74
4-75
4-76

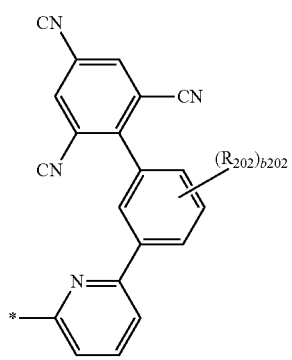
4-77
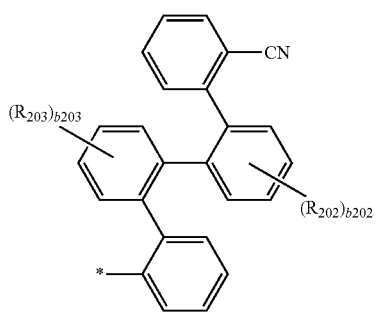
4-78
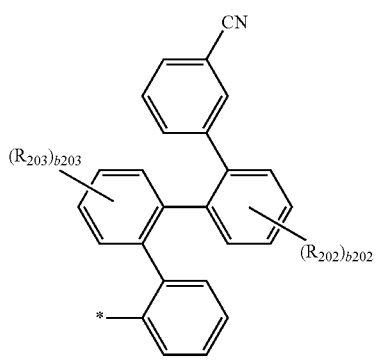
4-79
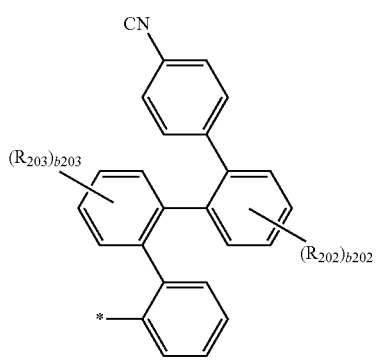
4-80
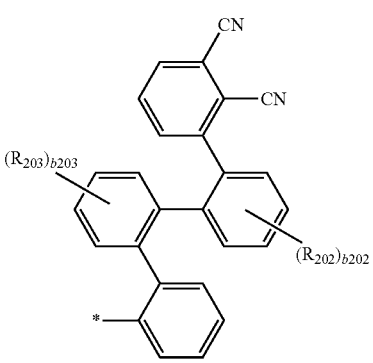
4-81
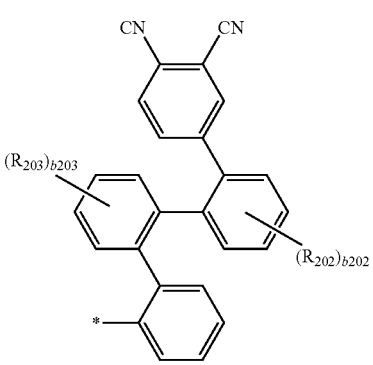
4-82
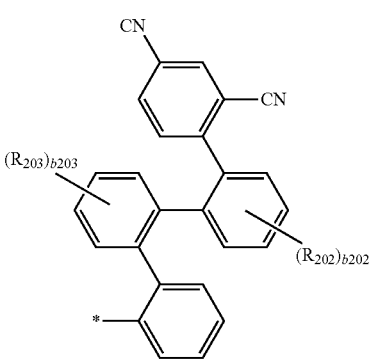
4-83
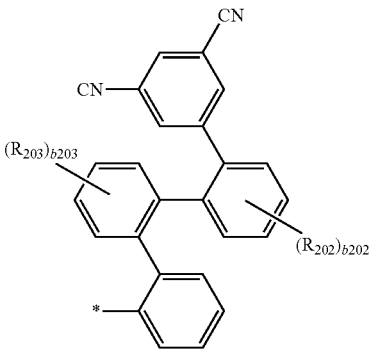
4-84

4-85
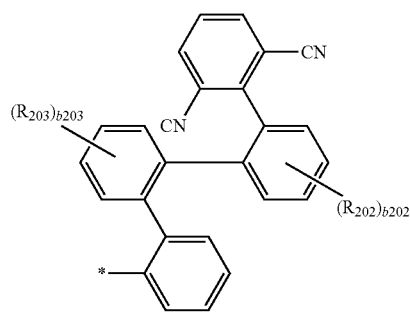
4-86
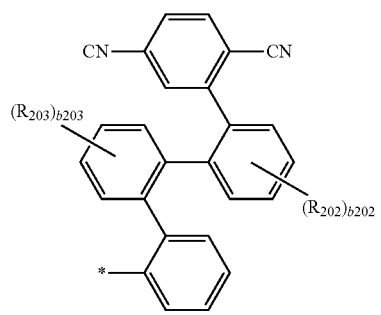
4-87
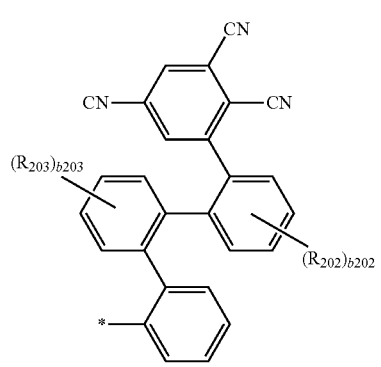
4-88
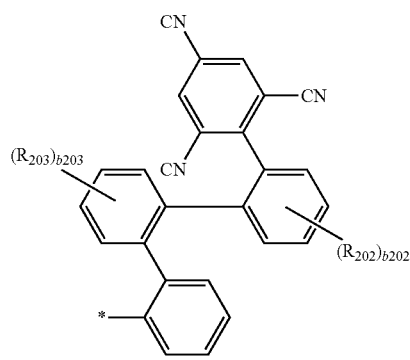
4-89
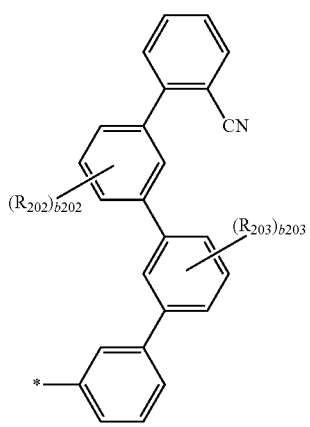
4-90
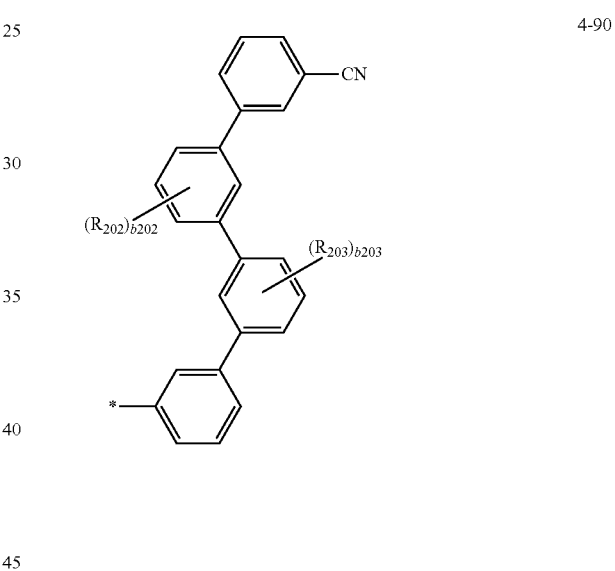
4-91
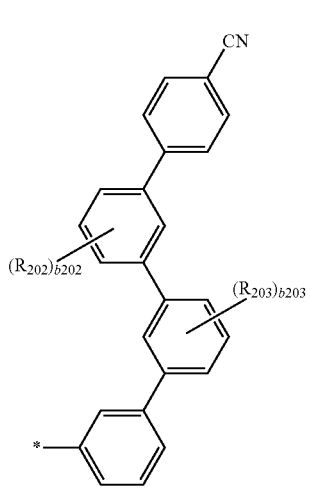

4-92 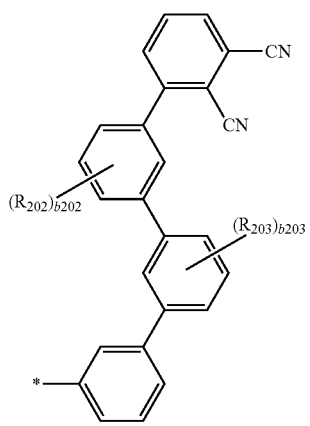 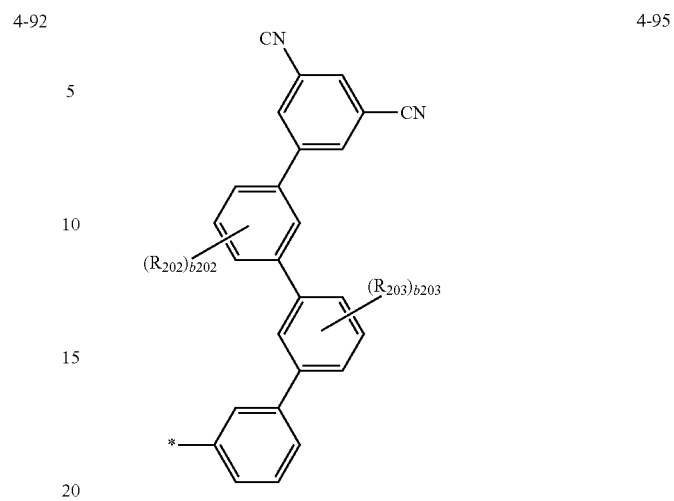 4-95
4-93 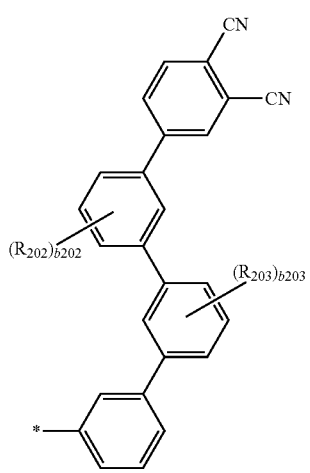 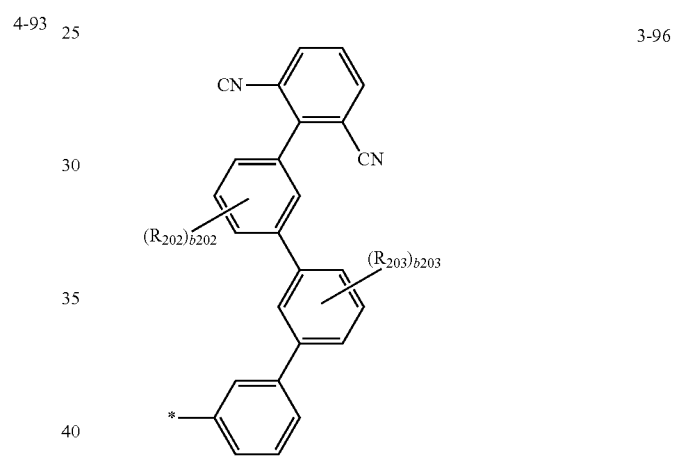 3-96
4-94 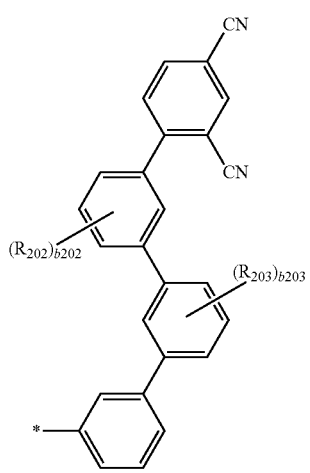 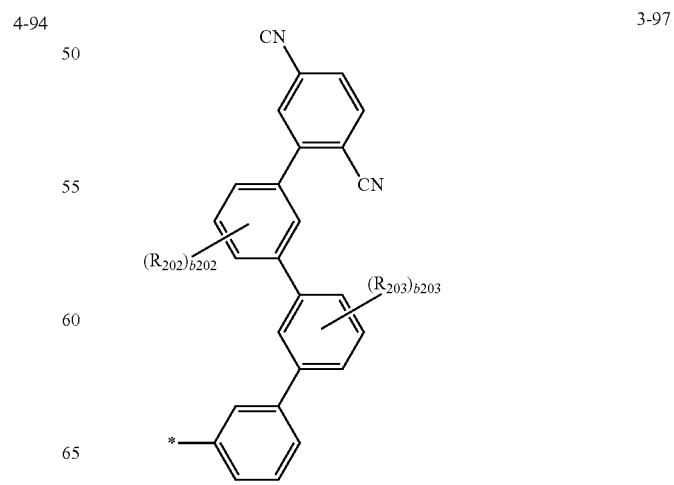 3-97

4-98
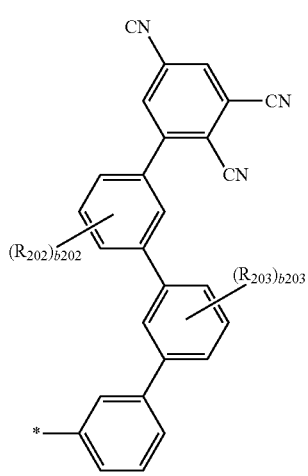
4-101
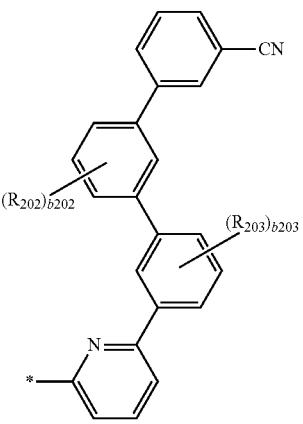
3-99
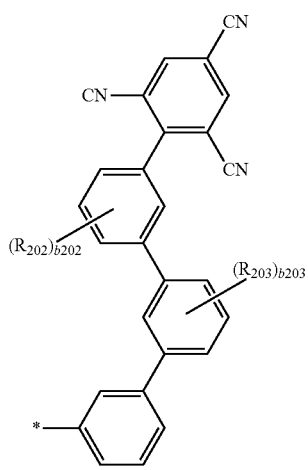
4-102
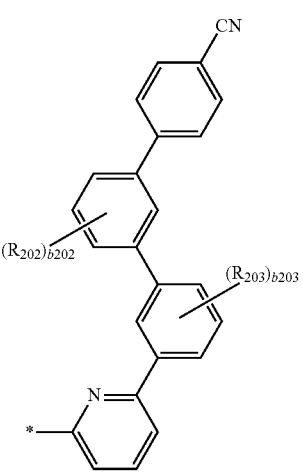
4-100
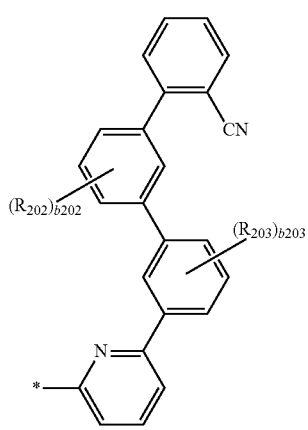
4-103
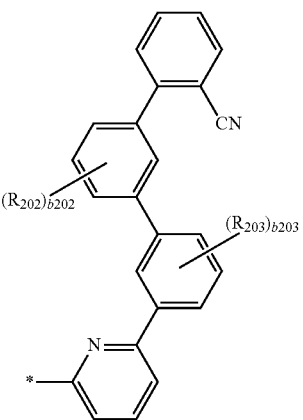

-continued
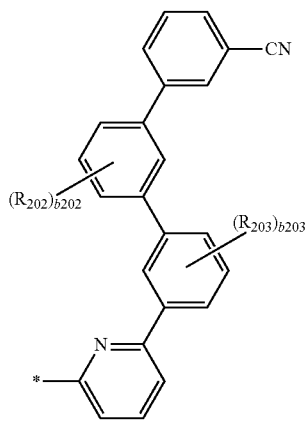
4-104
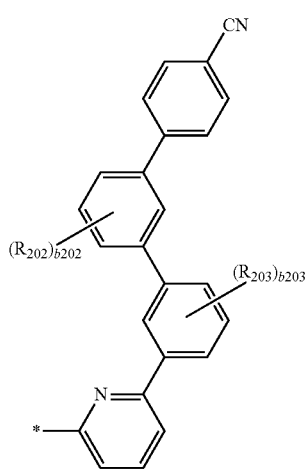
4-105
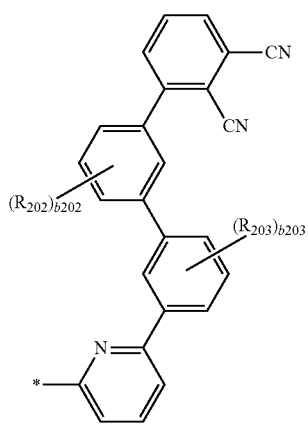
4-106
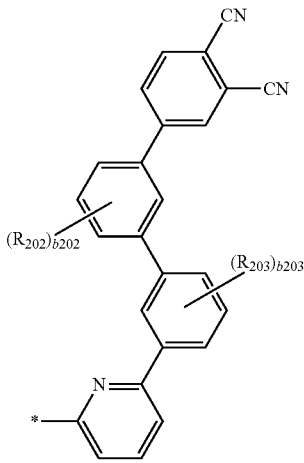
4-107
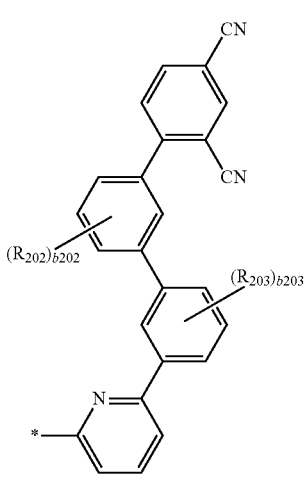
4-108
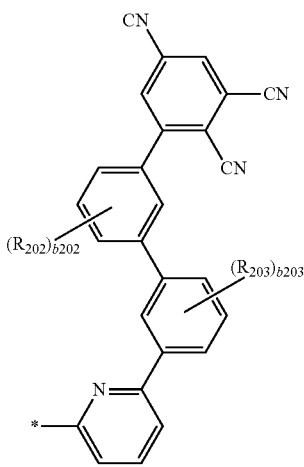
4-109

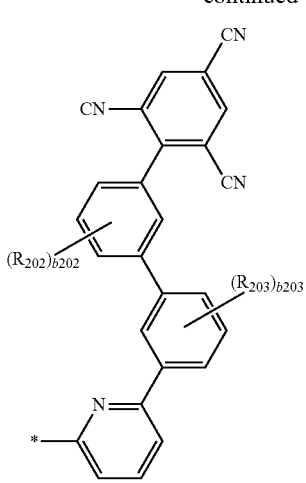

4-110 wherein, in Formulae 4-1 to 4-110,
* indicates a carbon atom in Formula 1, and
$R_{202}$, $R_{203}$, b202, and b203 are the same as in Formulae 2-1 to 2-10.

8. The condensed-cyclic compound of claim 1, wherein $A_{12}$ is selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a phenyl group, a pyridinyl group, a fluorenyl group, a dibenzofuranyl group, and a dibenzothiophenyl group; and
—Si($Q_{31}$)($Q_{32}$)($Q_{33}$),
wherein $Q_{31}$ to $Q_{33}$ are each independently selected from a $C_1$-$C_{10}$ alkyl group, a $C_1$-$C_{10}$ alkoxy group, a phenyl group, a naphthyl group, and a pyridinyl group.

9. The condensed-cyclic compound of claim 1, wherein $R_1$ to $R_8$, $R_{11}$ to $R_{18}$, $R_{101}$, $R_{102}$, $R_{21}$ to $R_{25}$, and $R_{201}$ to $R_{203}$ are each independently selected from
a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group;
a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and
—Si($Q_{11}$)($Q_{12}$)($Q_{13}$),
wherein $Q_{11}$ to $Q_{13}$ are each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

10. The condensed-cyclic compound of claim 1, wherein $R_1$ to $R_8$, $R_{11}$ to $R_{18}$, $R_{101}$, $R_{102}$, $R_{21}$ to $R_{25}$, and $R_{201}$ to $R_{203}$ are each independently selected from
a hydrogen, a deuterium, a cyano group, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group and —Si($Q_{11}$)($Q_{12}$)($Q_{13}$),
wherein $Q_{11}$ to $Q_{13}$ are each independently selected from a hydrogen, a $C_1$-$C_{20}$ alkyl group, a $C_1$-$C_{20}$ alkoxy group, and a phenyl group.

11. The condensed-cyclic compound of claim 1, wherein at least one of $X_3$, $X_6$, $X_{13}$, and $X_{16}$ is C(CN).

12. The condensed-cyclic compound of claim 1, wherein
$X_3$ is C(CN); or
$X_3$ and $X_6$ are C(CN).

13. The condensed-cyclic compound of claim 1, wherein $R_1$, $R_2$, $R_4$, $R_5$, $R_7$, $R_8$, $R_{11}$, $R_{12}$, $R_{14}$, $R_{15}$, $R_{17}$, and $R_{18}$ are not a cyano group.

14. The condensed-cyclic compound of claim 1, wherein the condensed-cyclic compound represented by Formula 1 is represented by one of Formulae 1-1 to 1-8:

1-1

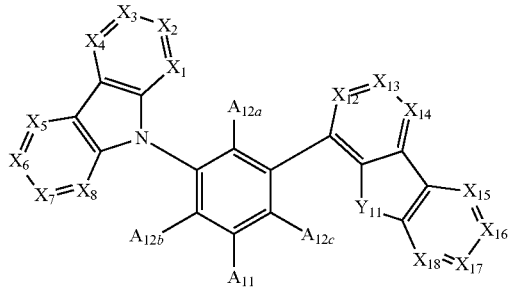

-continued
1-2
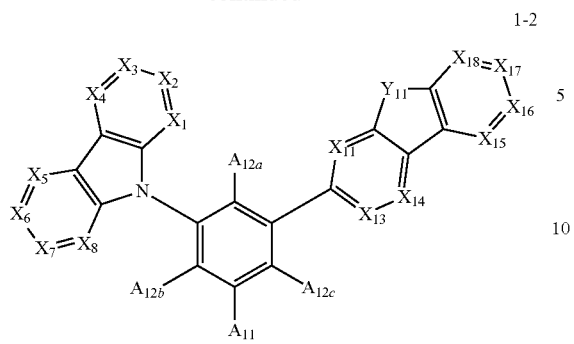
1-3
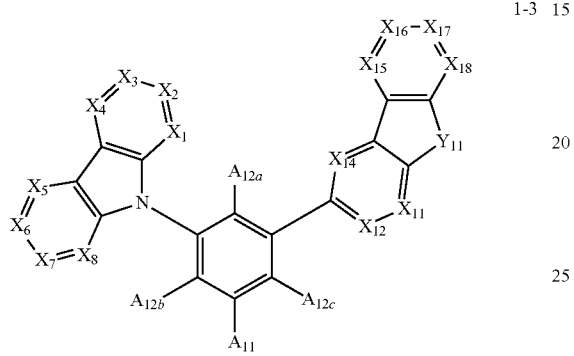
1-4
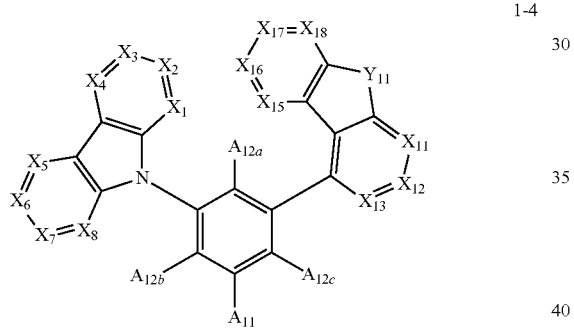
1-5
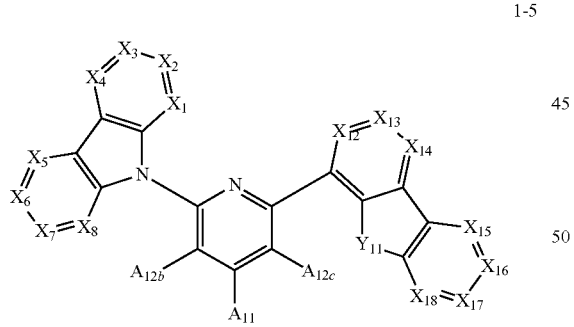
1-6
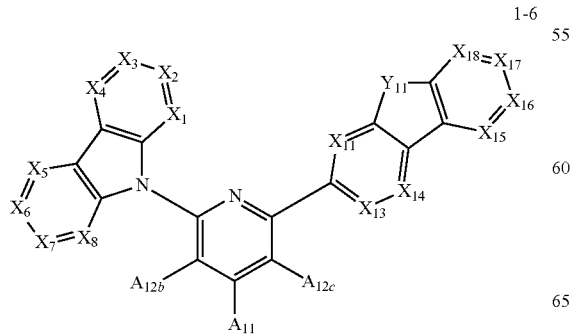
-continued
1-7
1-8
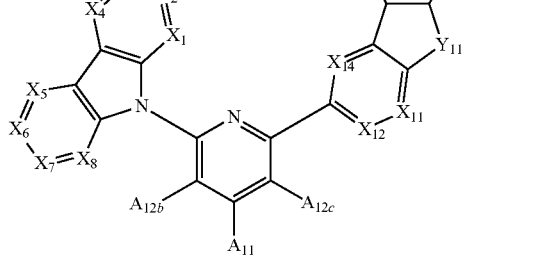
wherein, in Formulae 1-1 to 1-8,
$X_1$ to $X_8$ and $A_{11}$ are the same as in Formula 1;
$X_{11}$ to $X_{18}$ and $Y_{11}$ are the same as in Formulae 10-1 to 10-4; and
$A_{12a}$, $A_{12b}$, and $A_{12c}$ are each independently the same as $A_{12}$ in Formula 1.
15. The condensed-cyclic compound of claim 1, wherein the condensed-cyclic compound represented by Formula 1 is represented by one of Formulae 1-11 to 1-18, 1-21 to 1-28, and 1-31 to 1-38:
1-11
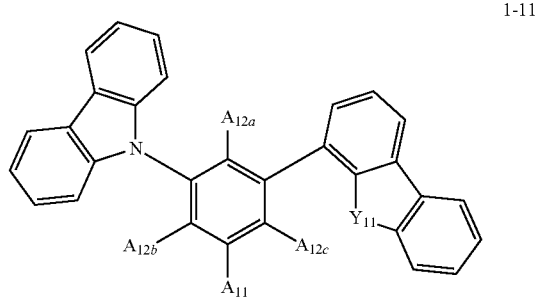
1-12
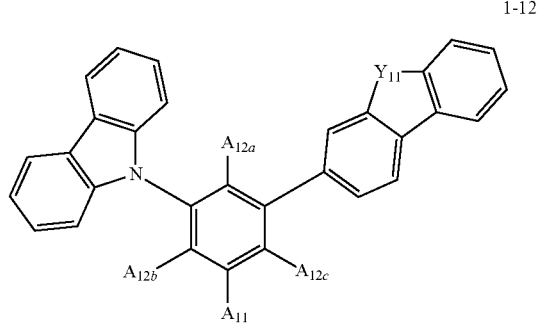

1-13
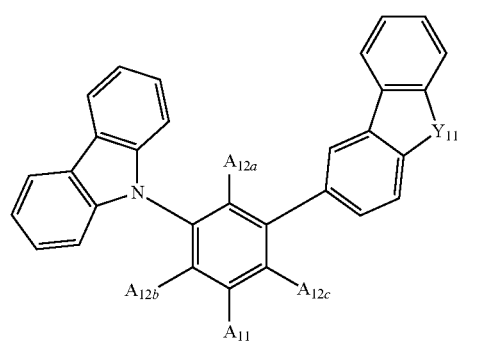
1-14
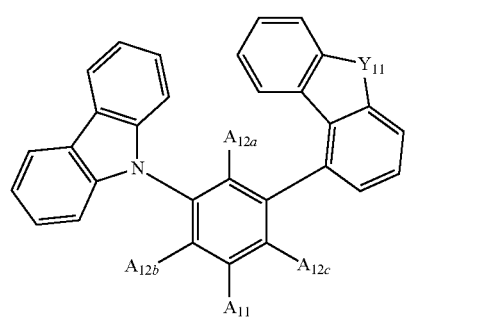
1-15
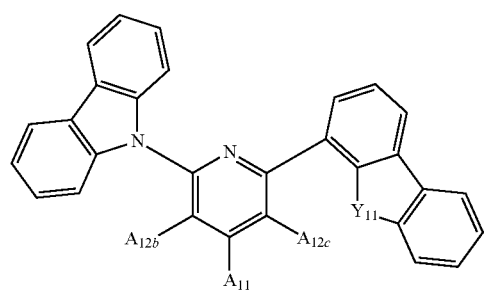
1-16
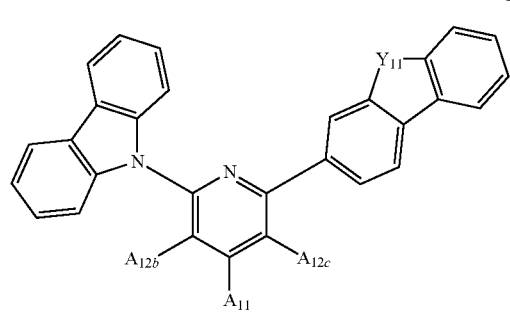
1-17
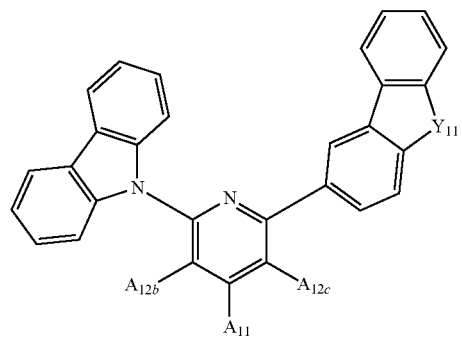
1-18
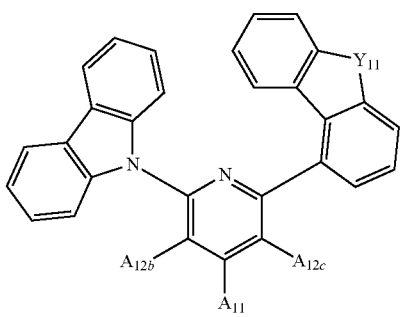
1-21
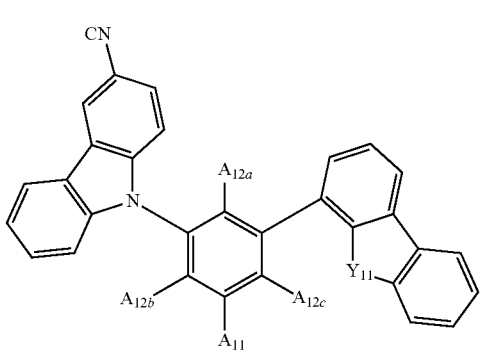
1-22
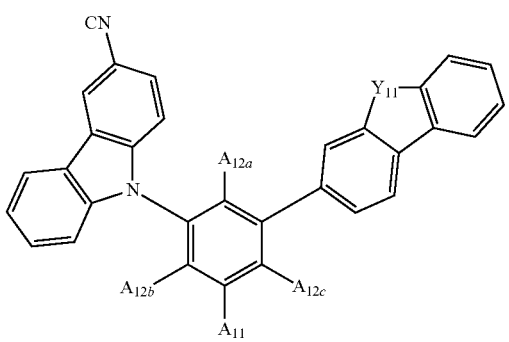
1-23
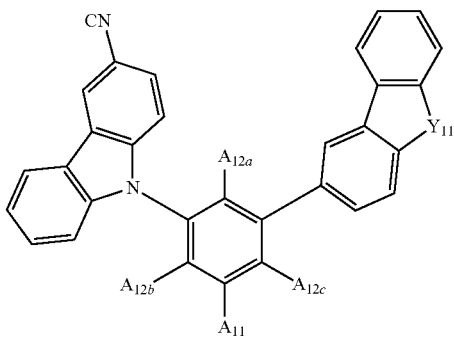

201
-continued
1-24
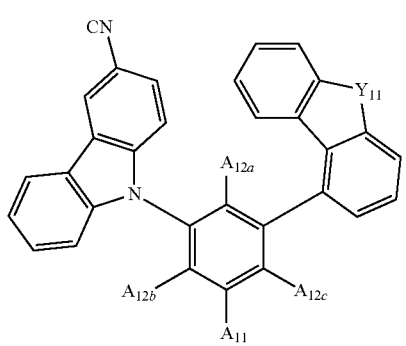
1-25
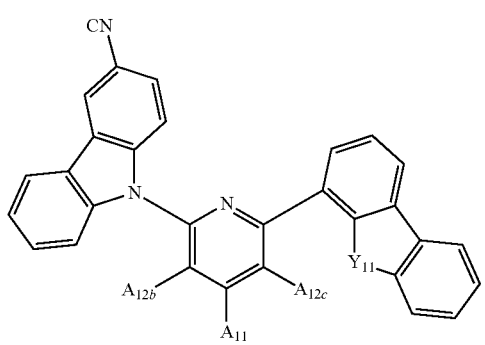
1-26
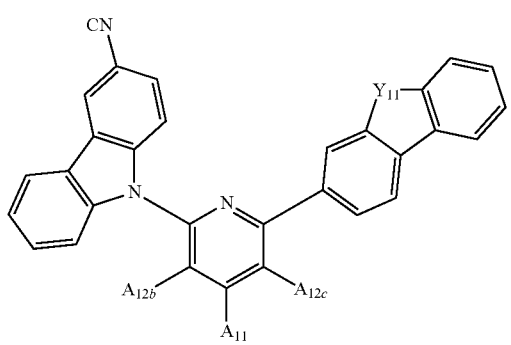
1-27
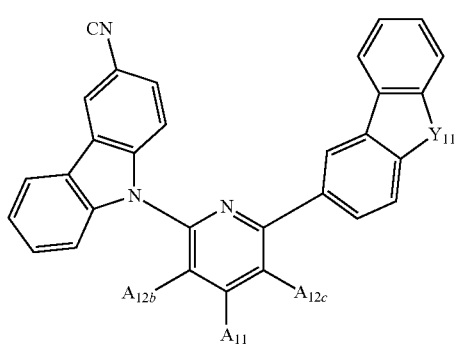
202
-continued
1-28
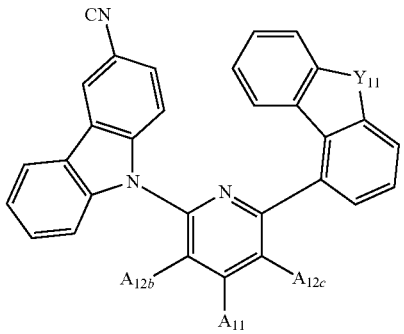
1-31
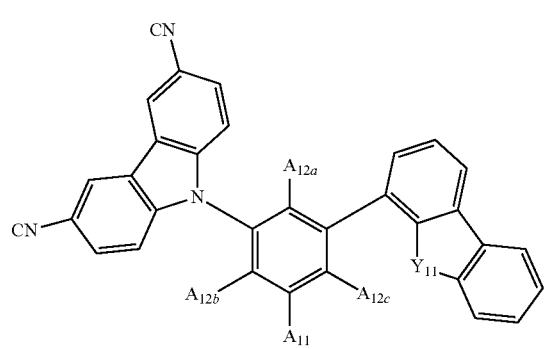
1-32
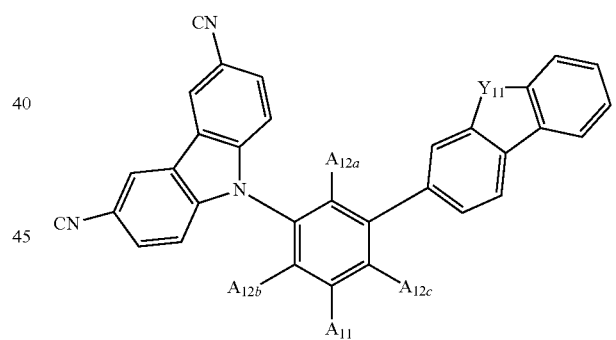
1-33
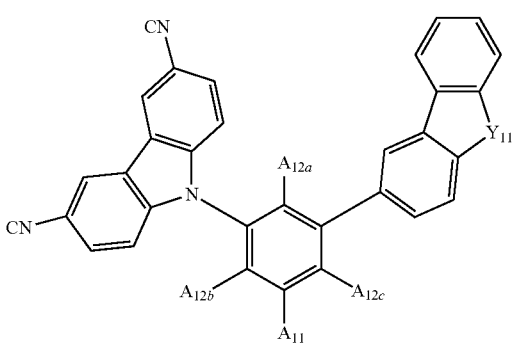

1-34
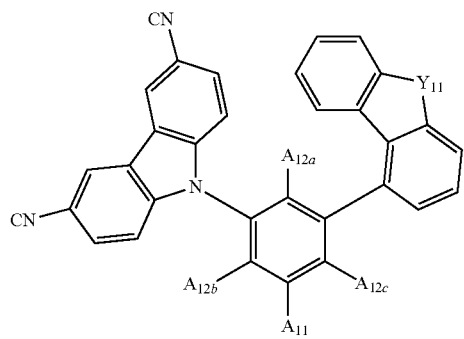
1-35
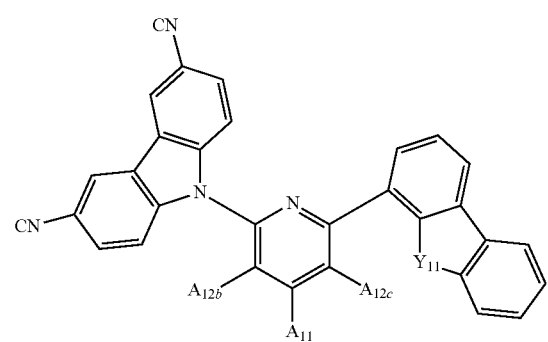
1-36
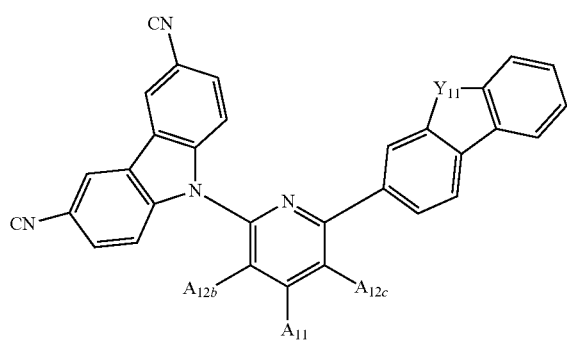
1-37
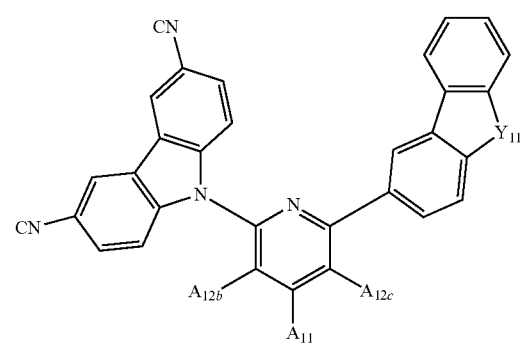
1-38
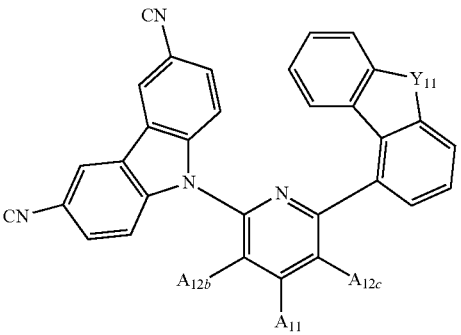
wherein, in Formulae 1-11 to 1-18, 1-21 to 1-28, and 1-31 to 1-38,
$A_{11}$ is the same as in Formula 1;
$Y_{11}$ is the same as in Formulae 10-1 to 10-4; and
$A_{12a}$, $A_{12b}$, and $A_{12c}$ are each independently the same as $A_{12}$ in Formula 1.
16. The condensed-cyclic compound of claim 1, wherein the condensed-cyclic compound represented by Formula 1 is represented by one of Formulae 1-41 to 1-48, 1-51 to 1-58, and 1-61 to 1-68:
1-41
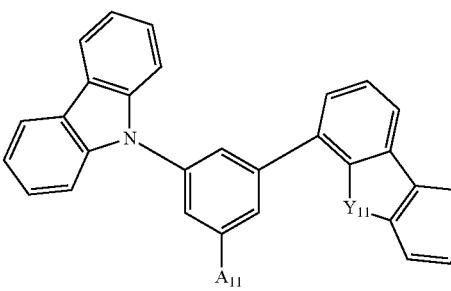
1-42
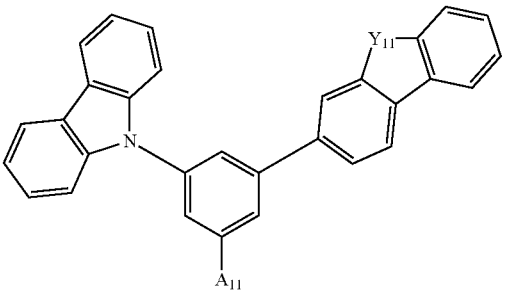
1-43
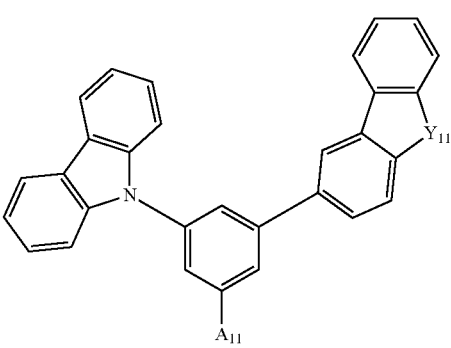

-continued
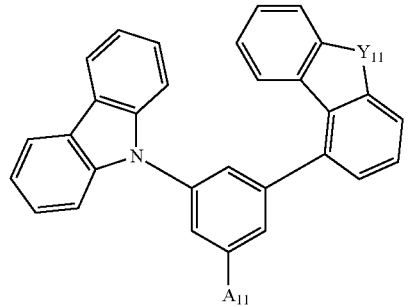
1-44
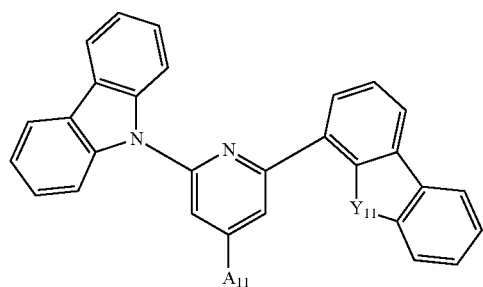
1-45
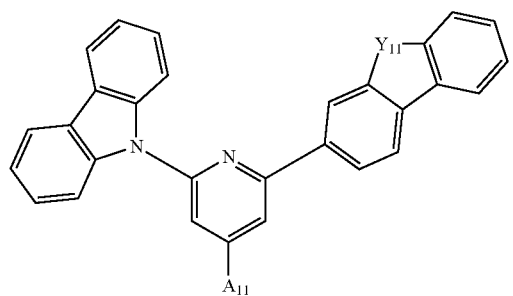
1-46
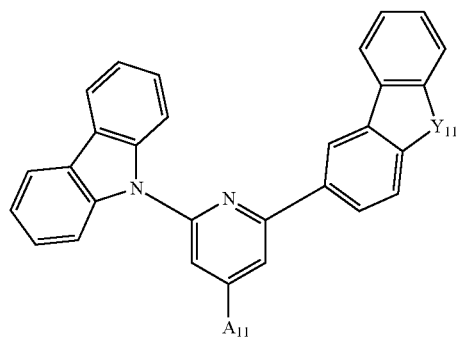
1-47
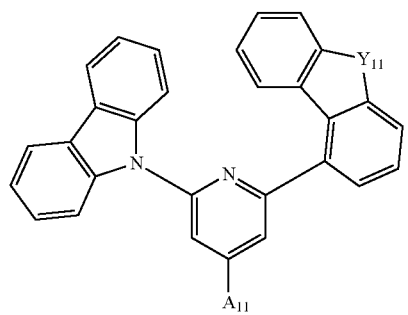
1-48
-continued
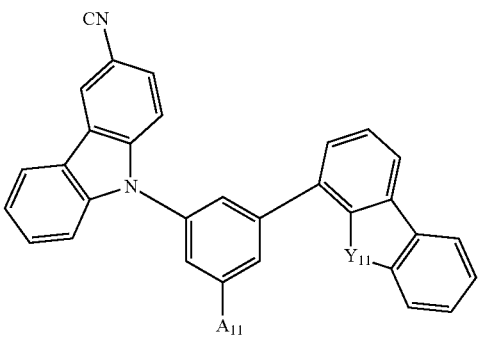
1-51
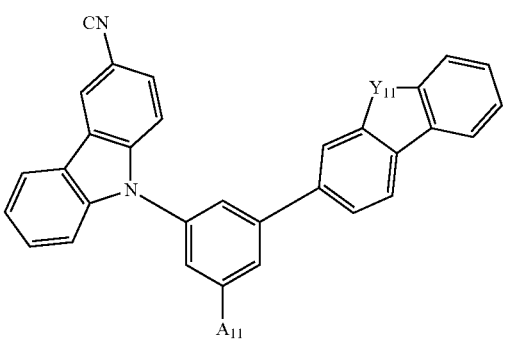
1-52
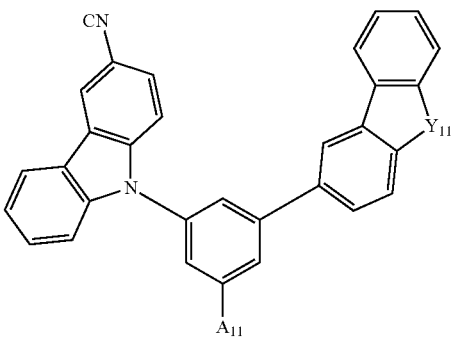
1-53
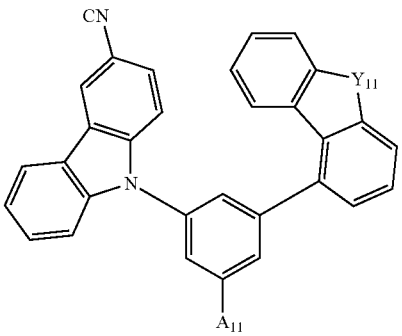
1-54

1-55

1-56

1-57

1-58

1-61

1-62

1-63

1-64

1-65
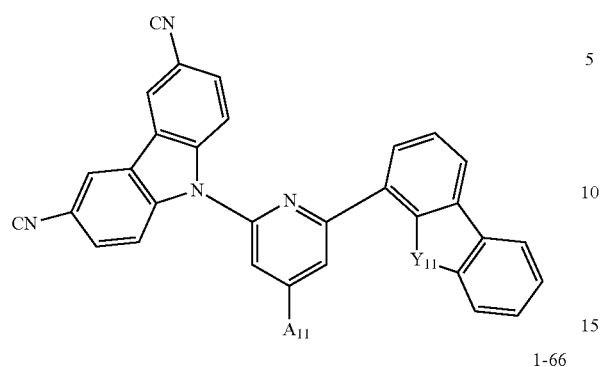
1-66
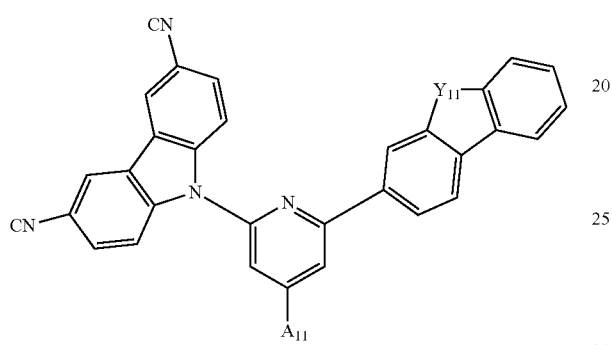
1-67
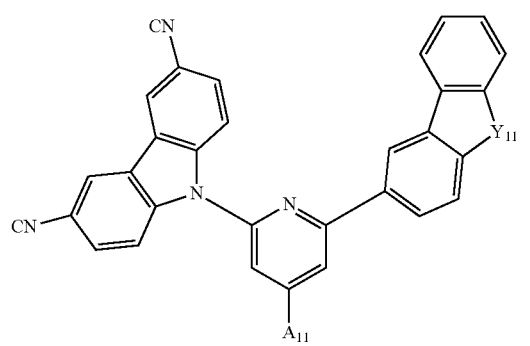
1-68
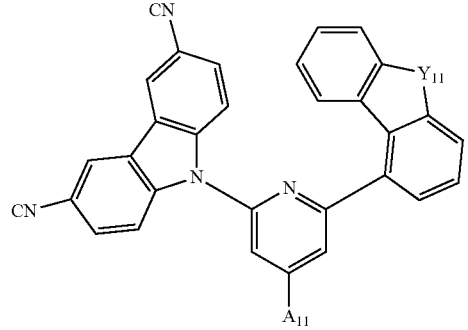
1
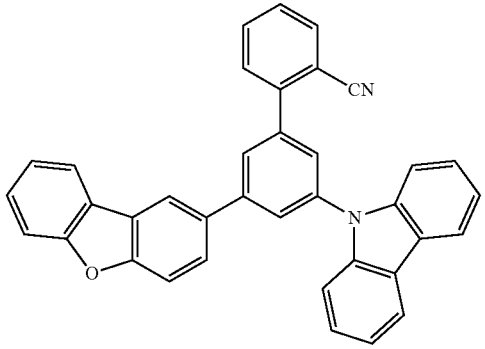
2
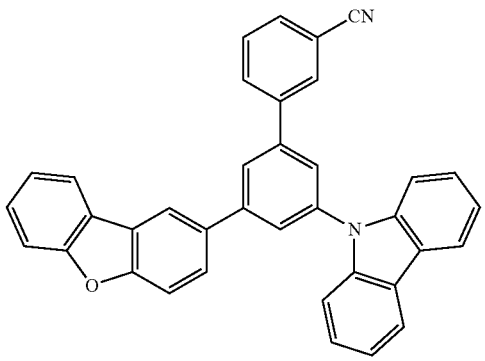
3
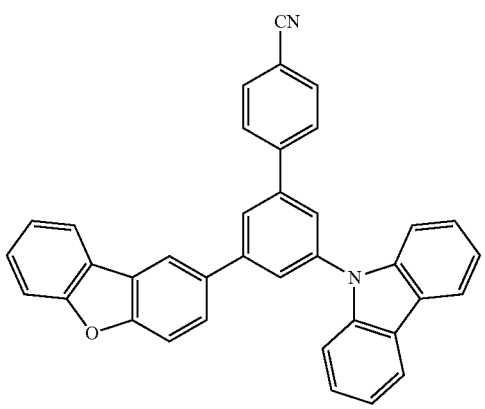
4
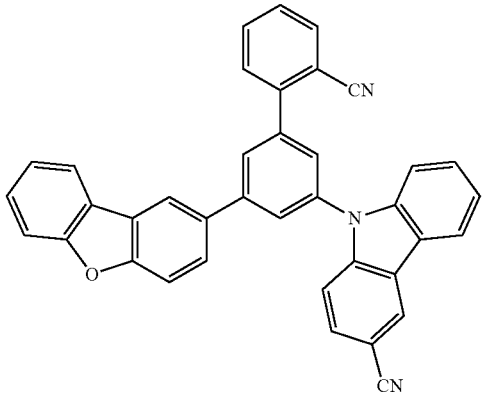
wherein, in Formulae 1-41 to 1-48, 1-51 to 1-58, and 1-61 to 1-68,
$A_{11}$ is the same as in Formula 1; and
$Y_{11}$ is the same as in Formulae 10-1 to 10-4.
17. The condensed-cyclic compound of claim 1, wherein the condensed-cyclic compound represented by Formula 1 is selected from Compounds 1 to 90:

211
-continued
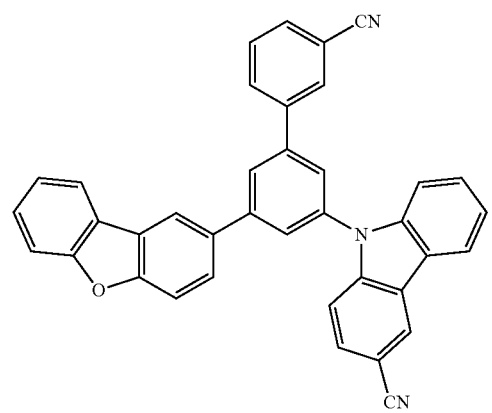
5
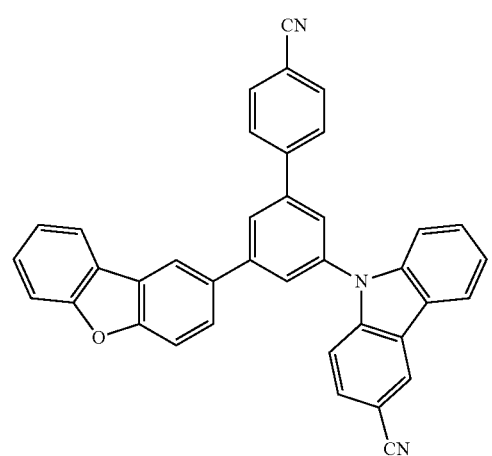
6
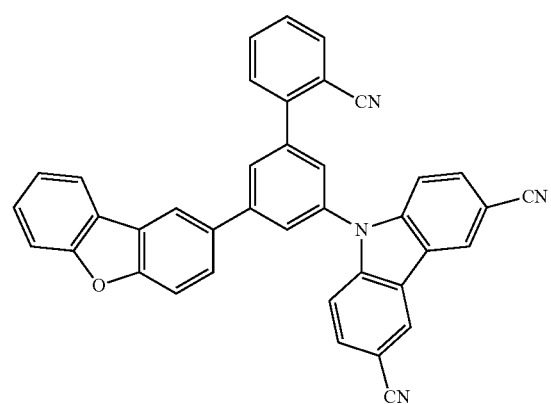
7
212
-continued
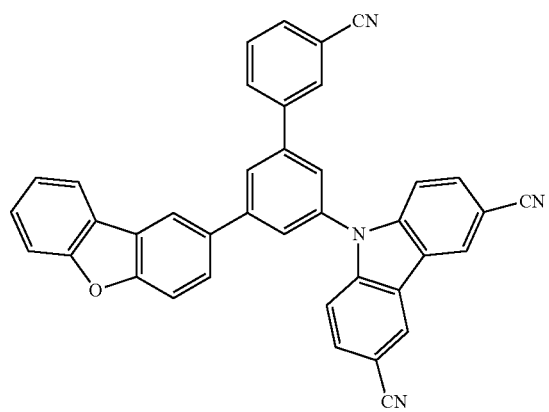
8

213
-continued
12
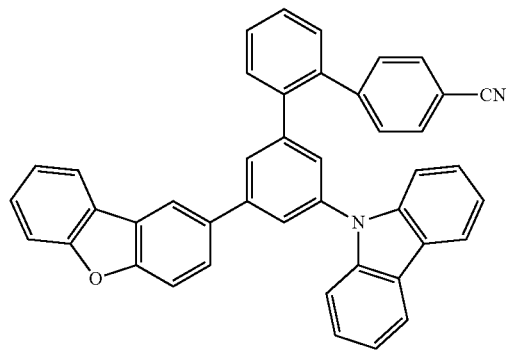
13
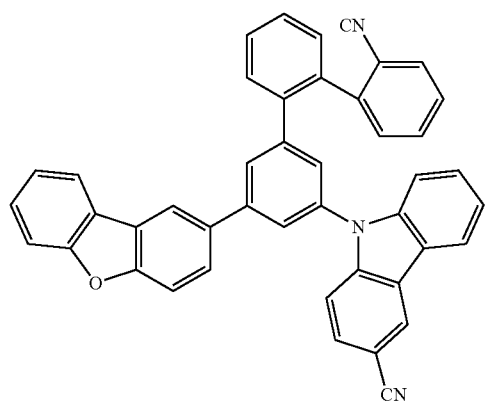
14
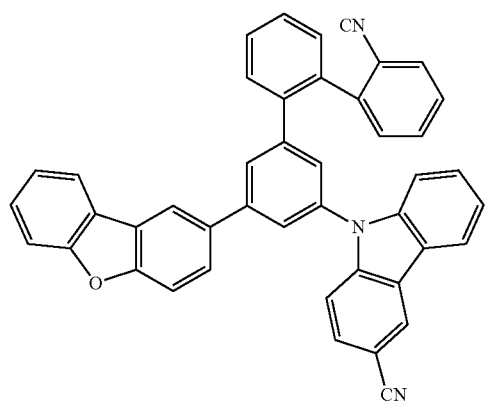
15
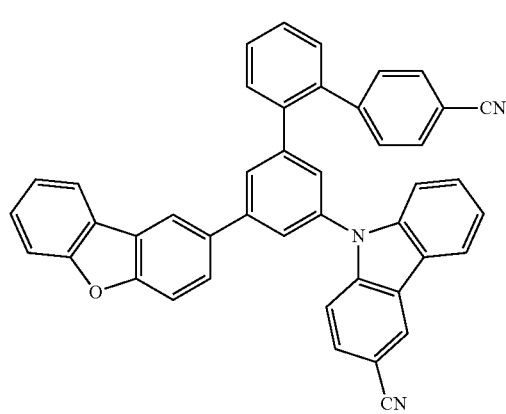
214
-continued
16
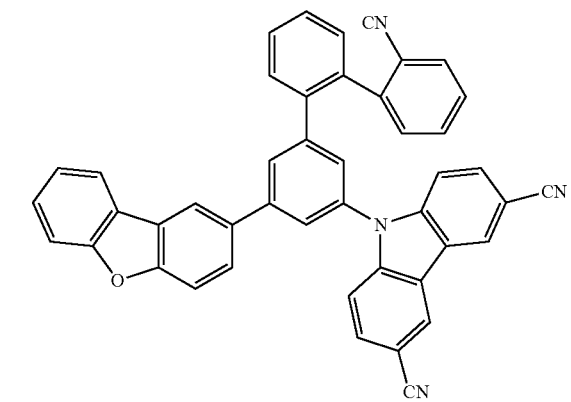
17
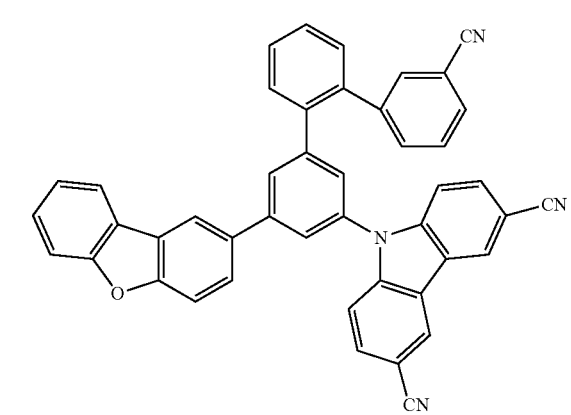
18
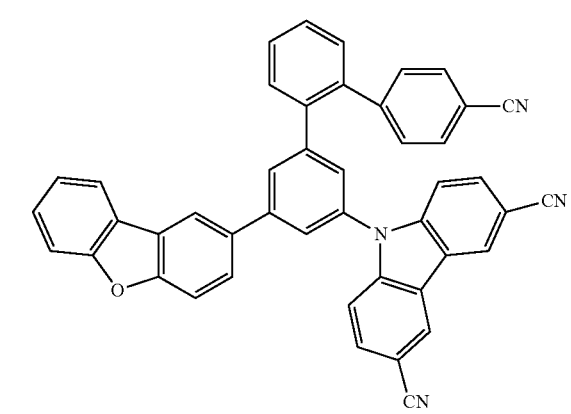

-continued
19
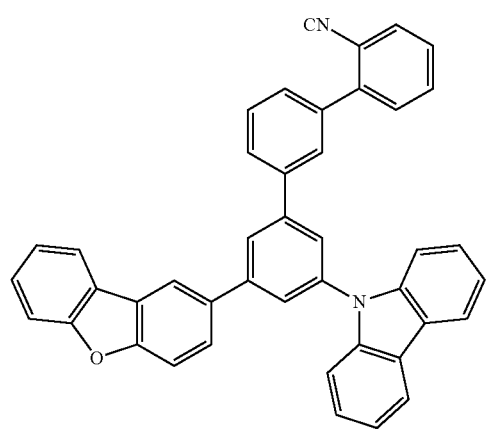
20
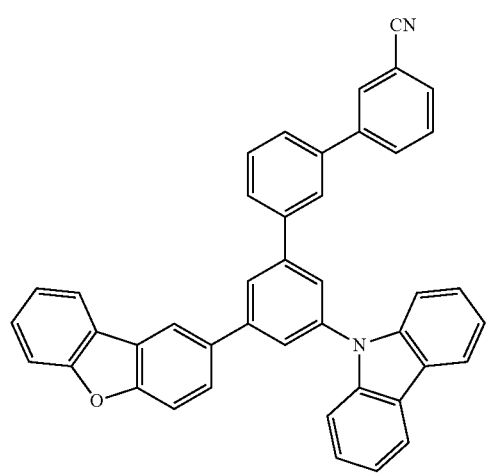
21
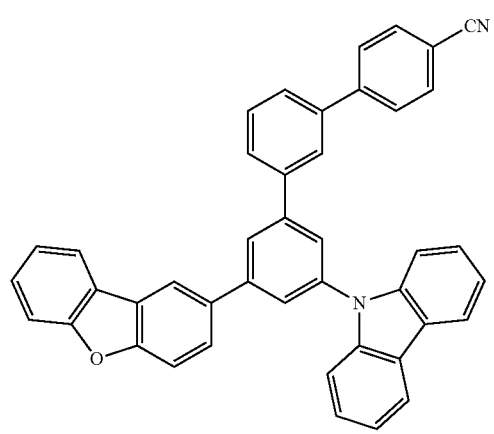
-continued
22
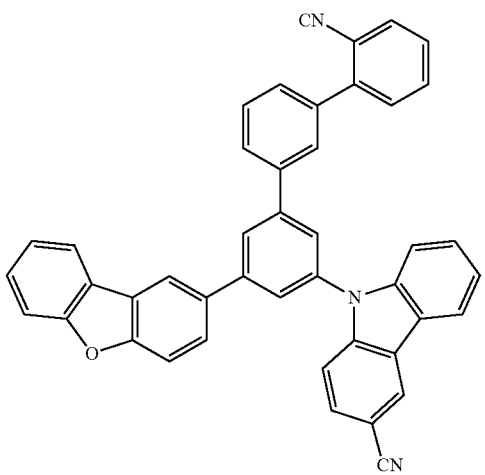
23
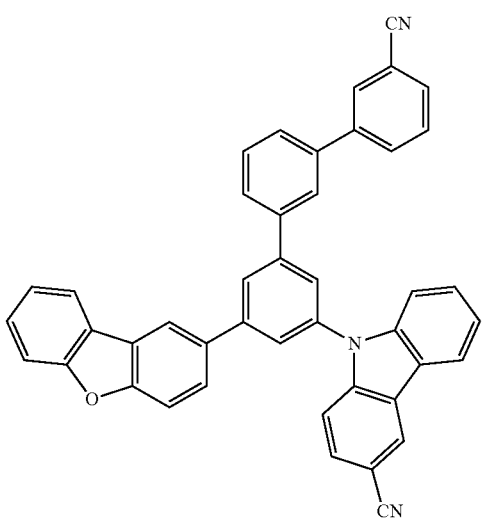
24

217
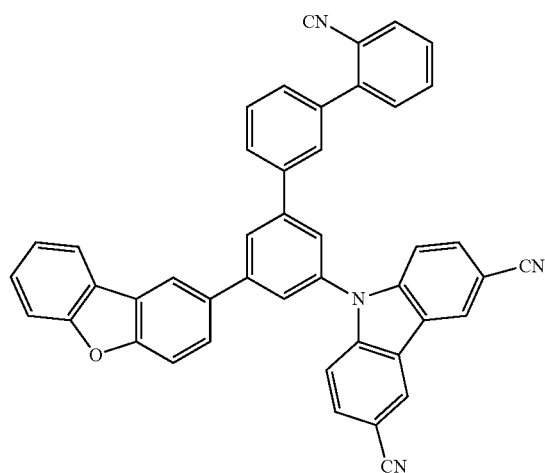
25
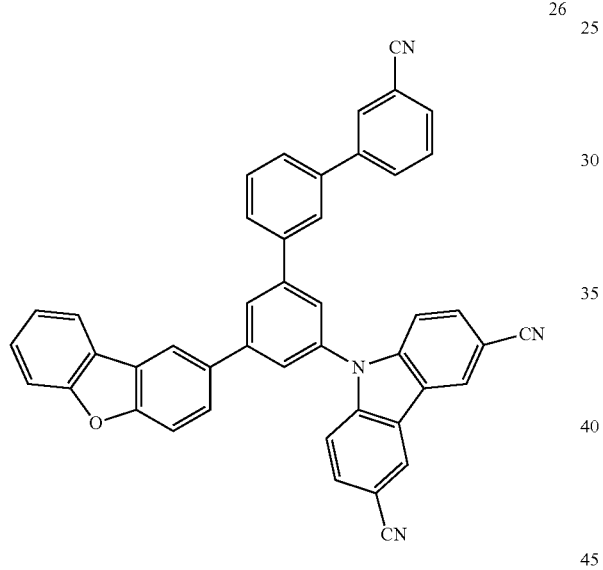
26
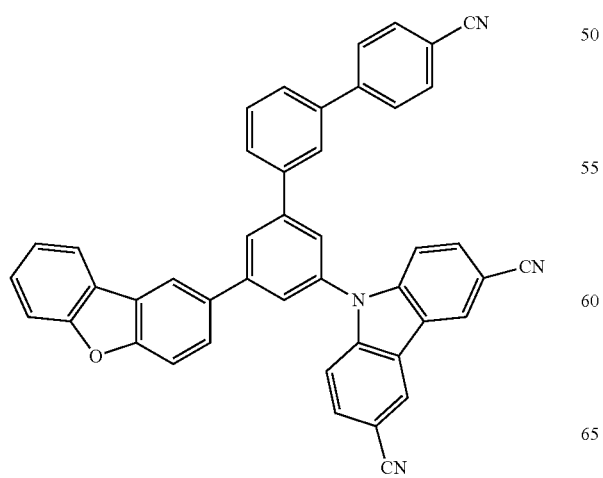
27
218
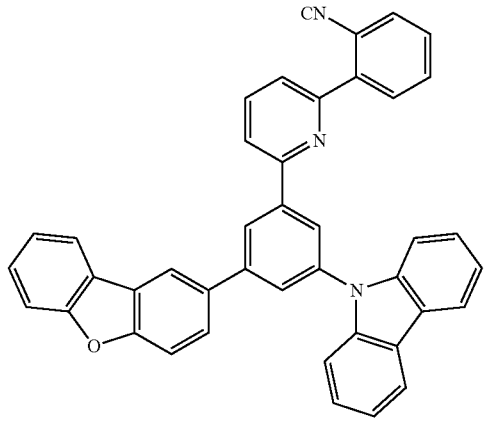
28
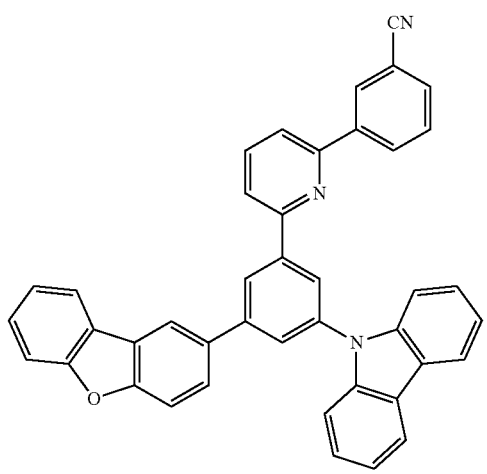
29
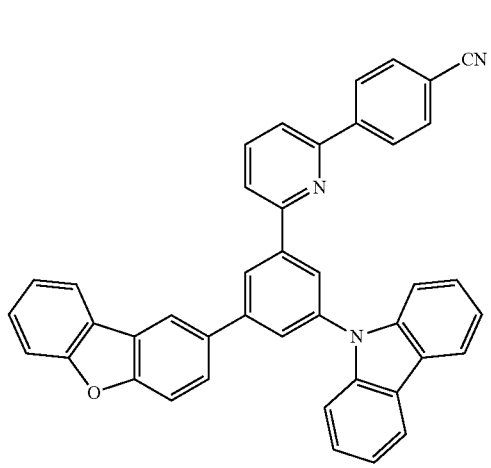
30

31
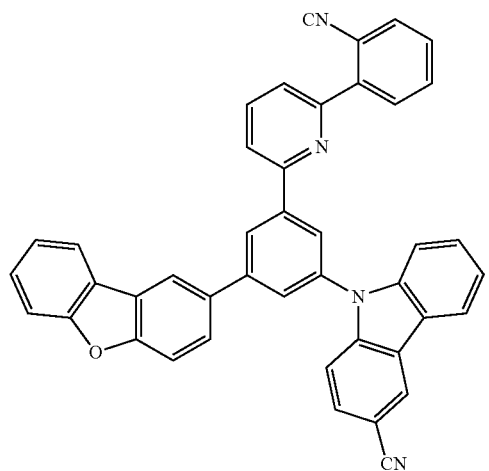
32
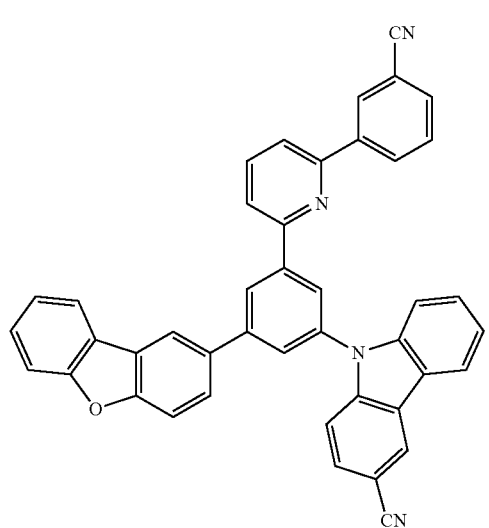
33
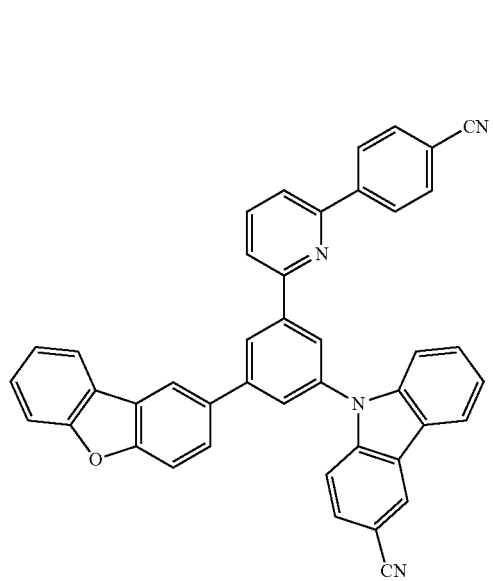
34
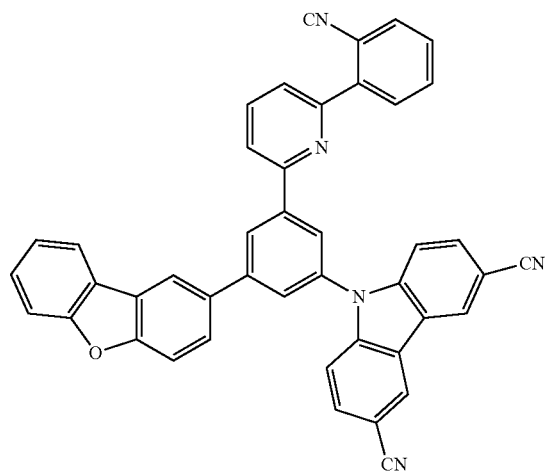
35
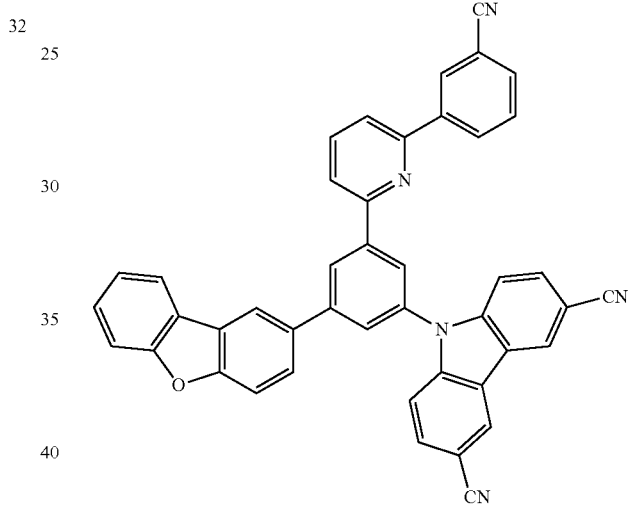
36
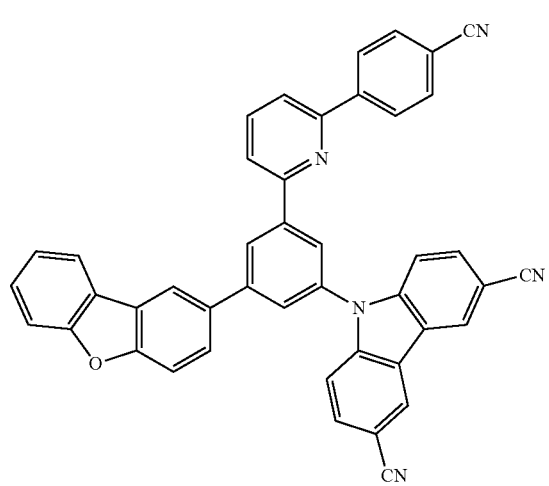

-continued
37
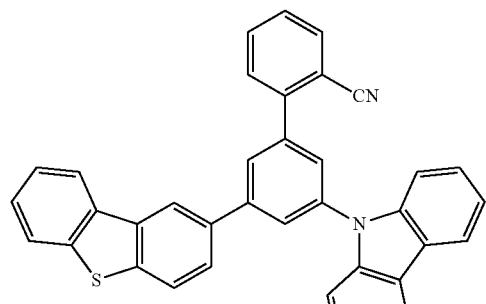
38
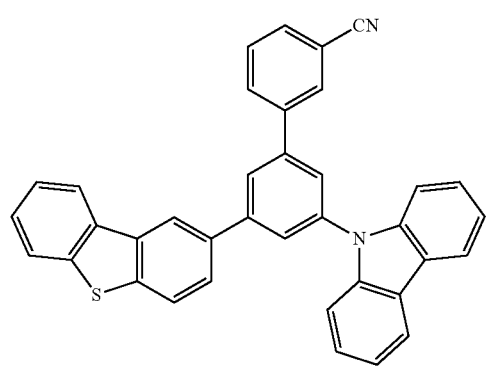
39
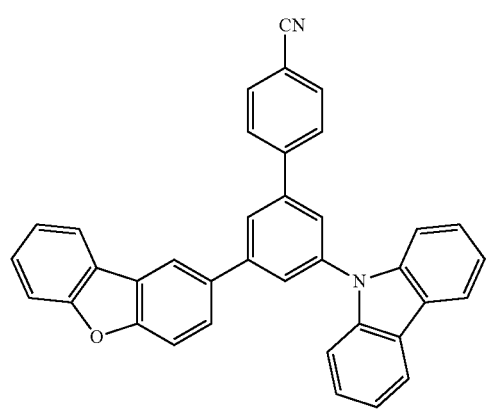
40
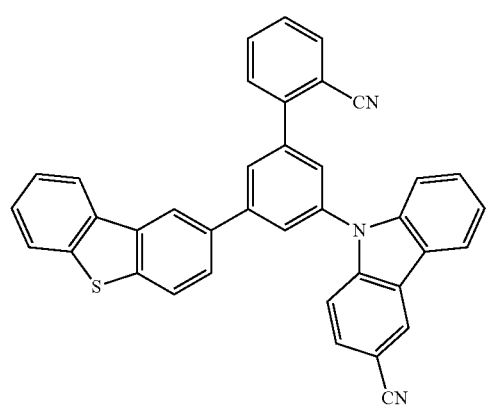
-continued
41
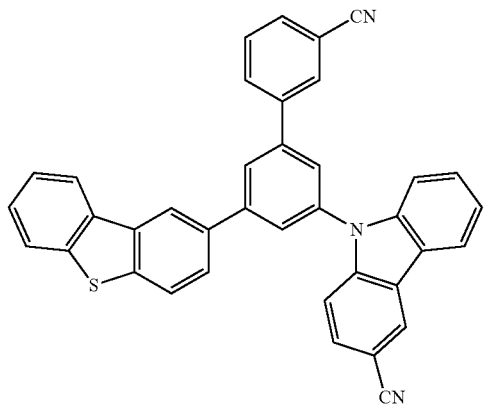
42
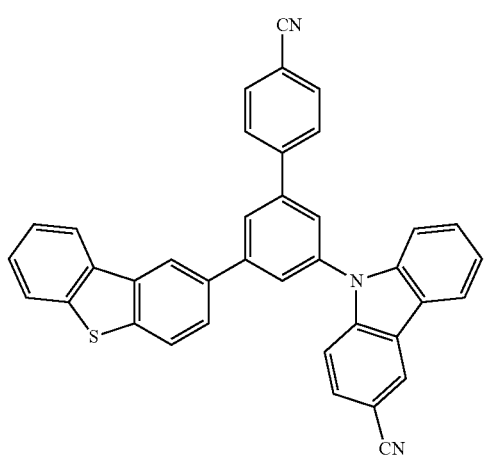
43
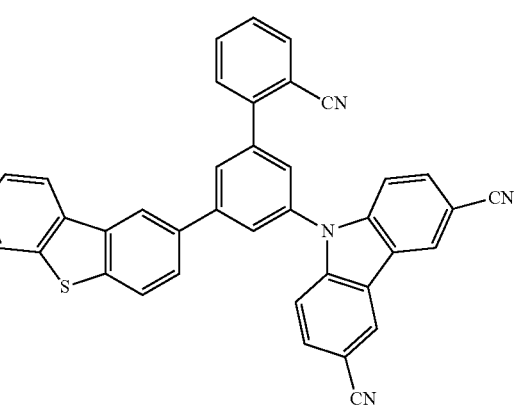

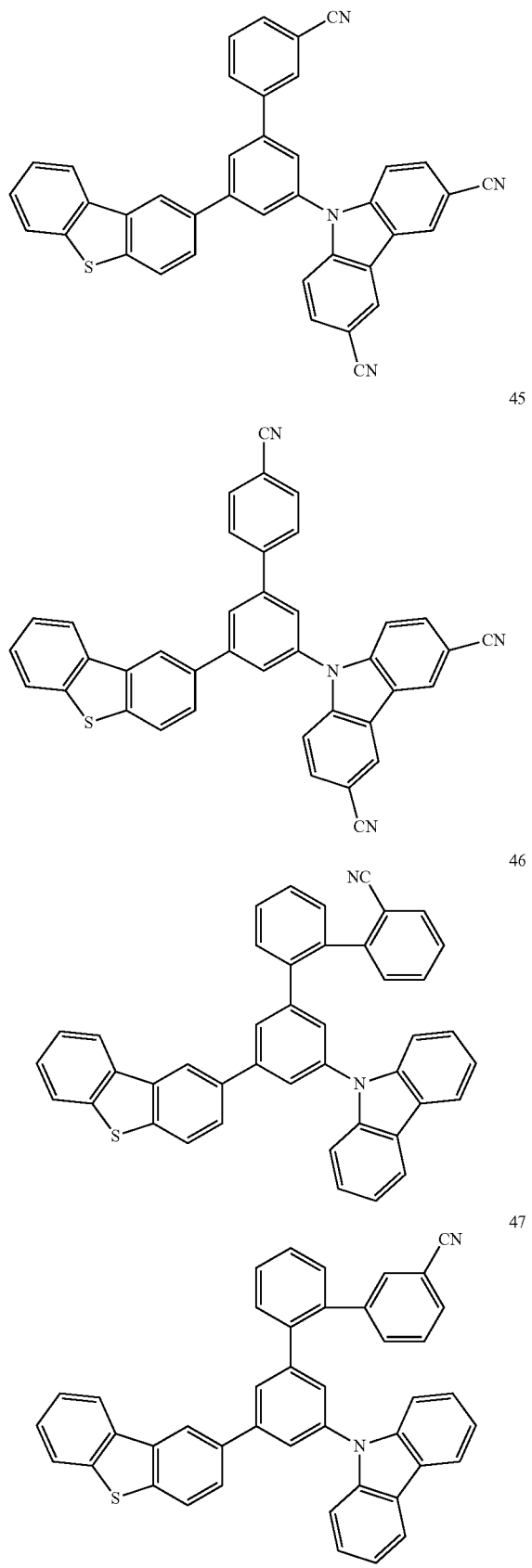
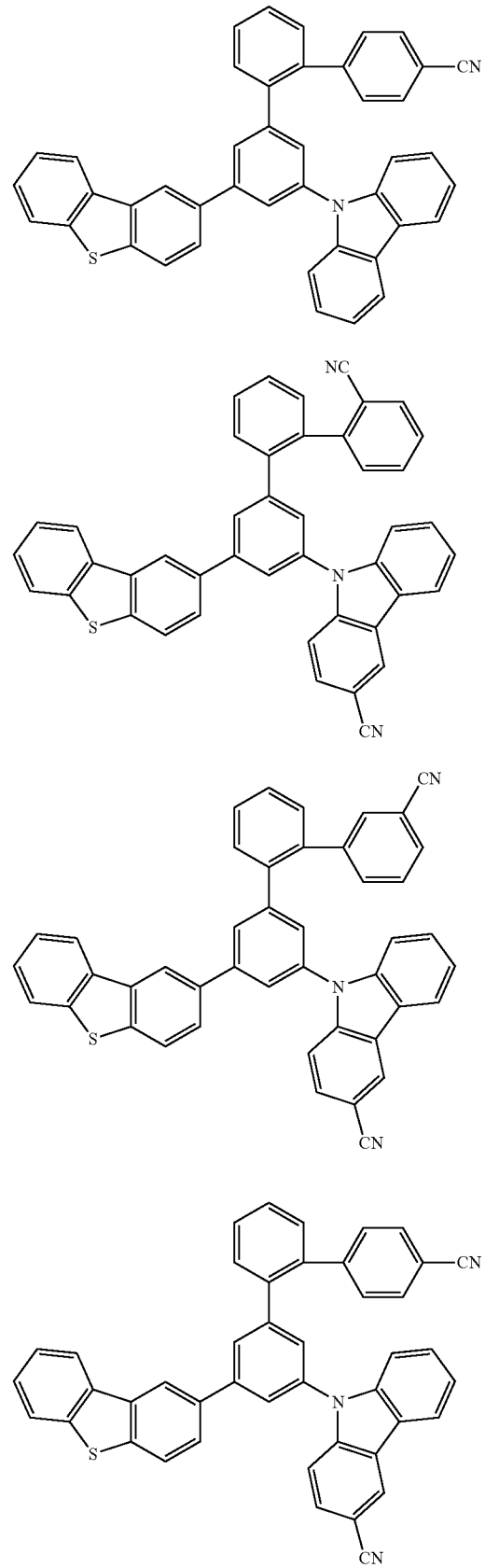

-continued
52
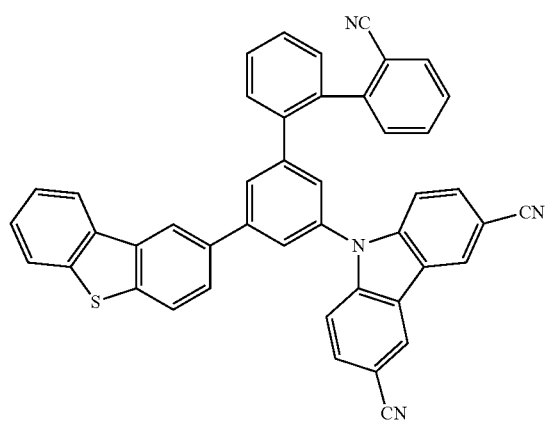
53
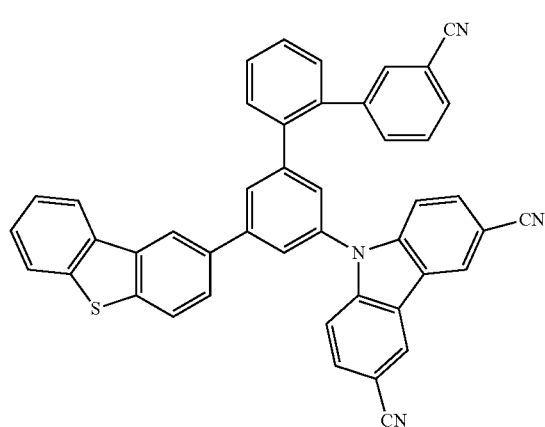
54
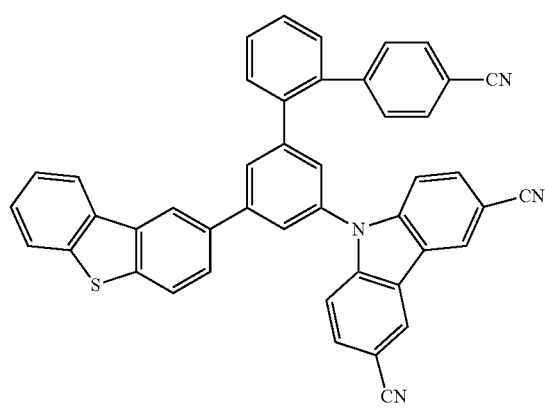
-continued
55
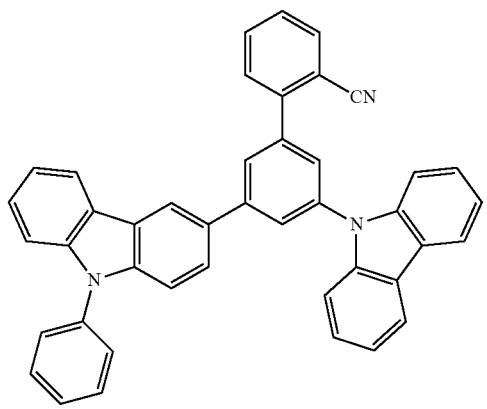
56
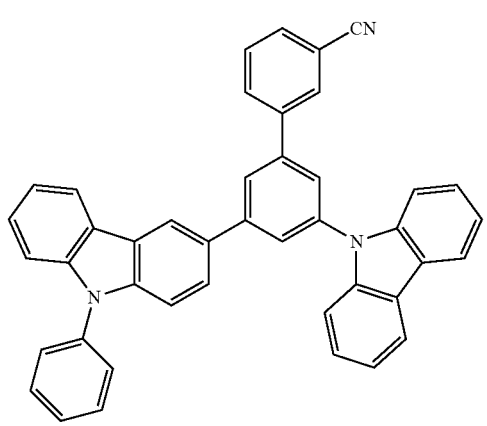
57
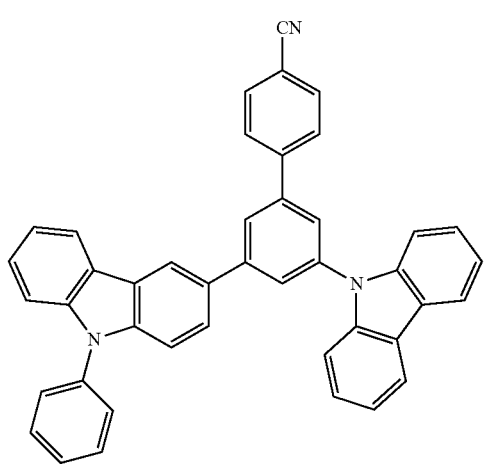

58
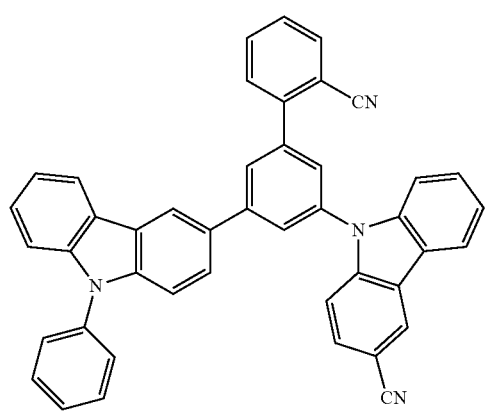
59
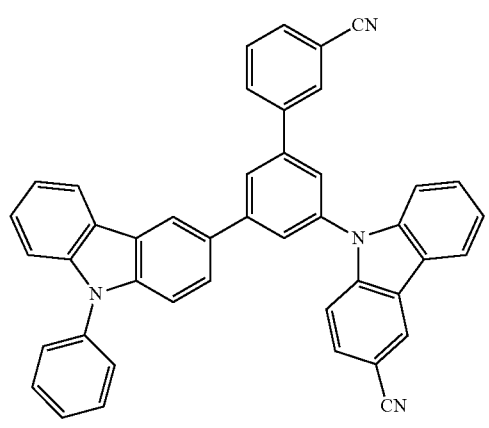
60
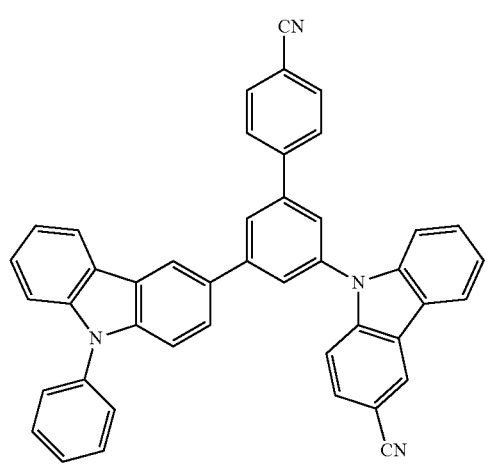
61
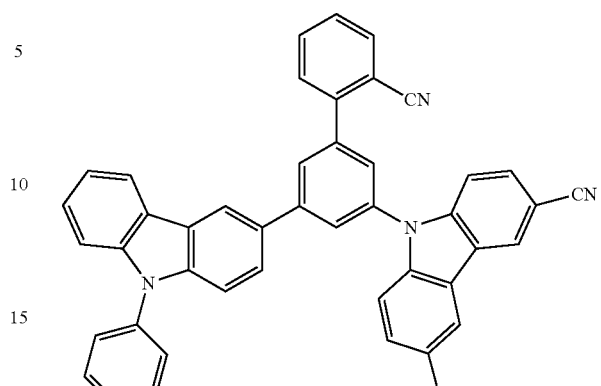
62
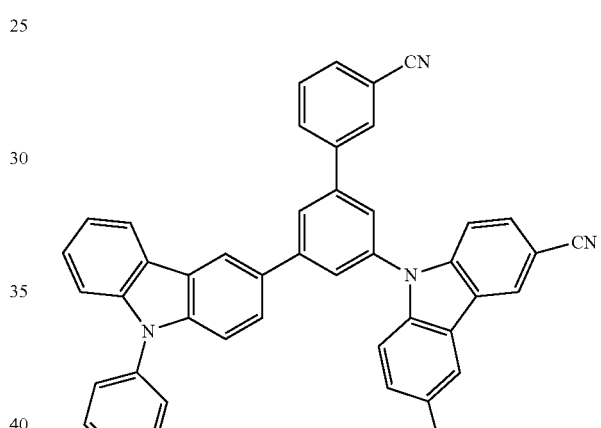
63
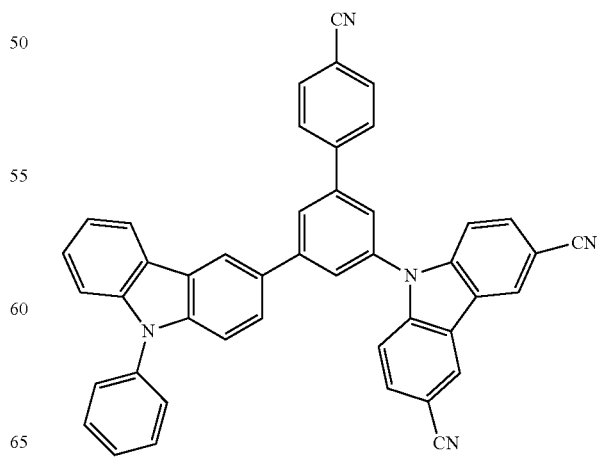

64
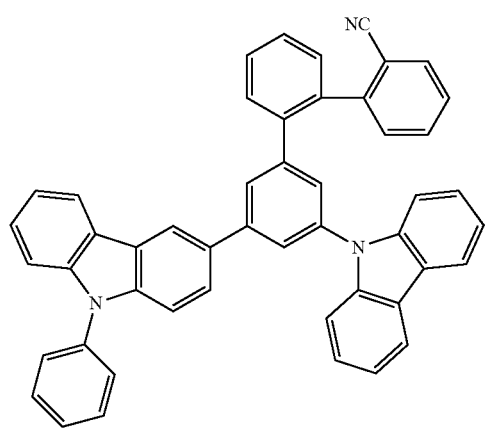
65
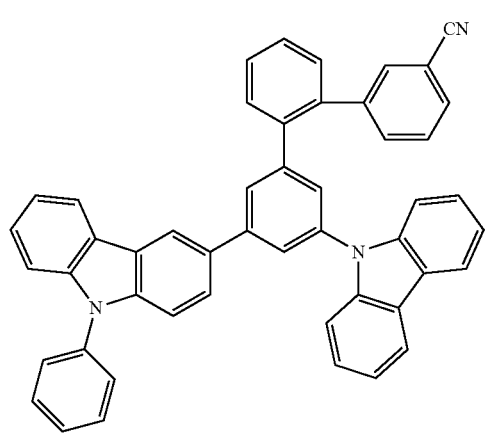
66
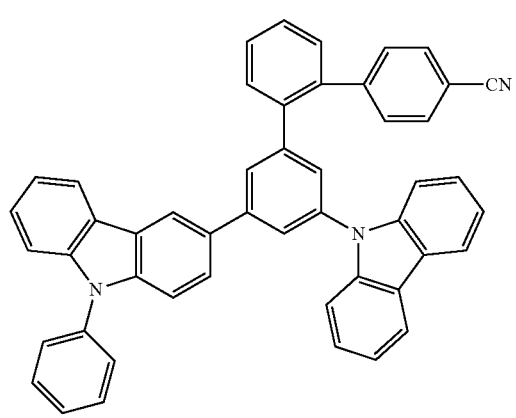
67
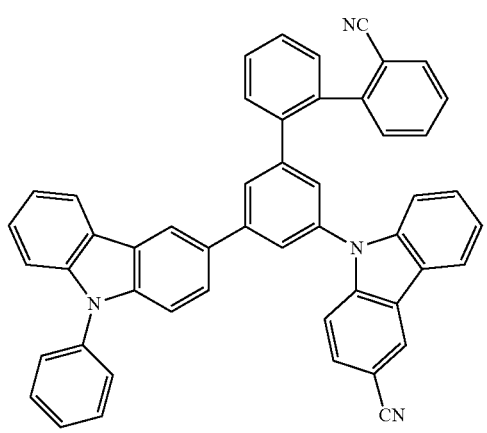
68
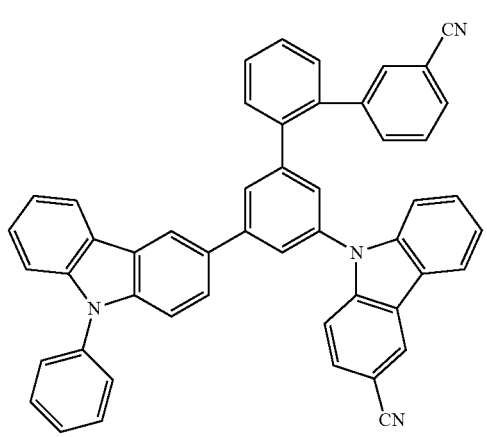
69
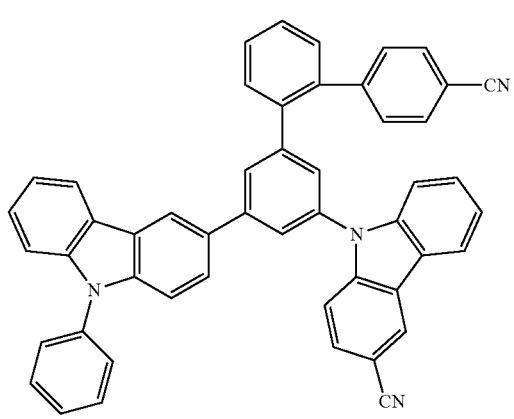

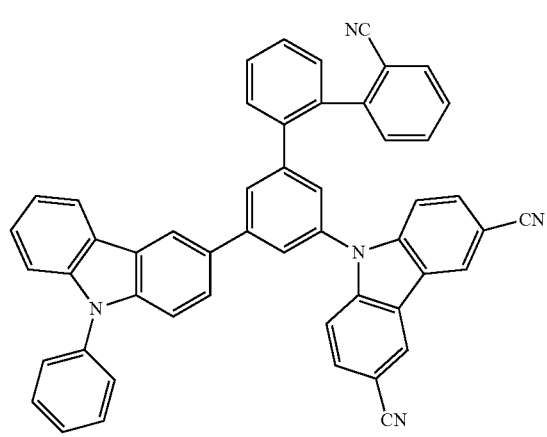
70
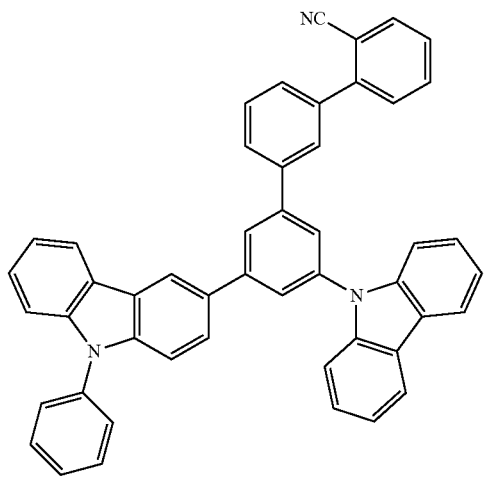
73
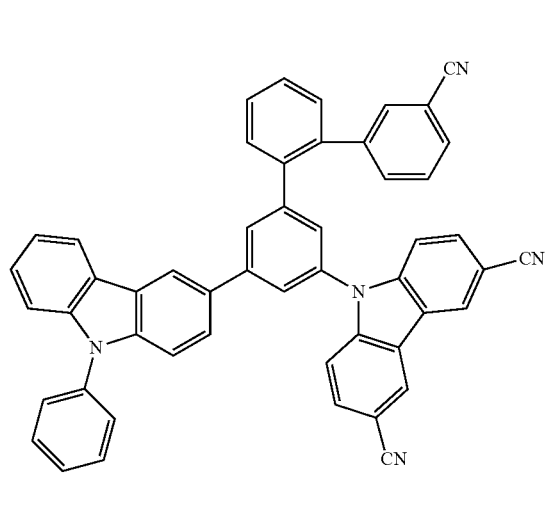
71
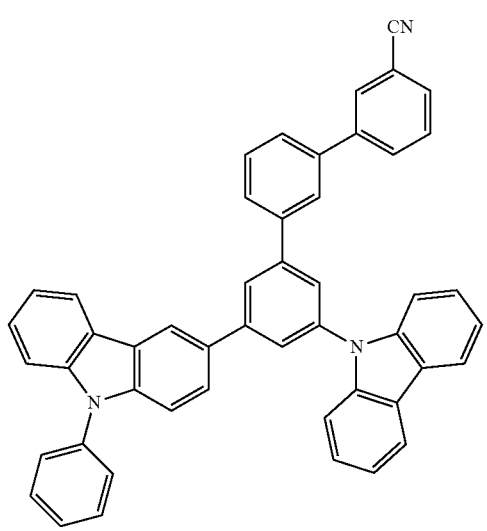
74
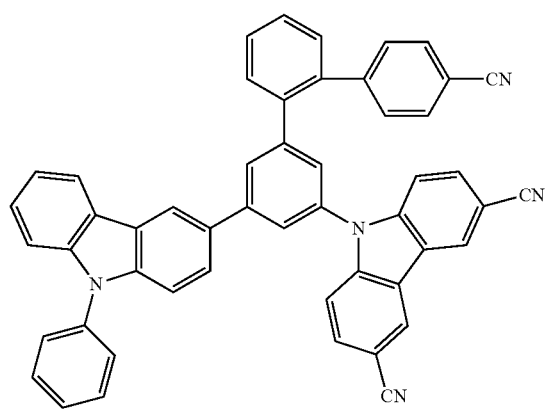
72
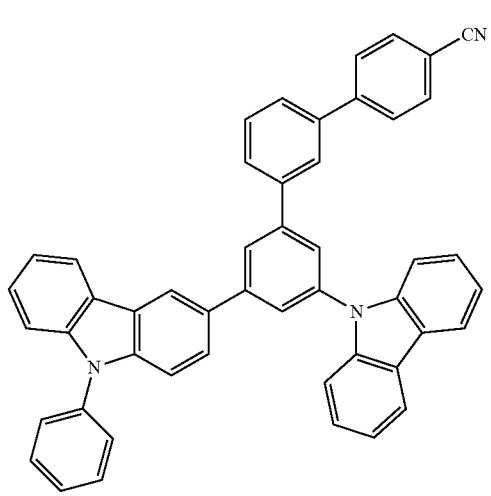
75

-continued
76
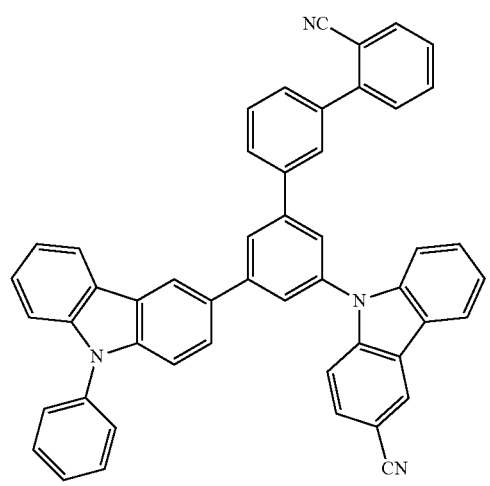
77
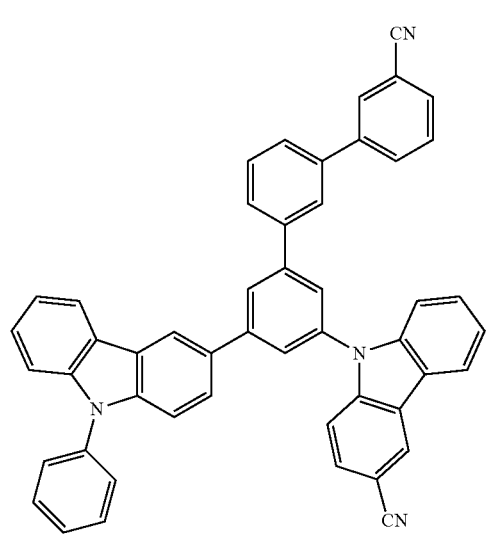
78
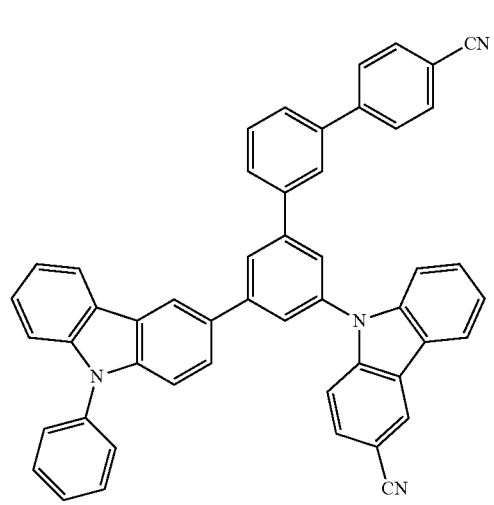
-continued
79
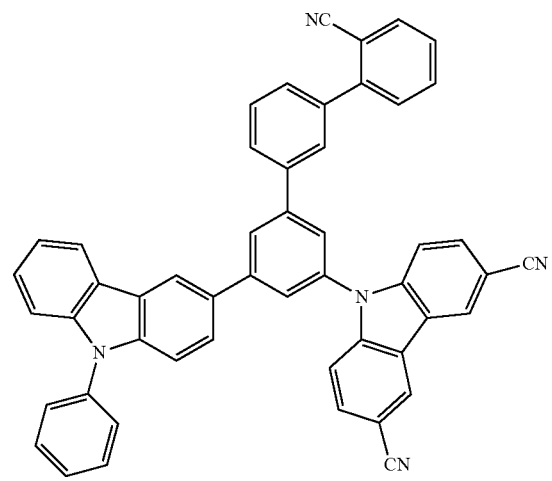
80
81
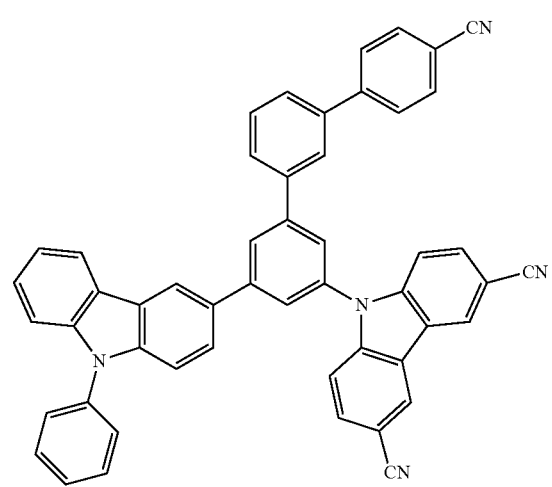

82
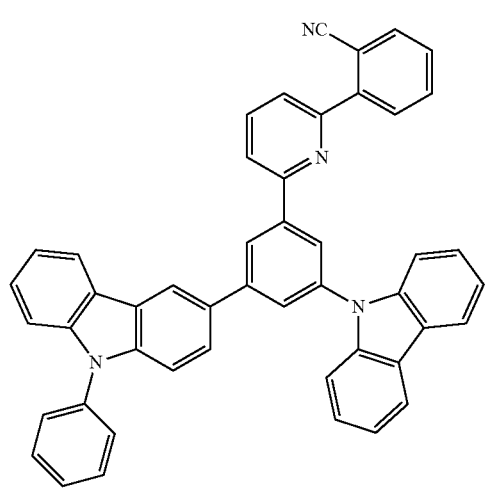
85
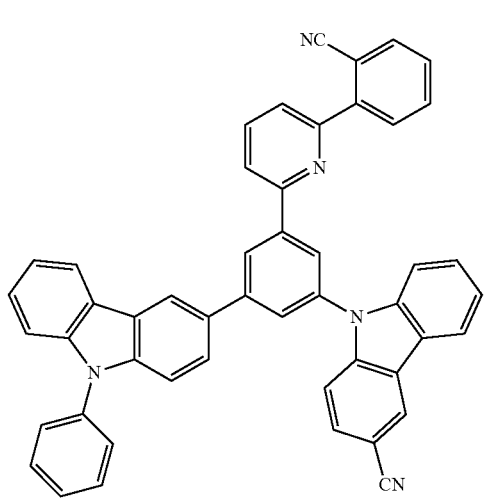
83
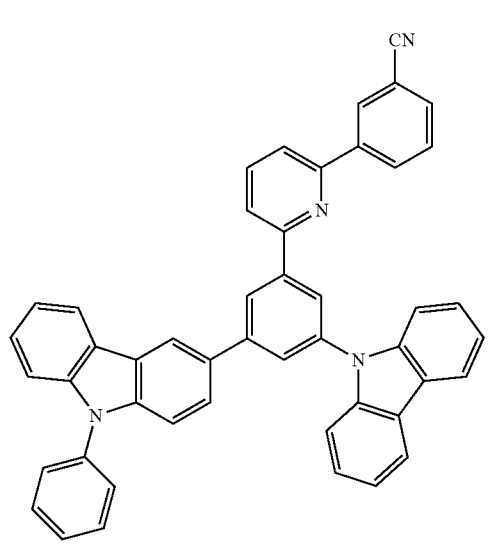
86
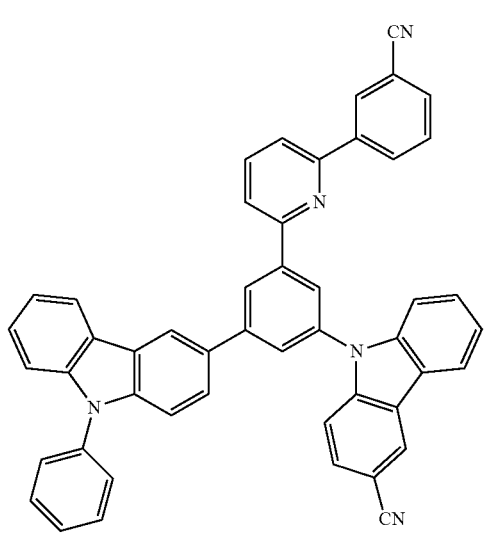
84
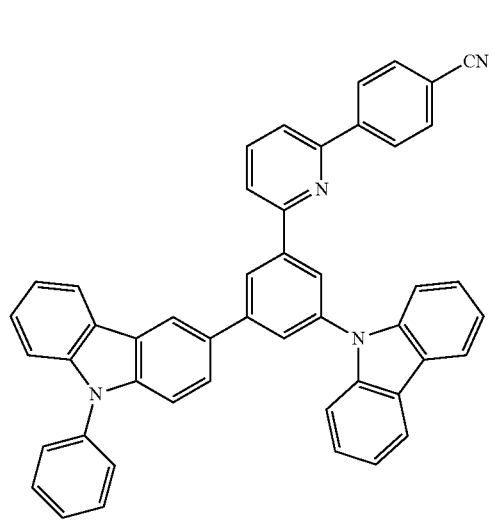
87
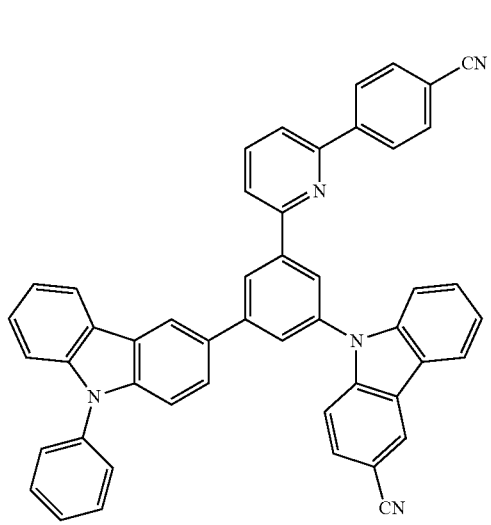

88

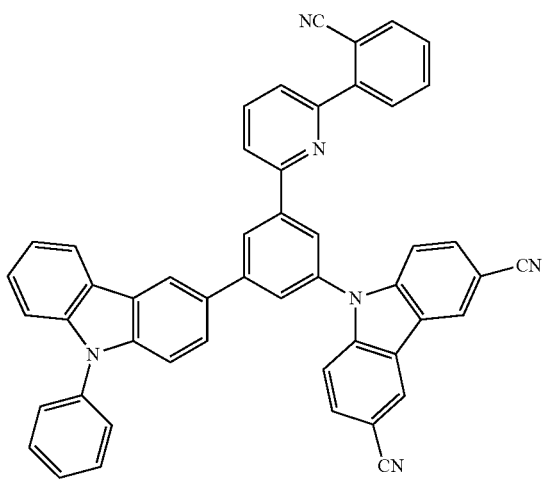

89

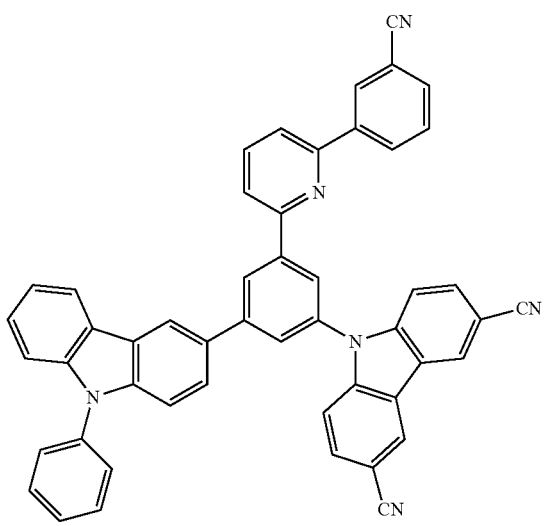

90

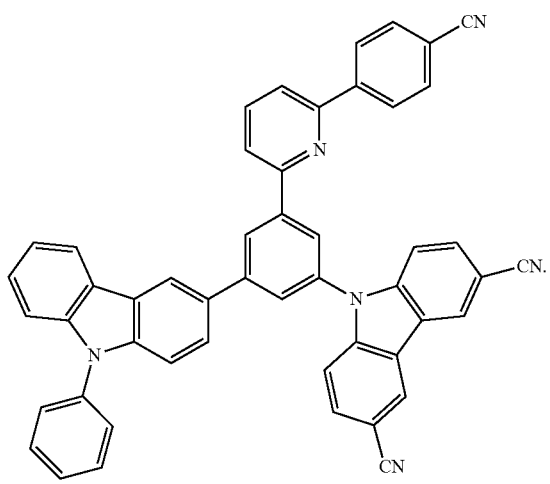

18. An organic light-emitting device comprising:
   a first electrode;
   a second electrode; and
   an organic layer disposed between the first electrode and the second electrode,
   wherein the organic layer comprises an emission layer and at least one condensed-cyclic compound of Formula 1 of claim 1.

19. The organic light-emitting device of claim 18, wherein the emission layer comprises the at least one condensed-cyclic compound of Formula 1.

20. The organic light-emitting device of claim 19, wherein the emission layer further comprises a phosphorescent dopant.

* * * * *